(12) United States Patent
Gallo et al.

(10) Patent No.: US 6,583,109 B1
(45) Date of Patent: *Jun. 24, 2003

(54) THERAPEUTIC POLYPEPTIDES FROM β-HCG AND DERIVATIVES

(76) Inventors: Robert C. Gallo, 8513 Thornden Ter., Bethesda, MD (US) 02817; Joseph Bryant, 732 Ivy League La., Rockville, MD (US) 20850; Yanto Lunardi-Iskandar, 226 Lee St., Gaithersburg, MD (US) 20877

( * ) Notice: Subject to any disclaimer, the term of this patent is extended or adjusted under 35 U.S.C. 154(b) by 0 days.

This patent is subject to a terminal disclaimer.

(21) Appl. No.: 09/220,415

(22) Filed: Dec. 24, 1998

Related U.S. Application Data

(63) Continuation-in-part of application No. PCT/US97/11210, filed on Jun. 24, 1997, and a continuation-in-part of application No. PCT/US97/11209, filed on Jun. 24, 1997, and a continuation-in-part of application No. PCT/US97/11448, filed on Jun. 24, 1997, and a continuation-in-part of application No. PCT/US97/11202, filed on Jun. 24, 1997.

(51) Int. Cl.⁷ ............................................. A01N 37/18
(52) U.S. Cl. ..................... 514/2; 514/14; 424/185.1; 424/198.1; 424/545; 530/324; 530/325; 530/326; 530/327; 530/328; 530/329; 530/330; 530/399
(58) Field of Search ........................... 424/185.1, 198.1, 424/545; 514/2, 14; 530/324–330, 399

(56) References Cited

U.S. PATENT DOCUMENTS

| | | |
|---|---|---|
| 4,161,519 A | 7/1979 | Talwar |
| 4,201,770 A | 5/1980 | Stevens ........................ 424/177 |
| 4,400,316 A | 8/1983 | Katsuragi et al. |
| 4,689,222 A | 8/1987 | McMichael |
| 4,691,006 A | 9/1987 | Stevens |
| 4,692,332 A | 9/1987 | McMichael |
| 4,713,366 A | 12/1987 | Stevens |
| 4,714,680 A | 12/1987 | Civin et al. |
| 4,762,913 A | 8/1988 | Stevens |
| 4,767,842 A | 8/1988 | Stevens |
| 4,780,312 A | 10/1988 | Talwar |
| 4,855,285 A | 8/1989 | Stevens |
| 4,880,626 A | 11/1989 | McMichael |
| 4,966,753 A | 10/1990 | McMichael |
| 5,004,681 A | 4/1991 | Boyse et al. |
| 5,141,867 A | 8/1992 | Ivanoff et al. |
| 5,192,553 A | 3/1993 | Boyse et al. |
| 5,380,668 A | 1/1995 | Herron |
| 5,445,968 A | 8/1995 | Pham ........................ 436/510 |
| 5,451,527 A | 9/1995 | Sarin et al. |
| 5,494,899 A | 2/1996 | Kincade et al. |
| 5,508,261 A | 4/1996 | Moyle et al. |
| 5,610,136 A | 3/1997 | McMichael |
| 5,614,612 A | 3/1997 | Haigwood et al. |
| 5,635,599 A | 6/1997 | Pastan et al. |
| 5,677,275 A | 10/1997 | Lunardi-Iskandar et al. |
| 5,700,781 A | 12/1997 | Harris |
| 5,811,390 A | 9/1998 | Bourinbaiar ................... 514/8 |
| 5,877,148 A | 3/1999 | Lunardi-Iskandar et al. ... 514/8 |

FOREIGN PATENT DOCUMENTS

| | | | |
|---|---|---|---|
| EP | 0 049 898 B2 | 4/1982 | |
| EP | 0 142 387 A1 | 5/1985 | |
| EP | 0 211 411 A2 | 2/1987 | |
| EP | 0323769 | 11/1988 | ........................ 7/6 |
| JP | 04300896 | 10/1992 | |
| WO | WO 86/04241 | 7/1986 | |
| WO | WO87/03487 | 6/1987 | |
| WO | WO 90/02759 | 3/1990 | |
| WO | WO9108228 | 6/1991 | ........................ 7/10 |
| WO | WO 91/09872 | 7/1991 | |
| WO | WO 91/16921 | 11/1991 | |
| WO | WO9222568 | 12/1992 | |
| WO | WO 92/22654 | 12/1992 | |
| WO | WO 94/20859 | 9/1994 | |
| WO | WO 94/24148 | 10/1994 | |
| WO | WO 96/04008 | 2/1996 | |
| WO | WO9749373 | 12/1997 | |
| WO | WO9906438 | 2/1999 | |
| WO | WO9925849 | 5/1999 | ........................ 15/62 |

OTHER PUBLICATIONS

1996 Sigma Product Catalogue, p. 1134.
Daar et al., Nat'l Acad Sci USA 87:6574–6579.
Strauss et al., 1986, Exp Hematol. 14:935–945.
Hammerskjold & Rekosh, 1989. Biochem. Biophys Acta. 989:269–280.
Abrams et al., 1983, J. Cell. Biochem. Supply A:53.
Aizawa and Tavassoli, 1986, Int. J. Cell Cloning 4:464–471.
Andrews et al., 1986, Blood 67;842–845.
Andrews et al., 1986, Blood 68;1030–1035.
Ballem et al., 1987, J. Clin. Invest. 80:33–40.
Ballem et al., 1992, New Eng. J. Med 327:1779–1784.
Barre–Sinoussi et al., 1983 Science 220:868–870.
Bauman et al., 1986, J. Cell Physiol. 128:133–142.
Bellet et al., 1984, Endocrinology 115:330–336.
Berchtold and Wenger, 1993, Blood 81:1246–1250.
Bidart et al., 1987, Mol. Immunology 24:339–345.
Bidart et al., 1987, J. Biol. Chem. 262:15483–15489.
Bidart et al., 1990, Science 248:736–739.

(List continued on next page.)

*Primary Examiner*—Jeffrey Stucker

(57) ABSTRACT

The present invention relates to peptides of one or more portions of the human chorionic gonadotropin β-chain peptides containing a sequence of one or more portions of the β-chain of human chorionic gonadotropin and derivatives and analogues thereof. The invention further relates to fractions of sources and or preparations of human chorionic gonadotropin, such as fractions of human early pregnancy urine, which fractions have anti-HIV activity, anti-cancer activity, and/or pro-hematopoietic activity. The present invention further relates to pharmaceutical compositions for treating and/or preventing HIV infection, cancer, and/or for promoting hematopoiesis.

102 Claims, 51 Drawing Sheets

OTHER PUBLICATIONS

Blazevic et al., 1985, AIDS Res. Hum. Retroviruses 11:1335–1342.
Bodger, et al., 1983, Blood 61:1006–1010.
Bolognesi, 1993, Semin. Immunol. 5:203–214.
Bourinbaiar and Nagorny, 1992, FEMS Microbiol. Lett. 96:27–30.
Bourinbaiar and Nagorny, 1992, FEBS Microbiol. Lett. 309:82–84.
Bourinbaiar and Lee–Huang, 1995, Immunol. Lett. 44:13–17.
Braunstein et al., 1978, J. Clin. Endocrinology and Metabolism 47:326–332.
Broxmeyer et al., 1984, J. Clin Invest. 73:939–953.
Broxmeyer, 1983, CRC Critical Reviews in Oncology/Hematology 1:227–257.
Broxmeyer, 1982, J. Clin Invest. 69:632–642.
Busch et al., 1987, Blut 54:179–188.
Cain et al., 1986, Transplantation 41:22–25.
Cao et al., 1982, J. Med. Genet. 19:81–87.
Caraux et al., 1985, J. Immun. 134:835–840.
Chak et al., 1988, J. Clin. Oncol. 6:863–867.
Chen et al., 1992, AIDS 6:533–539.
Clavel et al., 1986, Science, 233:343–346.
Cocchi et al., 1995, Science, 270–1811–1815.
Daffos, et al., 1983, am. J. Obstst. Gynecol. 146:985–987.
Daffos, et al., 1985, am. J. Obstst. Gynecol. 153:655–660.
Dalgleish et al., 1984, Nature 312:763–767.
De at al., 1997, J. Clin. Invest. 99:1484–1491.
Delli–Bovi et al., 1986, Cancer Res. 46:6333–6338.
Deshmukh et al., 1994, J. Clin. Immunol. 14:162–168.
Dexter et al., 1977, J. Cell. Physiol. 91:335–344.
Dickie et al. 1991, Virology, 185:109–119.
Dirnhofer et al. 1993, FASEB J. 7:1381–1385.
Dirnhofer et al. 1994, J. Endocrinology 141:153–162.
Emerson et al., 1985, J. Clin. Invest. 76:1286–1290.
Ensoli et al., 1989, Science 243:223–226.
Erickson, 1990, Science 249:527–533.
Evans et al., 1991, J. Immunotherapy 10:39–50.
Ferrero et al., 1983, Proc Natl. Acad. Sci. USA 80:4114.
Ferrero et al., 1986, Cancer Res. 46:975–980.
Franks et al., 1995, Pediatric Res. 37:56–63.
Friedman–Kien et al., 1981, J. Am. Acad. Dermatol. 5:468–473.
Gallo et al., 1984, Science 224:500–503.
Gelmann et al., 1987, Am. J. Med. 82:456–462.
Geller et al., 1985, Archs. Path. Lab. Met. 109:138–145.
Gill et al., 1990, Am. J. Clin. Oncol. 13:315–319.
Gill et al., 1991, Am. J. Med. 90:427–433.
Gill et al., 1994, AIDS, 8: 1695–1699.
Gill et al., 1996, New Eng. J. Med. 335:1261–1269.
Goldman et al., 1980, Br. J. Haematol. 45:221–223.
Guyader et al., 1987, Nature 326:662–669.
Hammerskjold and Rekosh, 1989, Biochem. Biophys. Acta 989:269–280.
Harris, 1995, Lancet 346:118–119.
Hermans, 1995, AIDS Res. Hum. Retroviruses S–96.
Hermans et al., 1995, Cell. Mol. Biol. 3:357–364.
Hershko et al., 1979, Lancet 1:945–947.
Heymsfield et al., Am. J. Clin. Nutr. 36:Oct. 1982, p. 680–690.
Hirokawa et al., 1982, Clin. Immumol. Immunopathol. 22:297–304.
Huang and Terstappen, 1992, Nature 360:745–749.
Hutchinson et al., 1978, J. Biol. Chem. 253:6551–6560.
Iyer et al. 1992, Int. J. Pepetide Protein Res. 39:137–144.
Juttner et al., 1985, Br. J. Haematol. 61:739–745.
Kahn et al., 1990, am. Ann. Med. 112:254–261.
Kardana et al., B. J. Cancer 1993 67:686–692.
Katz et al., 1985, Leukemia Res. 9:191–198.
Katz et al., 1986, Leukemia Res. 10:961–971.
Keating et al., 1984, Blood 64:1159–1162.
Kestler et al., 990, Science 248:1109–1112.
Keutmann et al., 1987, Proc. Natl. Acad. Sci. USA 84:2038–2042.
Keutmann et al., 1988, Biochemistry 27:8939–8944.
Klatzmann et al., 1984, Nature 312:767–768.
Kodo et al., 1984, J. Clin. Invest. 73:1377–1384.
Kopp et al., 1993, AIDS Res. Hum. Retroviruses 9:267–275.
Korbling et al., 1986, Blood 67:529–532
Kornyei et al., 1993, Biol. Reprod. 49:1149–1157.
Krown et al., 1990, Ann. Intern. Med. 112:812–821.
Lajtha, 1979, Differentiation 14:23–34.
Lajtha, 1979, Blood Cells 5:447–455.
Laphorn et al., 1994, Nature 369:455–461.
Leary et al., 1987, Blood 69:953–956.
Letvin et al., 1990, J. AIDS 3;1023–1040.
Longhi et al., 1986, J. Immunol. Meth. 92:89–95.
Lord and Spooncer, 1986, Lymphokine Res. 5:59–72.
LOuache et al., 1992, Blood 180:2991–2999.
Lu et al., 1983, Blood 61:250–256.
Lunardi–Iskandar et al., 1989, J. Clin. Invest. 83:610–615.
Lunardi–Iskandar et al., 1989, Leukemia Res. 13:573–581.
Lunardi–Iskandar et al., 1995, Nature 375:64–68.
Maddon et al., 1986, Cell 47:333–348.
Martin, 1991, *Basic and Chemical Endocrinology* (Appleton & Lange, East Norwalk) pp 543–567.
Masood et al., 1984, AIDS Res. Hum. Retroviruses 10:969–976.
McDougal et al., 1986, Science, 231:382–385.
Merrifield, 1963, J. Amer. Chem. Soc. 85:2149–2156.
Mitsuya et al., 1991, Science 249:1533–1544.
Moore et al., 1980, Blood 55:682–690.
Nakamura et al., 1988, Science 242:426–430.
Nicola et al., 1980, J. Cell. Physiol. 103:217–237.
Nicola et al., 1981, Blood 58:376–386.
Nijhof et al., 1983, J. Cell. Biol. 96:386–392.
Nijhof et al., 1984, Exp. Cell. Res. 155:583–587.
Nothdurft et al., 1977, Scand. J. Haematol. 19:470–481.
Ochs et al., 1981, Pediatr. Res. 15:601.
Paige et al., 1981, J. Exp. Med. 153:154–165.
Paul, 1994, Cell 82:177–182.
Perelson et al., 1966, Science 15:1582–1586.
Pierce et al., 1991, Rev. Biochem., 50:465–495.
Pillow et al., 1966, New Eng. J. Med. 275:94–97.
Popescu et al., 1995, JNCI 88:450–454.
Popovic et al., 1984, Science 224:497–500.
Prummer et al., 1985, Exp. Hematol. 13:891–898.
Puisieux et al., 1990, Endocrinology 126:687–694.
Raghavacher et al., 1983, J. Cell. Biochem. Suppl. 7A:78.
Reiffers et al., 1986, Exp. Hematol. 14:312–315.
Reisner et al., 1978, Proc. Natl. Acad. Sci. USA 75:2933–2936.
Reisner et al., 1982, Blood 59:360–363.
Robak et al., 1985, Leukemia Res. 9:1023–1029.
Rodeck, 1984, *Prenatal Diagnosis* (Royal College of Obstetricians and Gynaecologists, London).
Ryan et al., 1988, FASEB J. 2:2661–2669.

Salahuddin et al., 1988, Science 242:430–433.
Sarpel et al., 1979, Exp. Hematol. 7:113–120.
Schall, 1991, Cytokine 3:165–183.
Schooley et al., 1990, ann. Int. Med. 112:247–253.
Sherman, 1992, J. Mol. Endocrinol. 6:951–959.
Siegel et al., 1990, Cancer 65:492–498.
Smith et al., 1987, Science 238:1704–1707.
Smith and Broxmeyer, 1986, Br. J. Haematol. 63:29–34.
Stevens at al., 1986, Immunol. Lett. 12:11–18.
Strauss et al., 1986, Exp. Hematol. 14:878–886.
Strauss et al., 1986, Exp. Hematol. 14:935–945.
Terstappen et al., 1992, Leukemia 6:993–1000.
Thomas et al., 1972, Lancet 1(745):284–289.
Tilly et al., 1986, Lancet, Jul. 19 pp. 154–155.
To and Juttner, 1987, Br. J. Haematol. 66:285–288.
Torres et al., 1987, Immunol. Inv. 16:607–618.
Touraine, 1983, Birth Defects 19:139–142.
Triozzi et al., 1994, Int. J. Oncol. 5:1447–1453.
Tulunay et al., 1975, Proc. Natl. Acad. Sci USA 72:4100–4104.
Valenti, 1973, Am. J. Obstet. Gynecol. 115:851–853.
Van Gemen et al., 1994, J. virol. Methods 49:157–168.
Varmus et al., 1988, Science 240:1427–1439.
Vaslin et al., 1994, AIDS Res. Hum. Retroviruses 10:1241–1250.
Vickery et al., 1983, J. Parasitol. 69:478–485.
Visser et al., 1984, J. Exp. Med. 59:1576–1590.
Ward et al., 1991, *Reproduction in Domestic Animals* (Academic Press, New York) pp. 25–80.
Weinroth et al., 1995, Infectious Agents and disease 4:76–94.
Whitlock and Witte, 1982, Proc. Natl. Acad. Sci. USA 79:3608–3612.
Williams et al., 1987, Exp. Hematol. 15:243–250.
Winchester et al., 1977, Proc. Natl. Acad. Sci. USA 7414012–4016.
Xia, 1993, J. Mol. Endocrinol., Jun. 10:337–343.
Yarchoan et al., 1989, Proc. Vth Int. Conf. On AIDS, p. 564.
Yunis, 1983, Science 221:227–236.
Kotler et al., Am J. Clin. Nutr. 1985 42: 1255–65.
Kotler and Grunfeld, *AIDS Wasting Syndrome,* 229–275.
Kotler et al., Am J. Clin. Nutr. 1989; 50: 444–447.
Lunardi–Iskandar et al., J. Natl. Cancer Inst 87(13) 974–981.
Mastrangelo et al., Sem. Oncol 1996 23 (1): 4–21.
Mitsuya et al., FASEB 1991, 2369–2381.
Ott et al., Am J Clin Nutr 1993; 57:15–19.
Policastro et al., J Biol Chem 258: 11492–11499.
Russo and Russo, Cancer Letters 1995 90: 81–89.
Fink, et al., Amino Acid Sequence Elucidation of Human Acrosin–Trypsin Inhibitor (HUSI–II) Reveals that Kazal–type Proteinase Inhibitors are Structurally Related to β–subunits of Glycoprotein Hormones, FEBs Letters, vol. 270, No. 1,2, pp. 222–224.
Alfthan et al. (1992) Cancer Res. 52: 4628–4633.
Bagshawe (1992) Acta Oncol. 31: 99–106.
Bidart, J–M et al., "Human Chorionic Gonadotropin Molecular Forms, Detection, and Clinical Implications." TEM 4:285 (1993).
Birken, S. et al., "Structure of the Human Chorionic Gonadotropin .beta.–Subunit Fragment from Pregnancy Urine." Endocrinology 123:572 (1988).

Bourinbaiar, A.S. et al., "Pregnancy hormones, estrogen and progesterone, prevent HIV–1 synthesis in monocytes but not in lymphocytes." FEBS Letters 302:206 (1992).
Chen. W. et al., "Recombinant Carbohydrate Variant of Human Choriogonadotropin.beta.–Subunit (hCG.beta) Descarboxyl Terminus (115–145)." Journal of Biological Chemistry 266:6246 (1991).
Cole, L.A., et al., "The Deactivation of hCG by Nicking and Dissociation" Journal of Clinical Endocrinology and Metabolism 76:704 (1993).
Cole, Laurence A. et al., "The Heterogeneity of Human Chorionic Gonadotropin (hCG). III. The Occurrence and Biological and Immunological Activities of Nicked hCG." Endocrinology 129:1559 (1991).
Curti, Critical Reviews in Oncology/Hematology, vol. 14, pp. 29–39, 1993.
Danforth, D.N., Jr., M.D., "How Subsequent Pregnancy Affect Outcome in Women with a Prior Breast Cancer." Oncology 5:23 (1991).
Elford et al. (1993) AIDS 7: 1667–1671.
Freireich, E.J. et al., "Quantitative Comparison of Toxicity of Anticancer Agents in Mouse, Rat, Hamster, Dog, Monkey, and Man." Cancer Chemotherapy Reports 50:219 (1966).
Hirabayashi, M., M.D., "Early Gastric Cancer and a Concomitant Pregnancy", The American Surgeon 53:730 (1987).
Huang, J. et al., "Amino/Carboxyl–terminal Deletion Mutants of Human Choriogonadotropin.beta.." The Journal of Biological Chemistry 268:9311 (1993).
Huang, J. et al., "Mutagenesis of the 'determinant loop' region of human choriogonadotropin.beta.." Molecular and Cellular Endocrinology 90:211 (1993).
Jain, Scientific American, pp. 58–65, Jul. 1994.
Kumar, S. et al., "Necrosis and Inhibition of Growth of Human Lung Tumor by Anti–alpha.–Human Chorionic Gonadotropin Antibody." J. Natl Cancer Inst. 84:42 (1992).
Loosfelt, H. et al., "Cloning and Sequencing of Porcine LH–hCG Receptor cDNA: Variants Lacking Transmembrane Domain." Science 245:525 (1989).
Mann et al, Scand. J. Clin. Lab. Invest. , Suppl. vol. 216, pp. 97–104, 1993.
Marcillac et al. (1992) Cancer Res. 52: 3901–3907.
McFarland, K.C. et al., "Lutropin–Choriogonadotropin Receptor: An Unusual Member of the G Protein–Coupled Receptor Family." Science 245:494 (1989).
Nakhai, B. et al., "Over–expression and characterization of recombinant beta subunit of the human chorionic gonadotropin hormone synthesized in insect cells infected with a genetically engineered bAculovirus." Indian Journal of Biochemistry & Biophysics 29:315 (1992).
Northfeldt et al. (1991) Hematology/Oncology Clinics of North America 5: 297–310.
Ozturk, M. et al., "Ectopic .beta.–Human Chorionic Gonadotropin Production by a Human Hepatoma Cell Line (Focus): Isolation and Immunochemical Characterization." Endocrinology 120:559 (1987).
Ozturk, M. et al., "Physiological Studies of Human Chorionic Gonadotropin (hCG), .alpha.hCG, and .beta.hCG as Measured by Specific Monoclonal Immunoradiometric Assays." 120:549 (1987).
Ross et al., Immunology Today, vol. 11, No. 6, 1990.

Siemen, Rodent Tumor Models in Experimental Cancer Therapy, Edited by Kallman, Pergamon Press, pp. 12–15, 1987.

Sridhar, P. et al., "Differential secretion and glycosylation of recombinant human chorionic gonadotrophin (.beta.hCG) synthesized using different promoters in the baculovirus expression vector system." Gene (Netherlands) 131:261 (1993).

Stenman et al. (1993) Scand. J. Clin. Lab. Invest. Suppl. 216: 42–78.

Strickland et al. in Luteinizing hormone action and receptors, M. Ascoli, Ed., CRC Press, Boca Raton FL, 1985, p. 1.

Trott, Rodent Tumor Models in Experimental Cancer Therapy, Edited by Kallman, Pergramon Press, pp. 6–11, 1987.

Ward et al. in Reproduction in Domestic Animals, 4th ed., Cuppos, PT, ed., pp. 25–80, Academic Press, NY (1991).

Wass, M. et al., "Response of lymphocytes from cancer patients to human *chorionic* gonadotrophin", Lancet (England) 1:8004:171 (1977).

Yano, T. et al., "Inhibition of human epithelial ovarian cancer cell growth in vitro by agonistic and antagonistic analogues of luteinizing hormone–releasing hormone." Pro. Natl. Acad. Sci. USA 91:1701 (1994).

Cole, L.A. "The heterogeneity of human gonadotropin (hCG). III. The occurrence and biological and immunological activities of nicked hCG," Endocrinology, Sep. 1991, 129 (3):1559–1567.

Cole, L.A. et al., "The biological and clinical significance of nicks in human chorionic gonadotropin and its free beta–subunit," Yale J Biol Med. Nov.–Dec. 1991; 64 (6):627–37.

Cole, Laurence A. "hCG, Its Free Subunits and Its Metabolites—Roles in Pregnancy and Trophoblastic Disease," Journal of Reproductive Medicine, Jan. 1998 43 (1): 3–10.

Creighton, 1993, *Proteins, Structures and Molecular Principles* (W.H. Freeman & Co., New York) pp. 34–49.

Dirnhofer, S. et al., "Functional and immunological relevance of the COOH–terminal extension of human chorionic gonadotropin beta: implications for the WHO birth control vaccine," FASEB J Nov. 1993 7(14):1381–1385.

Ho, H.H. et al., "Characterization of human chorionic gonadotropin peptide variants with a radio–receptor assay using recombinant human luteinizing hormone/chorionic gonadotropin receptors," Early Pregnancy Sep. 3, 1997, (3):204–12.

Iyer, K.S. et al., "Search for peptide immunogens of the beta–subunit of human chorionic gonadotropin (hCG) capable of eliciting hormone specific and neutralizing antisera. Identification of an undecapeptide eliciting hCG–specific antisera," Int J Pept Protein Res Feb. 1992: 39(2):137–44.

James, John S. "New Approaches to HIV Treatment: Interview with Robert Gallo, M.D.," Aids Treatment News, Dec. 19, 1997, Issue 285, pp. 1–7 (www.immunet.org).

Kardana, A. et al., "Human chorionic gonadotropin beta–subunit nicking enzymes in pregnancy and cancer patient sErum," J Clin Endocrinol Metab, Sep. 1994, 79 (3):761–7.

"Chorionic Gonadotropin," U.S. Pharmacopia (USP23).

Kobata, Akira et al., "Structure, pathology and function of the N–linked sugar chains of human chorionic gonadotropin," Biochemica et Biophysica Acta 1455 (1999) 315–326.

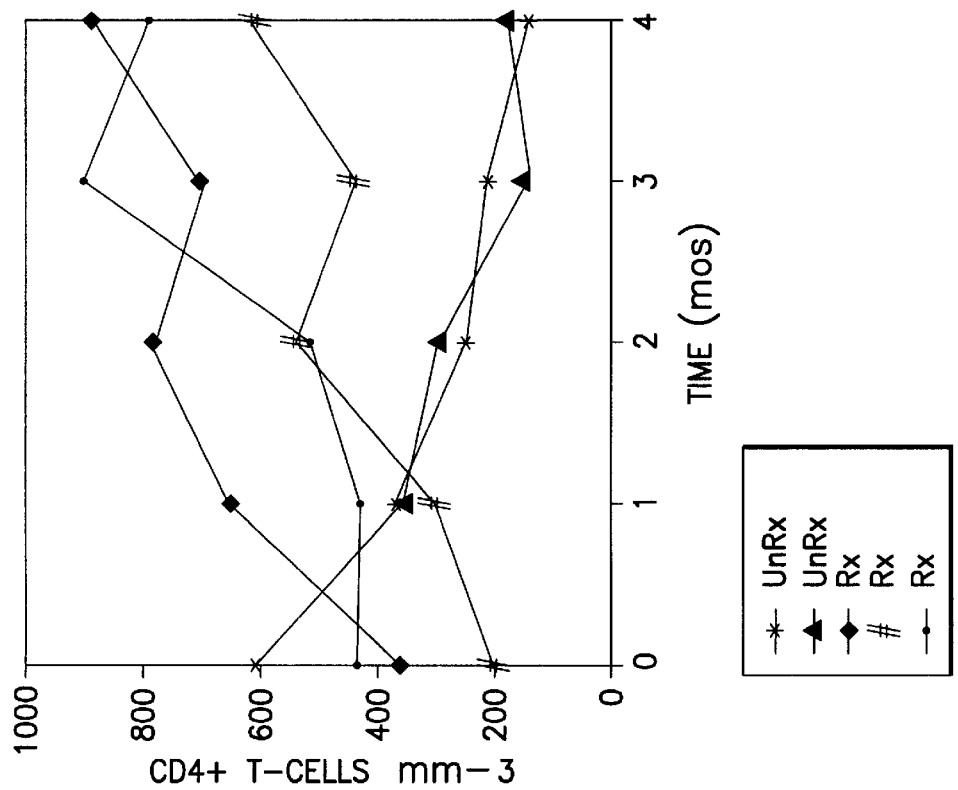
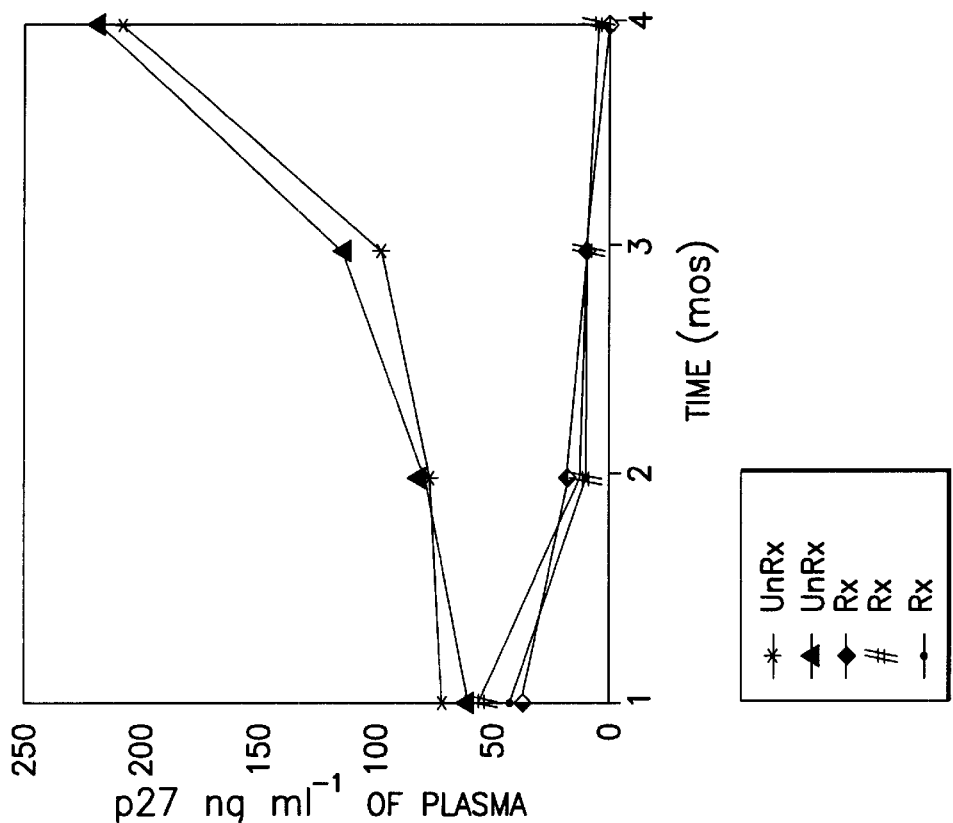
FIG.2B
FIG.2A

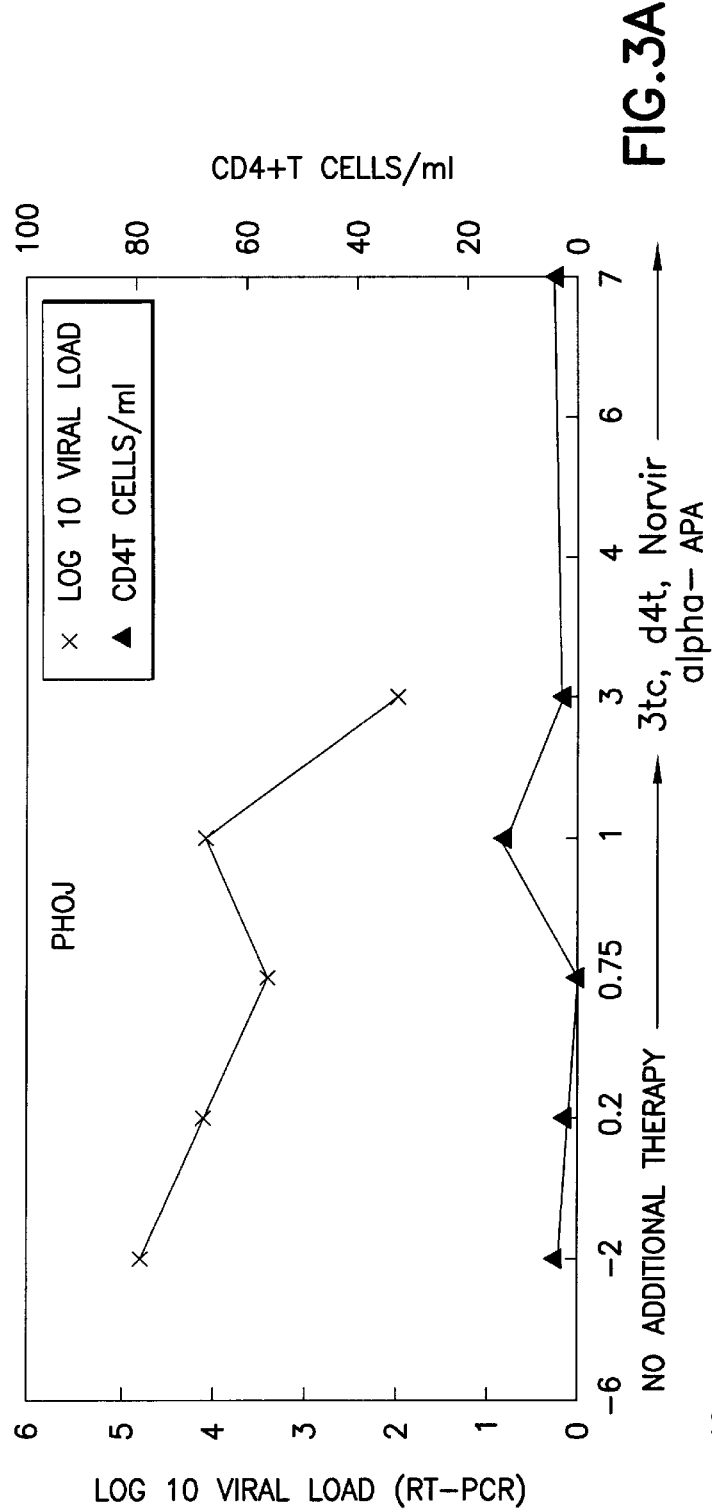
FIG.3A
FIG.3B

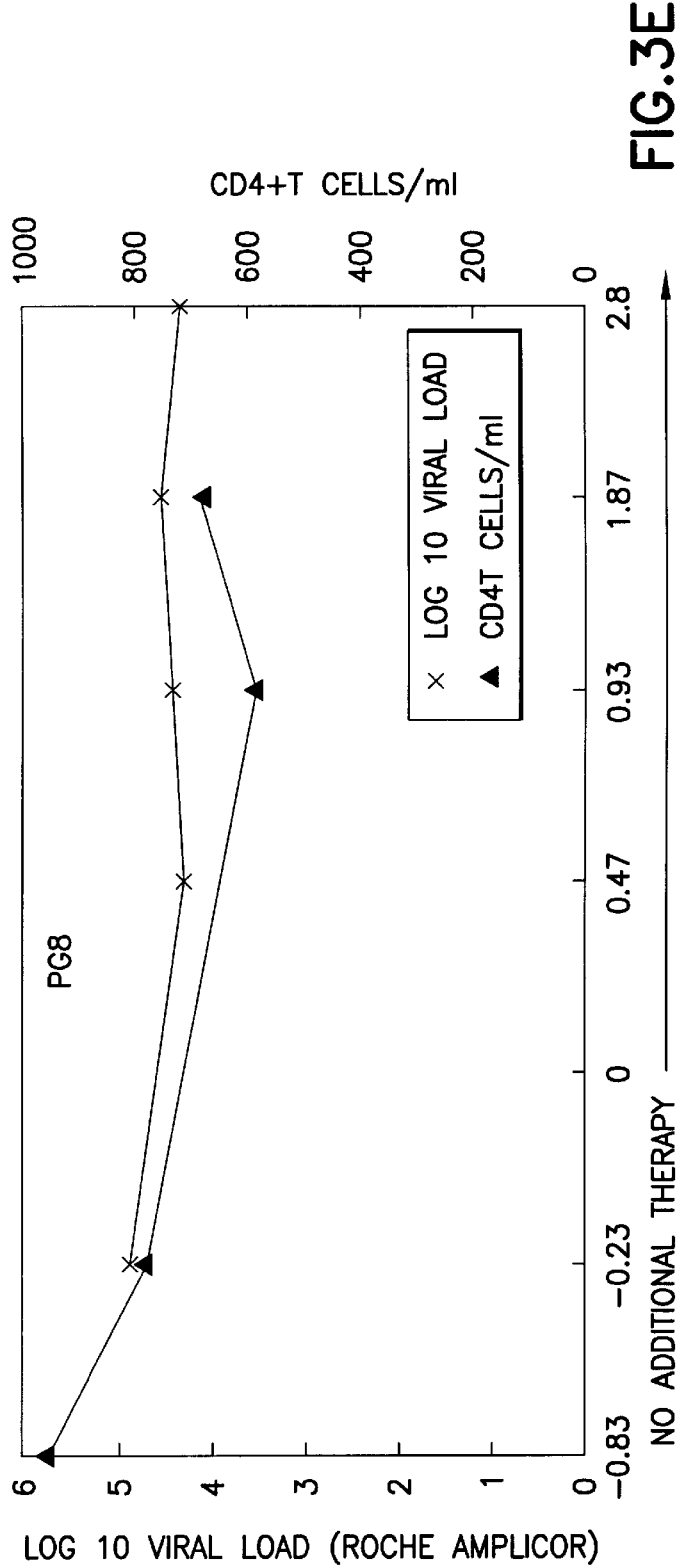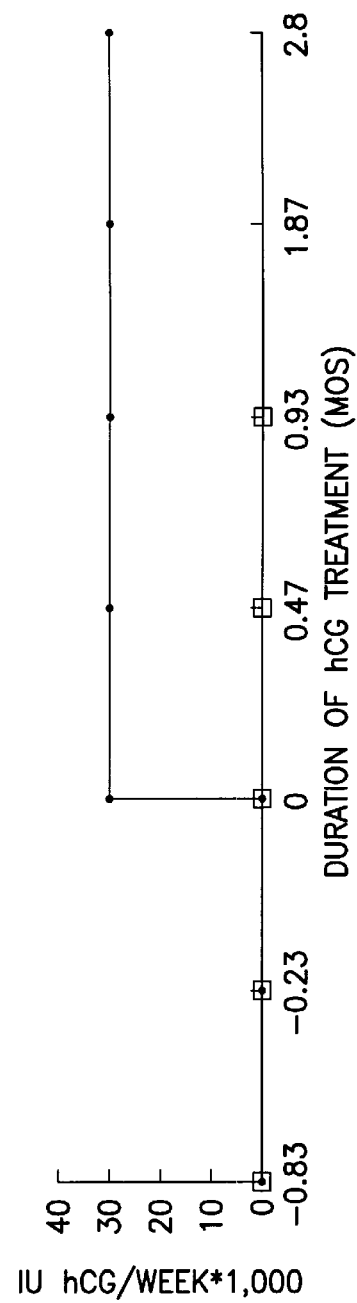
FIG.3E
FIG.3F

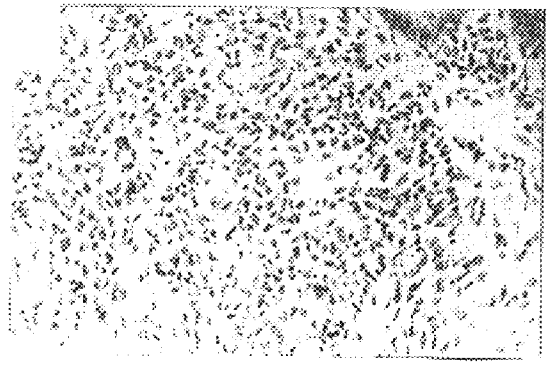 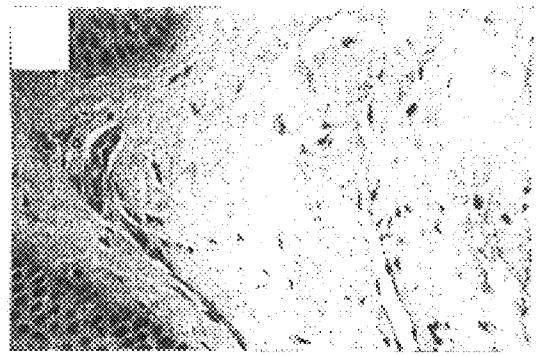
FIG.6F  FIG.6G
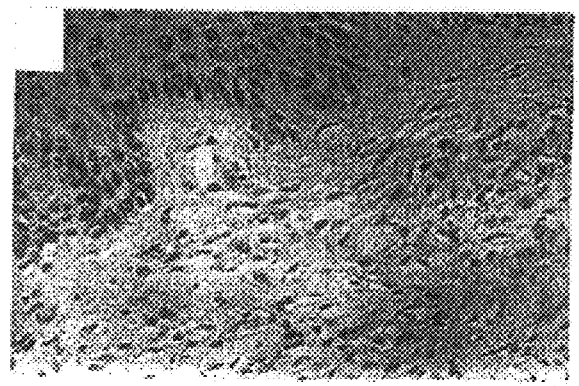
FIG.6H

```
                                                                                        52
AGACAAGGCA GGGGACGCAC CAAGG ATG GAG ATG TTC CAG GGG CTG CTG CTG
                                  Met Glu Met Phe Gln Gly Leu Leu Leu
                                  -20                    -15

TTG CTG CTG AGC ATG GGC ACA TGG GCA TCC AAG GAG CCG CTT          100
Leu Leu Leu Ser Met Gly Thr Trp Ala Ser Lys Glu Pro Leu
    -10                -5                  1

CGG CCA CGG TGC CGC CCC ATC AAT GCC ACC CTG GTG GAG AAG GAG      148
Arg Pro Arg Cys Arg Pro Ile Asn Ala Thr Leu Val Glu Lys Glu
                10                  15                  20

GGC TGC GTG TGC ATC ACC GTC AAC ACC ATC TGT GCC GGC TAC          196
Gly Cys Val Cys Ile Thr Val Asn Thr Ile Cys Ala Gly Tyr
    25                  30                  35

TGC CCC ACC ATG ACC CGC GTG CTG CAG GGG GTC CTG CCG GCC CTG CCT  244
Cys Pro Thr Met Thr Arg Val Leu Gln Gly Val Leu Pro Ala Leu Pro
        40                  45                  50

CAG GTG GTG TGC AAC TAC CGC GAT GTG CGC TTC GAG TCC ATC CGG CTC  292
Gln Val Val Cys Asn Tyr Arg Asp Val Arg Phe Glu Ser Ile Arg Leu
    55                  60                  65

CCT GGC TGC CCG CGC GGC CTG AAC CCC GTG GTC TAC TGC GTG GCT      340
Pro Gly Cys Pro Arg Gly Leu Asn Pro Val Val Tyr Ala Val Ala
70                  75                  80                  85
```

FIG.8A

```
CTC AGC TGT CAA TGT GCA CTC TGC CGC CGC AGC ACC ACT GAC TGC GGG     388
Leu Ser Cys Gln Cys Ala Leu Cys Arg Arg Ser Thr Thr Asp Cys Gly
                 90                  95                     100

GGT CCC AAG GAC CAC CCC TTG ACC TGT GAT GAC CCC CGC TTC CAG GAC     436
Gly Pro Lys Asp His Pro Leu Thr Cys Asp Asp Pro Arg Phe Gln Asp
            105                     110                     115

TCC TCT TCC TCA AAG GCC CCT CCC AGC CTT CCA AGC CCA TCC CGA         484
Ser Ser Ser Ser Lys Ala Pro Pro Ser Leu Pro Ser Pro Ser Arg
        120                     125                     130

CTC CCG GGG CCC TCG GAC ACC CCG ATC CTC CCA CAA TAAAGGCTTC          530
Leu Pro Gly Pro Ser Asp Thr Pro Ile Leu Pro Gln
        135                     140                 145

TCAATCCGC                                                            539
```

FIG.8B

| FIG.8A |
|--------|
| FIG.8B |

FIG.8

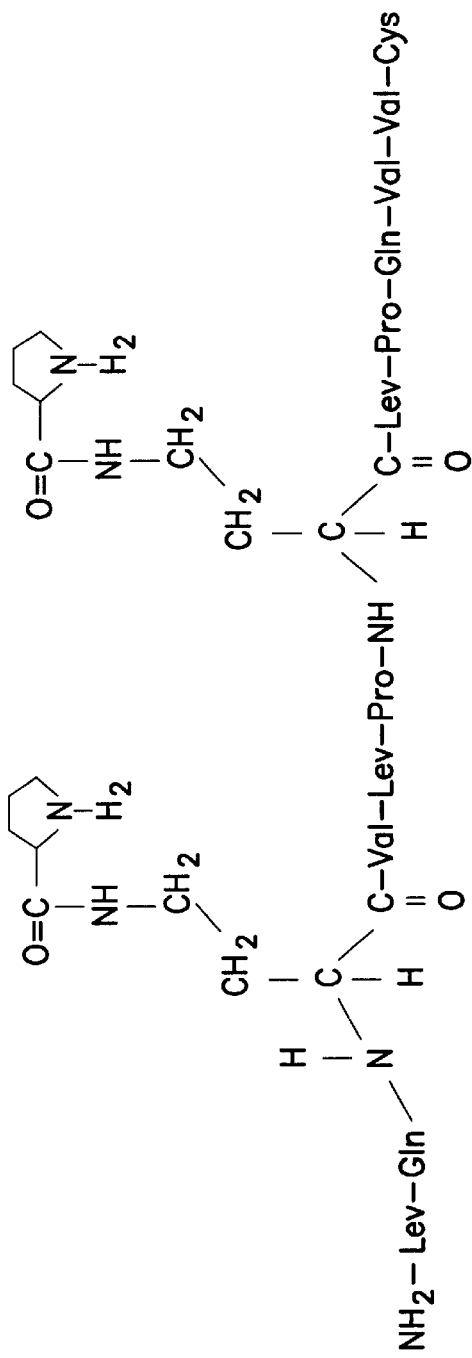
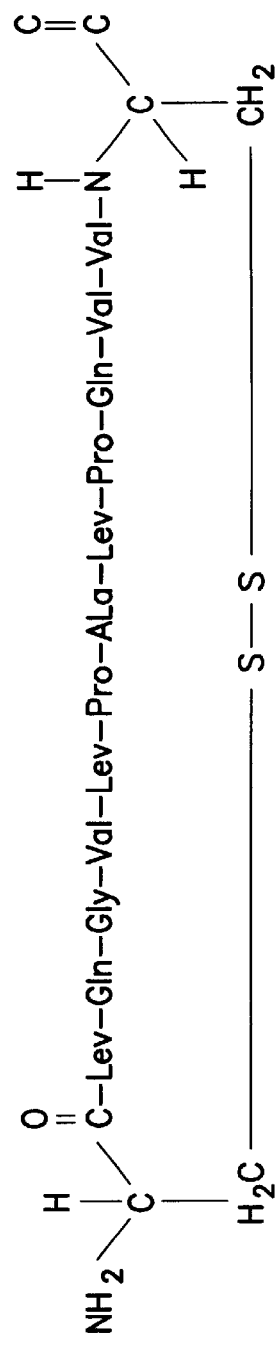
FIG.9A
FIG.9B

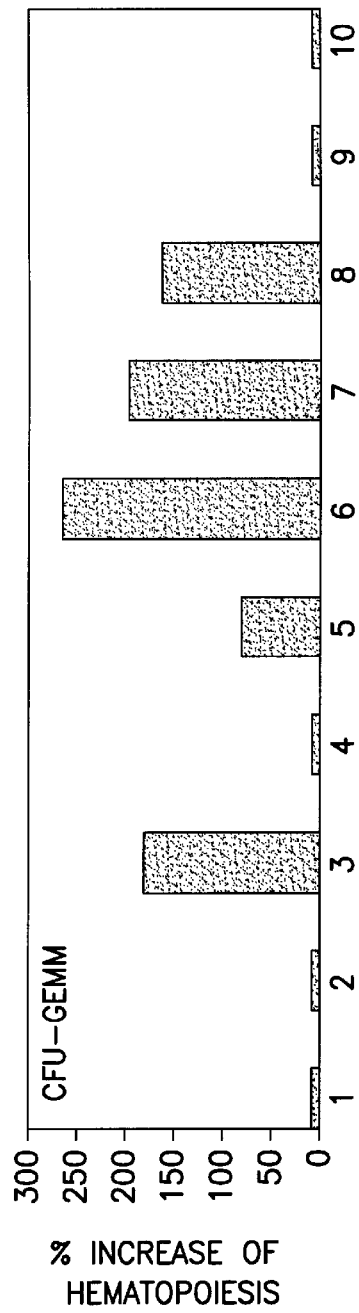
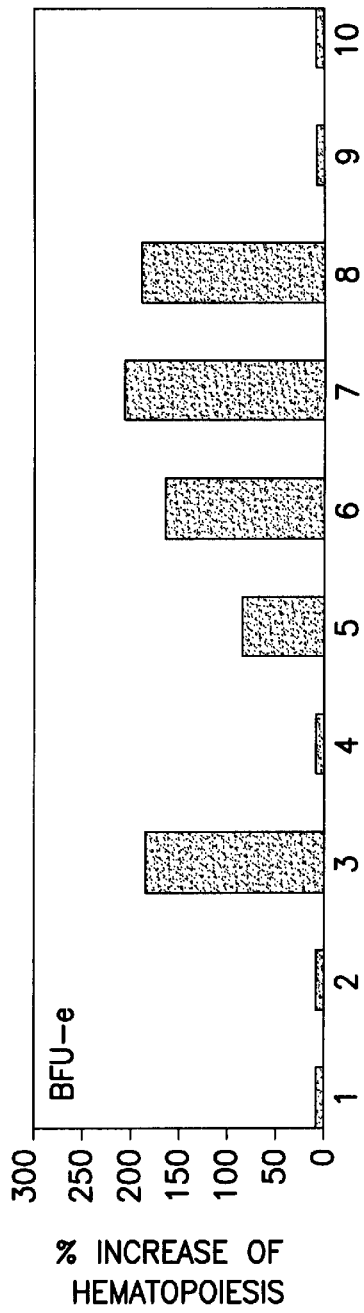
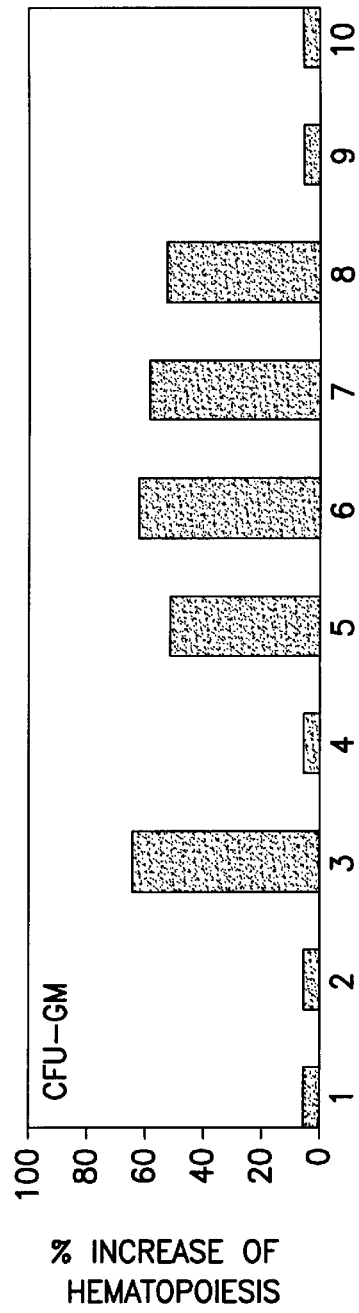

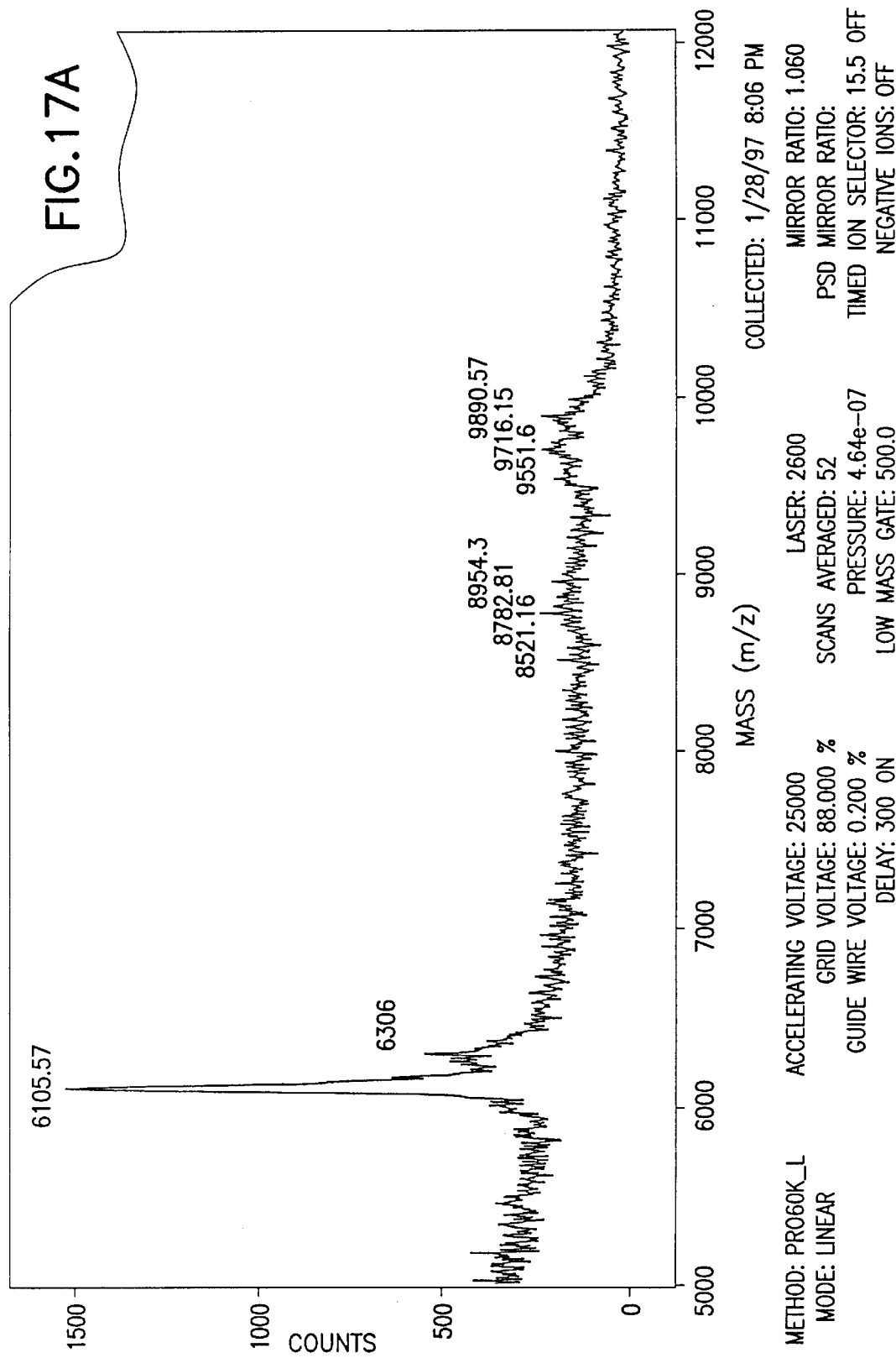

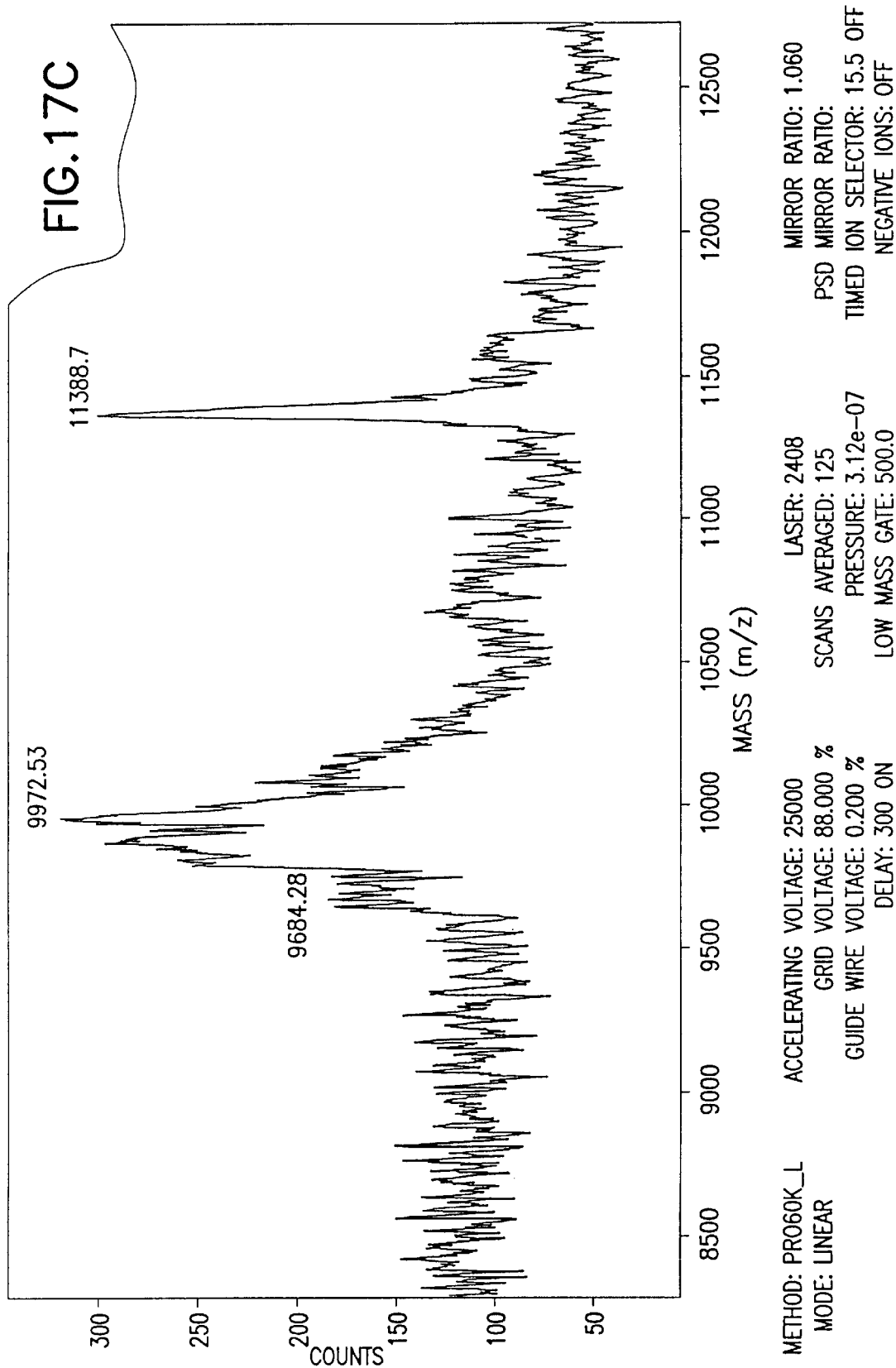

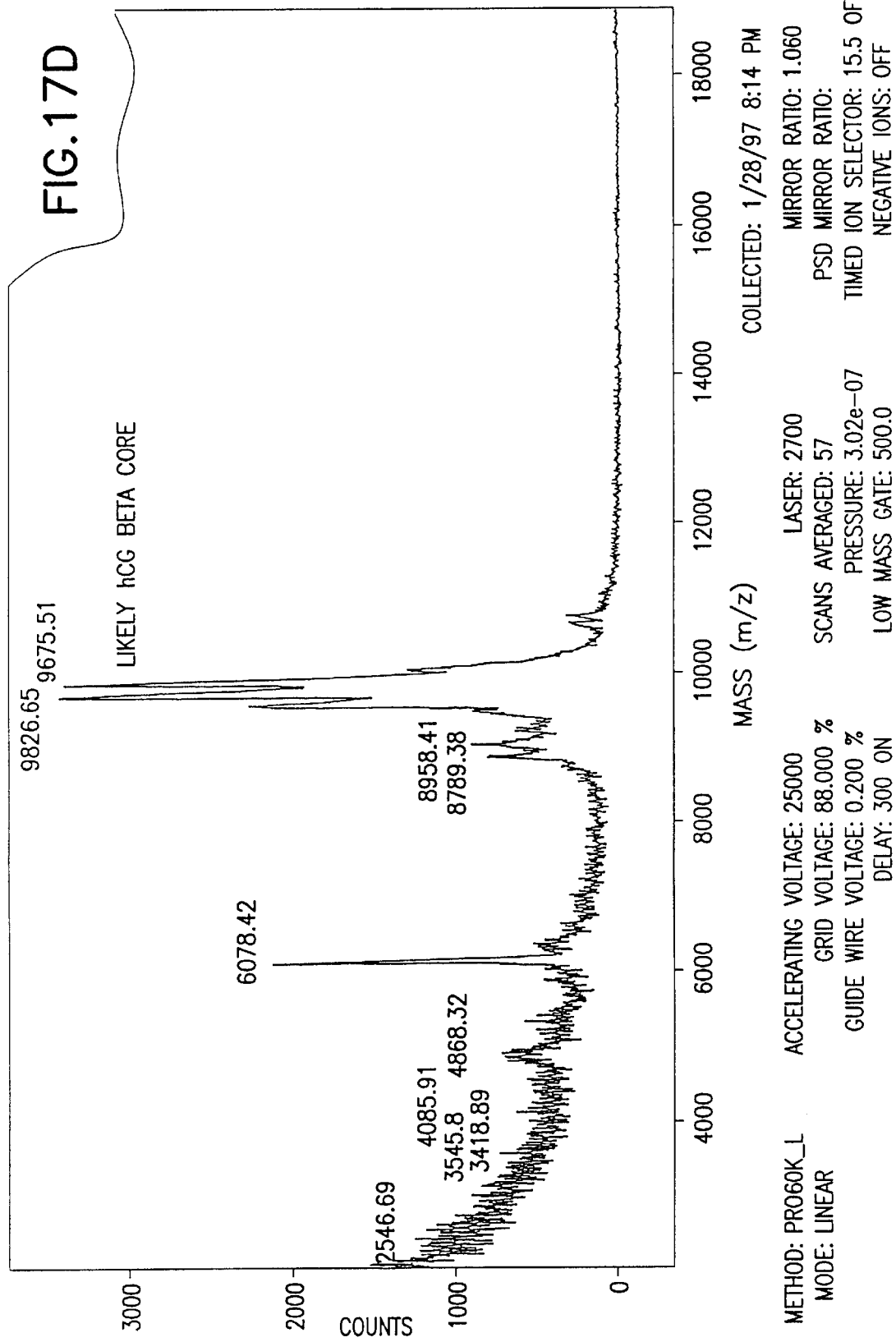

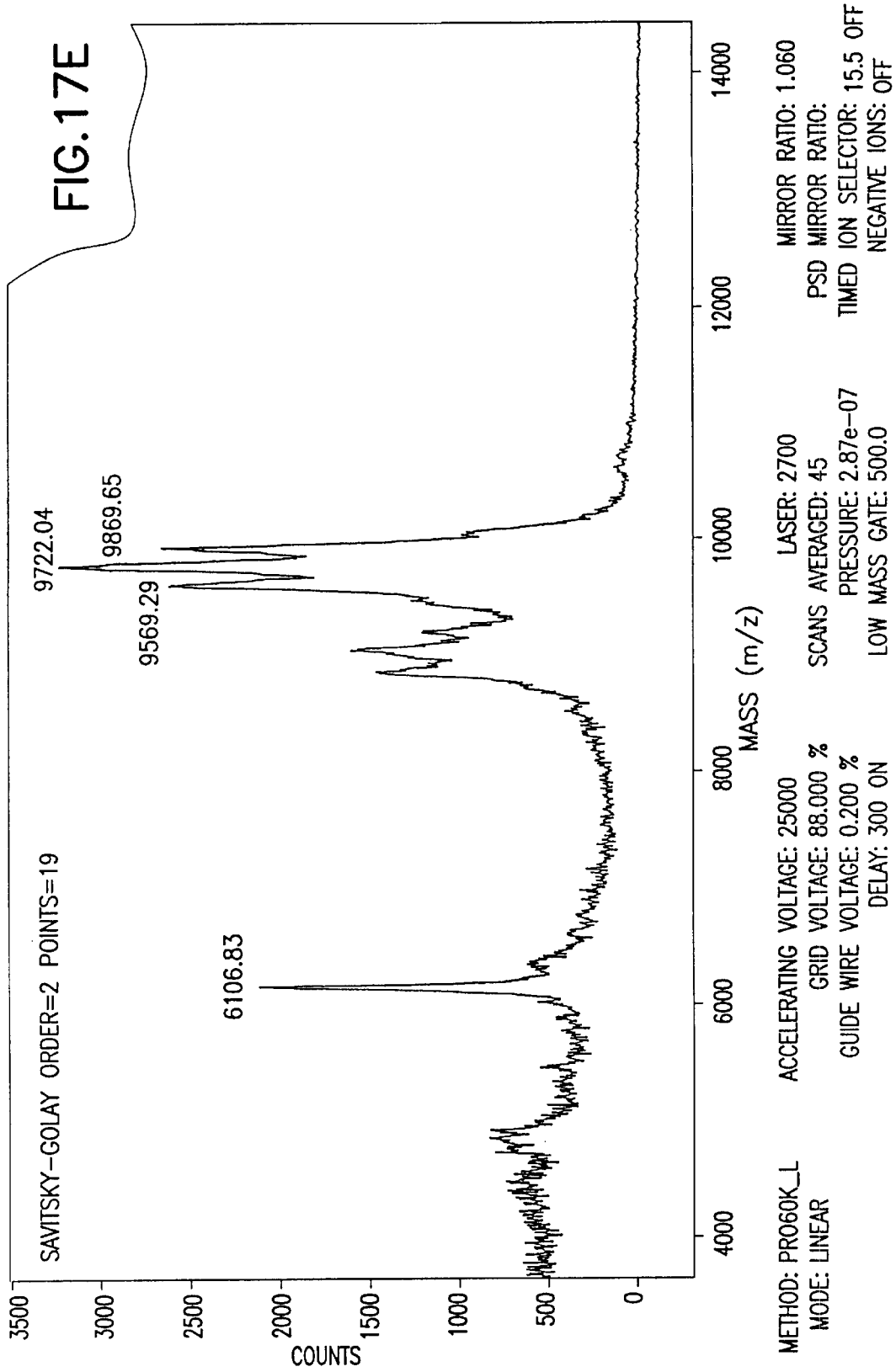

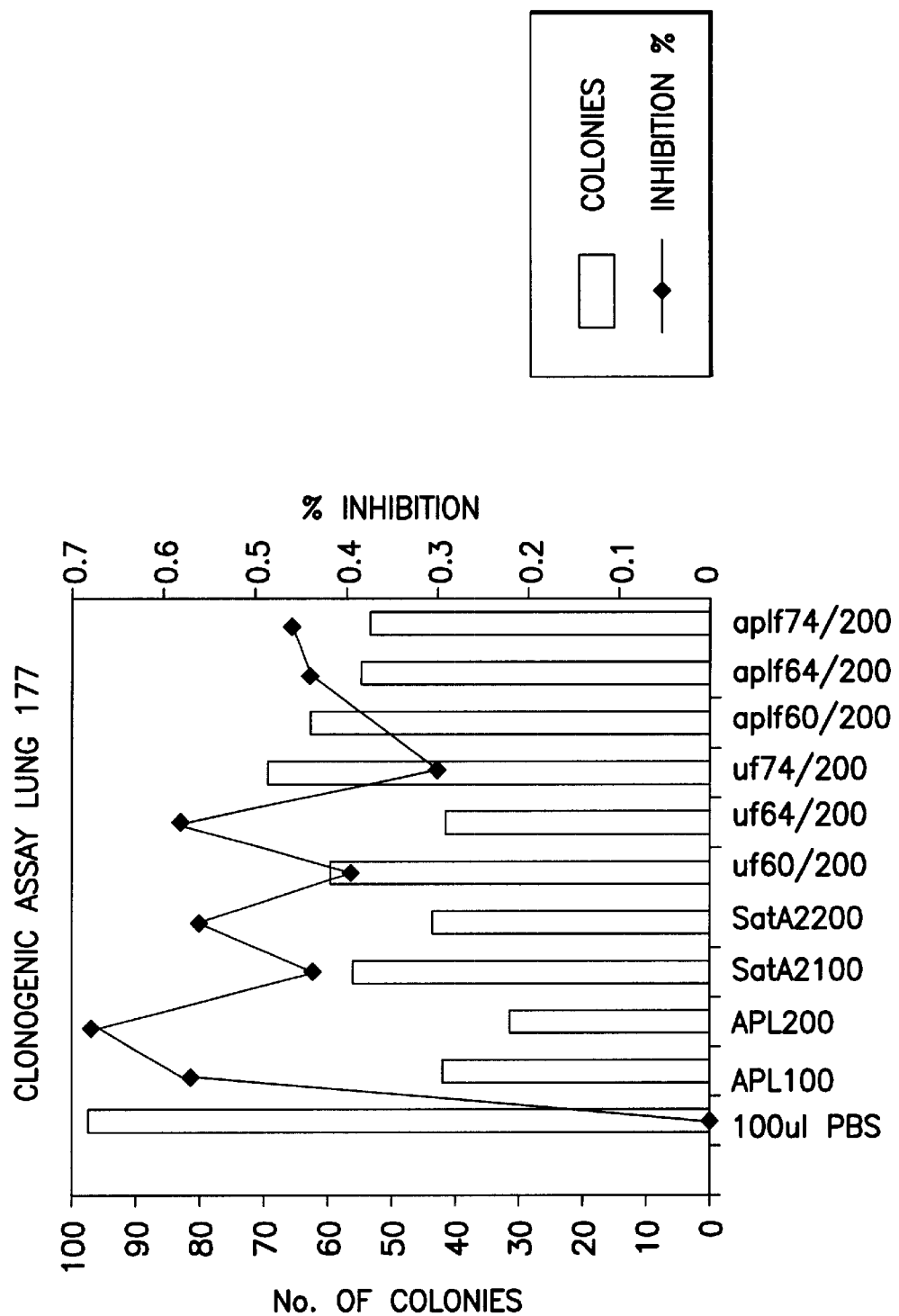

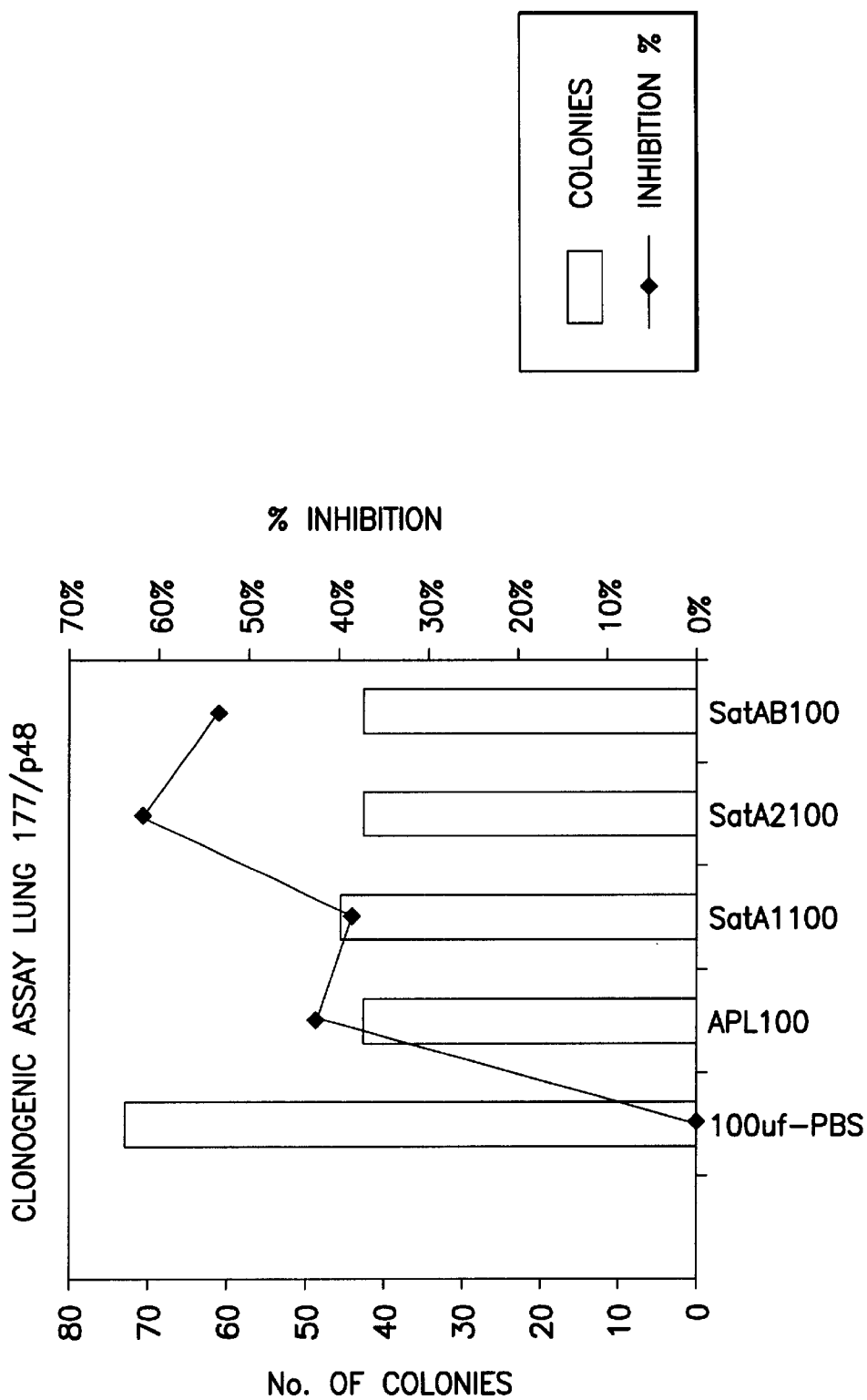

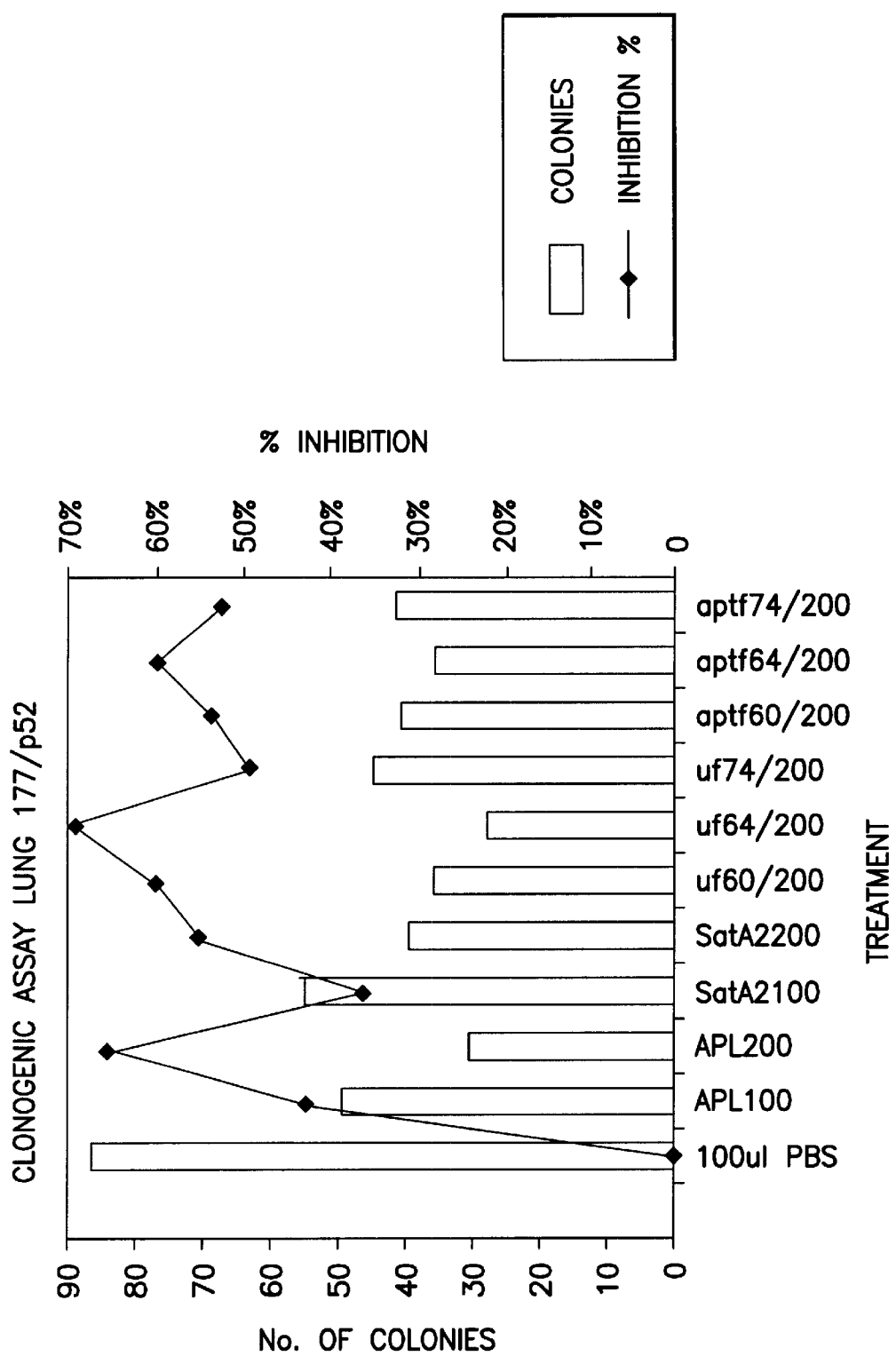

SEQUENCE LISTING (1) GENERAL INFORMATION:

(iii) NUMBER OF SEQUENCES: 37

(2) INFORMATION FOR SEQ ID NO:1:

(i) SEQUENCE CHARACTERISTICS:
      (A) LENGTH: 539 base pairs
      (B) TYPE: nucleic acid
      (C) STRANDEDNESS: single
      (D) TOPOLOGY: linear (ii) MOLECULE TYPE: DNA (ix) FEATURE:
      (A) NAME/KEY: CDS
      (B) LOCATION: 26..520

(xi) SEQUENCE DESCRIPTION: SEQ ID NO:1:

```
AGACAAGGCA GGGGACGCAC CAAGG ATG GAG ATG TTC CAG GGG CTG CTG CTG      52
                           Met Glu Met Phe Gln Gly Leu Leu Leu
                           -20                 -15
```

-continued

```
TTG CTG CTG CTG AGC ATG GGC GGG ACA TGG GCA TCC AAG GAG CCG CTT        100
Leu Leu Leu Leu Ser Met Gly Gly Thr Trp Ala Ser Lys Glu Pro Leu
    -10                 -5                   1

CGG CCA CGG TGC CGC CCC ATC AAT GCC ACC CTG GCT GTG GAG AAG GAG        148
Arg Pro Arg Cys Arg Pro Ile Asn Ala Thr Leu Ala Val Glu Lys Glu
                10                  15                  20

GGC TGC CCC GTG TGC ATC ACC GTC AAC ACC ACC ATC TGT GCC GGC TAC        196
Gly Cys Pro Val Cys Ile Thr Val Asn Thr Thr Ile Cys Ala Gly Tyr
            25                  30                  35

TGC CCC ACC ATG ACC CGC GTG CTG CAG GGG GTC CTG CCG GCC CTG CCT        244
Cys Pro Thr Met Thr Arg Val Leu Gln Gly Val Leu Pro Ala Leu Pro
        40                  45                  50

CAG GTG GTG TGC AAC TAC CGC GAT GTG CGC TTC GAG TCC ATC CGG CTC        292
Gln Val Val Cys Asn Tyr Arg Asp Val Arg Phe Glu Ser Ile Arg Leu
    55                  60                  65

CCT GGC TGC CCG CGC GGC GTG AAC CCC GTG GTC TCC TAC GCC GTG GCT        340
Pro Gly Cys Pro Arg Gly Val Asn Pro Val Val Ser Tyr Ala Val Ala
70                  75                  80                  85

CTC AGC TGT CAA TGT GCA CTC TGC CGC CGC AGC ACC ACT GAC TGC GGG        388
Leu Ser Cys Gln Cys Ala Leu Cys Arg Arg Ser Thr Thr Asp Cys Gly
                90                  95                 100

GGT CCC AAG GAC CAC CCC TTG ACC TGT GAT GAC CCC CGC TTC CAG GAC        436
Gly Pro Lys Asp His Pro Leu Thr Cys Asp Asp Pro Arg Phe Gln Asp
            105                 110                 115

TCC TCT TCC TCA AAG GCC CCT CCC CCC AGC CTT CCA AGC CCA TCC CGA        484
Ser Ser Ser Ser Lys Ala Pro Pro Pro Ser Leu Pro Ser Pro Ser Arg
        120                 125                 130

CTC CCG GGG CCC TCG GAC ACC CCG ATC CTC CCA CAA TAAAGGCTTC             530
Leu Pro Gly Pro Ser Asp Thr Pro Ile Leu Pro Gln
    135                 140                 145

TCAATCCGC                                                              539
```

(2) INFORMATION FOR SEQ ID NO:2:

(i) SEQUENCE CHARACTERISTICS:
        (A) LENGTH: 165 amino acids
        (B) TYPE: amino acid
        (D) TOPOLOGY: linear (ii) MOLECULE TYPE: protein (xi) SEQUENCE DESCRIPTION: SEQ ID NO:2:

```
Met Glu Met Phe Gln Gly Leu Leu Leu Leu Leu Leu Ser Met Gly
-20                 -15                 -10                 -5

Gly Thr Trp Ala Ser Lys Glu Pro Leu Arg Pro Arg Cys Arg Pro Ile
             1                   5                  10

Asn Ala Thr Leu Ala Val Glu Lys Glu Gly Cys Pro Val Cys Ile Thr
            15                  20                  25

Val Asn Thr Thr Ile Cys Ala Gly Tyr Cys Pro Thr Met Thr Arg Val
        30                  35                  40

Leu Gln Gly Val Leu Pro Ala Leu Pro Gln Val Val Cys Asn Tyr Arg
45                  50                  55                  60

Asp Val Arg Phe Glu Ser Ile Arg Leu Pro Gly Cys Pro Arg Gly Val
                65                  70                  75

Asn Pro Val Val Ser Tyr Ala Val Ala Leu Ser Cys Gln Cys Ala Leu
            80                  85                  90

Cys Arg Arg Ser Thr Thr Asp Cys Gly Gly Pro Lys Asp His Pro Leu
        95                 100                 105
```

```
Thr Cys Asp Asp Pro Arg Phe Gln Asp Ser Ser Ser Lys Ala Pro
    110                 115                 120
Pro Pro Ser Leu Pro Ser Pro Ser Arg Leu Pro Gly Pro Ser Asp Thr
125                 130                 135                 140
Pro Ile Leu Pro Gln
                145
```

(2) INFORMATION FOR SEQ ID NO:3:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (xi) SEQUENCE DESCRIPTION: SEQ ID NO:3:

```
Met Thr Arg Val Leu Gln Gly Val Leu Pro Ala Leu Pro Gln
1               5                   10
```

(2) INFORMATION FOR SEQ ID NO:4:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (xi) SEQUENCE DESCRIPTION: SEQ ID NO:4:

```
Leu Gln Gly Val Leu Pro Ala Leu Pro Gln
1               5                   10
```

(2) INFORMATION FOR SEQ ID NO:5:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (xi) SEQUENCE DESCRIPTION: SEQ ID NO:5:

```
Gly Val Leu Pro Ala Leu Pro
1               5
```

(2) INFORMATION FOR SEQ ID NO:6:

(i) SEQUENCE CHARACTERISTICS:
        (A) LENGTH: 13 amino acids
        (B) TYPE: amino acid
        (D) TOPOLOGY: linear (ii) MOLECULE TYPE: peptide (xi) SEQUENCE DESCRIPTION: SEQ ID NO:6:

```
Leu Gln Gly Val Leu Pro Ala Leu Pro Gln Val Val Cys
1               5                   10
```

(2) INFORMATION FOR SEQ ID NO:7:

(i) SEQUENCE CHARACTERISTICS:
        (A) LENGTH: 11 amino acids
        (B) TYPE: amino acid
        (D) TOPOLOGY: circular, linear (ii) MOLECULE TYPE: peptide (xi) SEQUENCE DESCRIPTION: SEQ ID NO:7:

Thr Cys Asp Asp Pro Arg Phe Gln Asp Ser Ser
1               5                   10

(2) INFORMATION FOR SEQ ID NO:8:

(i) SEQUENCE CHARACTERISTICS:
        (A) LENGTH: 13 amino acids
        (B) TYPE: amino acid
        (D) TOPOLOGY: linear (ii) MOLECULE TYPE: peptide (xi) SEQUENCE DESCRIPTION: SEQ ID NO:8:

Met Thr Arg Val Leu Gln Gly Val Leu Pro Ala Leu Pro
1               5                   10

(2) INFORMATION FOR SEQ ID NO:9:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (xi) SEQUENCE DESCRIPTION: SEQ ID NO:9:

Thr Arg Val Leu Gln Gly Val Leu Pro Ala Leu Pro
1               5                   10

(2) INFORMATION FOR SEQ ID NO:10:

(i) SEQUENCE CHARACTERISTICS:
        (A) LENGTH: 11 amino acids
        (B) TYPE: amino acid
        (D) TOPOLOGY: linear (ii) MOLECULE TYPE: peptide (xi) SEQUENCE DESCRIPTION: SEQ ID NO:10:

Arg Val Leu Gln Gly Val Leu Pro Ala Leu Pro
1               5                   10

(2) INFORMATION FOR SEQ ID NO:11:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (xi) SEQUENCE DESCRIPTION: SEQ ID NO:11:

Val Leu Gln Gly Val Leu Pro Ala Leu Pro
1               5                   10

(2) INFORMATION FOR SEQ ID NO:12:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (xi) SEQUENCE DESCRIPTION: SEQ ID NO:12:

Val Leu Gln Gly Val Leu Pro Ala Leu Pro Gln Val Val Cys
1               5                   10

```
(2) INFORMATION FOR SEQ ID NO:13:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (xi) SEQUENCE DESCRIPTION: SEQ ID NO:13:

Leu Gln Gly Val Leu Pro Ala Leu Pro
1               5

(2) INFORMATION FOR SEQ ID NO:14:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (xi) SEQUENCE DESCRIPTION: SEQ ID NO:14:

Gln Gly Val Leu Pro Ala Leu Pro
1               5

(2) INFORMATION FOR SEQ ID NO:15:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (xi) SEQUENCE DESCRIPTION: SEQ ID NO:15:

Leu Gln Gly Val Leu Pro Ala Leu Pro Gln
1               5                   10

(2) INFORMATION FOR SEQ ID NO:16:

(i) SEQUENCE CHARACTERISTICS:
        (A) LENGTH: 11 amino acids
        (B) TYPE: amino acid
        (D) TOPOLOGY: linear (ii) MOLECULE TYPE: peptide (xi) SEQUENCE DESCRIPTION: SEQ ID NO:16:

Leu Gln Gly Val Leu Pro Ala Leu Pro Gln Val
1               5                   10

(2) INFORMATION FOR SEQ ID NO:17:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (xi) SEQUENCE DESCRIPTION: SEQ ID NO:17:

Leu Gln Gly Val Leu Pro Ala Leu Pro Gln Val Val
1               5                   10
```

(2) INFORMATION FOR SEQ ID NO:18:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (xi) SEQUENCE DESCRIPTION: SEQ ID NO:18:

```
Leu Gln Gly Val Leu Pro Ala Leu Pro Gln Val Val Cys Asn
1               5                   10
```

(2) INFORMATION FOR SEQ ID NO:19:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (xi) SEQUENCE DESCRIPTION: SEQ ID NO:19:

```
Gly Val Leu Pro Ala Leu Pro Gln
1               5
```

(2) INFORMATION FOR SEQ ID NO:20:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (xi) SEQUENCE DESCRIPTION: SEQ ID NO:20:

```
Gly Val Leu Pro Ala Leu Pro Gln Val
1               5
```

(2) INFORMATION FOR SEQ ID NO:21:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (xi) SEQUENCE DESCRIPTION: SEQ ID NO:21:

```
Gly Val Leu Pro Ala Leu Pro Gln Val Val
1               5                   10
```

(2) INFORMATION FOR SEQ ID NO:22:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (xi) SEQUENCE DESCRIPTION: SEQ ID NO:22:

```
Gly Val Leu Pro Ala Leu Pro Gln Val Val Cys Asn
1               5                   10
```

(2) INFORMATION FOR SEQ ID NO:23:

(i) SEQUENCE CHARACTERISTICS:
        (A) LENGTH: 98 amino acids
        (B) TYPE: amino acid
        (D) TOPOLOGY: linear (ii) MOLECULE TYPE: peptide (xi) SEQUENCE DESCRIPTION: SEQ ID NO:23:

```
Val Leu Pro Ala Leu Pro Gln Val Val Cys Asn Tyr Arg Asp Val Arg
 1               5                  10                  15

Phe Glu Ser Ile Arg Leu Pro Gly Cys Pro Arg Gly Leu Asn Pro Val
                20                  25                  30

Val Ser Tyr Ala Val Ala Leu Ser Cys Gln Cys Ala Leu Cys Arg Arg
            35                  40                  45

Ser Thr Thr Asp Cys Gly Gly Pro Lys Asp His Pro Leu Thr Cys Asp
50                  55                  60

Asp Pro Arg Phe Gln Asp Ser Ser Ser Lys Ala Pro Pro Pro Ser
65                  70                  75                  80

Leu Pro Ser Pro Ser Arg Leu Pro Gly Pro Ser Asp Thr Pro Ile Leu
                85                  90                  95

Pro Gln
```

(2) INFORMATION FOR SEQ ID NO:24:

(i) SEQUENCE CHARACTERISTICS:
        (A) LENGTH: 88 amino acids
        (B) TYPE: amino acid
        (D) TOPOLOGY: linear (ii) MOLECULE TYPE: peptide (xi) SEQUENCE DESCRIPTION: SEQ ID NO:24:

```
Asn Tyr Arg Asp Val Arg Phe Glu Ser Ile Arg Leu Pro Gly Cys Pro
 1               5                  10                  15

Arg Gly Leu Asn Pro Val Val Ser Tyr Ala Val Ala Leu Ser Cys Gln
                20                  25                  30

Cys Ala Leu Cys Arg Arg Ser Thr Thr Asp Cys Gly Gly Pro Lys Asp
            35                  40                  45

His Pro Leu Thr Cys Asp Asp Pro Arg Phe Gln Asp Ser Ser Ser Ser
        50                  55                  60

Lys Ala Pro Pro Pro Ser Leu Pro Ser Pro Ser Arg Leu Pro Gly Pro
65                  70                  75                  80

Ser Asp Thr Pro Ile Leu Pro Gln
                85
```

(2) INFORMATION FOR SEQ ID NO:25:

(i) SEQUENCE CHARACTERISTICS:
        (A) LENGTH: 37 amino acids
        (B) TYPE: amino acid
        (D) TOPOLOGY: linear (ii) MOLECULE TYPE: peptide (xi) SEQUENCE DESCRIPTION: SEQ ID NO:25:

```
Thr Cys Asp Asp Pro Arg Phe Gln Asp Ser Ser Ser Lys Ala Pro
 1               5                  10                  15

Pro Pro Ser Leu Pro Ser Pro Ser Arg Leu Pro Gly Pro Ser Asp Thr
                20                  25                  30
```

Pro Ile Leu Pro Gln
          35

(2) INFORMATION FOR SEQ ID NO:26:

(i) SEQUENCE CHARACTERISTICS:
        (A) LENGTH: 14 amino acids
        (B) TYPE: amino acid
        (D) TOPOLOGY: circular (ii) MOLECULE TYPE: peptide (xi) SEQUENCE DESCRIPTION: SEQ ID NO:26:

Cys Leu Gln Gly Val Leu Pro Ala Leu Pro Gln Val Val Cys
1               5                   10

(2) INFORMATION FOR SEQ ID NO:27:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:27:

Cys Asp Asp Pro Arg Phe Gln Asp Ser Ser
1               5                   10

(2) INFORMATION FOR SEQ ID NO:28:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:28:

Gly Val Leu Pro Ala Leu Pro Gln Val Val Cys
1               5                   10

(2) INFORMATION FOR SEQ ID NO:29:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:29:

Leu Thr Cys Asp Asp Pro Arg Phe Gln Asp Ser Ser
1               5                   10

(2) INFORMATION FOR SEQ ID NO:30:

(i) SEQUENCE CHARACTERISTICS:
        (A) LENGTH: 24 amino acids
        (B) TYPE: amino acid
        (C) STRANDEDNESS: single
        (D) TOPOLOGY: linear (ii) MOLECULE TYPE: protein -continued (xi) SEQUENCE DESCRIPTION: SEQ ID NO:30:

Leu Gln Gly Val Leu Pro Ala Leu Pro Gln Val Val Cys Thr Cys Asp
 1               5                  10                  15
Asp Pro Arg Phe Gln Asp Ser Ser
             20

(2) INFORMATION FOR SEQ ID NO:31:

(i) SEQUENCE CHARACTERISTICS:
        (A) LENGTH: 23 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:31:

Cys Asp Asp Pro Arg Phe Gln Asp Ser Ser Leu Gln Gly Val Leu Pro
 1               5                  10                  15
Ala Leu Pro Gln Val Val Cys
             20

(2) INFORMATION FOR SEQ ID NO:32:

(i) SEQUENCE CHARACTERISTICS:
        (A) LENGTH: 23 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:32:

Gly Val Leu Pro Ala Leu Pro Gln Val Val Cys Leu Thr Cys Asp Asp
 1               5                  10                  15
Pro Arg Phe Gln Asp Ser Ser
             20

(2) INFORMATION FOR SEQ ID NO:33:

(i) SEQUENCE CHARACTERISTICS:
        (A) LENGTH: 34 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:33:

Pro Arg Cys Arg Pro Ile Asn Ala Thr Leu Ala Val Glu Lys Glu Gly
 1               5                  10                  15
Cys Pro Val Cys Ile Thr Val Asn Thr Thr Ile Cys Ala Gly Tyr Cys
             20                  25                  30
Pro Thr (2) INFORMATION FOR SEQ ID NO:34:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: protein -continued (xi) SEQUENCE DESCRIPTION: SEQ ID NO:34:

Gln Gly Val Leu Pro Ala Leu Pro Gln Val Val Cys Asn Tyr Arg Asp
1               5                   10                  15

Val Arg Phe Glu
            20

(2) INFORMATION FOR SEQ ID NO:35:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:35:

Val Leu Pro Ala Leu Pro Gln Val Val
1               5

(2) INFORMATION FOR SEQ ID NO:36:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:36:

Cys Val Ala Gln Pro Gly Pro Gln Val Leu Leu Val Leu Cys
1               5                   10

(2) INFORMATION FOR SEQ ID NO:37:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:37:

Cys Val Ala Gln Gly Val Leu Pro Ala Leu Pro Gln Val Val Cys
1               5                   10                  15

THERAPEUTIC POLYPEPTIDES FROM β-HCG AND DERIVATIVES

CROSS-REFERENCE TO RELATED APPLICATIONS

This application is a continuation-in-part of the following applications, the entire disclosures of which are incorporated herein by reference: PCT/US97/11210, entitled "Treatment and Prevention of Cancer by Administration of Derivatives of Human Chorionic Gonadotropin", filed on Jun. 24, 1997 which is based on and claims priority to the priority following priority documents: U.S. patent application Ser. No. 08/669,676, filed Jun. 24, 1996, now abandoned, and U.S. patent application Ser. No. 08/709,925, filed Sep. 9, 1996, now U.S. Pat. No. 5,997,871;

PCT/US97/11209, entitled "Methods of Promoting Hematopoiesis using Derivatives of Human Chorionic Gonadotropin", filed on Jun. 24, 1997, which is based on and claims priority to the priority following priority documents: U.S. patent application Ser. No. 08/669,654, filed Jun. 24, 1996, now abandoned, and U.S. patent application Ser. No. 08/709,924, filed Sep. 9, 1996, now U.S. Pat. No. 5,968,513;

PCT/US97/11448 "Treatment and Prevention of Wasting Syndrome Based on Administration of Derivatives of Human Chorionic Gonadotropin", filed on Jun. 24, 1997, which is based on and claims priority to the priority following priority documents: U.S. patent application Ser. No. 08/669,675, filed Jun. 24, 1996, now abandoned, and U.S. patent application Ser. No. 08/709,933, filed Sep. 9, 1996, now abandoned; and PCT/US97/11202, entitled "Treatment and Prevention of HIV Infection by Administration of Derivatives of Human Chronic Gonadotropin," filed on Jun. 24, 1997, which is based on and claims priority to the priority following priority documents: U.S. patent application Ser. No. 08/669, 681, filed Jun. 24, 1996, now abandoned, and U.S. patent application Ser. No. 08/709,948, filed Sep. 9, 1996, now U.S. Pat. No. 6,319,504.

FIELD OF THE INVENTION

The present invention relates to peptides of one or more portions of the human chorionic gonadotropin β-chain as well as methods for treatment and prevention of diseases, including HIV infection, cancer and wasting syndrome, and methods of promoting hematopoiesis using human chorionic gonadotropin, employing the β-chain of human chorionic gonadotropin, peptides containing a sequence of one or more portions of the β-chain of human chorionic gonadotropin and derivatives and analogues thereof. The invention further relates to fractions of sources and or preparations of human chorionic gonadotropin, such as fractions of human early pregnancy urine, which fractions have anti-HIV activity, anti-cancer activity, anti-wasting activity, and/or pro-hematopoietic activity. The present invention further relates to pharmaceutical compositions for treating and/or preventing HIV infection, cancer, and/or wasting, and/or for promoting hematopoiesis.

BACKGROUND OF THE INVENTION

The Human Immunodeficiency Virus

The human immunodeficiency virus (HIV) has been implicated as the primary cause of the slowly degenerative immune system disease termed acquired immune deficiency syndrome (AIDS) (Barre-Sinoussi, F., et al., 1983, Science 220:868–870; Gallo, R., et al., 1984, Science 224:500–503). There are at least two distinct types of HIV: HIV-1 (Barre-Sinoussi, F., et al., 1983, Science 220:868–870; Gallo, R., et al., 1984, Science 224:500–503) and HIV-2 (Clavel, F., et al., 1986, Science 233:343–346; Guyader, M., et al., 1987, Nature 326:662–669). Further, a large amount of genetic heterogeneity exists within populations of each of these types. In humans, HIV replication occurs prominently in $CD4^+$ T lymphocyte populations, and HIV infection leads to depletion of this cell type and eventually to immune incompetence, opportunistic infections, neurological dysfunctions, neoplastic growth, and ultimately death.

HIV is a member of the lentivirus family of retroviruses (Teich, N., et al., 1984, RNA Tumor Viruses, Weiss, R., et al., eds., CSH-Press, pp. 949–956). Retroviruses are small enveloped viruses that contain a single-stranded RNA genome and replicate via a DNA intermediate produced by a virally-encoded reverse transcriptase, an RNA-dependent DNA polymerase (Varmus, H., 1988, Science 240:1427–1439).

The HIV viral particle comprises a viral core, composed in part of capsid proteins, together with the viral RNA genome and those enzymes required for early replicative events. Myristylated gag protein forms an outer shell around the viral core, which is, in turn, surrounded by a lipid membrane envelope derived from the infected cell membrane. The HIV envelope surface glycoproteins are synthesized as a single 160 kilodalton precursor protein which is cleaved by a cellular protease during viral budding into two glycoproteins, gp41 and gp120. gp41 is a transmembrane glycoprotein and gp120 is an extracellular glycoprotein which remains non-covalently associated with gp41, possibly in a trimeric or multimeric form (Hammarskjold, M., & Rekosh, D., 1989, Biochem. Biophys. Acta 989:269–280).

HIV is targeted to $CD4^+$ cells because a CD4 cell surface protein (CD4) acts as the cellular receptor for the HIV-1 virus (Dalgleish, A., et al., 1984, Nature 312:763–767; Klatzmann et al., 1984, Nature 312:767–768; Maddon et al., 1986, Cell 47:333–348). Viral entry into cells is dependent upon gp120 binding the cellular CD4 receptor molecules (McDougal, J. S., et al., 1986, Science 231:382–385; Maddon, P. J., et al., 1986, Cell 47:333–348), explaining HIV's tropism for $CD4^+$ cells, while gp41 anchors the envelope glycoprotein complex in the viral membrane. While these virus:cell interactions are necessary for infection, there is evidence that additional virus:cell interactions are also required.

HIV Treatment

HIV infection is pandemic and HIV-associated diseases represent a major world health problem. Although considerable effort is being put into the design of effective Therapeutics, currently no curative anti-retroviral drugs against AIDS exist. In attempts to develop such drugs, several stages of the HIV life cycle have been considered as targets for therapeutic intervention (Mitsuya, H., et al., 1991, FASEB 1. 5:2369–2381). Many viral targets for intervention with HIV life cycle have been suggested, as the prevailing view is that interference with a host cell protein would have deleterious side effects. For example, virally encoded reverse transcriptase has been one focus of drug development. A number of reverse-transcriptase-targeted drugs, including 2',3'-dideoxynucleoside analogs such as AZT, ddl, ddC, and d4T have been developed which have been shown to been active against HIV (Mitsuya, H., et al., 1991, Science 249:1533–1544).

The new treatment regimens for HIV-1 show that a combination of anti-HIV compounds, which target reverse transcriptase (RT), such as azidothymidine (AZT), lamivudine (3TC), dideoxyinosine (ddl), dideoxycytidine (ddC)

used in combination with an HIV-1 protease inhibitor have a far greater effect (2 to 3 logs reduction) on viral load compared to AZT alone (about 1 log reduction). For example, impressive results have recently been obtained with a combination of AZT, ddI, 3TC and ritonavir (Perelson, A. S., et al., 1996, *Science* 15:1582–1586). However, it is likely that long-term use of combinations of these chemicals will lead to toxicity, especially to the bone marrow. Long-term cytotoxic therapy may also lead to suppression of $CD8^+$ T cells, which are essential to the control of HIV, via killer cell activity (Blazevic, V., et al., 1995, *AIDS Res. Hum. Retroviruses* 11:1335–1342) and by the release of suppressive factors, notably the chemokines Rantes, MIP-1α and MIP-1β (Cocchi, F., et al., 1995, *Science* 270:1811–1815). Another major concern in long-term chemical anti-retroviral therapy is the development of HIV mutations with partial or complete resistance (Lange, J. M., 1995, *AIDS Res. Hum. Retroviruses* 10:S77–82). It is thought that such mutations may be an inevitable consequence of anti-viral therapy. The pattern of disappearance of wild-type virus and appearance of mutant virus due to treatment, combined with coincidental decline in $CD4^+$ T cell numbers strongly suggests that, at least with some compounds, the appearance of viral mutants is a major underlying factor in the failure of AIDS therapy.

Attempts are also being made to develop drugs which can inhibit viral entry into the cell, the earliest stage of HIV infection. Here, the focus has thus far been on CD4, the cell surface receptor for HIV. Recombinant soluble CD4, for example, has been shown to inhibit infection of $CD4^+$ T cells by some HIV-1 strains (Smith, D. H., et al., 1987, *Science* 238:1704–1707). Certain primary HIV-1 isolates, however, are relatively less sensitive to inhibition by recombinant CD4 (Daar, E., et al., 1990, *Proc. Nati. Acad. Sci. USA* 87:6574–6579). In addition, recombinant soluble CD4 clinical trials have produced inconclusive results (Schooley, R., et al., 1990, *Ann. Int. Med.* 112:247–253; Kahn, J. O., et al., 1990, *Ann. Int. Med.* 112:254–261; Yarchoan, R., et al., 1989, *Proc. Vth Int. Conf. on AIDS, p.* 564, MCP 137).

The late stages of HIV replication, which involve crucial virus-specific processing of certain viral encoded proteins, have also been suggested as possible anti-HIV drug targets. Late stage processing is dependent on the activity of a viral protease, and drugs are being developed which inhibit this protease (Erickson, J., 1990, *Science* 249:527–533).

Recently, chemokines produced by $CD8^+$ T cells have been implicated in suppression of HIV infection (Paul, W. E., 1994, *Cell* 82:177; Bolognesi, D. P., 1993, *Semin. Immunol.* 5:203). The chemokines RANTES, MIP-1α and MIP-1β, which are secreted by $CD8^+$ T cells, were shown to suppress HIV-1 p24 antigen production in cells infected with HIV-1 or HIV-2 isolates in vitro (Cocchi, F, et al., 1995, *Science* 270:1811–1815). Thus, these and other chemokines may prove useful in therapies for HIV infection. The clinical outcome, however, of all these and other candidate drugs is still in question.

Attention is also being given to the development of vaccines for the treatment of HIV infection. The HIV-1 envelope proteins (gp160, gp120, gp41) have been shown to be the major antigens for anti-HIV antibodies present in AIDS patients (Barin et al., 1985, *Science* 228:1094–1096). Thus far, therefore, these proteins appear to be the most promising candidates to act as antigens for anti-HIV vaccine development. Several groups have begun to use various portions of gp160, gp120, and/or gp41 as immunogenic targets for the host immune system. See for example, Ivanoff, L., et al., U.S. Pat. No. 5,141,867; Saith, G., et al., WO92/22,654; Shafferman, A., WO91/09,872; Formoso, C., et al., WO90/07,119. Vaccines directed against HIV proteins are problematic in that the virus mutates rapidly rendering many of these vaccines ineffective. Thus, although a great deal of effort is being directed to the design and testing of anti-retroviral drugs, effective, non-toxic treatments are still needed.

Hematopoietic Cell Production

The morphologically recognizable and functionally capable cells circulating in blood include erythrocytes, neutrophilic, eosinophilic, and basophilic granulocytes, B-, T-, non B-, non T-lymphocytes, and platelets. These mature hematopoietic cells derive from and are replaced, on demand, by morphologically recognizable dividing precursor cells for the respective lineages such as erythroblasts for the erythrocyte series, myeloblasts, promyelocytes and myelocytes for the granulocyte series, and megakaryocytes for the platelets. The precursor cells derive from more primitive cells that can simplistically be divided into two major subgroups: stem cells and progenitor cells (for review, see Broxmeyer, H. E., 1983, "Colony Assays of Hematopoietic Progenitor Cells and Correlations to Clinical Situations," *CRC Critical Reviews in Oncology/Hematology* 1:227–257).

The definitions of stem and progenitor cells are operational and depend on functional, rather than on morphological, criteria. Stem cells have extensive self-renewal or self-maintenance capacity (Lajtha, L. G., 1979, *Differentiation* 14:23), a necessity since absence or depletion of these cells could result in the complete depletion of one or more cell lineages, events that would lead within a short time to disease and death. Some of the stem cells differentiate upon need, but some stem cells or their daughter cells produce other stem cells to maintain the pool of these cells. Thus, in addition to maintaining their own kind, pluripotential stem cells are capable of differentiation into several sub-lines of progenitor cells with more limited self-renewal capacity or no self-renewal capacity. These progenitor cells ultimately give rise to the morphologically recognizable precursor cells. The progenitor cells are capable of proliferating and differentiating along one, or more than one, of the myeloid differentiation pathways (Lajtha, L. G. (Rapporteur), 1979, *Blood Cells* 5:447).

A variety of infectious agents, genetic abnormalities and environmental factors can cause a deficiency in one or more hematopoietic cell types. For example, hematological abnormalities have been observed in HIV-1 infected individuals (the human immunodeficiency virus (HIV) has been implicated as the primary cause of the slowly degenerative immune system disease termed acquired immune deficiency syndrome (AIDS)) (Barre-Sinoussi, F., et al., 1983, *Science* 220:868–870; Gallo, R., et al., 1984, *Science* 224:500–503)), particularly in the late stages of disease (Lunardi-Iskandar, Y. et al., 1989, *J. Clin. Invest* 83:610–615). These abnormalities include a reduction in $CD4^+$ T cells as well as cytopenias of one or more hematopoietic lineages, often associated with bone marrow morphologic abnormalities and deficient progenitor cell growth (Lunardi-Iskandar, Y. et al., 1989, *J. Clin. Invest* 83:610–615; Louache, F. et al., 1992, *Blood* 180:2991–2999). Idiopathic thrombocytopenic purpura (ITP), characterized by significant reduction in platelet numbers, often afflicts subjects infected with HIV (Ballem, P. J. et al., 1992, *N. Engl. J. Med.* 327:1779). The destruction of platelets in sufferers of ITP appears to be mediated by platelet associated autoantibodies (Berchtold, P. and Wenger, M., 1993, *Blood* 81:1246; Ballem, P. J. et al., 1987,

*J. Clin. Invest.* 80:33). Thus, because management of ITP generally involves immunosuppression, treatment of ITP in HIV infected patients is complicated as administration of immunosuppressive drugs is extremely detrimental in HIV infection.

Additionally, chemotherapy and radiation therapy used in the treatment of cancer and certain immunological disorders can cause pancytopenias or combinations of anemia, neutropenia and thrombocytopenia. Thus, the increase or replacement of hematopoietic cells is often crucial to the success of such treatments. (For a general discussion of hematological disorders and their causes, see, e.g., "Hematology" in Scientific American Medicine, E. Rubenstein and D. Federman, eds., Volume 2, chapter 5, Scientific American, New York (1996)).

Furthermore, aplastic anemia presents a serious clinical condition as the overall mortality of all patients with aplastic anemias, in the absence of stem cell therapy, is high. Approximately 60–75% of individuals suffering from the disorder die within 12 months, in the absence of new stem cells. The overall incidence of these diseases is approximately 25 new cases per million persons per year. Although it is extremely unlikely that a single pathogenic mechanism accounts for all aplastic anemias, it is clear that provision of new hematopoietic stem cells is usually sufficient to allow permanent recovery, since transplantation of patients with aplastic anemia with bone marrow obtained from identical twins (i.e., syngeneic) (Pillow, R. P., et al., 1966, *N. Engl. J. Med.* 275:94–97) or from HLA-identical siblings (i.e., allogeneic) (Thomas, E. D., et al., Feb. 5, 1972, *The Lancet, pp.* 284–289) can fully correct the disease. However, some patients with aplastic anemia reject the transplanted marrow. This complication is particularly common among patients who have been immunologically sensitized as a result of multiple therapeutic blood, transfusions.

The current therapy available for many hematological disorders as well as the destruction of the endogenous hematopoietic cells caused by chemotherapy or radiotherapy is bone marrow transplantation. However, use of bone marrow transplantation is severely restricted since it is extremely rare to have perfectly matched (genetically identical) donors, except in cases where an identical twin is available or where bone marrow cells of a patient in remission are stored in a viable frozen state. Except in such autologous cases, there is an inevitable genetic mismatch of some degree, which entails serious and sometimes lethal complications. These complications are two-fold. First, the patient is usually immunologically incapacitated by drugs beforehand, in order to avoid immune rejection of the foreign bone marrow cells (host versus graft reaction). Second, when and if the donated bone marrow cells become established, they can attack the patient (graft versus host disease), who is recognized as foreign. Even with closely matched family donors, these complications of partial mismatching are the cause of substantial mortality and morbidity directly due to bone marrow transplantation from a genetically different individual.

Peripheral blood has also been investigated as a source of stem cells for hematopoietic reconstitution (Nothdurtt, W., et al., 1977, *Scand. J. Haematol.* 19:470–481; Sarpel, S. C., et al., 1979, *Exp. Hematol.* 7:113–120; Ragharachar, A., et al., 1983, *J. Cell. Biochem. Suppl.* 7A:78; Juttner, C. A., et al., 1985, *Brit. J. Haematol.* 61:739–745; Abrams, R. A., et al., 1983, *J. Cell. Biochem. Suppl.* 7A:53; Prummer, O., et al., 1985, *Exp. Hematol.* 13:891–898). In some studies, promising results have been obtained for patients with various leukemias (Reiffers, J., et al., 1986, *Exp. Hematol.* 14:312–315; Goldman, J. M., et al., 1980, *Br. J. Haematol.* 45:223–231; Tilly, H., et al., July 19, 1986, *The Lancet, pp.* 154–155; see also To, L. B. and Juttner, C. A., 1987, *Brit. J. Haematol.* 66: 285–288, and references cited therein); and with lymphoma (Korbling, M., et al., 1986, *Blood* 67:529–532). Other studies using peripheral blood, however, have failed to effect reconstitution (Hershko, C., et al., 1979, *The Lancet* 1:945–947; Ochs, H. D., et al., 1981, *Pediatr. Res.* 15:601). Studies have also investigated the use of fetal liver cell transplantation (Cain, G. R., et al., 1986, *Transplantation* 41:32–25; Ochs, H. D., et al., 1981, *Pediatr. Res.* 15:601; Paige, C. J., et al., 1981, *J. Exp. Med.* 153:154–165; Touraine, J. L., 1980, *Excerpta Med.* 514:277; Touraine, J. L., 1983, *Birth Defects* 19:139; see also Good, R. A., et al., 1983, *Cellular Immunol.* 82:44–45 and references cited therein) or neonatal spleen cell transplantation (Yunis, E. J., et al., 1974, *Proc. Natl. Acad. Sci. U.S.A.* 72:4100) as stem cell sources for hematopoietic reconstitution. Cells of neonatal thymus have also been transplanted in immune reconstitution experiments (Vickery, A. C., et al., 1983, *J. Parasitol.* 69(3):478–485; Hirokawa, K., et al., 1982, *Clin. Immunol. Immunopathol.* 22:297–304).

Clearly, there is a tremendous need for methods of expanding blood cells in vitro or therapies which increase the production of hematopoietic cells in vivo.

Wasting Syndromes

Wasting syndrome is a serious clinical problem characterized by a decrease in body mass of more than 10% from baseline body weight and a disproportionate loss of body mass with respect to body fat (Weinroth et al., 1995, *Infectious Agents and Disease* 4:76–94; Kotler and Grunfeld, 1995, *AIDS Clin. Rev.* 96:229–275). Thus, wasting is distinguished from starvation in which higher levels of body fat than body cell mass are depleted (Kotler et al., 1985, *Am J. Clin. Nutr.* 42:1255–1265; Cahill, 1970, *N. Engl. J. Med.* 282:668–675). Wasting is associated with a variety of conditions, including HIV infection (human immunodeficiency virus (HIV) has been implicated in acquired immune deficiency syndrome (AIDS) (Barre-Sinoussi, F., et al., 1983, *Science* 220:868–870; Gallo, R., et al., 1984, *Science* 224:500–503)), other infectious diseases, sepsis, cancer, chronic cardiovascular disease and diarrhea (Kotler et al., 1989, *Am. J. Clin. Nutr.* 50:444–447; Heymsfield et al., 1982, *Am. J. Clin. Nutr.* 36:680–690). Importantly, wasting is a significant factor in the mortality of patients suffering from infections or cancer. In fact, body cell mass depletion has a linear relationship to time of survival in AIDS patients (Kotler et al., 1989, *Am. J. Clin. Nutr.* 50:444–447).

The cause of wasting syndrome in AIDS and other conditions is unclear and is most likely multifactorial. Metabolic abnormalities, irregular levels of hormones and cytokines, and malabsorption have all been implicated in wasting syndrome. Not all AIDS patients suffer from wasting, suggesting that the cause of the wasting is not HIV itself. Most cases of HIV associated wasting syndrome are apparently caused by complications of AIDS, such as secondary infections and gastrointestinal disease (Kotler and Grunfeld, 1995, *AIDS Clin. Rev.* 96:229–275).

Current and potential therapies for wasting syndromes include nutritional support, appetite enhancers such as dronabinol and megestrol acetate, anabolic therapies, such as growth hormone, and cytokine inhibitors. However, mixed results have been obtained with nutritional support and appetite enhancers in that patients tended to gain only fat and not overall body mass. Administration of growth hormone, and cytokine inhibitors are still being tested and may pose a risk of side effects (Kotler and Grunfeld, 1995, *AIDS Clin. Rev.* 96:229–275; Weinroth et al., 1995, *Infectious Agents and Disease* 4:76–94).

Thus, treatment of wasting is critical to the survival and well-being of patients suffering from serious diseases such as cancer and AIDS; thus, there is a need for safe and effective therapies for wasting syndrome associated with cancer, AIDS and other infectious diseases.

Cancer

A neoplasm, or tumor, is a neoplastic mass resulting from abnormal uncontrolled cell growth, which may cause swelling on the body surface, and which can be benign or malignant. Benign tumors generally remain localized. Malignant tumors are collectively termed cancers. The term "malignant" generally means that the tumor can invade and destroy neighboring body structures and spread to distant sites to cause death (for review, see Robbins and Angell, 1976, *Basic Pathology*, 2d Ed., W. B. Saunders Co., Philadelphia, pp. 68–122). Treatment options, such as surgery, chemotherapy and radiation treatment, are either ineffective or present serious side effects. Thus, there is a need for development of new drugs for the treatment of cancer.

Kaposi's Sarcoma (KS) is a rare type of cancer, the incidence of which is greatly increased in HIV infected people (Lunardi-Iskandar, Y., et al., 1995, *Nature* 375:64–68; Friedman-Kien, A. E., et al., 1981, *J. Am. Acad. Dermatol.* 5:468–473). The tumors appear to be comprised of hyperplastic cells derived from vascular endothelial cells (Nakamura, S., et al., 1988, *Science* 242:426–430; Ensoli, B., et al 1989, *Science* 243:223–226; Salahuddin, S. Z., et al., 1988, *Science* 242:430–433; Masood, R., et al., 1994, *AIDS Res. Hum. Retroviruses* 10:969–976; Lunardi-Iskandar, Y., et al., 1995, *JNCI* 88:450–454). In some cases, neoplastic cells with chromosomal abnormalities are also present in the tumors (Lunardi-Iskandar, Y., et al., 1995, *JNCI* 87:974–981; Delli-Bovi, P., et al., 1986, *Cancer Res.* 46:6333–6338; Siegal, B., et al., 1990, *Cancer* 65:492–498; Yunis, J. J., 1983, *Science* 221:227–236; Popescu, N. C., et al., 1995, *JNCI* 88:450–454). Therapies for KS include radiotherapy, α-interferon and systemic chemotherapy (Chak, L. Y., et al., 1988, *J. Clin. Oncol.* 6:863–7; Evans, L. M., et al., 1991, *J. Immunother.* 10:39–50; Kovas, J., et al., 1990, *Ann. Intern. Med.* 112:812–21; Gelmann, E. D., et al., 1987, *Am. J. Med.* 82:456–62; Gill, P. S., et al., 1991, *Am. J. Med.* 90:427–33; Gill, P. S., et al., 1990; *Am. J. Clin. Oncol.* 13:315–9; Gill, P. S., et al., 1994, *AIDS* 8:1695–9). However, hematological and non-hematological toxicities limit the prolonged use of chemotherapy and α-interferon in conjunction with anti-retroviral agents commonly used in the treatment of AIDS (Kovas, J., et al., 1990, *Ann. Intern. Med.* 112:812–21; Gill, P. S., et al., 1991, *Am. J. Med.* 90:427–33; Gill, P. S., et al., 1994, *AIDS* 8:1695–9). Thus, new drugs, preferably drugs compatible with AIDS therapeutics, are needed for the treatment of KS.

Human Chorionic Gonadotropin

Human chorionic gonadotropin (hCG), which is required for the maintenance of pregnancy, is a member of the glycoprotein hormone family. The glycoprotein hormones, which also include follicle-stimulating hormone (FSH), luteinizing hormone (LH) and thyroid-stimulating hormone (TSH), consist of two sub-units, α and β. These subunits are non-covalently linked to form a heterodimer, and heterodimer formation has been shown to be required for receptor binding. Within a particular species, the α-subunits are identical among the glycoprotein hormones while the β-subunits differ and determine the receptor binding specificity of the particular hormone (Kornyei, J. L., et al., 1993, *Biol. Reprod.* 49:1149). The β-subunits of the glycoprotein hormones exhibit a high degree of sequence similarity within the N-terminal 114 amino acids. LH is the most similar to hCG with 85% sequence homology within the first 114 amino acids, and both proteins bind the same receptor. hCG, however, contains a C-terminal extension not present in the other glycoprotein β-chains (Lapthorn, A. J., et al., 1994, *Science* 369:455–461).

From the three dimensional crystal structure of hCG, it has been determined that hCG, like the growth factors nerve growth factor (NGF), transforming growth factor-β (TGF-β) and platelet-derived growth factor-β (PDGF-β), is a cysteine-knot glycoprotein. Proteins containing such a cysteine-knot motif have at least three disulfide bridges, two of which join adjacent anti-parallel strands of the peptide, thus, forming a ring, and one of which joins the peptide chain through the ring. Particular structures in the hCG β-chain include the determinant loop sequence (β93–100) which has been implicated in subunit association and the longest inter-cysteine loop (β38–57) which may play a role in receptor binding. Residues 47–53 appear to be exposed at the surface of this inter-cysteine loop (Lapthorn et al., 1994, *Nature* 369:455–461).

Previously, purified preparations of heterodimeric hCG have been shown to reduce the reverse transcriptase activity in HIV-1 infected lymphocytes and monocytes in culture (Bourinbaiar, A. S., and Nagorny, R., 1992, *FEMS Microbiology Letters* 96:27–30) and to prevent transmission of HIV from lymphocytes to trophoblasts in vitro (Bourinbaiar, A. S., and Nagorny, R., 1992, *FEBS Letters* 309:82–84). Additionally, the β-subunit of hCG (β-hCG) has been demonstrated to reduce HIV production in lymphocytes at doses from 100 pg/ml to 100 µg/ml and in monocytes at doses up to approximately 10 µg/ml, with higher doses actually increasing the level of viral production in monocytes (Bourinbaiar, A. S., and Lee-Huang, S., 1995, *Immunology Letters* 44:13–17). However, none of these reports disclose the potential efficacy of β-hCG peptides in HIV inhibition in vitro or of hCG or any portion or derivative thereof in HIV treatment or prevention in vivo.

Furthermore, doses of hCG below those necessary to induce a humoral immune response have been proposed for treatment of HIV infection based on observations of therapeutic effects of such doses on cats and cows infected with feline leukemia and bovine leukemia viruses respectively (U.S. Pat. No. 4,880,626). This patent suggested use of the hCG dimer at very low doses (approximately 2 I.U. per treatment).

Lunardi-Iskandar et al. (1995, *Nature* 375:64–68 and PCT Application WO96/04008) reported that hCG, β-hCG, as well as a β-hCG carboxy-terminal peptides of amino acids 109–145 (SEQ ID NO:25) and 109–119 (SEQ ID NO:7) are efficacious in the treatment of Kaposi's Sarcoma. However, neither reference discloses or even suggests that hCG, β-hCG or β-hCG peptides of amino acids 109–145 or 109–119 (SEQ ID NOS:7 and 25, respectively) have any viral anti-activity or that other β-hCG peptides have any therapeutic activity.

Finally, Harris (1995, *The Lancet* 346:118–119) reported that treatment with hCG improved T cell counts and physical symptoms in certain HIV infected subjects.

The present invention fulfills a need for safe and effective therapies for HIV, wasting syndrome associated with AIDS, other infectious diseases and cancer, as well as methods for promoting hematopoiesis.

Citation of references hereinabove shall not be construed as an admission that such references are prior art to the present invention.

SUMMARY OF THE INVENTION

The present inventors have found that hCG preparations, β-hCG preparations, certain peptides of β-hCG, certain combinations of β-hCG peptides linked via their N-termini and C-termini by peptide bond(s), and certain gel filtration chromatography fractions of commercial hCG preparations and human early (i.e. first trimester) pregnancy urine exhibit anti-viral activities, including anti-HIV activities. In particular, hCG and β-hCG preparations and certain gel filtration chromatography fractions of commercial hCG preparations and of human early pregnancy urine, as described by way of example hereinbelow, and specific peptides thereof inhibit HIV-1 replication in vitro, inhibit HIV-1 gene-expression in HIV-1 transgenic mice, reduce plasma virus levels in SIV infected monkeys and in AIDS patients, and increase $CD4^+$ T cells in HIV transgenic mice, SIV infected monkeys and AIDS patients. The present inventors have further found that the subjects tolerated treatment with hCG and β-hCG preparations very well and that the virus did not become resistant to treatment after exposure to hCG or β-hCG. The present invention fills a tremendous need for a non-toxic, long-term treatment of HIV infection and its sequelae, ARC and AIDS.

The present invention relates to proteins having a sequence of one or more portions of the β-chain of hCG (β-hCG), particularly proteins having the sequence of amino acid numbers 41–54, 45–54, 47–53, 45–57 and 109–119 (SEQ ID NOS:3–7, respectively). The present invention also relates to proteins comprising or, alternatively, consisting of, the sequence of two or more portions of β-hCG, e.g., wherein said portions are linked via their N-termini and C-termini by peptide bond(s), particularly proteins having the sequence of amino acid numbers 45–57 (SEQ ID NO:6) linked via a peptide bond at the C-terminus to the N-terminus of a peptide of amino acid numbers 109–119 (SEQ ID NO:7) or linked at the N-terminus to the C-terminus of a peptide of amino acid numbers 110–119 (SEQ ID NO:27); or a peptide of amino acid numbers 47–57 (SEQ ID NO:28) linked by a peptide bond at the C-terminus to the N-terminus of a peptide of amino acid numbers 108–119 (SEQ ID NO:29) of β-hCG as depicted in FIG. 8 (a portion of SEQ ID NO:2), i.e. the peptides denoted 45–57::109–119, 110–119::45–57, or 47–57::108–119 (SEQ ID NOS:30–32, respectively). The present invention also relates to certain fractions (i.e. components of a source of hCG or β-hCG isolated away from other components in the source of hCG or β-hCG by a separation technique known in the art) of any source of hCG or β-hCG, such as commercial hCG preparations and human (preferably early, i.e., first trimester) pregnancy urine, which fractions have anti-HIV and/or anti-Kaposi's Sarcoma activity.

The present invention further relates to therapeutic methods and compositions for treatment and prevention of diseases and disorders associated with HIV infection based on hCG and β-hCG preparations, therapeutically and prophylactically effective fractions of a source of hCG or β-hCG (preferably a source of native hCG or native β-hCG, i.e. a source of naturally occurring hCG or β-hCG, not recombinantly produced hCG or β-hCG) and therapeutically and prophylactically effective proteins containing a sequence of one or more portions (i.e., a fusion protein comprising more than one β-hCG peptide sequence either as non-contiguous or contiguous sequences, e.g., having an amino acid sequence of one β-hCG peptide linked via a peptide bond to another β-hCG peptide) of β-hCG, and related derivatives and analogs. The invention provides for treatment and prevention of HIV infection by administration of a therapeutic compound of the invention. The therapeutic compounds of the invention include: hCG, β-hCG, therapeutically and prophylactically effective fractions of a source of hCG or β-hCG, therapeutically and prophylactically effective peptides having a sequence of a one or more portions of β-hCG, modified derivatives of hCG, β-hCG and β-hCG peptides, and nucleic acids encoding β-hCG and therapeutically and prophylactically effective peptides having a sequence of one or more portions of β-hCG, and derivatives and analogs of the foregoing. The invention also provides in vitro and in vivo assays for assessing the efficacy of therapeutics of the invention for treatment or prevention of HIV. The invention also provides pharmaceutical compositions and methods of administration of therapeutics of the invention for treatment or prevention of HIV infection.

The present invention further relates to therapeutic methods and compositions having anti-wasting activity for treatment and prevention of wasting syndromes based on hCG and β-hCG preparations, therapeutically and prophylactically effective fractions of a source of native hCG or native β-hCG and therapeutically and prophylactically effective proteins containing a sequence of a portion or portions (i.e., a fusion protein comprising more than one β-hCG peptide sequence, e.g., having an amino acid sequence of one β-hCG peptide linked via a peptide bond to another β-hCG peptide) of β-hCG, and related derivatives and analogs. The invention provides for treatment and prevention of wasting syndromes by administration of a therapeutic compound of the invention. The therapeutic compounds of the invention include: hCG, β-hCG, therapeutically and prophylactically effective fractions of a source of hCG or β-hCG (preferably a source of native hCG or native β-hCG, i.e. a source of naturally occurring hCG or β-hCG and not recombinantly produced hCG or β-hCG), therapeutically and prophylactically effective peptides having a sequence of a portion or portions of β-hCG (i.e. a fusion protein comprising more than one β-hCG peptide sequence either as non-contiguous or contiguous sequences, e.g. having an amino acid sequence of one β-hCG peptide linked via a peptide bond to another β-hCG peptide), modified derivatives of hCG, β-hCG and β-hCG peptides, and nucleic acids encoding β-hCG and therapeutically and prophylactically effective peptides having a sequence of a portion or portions of β-hCG, and derivatives and analogs of the foregoing.

The present invention also relates to the use of certain fractions (i.e. components of a source of hCG or β-hCG isolated away from other components in the source of hCG or β-hCG by a separation technique known in the art) of any source of hCG or β-hCG, such as commercial hCG preparations and human (preferably early, i.e., first trimester) pregnancy urine, which fractions have anti-HIV, anti-cancer activity (such as anti-Keposi's Sarcoma activity), anti-wasting activity and/or pro-hematopoeitic activity.

The invention also provides in vitro and in vivo assays for assessing the efficacy of therapeutics of the invention for treatment or prevention of HIV infection, cancer, and/or wasting syndromes.

The invention also provides pharmaceutical compositions and methods of administration of Therapeutics of the invention for treatment.

The present invention also relates to therapeutic methods and compositions for treatment and prevention of diseases and disorders in which an increase in one or more types of hematopoietic cells is desirable. The therapeutic compounds of the invention are hCG and β-hCG preparations, therapeutically and prophylactically effective fractions of a source of native hCG or native β-hCG and therapeutically and prophylactically effective proteins containing a sequence of one or more portions (i.e., a fusion protein comprising more than one β-hCG peptide sequence either as non-contigous or contiguous sequences, e.g., having an amino acid sequence of one β-hCG peptide linked via a peptide bond to another β-hCG peptide) of β-hCG, and related derivatives and analogs. The present invention also relates to use of certain fractions (i.e. components of a source of hCG or β-hCG (preferably native hCG or β-hCG, i.e. not recombinantly produced) isolated away from other components in the source of hCG or β-hCG by a separation technique known in the art) of any source of hCG or β-hCG, such as commercial hCG preparations and human (preferably early, i.e., first trimester) pregnancy urine, which fractions have anti-HIV, anti-cancer activity (such as anti-Kaposi's Sarcoma activity) anti-wasting activity and/or pro-hematopoietic activity.

The invention provides for treatment and prevention of diseases and disorders (e.g., involving hematopoietic cell deficiencies) by administration either of a therapeutic compound of the invention or of hematopoietic cells, the numbers of which have been increased in vitro by contact with a therapeutic compound of the invention. The invention thus also provides in vitro methods of expanding hematopoietic cells. The therapeutic compounds of the invention include: hCG, β-hCG, therapeutically and prophylactically effective fractions of a source of native hCG or native β-hCG, therapeutically and prophylactically effective peptides having a sequence of one or more portions of β-hCG, modified derivatives of hCG, β-hCG and β-hCG peptides, and nucleic acids encoding β-hCG and therapeutically and prophylactically effective peptides having a sequence of one or more portions of β-hCG, and derivatives and analogs of the foregoing.

In a specific embodiment, gene therapy methods are provided using hCG and β-hCG preparations, therapeutically and prophylactically effective fractions of a source of hCG or β-hCG and therapeutically and prophylactically effective proteins containing a sequence of one or more portions of β-hCG, and related derivatives and analogs to induce proliferation of hematopoietic progenitor or stem cells into which cells a nucleic acid of interest is introduced either before or after proliferation. The proliferation induced by the methods of the invention can be with or without concomitant hematopoietic cell differentiation, and, in a preferred embodiment, is proliferation followed by differentiation of the cells.

The present invention further relates to therapeutic methods and compositions for treatment and prevention of cancers based on hCG and β-hCG preparations, therapeutically and prophylactically effective fractions of a source of native hCG or native β-hCG and therapeutically and prophylactically effective proteins containing a sequence of one or more portions (i.e., a fusion protein comprising more than one β-hCG peptide sequence either as non-contiguous or contiguous sequences, e.g., having an amino acid sequence of one β-hCG peptide linked via a peptide bond to another β-hCG peptide) of β-hCG, and related derivatives and analogs. The invention provides for treatment and prevention of cancers by administration of a therapeutic compound of the invention. The therapeutic compounds of the invention include: hCG, β-hCG, therapeutically and prophylactically effective fractions of a source of native hCG or native β-hCG, therapeutically and prophylactically effective peptides having a sequence of one or more portions of β-hCG, modified derivatives of hCG, β-hCG and β-hCG peptides, and nucleic acids encoding β-hCG and therapeutically and prophylactically effective peptides having a sequence of one or more portions of β-hCG, and derivatives and analogs of the foregoing.

The present invention also relates to certain fractions (i.e. components of a source of hCG or β-hCG isolated away from other components in the source of hCG or β-hCG by any separation technique known in the art) of any source of hCG or β-hCG, such as commercial hCG preparations and human (preferably early, i.e., first trimester) pregnancy urine, which fractions have anti-HIV and or anti-Kaposi's Sarcoma activity. The invention also provides in vitro and in vivo assays for assessing the efficacy of therapeutics of the invention for treatment or prevention of cancers.

The invention also provides pharmaceutical compositions and methods of administration of Therapeutics of the invention for treatment.

The invention also provides methods of administration and pharmaceutical compositions containing a Therapeutic of the invention.

Definitions

As used herein, the following terms shall have the meaning indicated.

AIDS=Acquired Immune Deficiency Syndrome

ARC=AIDS-Related Complex

BFU-E=burst forming unit-erythroid. A hematopoietic progenitor cell which is capable of producing a colony of erythroid progeny cells in semi-solid medium.

CFU=colony forming unit. A cell which is capable of producing a colony of progeny cells in semi-solid medium.

CFU-GEMM=colony forming unit-granulocyte, erythrocyte, monocyte/macrophage, megakaryocyte. A multipotential hematopoietic progenitor cell which is capable of producing a colony composed of granulocyte, erythrocyte, monocyte/macrophage, and megakaryocyte progeny in semi-solid medium.

CFU-GM=colony forming unit-granulocyte, macrophage. A hematopoietic progenitor cell which is capable of producing a colony composed of granulocyte and macrophage progeny in semi-solid medium.

CFU-MK=colony forming unit-megakaryocyte. A hematopoietic progenitor cell which is capable of producing a colony composed of megakaryocyte progeny in semi-solid medium.

CFU-S=colony forming unit-spleen. A multipotential stem cell with self-renewal capacity, which, upon inoculation into a lethally irradiated mouse, is capable of producing a colony (module) on the spleen. CFU-S is not a marrow-repopulating cell; it is a less primitive stem cell which does not provide long-term engraftment in an animal.

CSF=colony stimulating factor

Epo=erythropoietin

FBS=fetal bovine serum. Also known as fetal calf serum.

G-CSF=granulocyte colony stimulating factor

GM-CSF=granulocyte-macrophage colony stimulating factor

HCG=Human Chorionic Gonadotropin

KS=Kaposi's Sarcoma

OI=Opportunistic Infection

ITP=Idiopathic thrombocytopenic purpura (a severe platelet deficiency)

PB=peripheral blood
PBMC=Peripheral Blood Mononuclear Cell

DESCRIPTION OF THE FIGURES

FIGS. 2A–D. Effects of an hCG preparation on indicators of SIV infection in SIV-infected macaques. SIV was given intravenously at a dose of $10^{4.5}$ $TCID_{50}$ per ml. (A) SIV titer was monitored over time in months by quantifying the p27 gag protein (Organon Teknika assay) as nanograms (ng) of p27/ml of plasma from the plasma of the SIV infected macaques. Treated SIV-infected macaques (indicated as Rx) were given hCG APL™, 3000 IU, 2×weekly. Plasma levels of p27 gag in these treated monkeys are indicated on the graph by lines with diamonds, number (#) signs or filled circles. Results with the untreated SIV-infected macaques (indicated UnRx) are indicated by the lines with either stars or triangles. (B) $CD4^+$ T cell levels were determined in cells/mm³ in SIV-infected macaques either treated with hCG or untreated over time in months. Results from the SIV-infected monkeys treated with hCG (APL™) (Rx) are indicated by lines with diamonds, number (#) signs or filled circles, while results with the untreated monkeys (UnRx) are indicated by lines with stars or triangles. (C) Change in weight in kilograms (kg) was monitored in treated and untreated SIV-infected monkeys over time in months. Weight changes in the SIV-infected monkeys treated with hCG (APL™) (Rx) are indicated by lines with diamonds, # signs or filled circles, while results in the untreated monkeys (UnRx) are indicated by lines with stars or triangles. (D) Levels of $CD4^+$ T cells were monitored in normal uninfected monkeys either treated with hCG (APL™) or untreated over time in months. $CD4^+$ T cell levels in the untreated monkeys are indicated by lines with sun-like figures or squares, and the results in the treated monkeys are indicated by lines with pentagonal figures or with filled inverted triangles.

FIGS. 3A–J. Effects of administration of hCG preparations on HIV-1 viral load and $CD4^+$ T cell levels in individual patients in the clinical study described herein. Figures A and B are data from patient PHOJ, C and D from patient PG1, E and F from patient PG3, G and H from patient PHVE, and I and J from patient PG17. In panels A, C, E, G and I, viral load and $CD4^+$ T Cell counts are plotted over time (in months). Viral load (measured by RT-PCR in panels A and G and by the Roche Amplicor test in panels C, E and I) is plotted as the logarithm of the viral load (represented by line with "X" data points). The $CD4^+$ T Cell levels are plotted as $CD4^+$ T Cells/ml (represented by line with triangle data points). Panels B, D, F, H, and J plot the dosage of hCG in IU (×1000) per week over time in months, with the timing of other therapies indicated above the graph with a thick arrow.

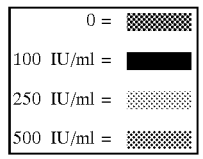

(C) The viability of Hut 78 cells in the presence of hCG at 0 IU/ml, 250 IU/ml and 500 IU/ml under the conditions used in the transient expression assays shown in Figures A and B was determined using a coulter cell counter. Results are presented as a bar graph in terms of cell number×10,000 and the hCG concentrations are indicated as shown below:

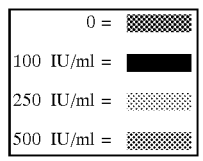

FIGS. 6A–H. Effect of hCG preparations and peptides on KS colony growth in vitro and KS tumors in vivo. (A) Comparison of the anti-KS in vitro effects (tumor cell killing) of purified hCG and β-hCG peptides in KS clonogenic assays using KS Y-12 and KS Y-12 "SKL" 18 cells depicted in a bar graph in terms of number of colonies. The results are averages of 3 sets of results with less than 10% variation and are representative of multiple experiments. Results with no hCG or hCG peptides are represented by open bars, the results with the β-hCG peptide of amino acids 109–119 (SEQ ID NO:7) are represented by stippled bars, the results with the β-hCG peptide of amino acids 109–145 (SEQ ID NO:25) are represented by the bars with horizontal stripes, the results with the circular β-hCG peptide of amino acids 44–57 (SEQ ID NO:26) where the amino acid at position 44 is a cysteine are represented by the bars with diagonal stripes, and the results with the highly purified hCG preparation, CR 127, are represented by solid bars. (B–H) Thin sections of KS tumors induced in nude mice by inoculation with 106 neoplastic KS Y-1 cells. (B) Thin section of tumors from mice that were not treated with hCG or hCG subunits or peptides (C) Thin section of a tumor from a mouse after treatment with crude hCG APL™ (100 IU) subcutaneously daily for 7 days. (D) Thin section of a tumor from a mouse treated with the β-hCG peptide of amino acids 45–57 (SEQ ID NO:6), 10 μg/ml/daily (6.7 nmoles) for 5 days. (E) Thin section of a tumor from a mouse after 5 days of treatment with the circularized β-hCG peptide 44–57 where cysteine has been substituted at position 44 (SEQ ID NO:26), at 10 μg per day. (F) This panel shows the thin tissue section of KS tumor from AIDS-KS patients treated with 1 ml of diluent alone shows less than 2% cell death as detected by specific apoptosis in situ immunostaining. (G) Thin tissue section of KS tumor from an AIDS-KS patient after hCG preparation therapy of intralesional injections of 2000 IU, 3 times weekly for 2–3 weeks, shows evidence of apoptosis in all cells. (H) Thin tissue section of KS tumor from an AIDS-KS patient after hCG preparation therapy, 500 IU, 3 times weekly for 3 weeks.

Figure 7B:
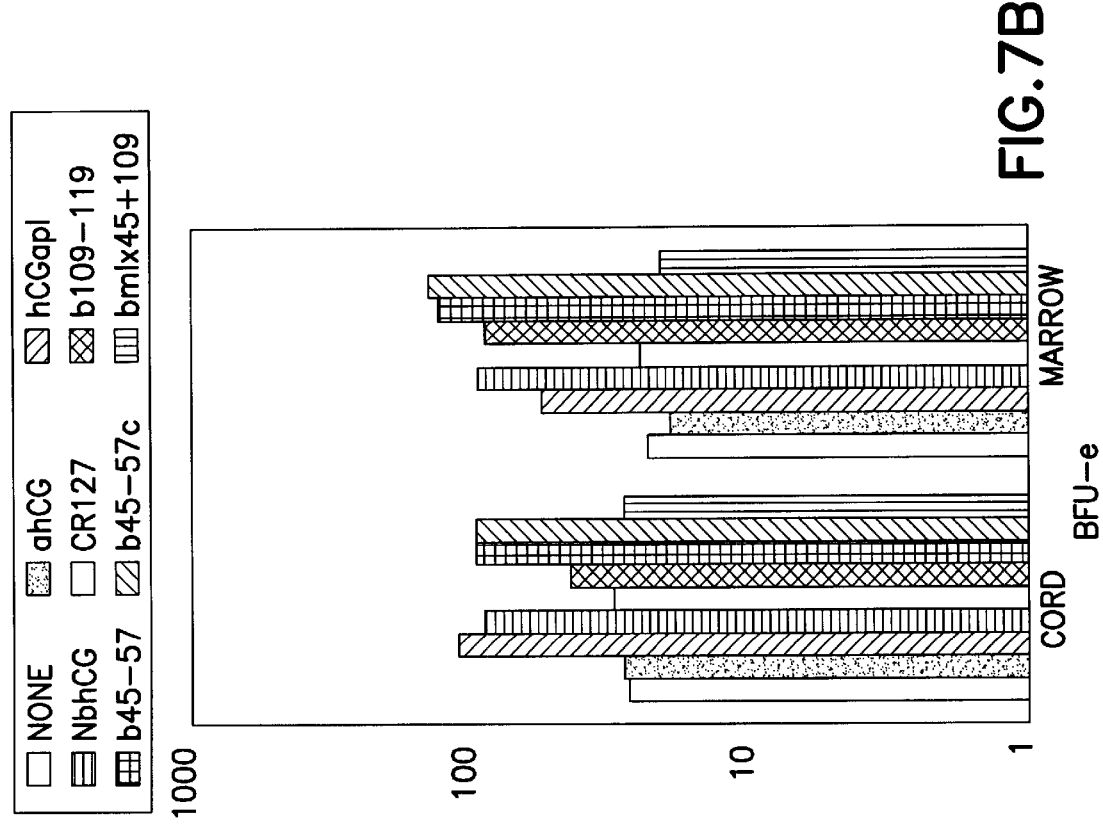
Figure 7A:
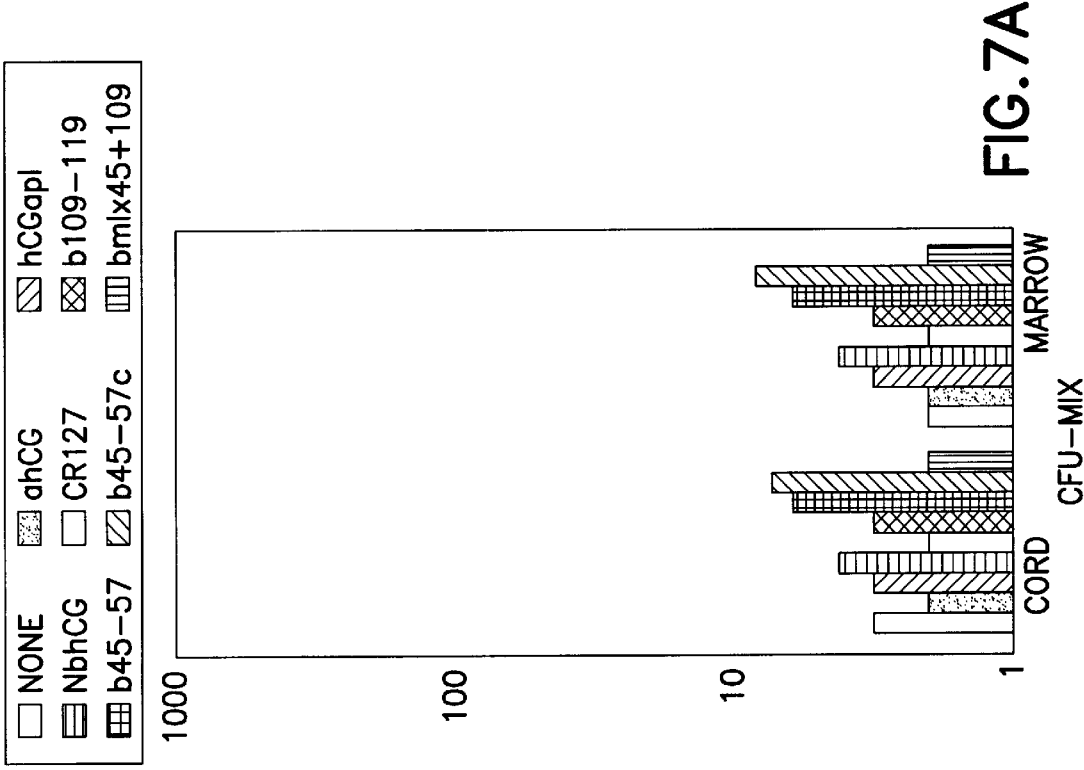
Figure 7C:
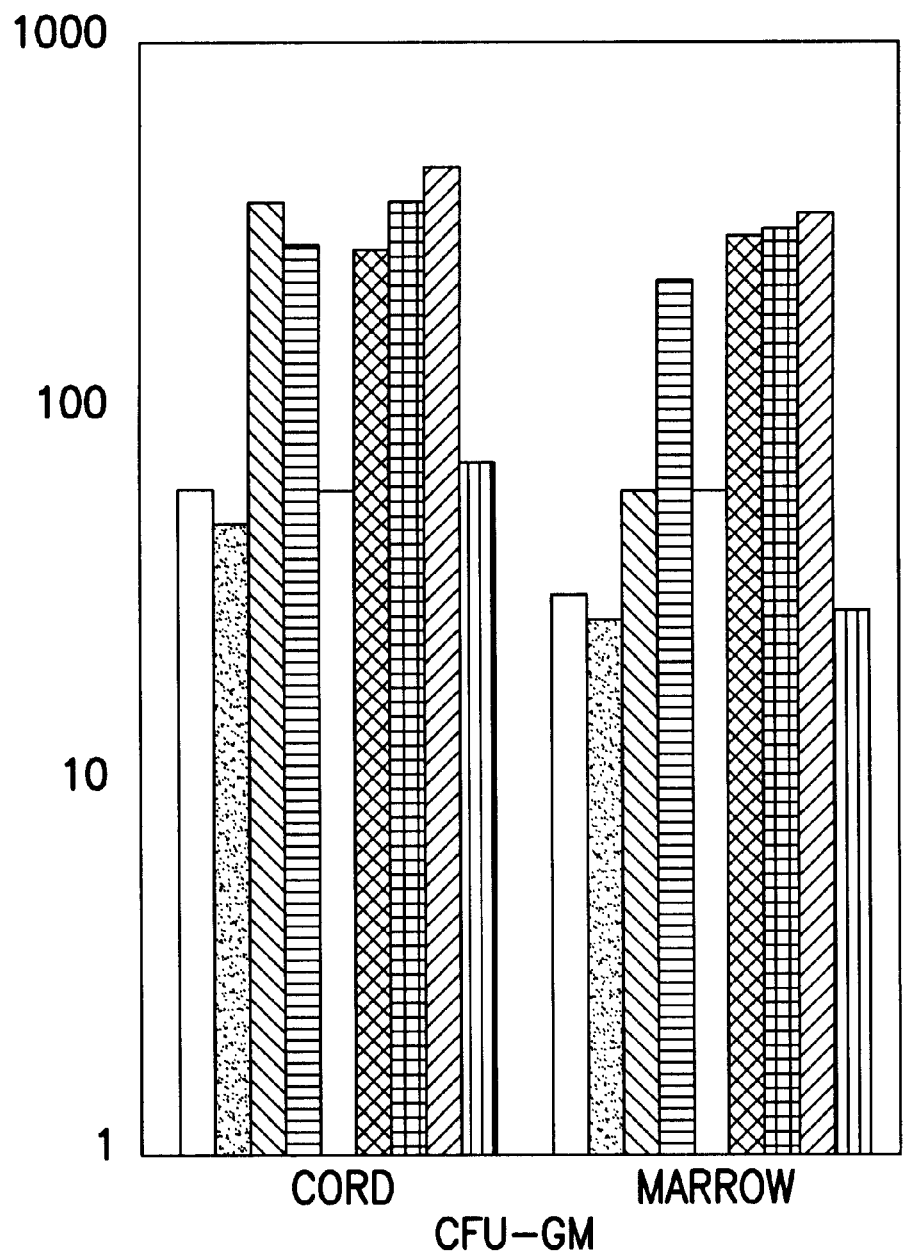

FIGS. 7A–C. These bar graphs demonstrate the effects of hCG preparations and peptides on hematopoiesis in vitro. (A) This bar graph depicts results of colony assays in terms of number of colonies for CFU-MIX (colony forming units of megakaryocytes, erythrocytes, granulocytes and monocytes). (B) This bar graph presents data from colony assays for BFU-e (Burst forming units of erythrocytes) in terms of number of colonies. (C) This bar graph presents results from colony assays of CFU-GM (colony forming units of granulo-macrophages) in terms of number of colonies. For all three graphs, results are shown for cells isolated from cord blood ("cord") and bone marrow ("marrow"). The results are averages of 3 sets of results with less than 10% variation and are representative of multiple experiments. The results from no treatment are indicated by open bars; the results with α-hCG are represented by solid bars; the results with APL™ hCG (hCGapl) are represented by bars with a lattice pattern; the results with native β-hCG preparation (NbhCG) are represented by cross-hatched bars; the results with the highly purified hCG preparation (CR127) are represented by open bars; the results with the β-hCG peptide of amino acids 109–119 (SEQ ID NO:7) (b109–119) are shown by the diagonally stippled bars; the results with the β-hCG peptide of amino acids 45–57 (SEQ ID NO:6) (b45–57) are shown by the bars with the diamonds; the results with the circularized β-hCG peptide of amino acids 44–57 with cysteine substituted for the amino acid at position 44 (SEQ ID NO:26) (b45–57c) are represented by the diagonally striped bars; and the results with the mixture of scrambled β-hCG peptides of amino acids 45–57 and 109–119 (bmix45+109) are represented by the vertically striped bars.

FIG. 8. Nucleotide (SEQ 1D NO:1) and amino acid (SEQ 1D NO:2) sequence of β-hCG.

FIGS. 9A and B. Schematic depiction of the structures of (A) the linear peptide of amino acids 45–57 (SEQ ID NO:6) of the β-hCG sequence depicted in FIG. 8 (SEQ ID NO:2) where the amino acid residues at positions 47 and 51 are substituted by a branch made up of diaminobutyric acid peptide bonded to proline, and (B) the circularized peptide of amino acids 44–57 (SEQ ID NO:26) with valine at position 44 substituted with cysteine, which protein is circularized via a disulfide bond between its amino- and carboxy-terminal cysteines. In both A and B, amino acids are represented by their three letter amino acid code, except for the branched residues and the terminal cysteines, for which the structure is depicted.

FIGS. 10A–F. These graphs depict results from the fractionation by Superdex 200 gel filtration of a commercial hCG preparation APL™ (Wyeth Ayerst) and early pregnancy urine. (A) and (D). These graphs depicts the relative amount of protein in mg/ml in each fraction identified by fraction number in the hCG APL™ fractionation (A) and early pregnancy urine fractionation (D). The fractions containing the hCG dimer and β-core protein are identified with arrows and the labels "hCG" and "β-core" respectively. (B) and (E). These graphs present the percent inhibition of growth of cultured KS cells by the individual fractions from the hCG APL™ (B) and early pregnancy urine (E) using KS cell clonogenic assays. The results are plotted as percent inhibition versus fraction number. (C) and (F). These graphs depict the effect of the hCG APL™ (C) and early pregnancy urine (F) fractions on HIV replication in vitro. Specifically, this graph presents data on the percentage inhibition of HIV-1 IIIB viral infection of PBMCs as a function of fraction number.

Figure 11:
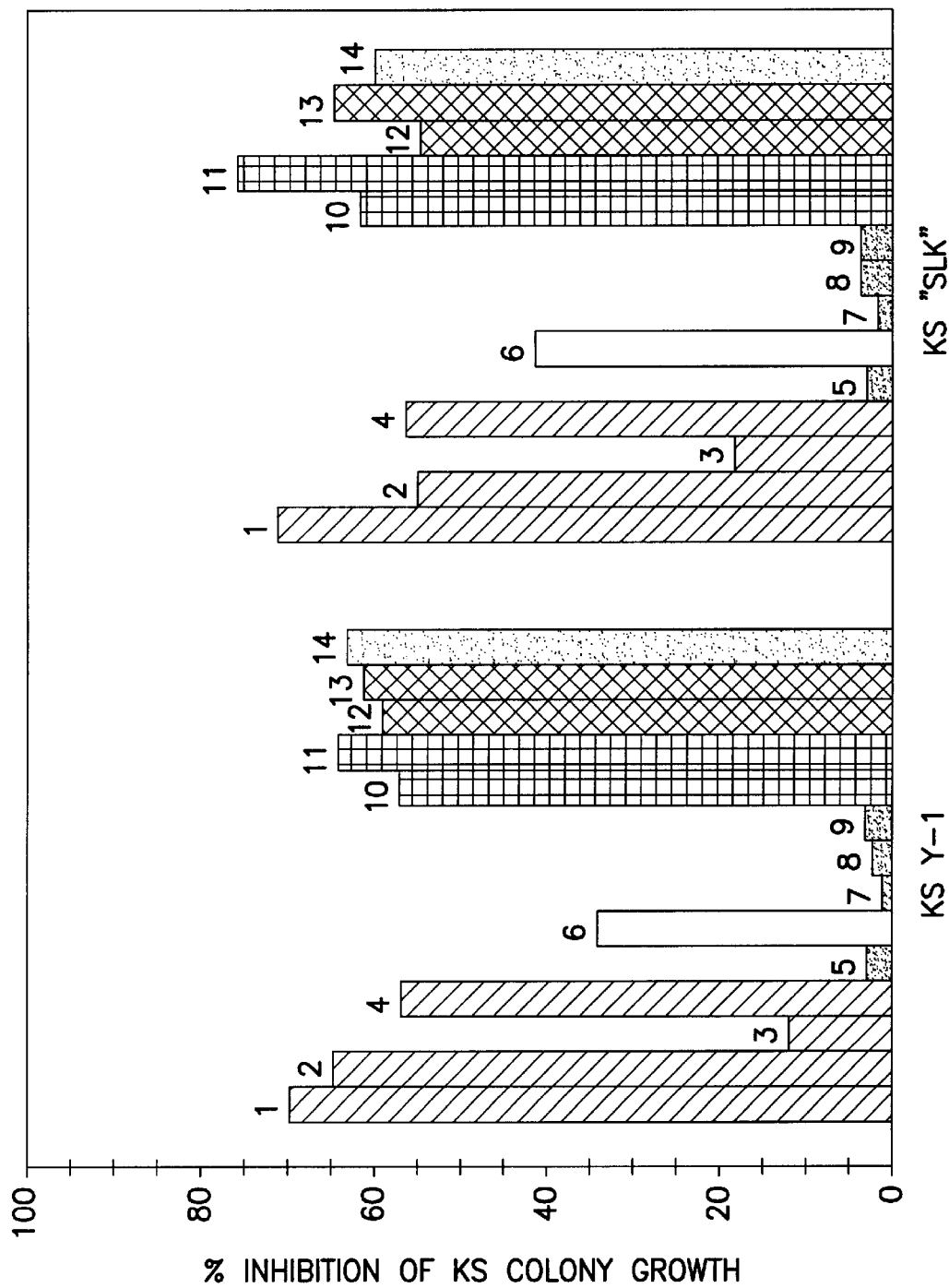

FIG. 11. Effect of hCG preparations, hCG and early pregnancy urine fractions, and β-hCG peptides on KS cell growth in vitro. Results for clonogenic assays using the cell lines KS Y-1 (bars labeled "KS Y-1") and KS SLK (labeled "KS SLK") are presented on a bar graph as percent inhibition of KS Colony Growth. Bars 1–4 represent cells treated with 200 IU/ml of the commercial hCG preparations hCG APL™, hCG CG10 (Sigma), hCG PROFASI™, and hCG PREGNYL™, respectively; bar 5 represents treatment with 50 µg/ml β-hCG core protein; bar 6, 50 µg/ml native β-hCG; bar 7, 50 µg/ml native α-hCG; bar 8, 200 IU/ml highly purified hCG preparation CR 127; bar 9, 50 µg/ml recombinantly produced hCG (Sigma); bars 10 and 11, 50–100 µl/ml of fractions 65 and 76, respectively, of the early pregnancy urine fractionation; bars 12 and 13, 50–100 µl/ml of fractions 65 and 76, respectively, of the hCG APL™ fractionation; and bar 14, 100 µg/ml of the circularized β-hCG peptide 44–57 (with cysteine substituted at position 44; SEQ ID NO:26).

FIGS. 12A–C. These bar graphs demonstrate the effects of hCG preparations, fractions and peptides on hematopoiesis in vitro. (A) Results of colony assays in terms of percent increase of hematopoiesis for CFU-GEMM (colony forming units of megakaryocytes, erythrocytes, granulocytes and monocytes). (B) Data from colony assays for BFU-e (Burst forming units of erythrocytes) in terms of percent increase of hematopoiesis. (C) Results from colony assays of CFU-GM (colony forming units of granulo-macrophages) in terms of percent increase of hematopoiesis. In all three graphs, bar 1 represents results from treatment with PBS alone; bar 2, the results with 100 µg/ml α-hCG; bar 3, with 200 IU/ml APL™ hCG; bar 4, 200 IU/ml of the highly purified hCG preparation CR 127; bar 5, 100 µg/ml native β-hCG preparation; bar 6, 100 µg/ml of the circularized β-hCG peptide of amino acids 44–57 with cysteine substituted for the amino acid at position 44 (SEQ ID NO:26); bar 7, 100 µl/ml of fraction 65 of the hCG APL™ fractionation; bars 8 and 9, 100 µl/ml of fractions 65 and 26, respectively, of the early pregnancy urine fractionation; and bar 10, 100 µg/ml of the β-hCG core protein.

Figure 13:
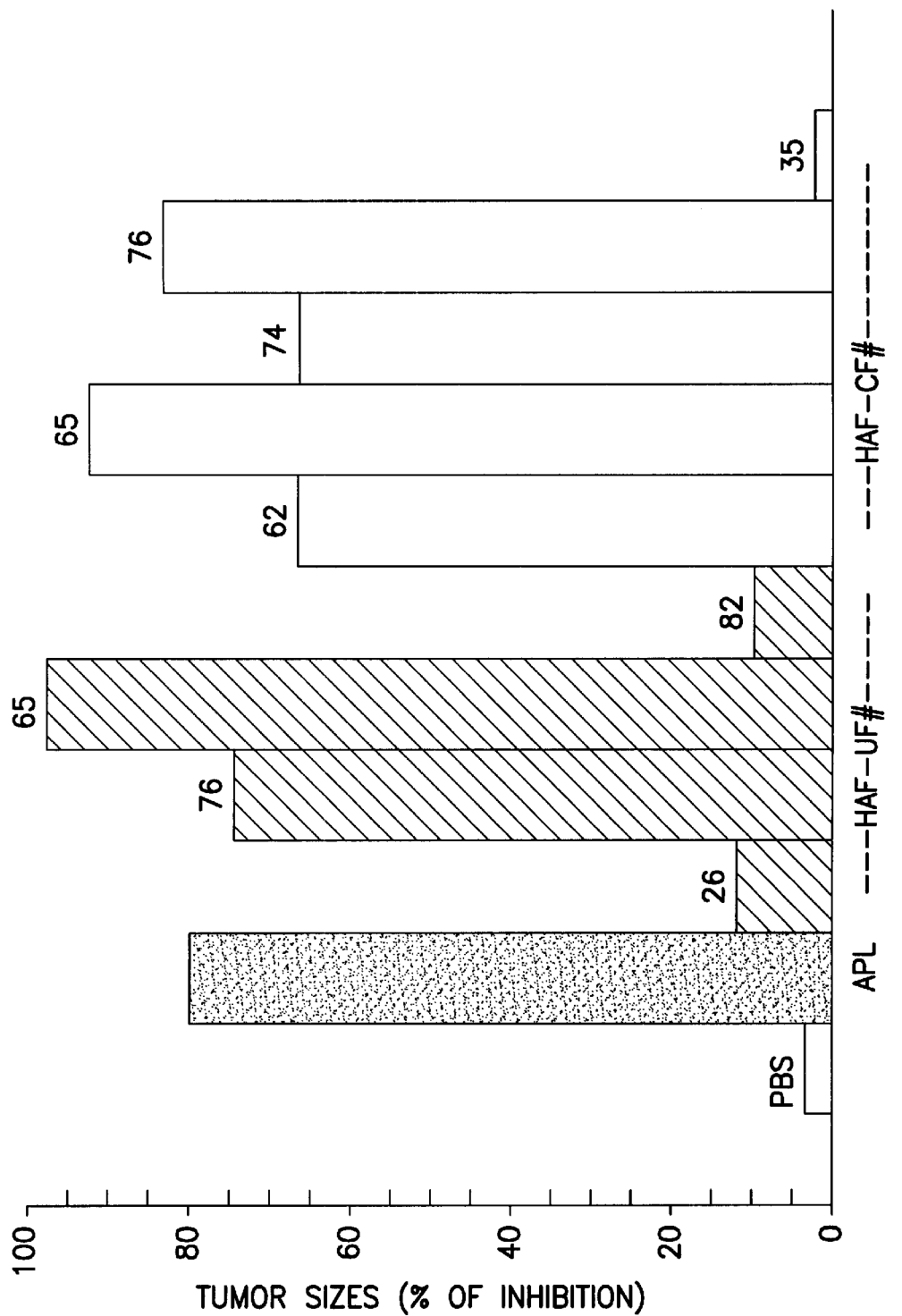

FIG. 13. Effect of treatment with hCG commercial preparation and early pregnancy urine fractions on KS tumors in mice. Results are plotted as percent inhibition of tumor size as compared to control tumors. The open bar represents mice treated with PBS alone; the solid bar with 100 IU per day of hCG APL™; diagonally striped bars with 200 µl per day of fractions 26, 76, 65, and 82 (as labeled on top of the bars) of the early pregnancy urine fractionation ("HAF-UF#"); and open bars with 200 µl per day of fractions 62, 65, 74, 76 and 35 (as labeled on top of the bars) of the hCG APL™ fractionation ("HAF-CF#").

Figure 14:
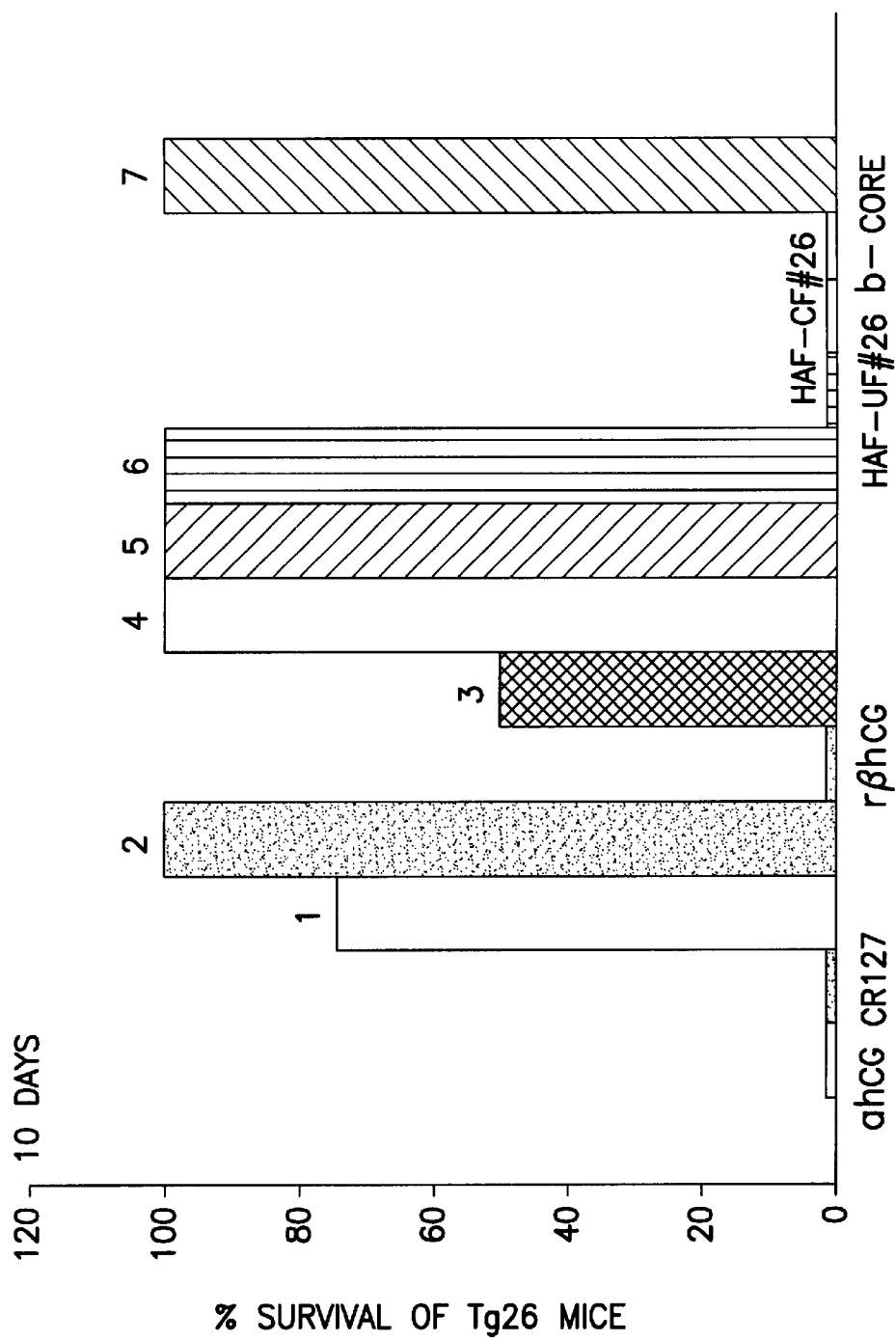

FIG. 14. Effect of hCG preparations, peptides and fractions on survival of HIV-1 transgenic mice. Data is plotted on a bar graph as "% Survival of Tg26 mice" 10 days after birth, each bar representing 4 mice. None of the untreated mice survived. Bar labeled "ahCG" represents mice treated with 200 µg per day native α-hCG; bar labeled "CR127", with 300 IU per day of the highly purified hCG preparation CR 127; bar 1, 200 µg per day native β-hCG; bar 2, 300 IU per day hCG APL™; bar labeled "rβhCG", with 200 µg per day recombinant β-hCG; bar 3, with 50 µg per day LH (leutinizing hormone); bar 4, with 200 µl per day fraction 65 of the hCG APL™ fractionation; bars 5 and 6, 200 µl per day fractions 65 and 76, respectively, of the early pregnancy urine fractionation; bars labeled "HAF-UF#26 and "HAF-CF#26", 200 µl per day fraction 26 from the early pregnancy urine and hCG APL™ fractionations, respectively; bar labelled "b-core", 50 µg per day β-hCG core peptide; and bar 7, with 300 µg per day circularized β-hCG peptide 44–57 (with cysteine substituted at position 44; SEQ ID NO:26).

Figure 15A:
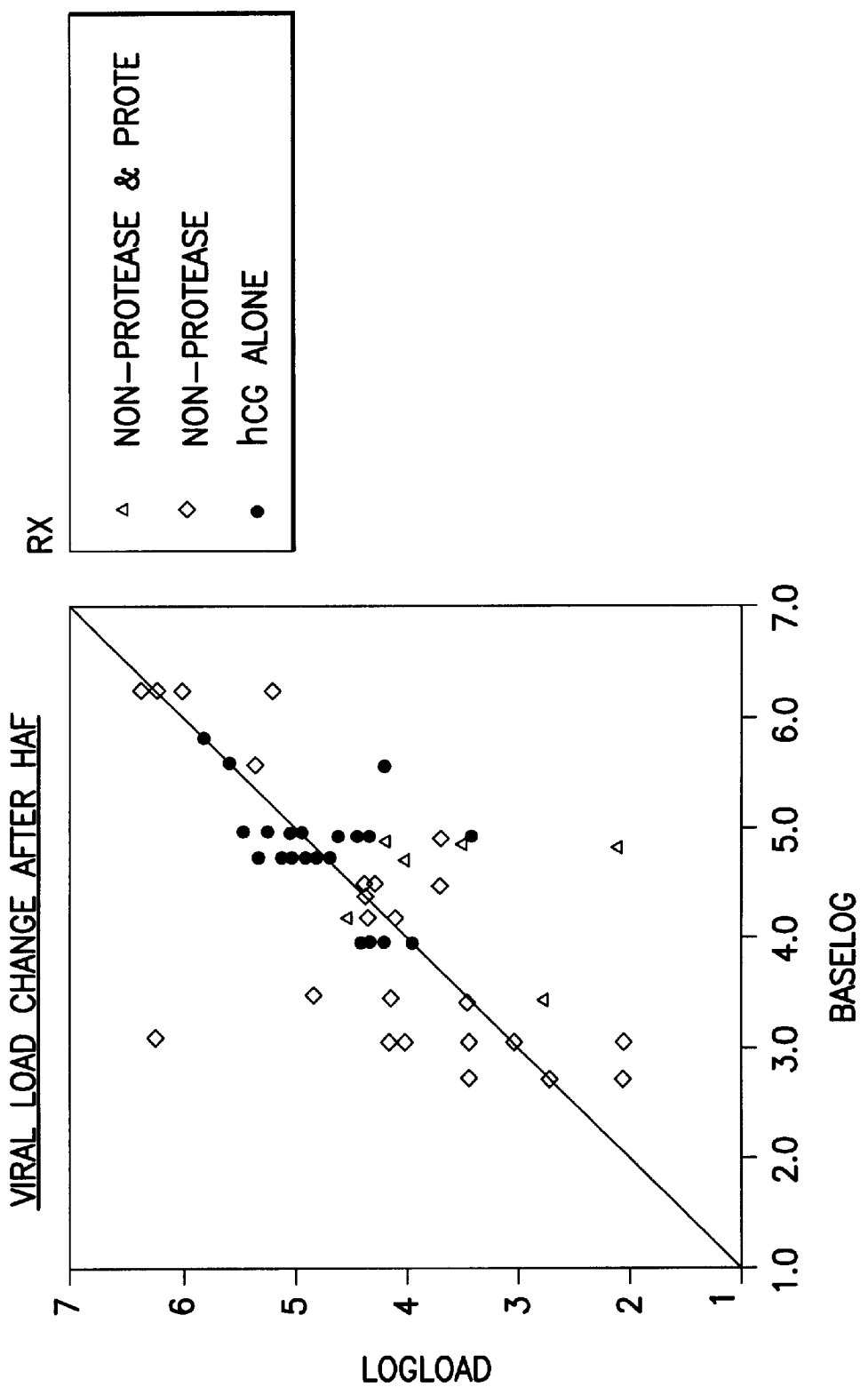
Figure 15B:
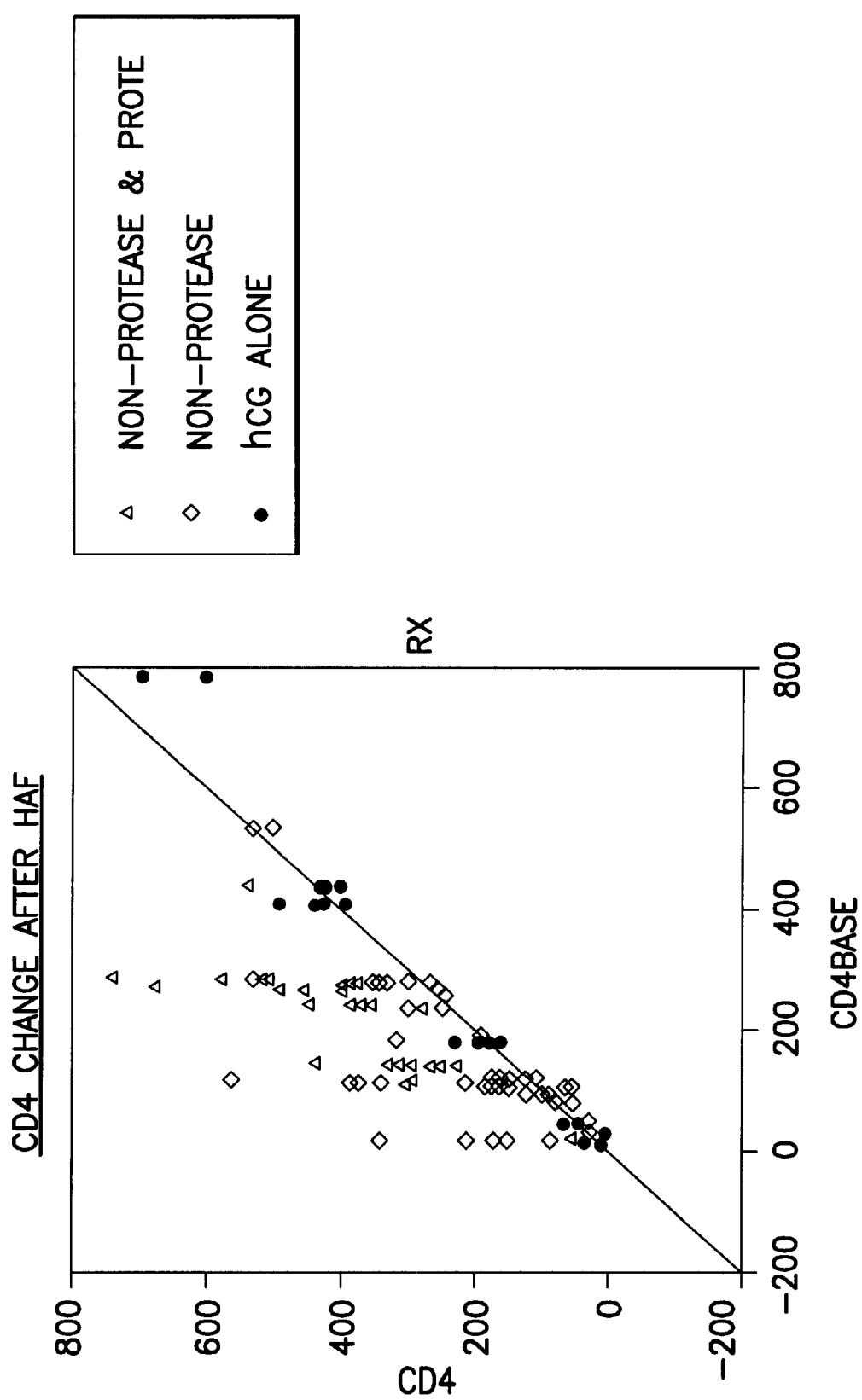
Figure 15C:
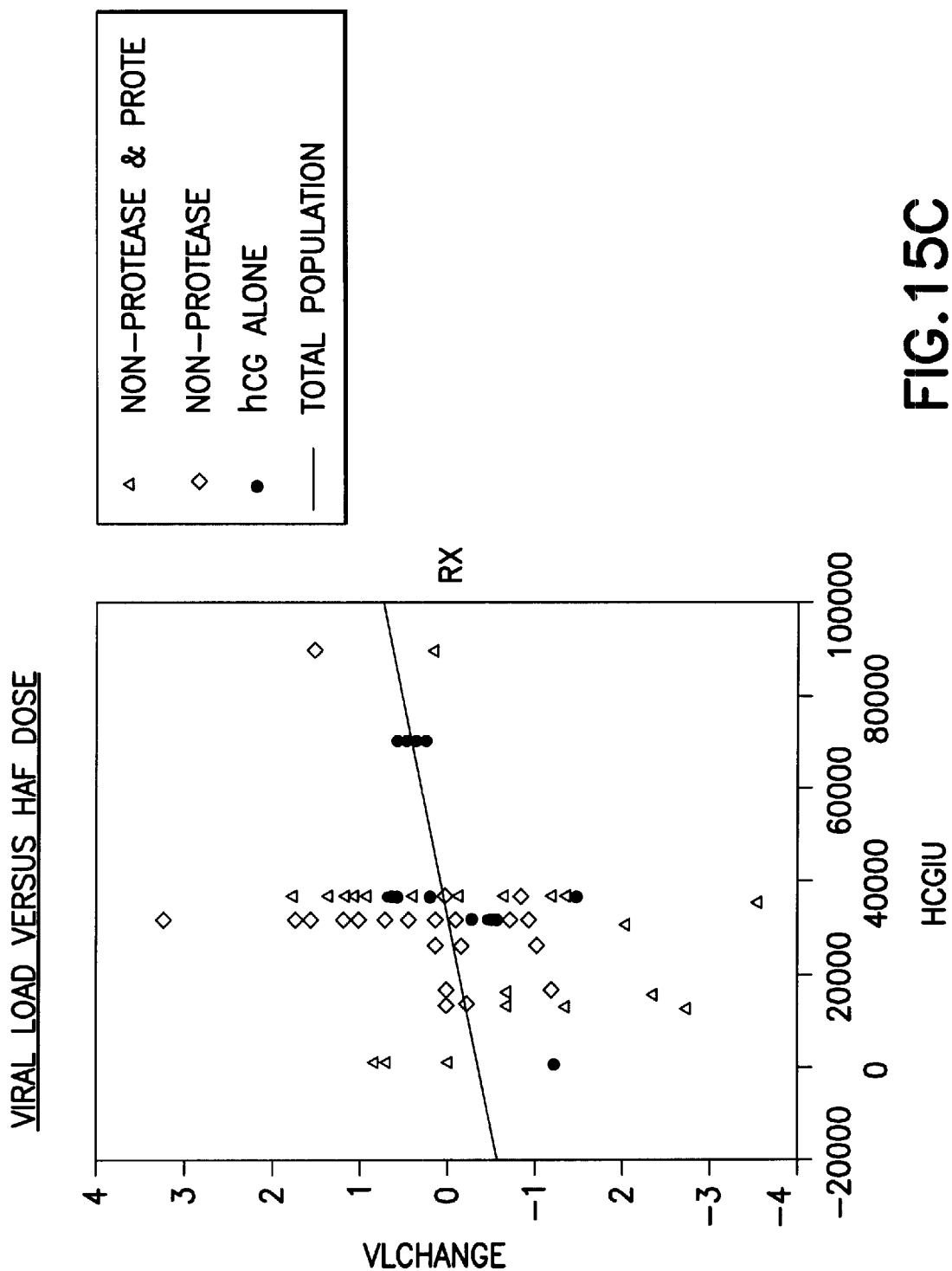

FIGS. 15A–C. Graphs of change in viral load and CD4$^+$ T cell levels with hCG therapy. (A) The change in viral load is plotted as the logarithm of viral load after therapy ("Logload") as a function of viral load before therapy ("Baselog"). (B) The change in CD4$^+$ T cell levels is plotted as CD4$^+$ T cell levels after therapy (in CD4$^+$ T cells/ml) ("CD4") as a function of CD4$^+$ T cell levels before therapy (in CD4$^+$ T cells/ml) ("CD4Base"). (C) Plot of linear regression analysis of the change in viral load ("vlchange") as a function of weekly dose of hCG in IU ("HCGIU"). For all three panels, data points for patients on hCG therapy as well as non-protease and protease inhibitors are represented by open triangles, those on hCG therapy and non-protease inhibitors by open diamonds, and those on hCG alone by solid circles.

Figure 16A:
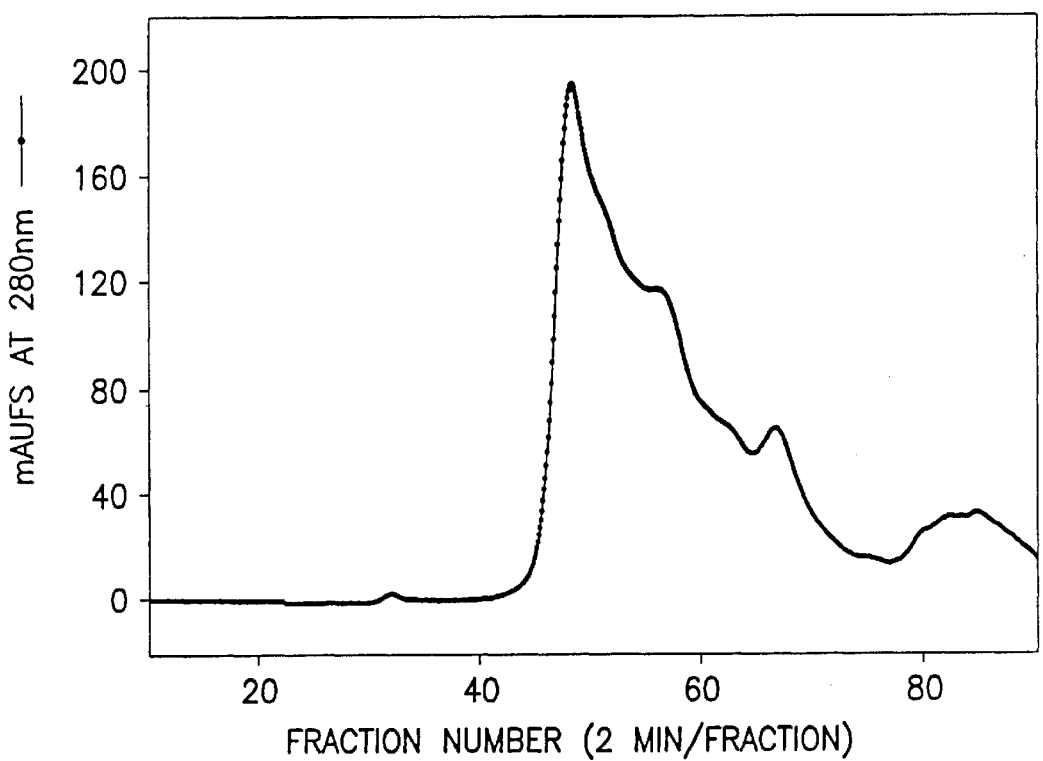
Figure 16B:
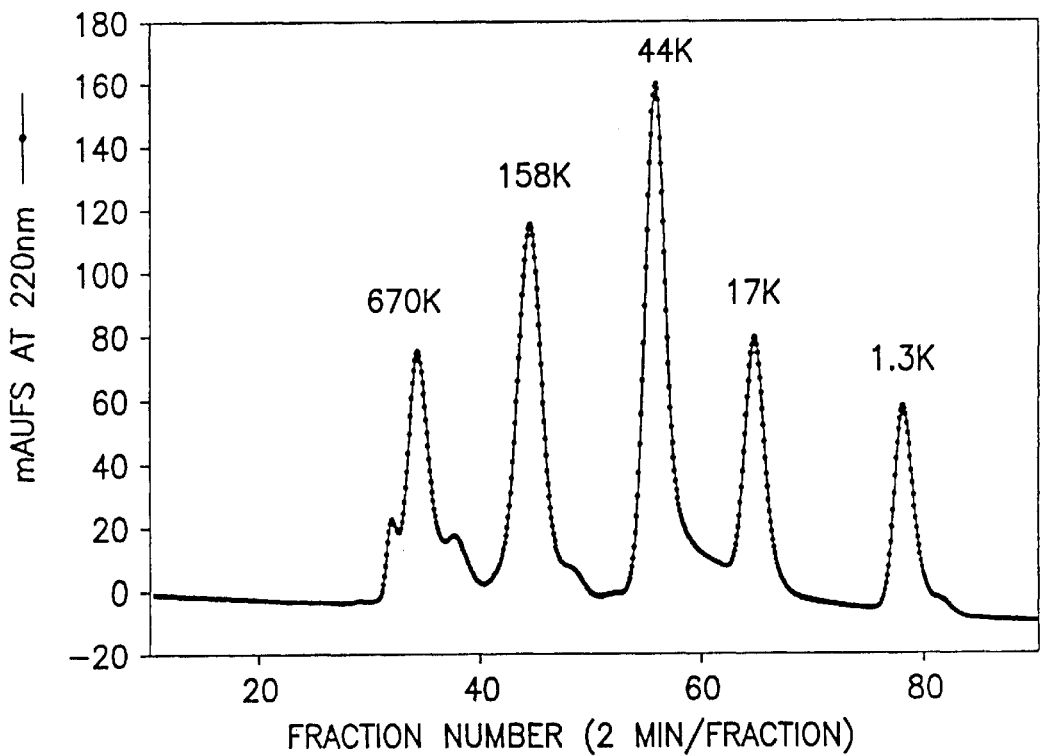
Figure 17B:
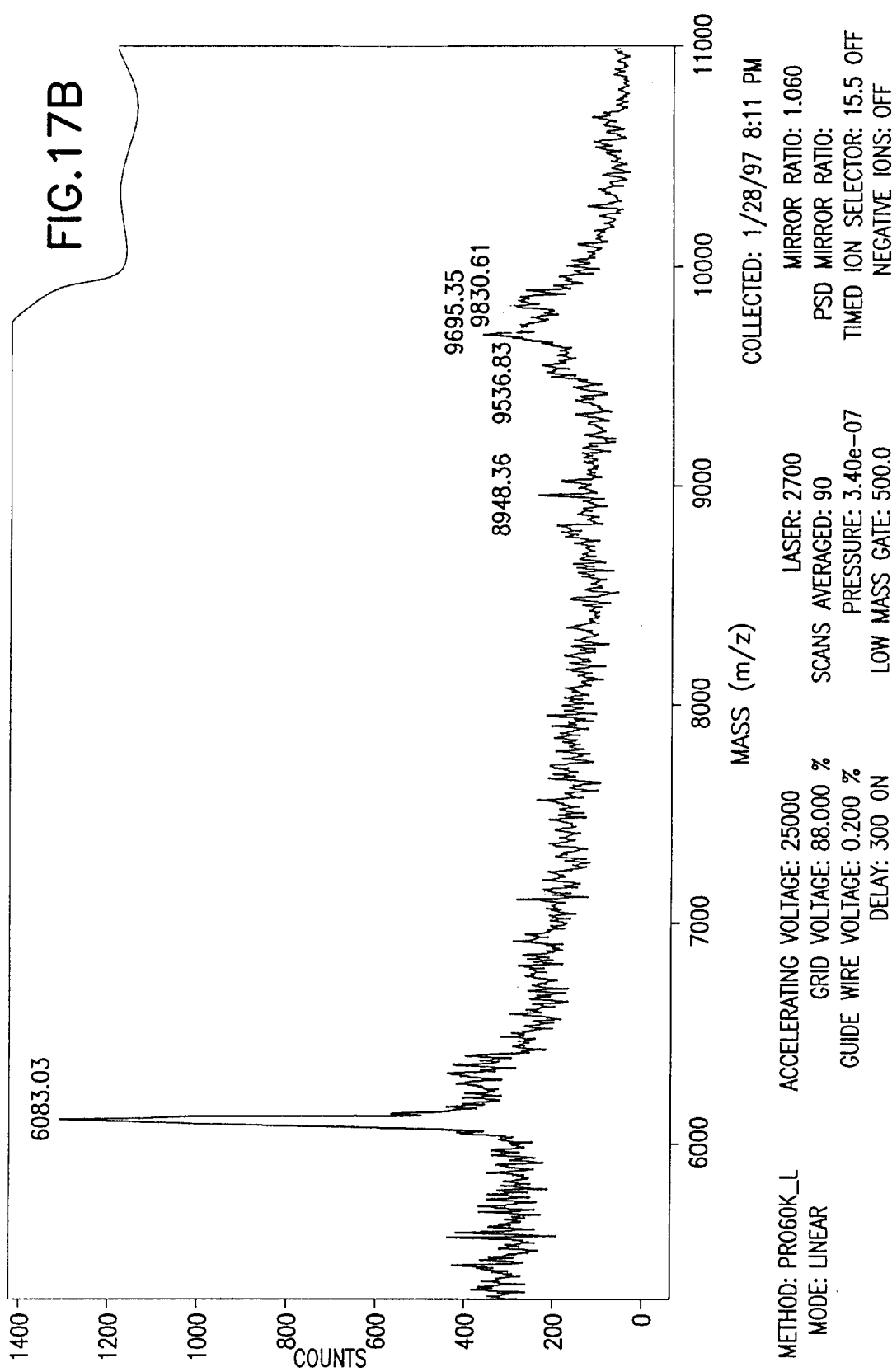

FIGS. 16A and B. (A) Plot of protein concentration (as mAUFS, milli absorbance units, at 280 nm) as a function of the fraction number of the hCG APL™ preparation Superdex 200 fractionation. (B) Plot of protein concentration (as mAUFS, milli absorbance units, at 280 nm) of molecular weight markers of 670 kD, 158 kD, 44 kD, 17 kD and 1.3 kD (as indicated above the plot) as a function of fraction number of a Superdex 200 column run under the same conditions as the fractionation plotted in panel A.

FIGS. 17A–E. Mass spectrometry profiles of fractions 61, 63, 64, 65, and 67 in panels A–E, respectively.

FIGS. 18 A–H. Visualization by confocal microscopy of apoptosis of prostate cancer cells treated with hCG and hCG related preparations for 48 hours and stained with both actin monoclonal antibody labeled with FITC and propidium iodine. Panel A shows a confocal micrograph of cultured prostate tumor cells untreated; Panel B, prostate tumor cells treated with 200 IU hCG APL™; Panel C, prostate tumor cells treated with 200 µg of the circularized β-hCG peptide of amino acids 44–57 with cysteine substituted at position 44 (SEQ ID NO:26); Panel D, prostate tumor cells treated with 100 µl of fraction number 64 of the early pregnancy urine; Panels E–H are controls treated with PBS alone.

Figure 19:
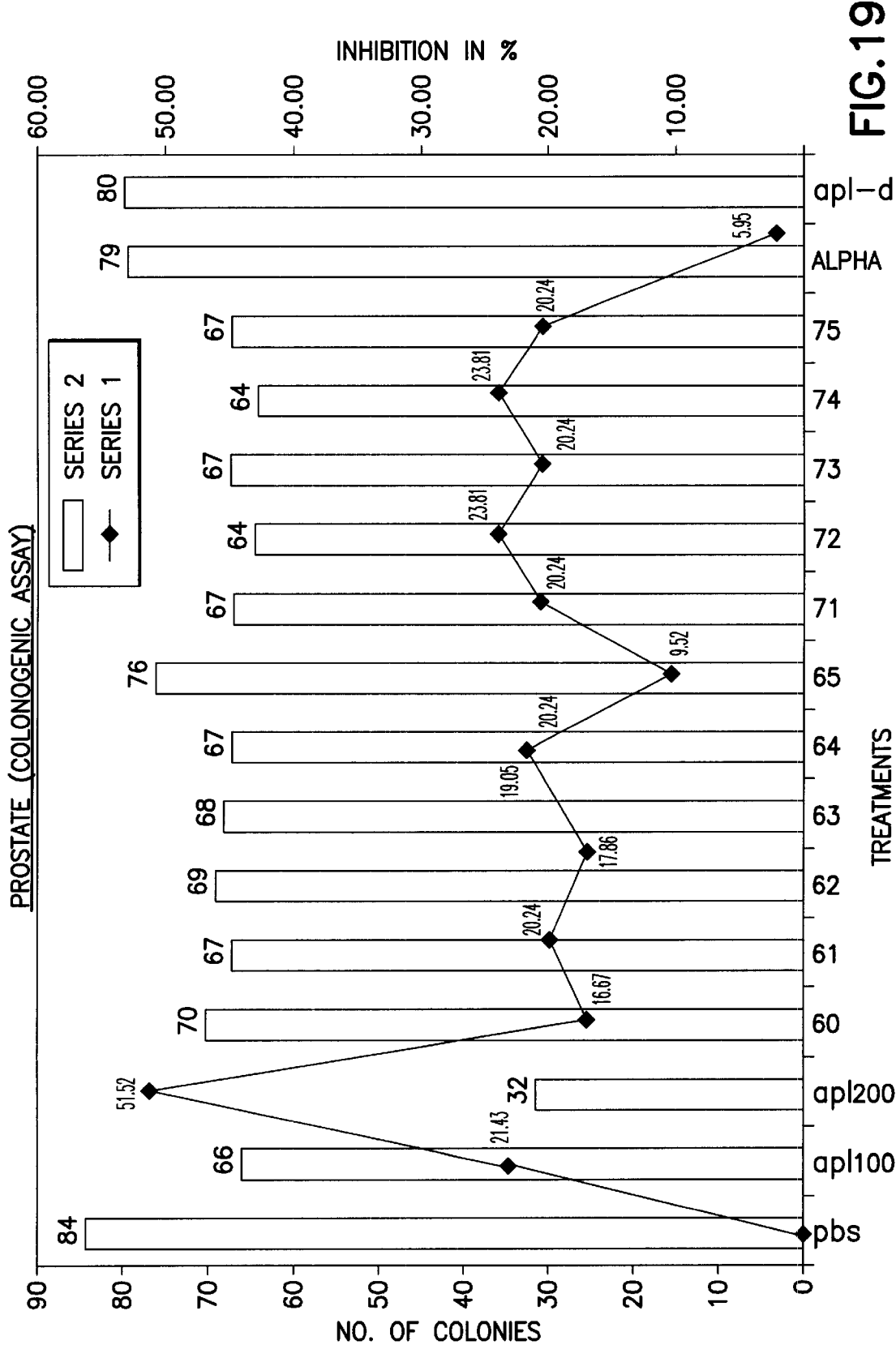

FIG. 19. Results of clonogenic assays on prostate tumor cells with hCG preparations and fractions of the hCG APL™ preparations. Results are plotted both as number of colonies (bars) and percent inhibition of colony formation (line with solid diamonds) for each test substance. "PBS" are cells treated with PBS alone; "apl100" and "apl200" are cells treated with 100 IU and 200 IU of the hCG APL™ preparation, respectively; the numbers are cells treated with those fraction numbers of the fractionation of the hCG APL™ preparation; "alpha" are those cells treated with a native α-hCG preparation; and "apl-d" are those cells treated with the hCG APL™ diluent alone (i.e., a control without hCG).

Figure 20A:
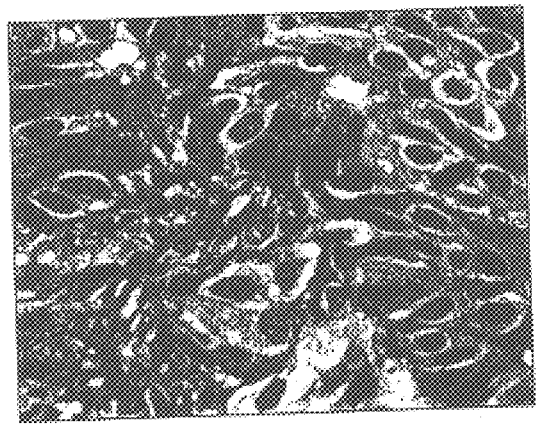
Figure 20B:
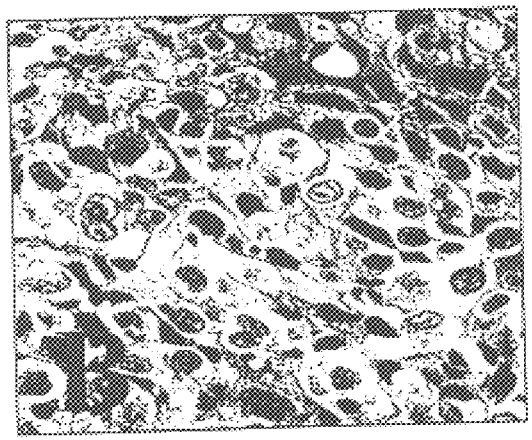
Figure 20C:
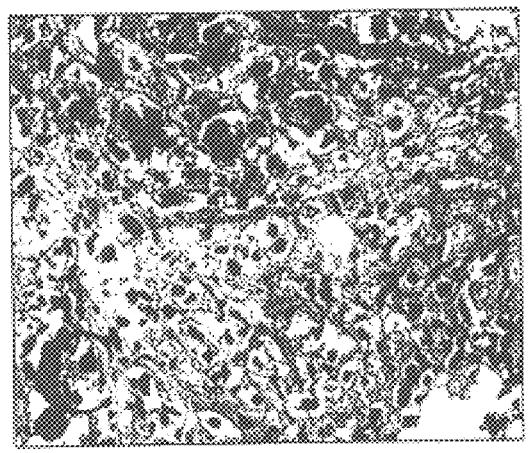

FIGS. 20A–C. Photographs showing the levels of apoptosis in tumor cells in nude mice in response to treatment with hCG preparations or β-hCG peptides. Panel A presents tumor cells from untreated mice. Panel B presents tumor cells from mice treated with 100 µg/day of the circularized β-hCG peptide of amino acids 44–57 with cysteine substituted at position 44 (SEQ ID NO:26). Panel C presents tumor cells from mice treated with 100 IU per day of hCG APL™.

Figure 21:
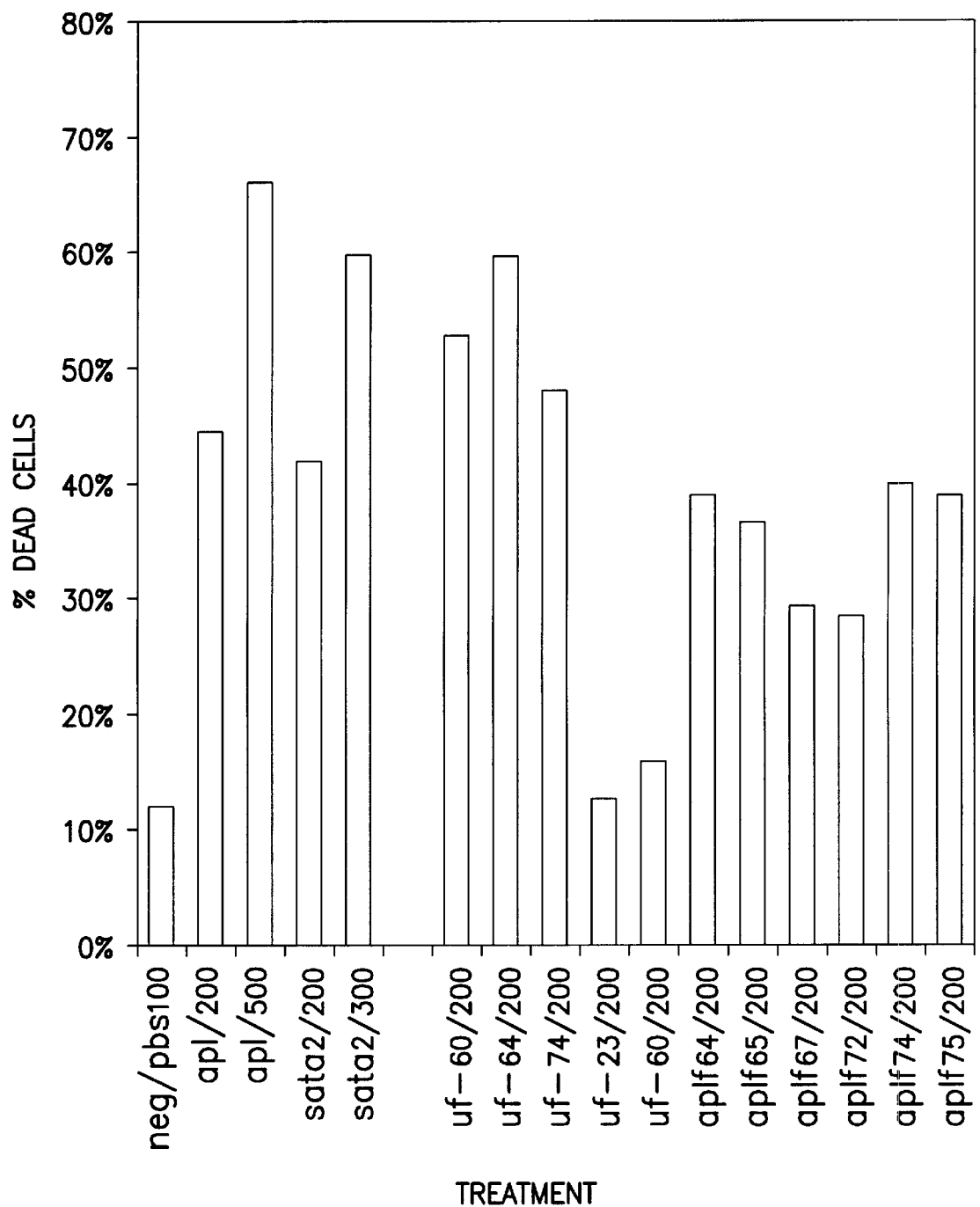

FIG. 21. Bar graph depicting the percent of dead lung cancer cells as measured by Trypan Blue assay in response to hCG preparations, hCG fractions, and β-hCG peptides. Treatments are indicated as follows: "neg/pbs100" is control treated with PBS alone; "apl/200" and "apl/500" were treated with 200 IU and 500 IU, respectively, of the hCG APL™ preparation; "sata2/200" and "sata2/300" were treated with 200 μg/ml and 300 μg/ml, respectively, of the circularized β-hCG peptide of amino acids 44–57, with cysteine substituted for position 44 (SEQ ID NO:26); "uf-60/200", "uf-64/200", "uf-74/200", "uf-23/200" and "uf-80/200" were treated with 200 μg/ml of the early pregnancy urine SUPERDEX™ 200 fractions 60, 64, 74, 23, and 80, respectively; "apl-64/200", "apl-65/200", "apl-67/200", "apl-72/200", "apl-74/200" and "apl-75/200" were treated with 200 μg/ml of the hCG APL™ SUPERDEX™ 200 fractions 64, 65, 67, 72, 74, and 75, respectively.

FIGS. 22A–C. Results of clonogenic assays on lung tumor cells with hCG preparations, fractions of hCG preparations, and β-hCG peptides. Results are plotted both as number of colonies (bars) and percent inhibition of colony formation (line with solid diamonds) for each test substance. (A) Treatments are indicated as follows: "100 ul PBS" is control treated with PBS alone; "APL100" and "APL200" were treated with 100 IU and 200 IU, respectively, of the hCG APL™ preparation; "SATA2100" and "SATA2200" were treated with 100 μg/ml and 200 μg/ml, respectively, of the circularized β-hCG peptide of amino acids 44–57, with cysteine substituted for position 44 (SEQ ID NO:26); "uf-60/200", "uf-64/200", and "uf-74/200" were treated with 200 μg/ml of the early pregnancy urine SUPERDEX™ 200 fractions 60, 64, and 74, respectively; "apl-60/200", "apl-64/200" and "apl-74/200" were treated with 200 μg/ml of the hCG APL™ SUPERDEX™ 200 fractions 60, 64, and 74, respectively. (B) Results after 6 days of treatment. Treatments are indicated as follows: "100 ul PBS" is control treated with PBS alone; "APL100" and was treated with 100 IU of the hCG APL™ preparation; "SATA100" was treated with 100 μg/ml of the β-hCG peptide of amino acids 45–57 (SEQ ID NO: 6); "SATA2100" was treated with 100 μg/ml of the circularized β-hCG peptide of amino acids 44–57, with cysteine substituted for position 44 (SEQ ID NO:26); and "SATAB100" was treated with 100 μg/ml of the fused β-hCG peptide 45–57::109–119 (SEQ ID NO:30). (C) Results after 5 days of treatment. Treatments are indicated as follows: "100 looul PBS" is control treated with PBS alone; "APL100" and "APL200" were treated with 100 IU and 200 IU, respectively, of the hCG APL™ preparation; "SATA2100" and "SATA2200" were treated with 100 μg/ml and 200 μg/ml, respectively, of the circularized β-hCG peptide of amino acids 44–57, with cysteine substituted for position 44 (SEQ ID NO:26); "uf-60/200", "uf-64/200", and "uf-74/200" were treated with 200 μg/ml of the early pregnancy urine SUPERDEX™ 200 fractions 60, 64, and 74, respectively; "apl-60/200", "apl-64/200" and "apl-74/200" were treated with 200 μg/ml of the hCG APL™ SUPERDEX™ 200 fractions 60, 64, and 74, respectively.

FIGS. 23 A–F. Visualization by confocal microscopy of apoptosis of lung cancer cells treated with hCG and hCG related preparations for 48 hours and stained with both actin monoclonal antibody labeled with FITC and propidium iodine. Panel A shows a confocal micrograph of cultured lung tumor cells untreated; Panel B, lung tumor cells treated with 200 IU hCG APL™; Panel C, lung tumor cells treated with 200 μg of the circularized β-hCG peptide of amino acids 44–57 with cysteine substituted at position 44 (SEQ ID NO:26); Panel D, lung tumor cells treated with fraction number 64 of the early pregnancy urine; Panels E–F are controls treated with PBS alone.

FIGS. 24 A–I. Visualization by confocal microscopy of apoptosis of kidney (renal) cancer cells treated with hCG APL™ preparation and stained with both actin monoclonal antibody labeled with FITC and propidium iodine. Panels A–C show a confocal micrograph of cultured kidney cancer cells treated with PBS alone; Panels D–F, cultured kidney cancer cells treated for 48 hours with 100 IU hCG APL™; Panels G–I, cultured kidney cancer cells treated with 300 IU hCG APL™ for 48 hours.

DETAILED DESCRIPTION OF THE INVENTION

The present invention relates to proteins (including peptides) containing a sequence of one or more portions of β-hCG (β-hCG peptides) that are effective at inhibiting HIV replication and/or infection in vitro or in vivo, decreasing viral load, and/or treating or preventing disorders associated with HIV infection. In specific embodiments, the invention provides an isolated protein, comprising, or alternatively, consisting of an amino acid sequence amino acid numbers 41–54, 45–54, 47–53 or 45–57 (SEQ ID NOS:3–6, respectively) of the β-hCG sequence depicted in FIG. 8 (a portion of SEQ ID NO:2), particularly to an isolated protein or peptide comprising an amino acid sequence consisting of amino acids 45–57 (SEQ ID NO:5) of FIG. 8 (a portion of SEQ ID NO:2). The invention also provides isolated proteins comprising or, alternatively, consisting of, the amino acid sequence of two or more portions (preferably non-naturally contiguous portions) of β-hCG, e.g., wherein such portions are linked at the C-termini and N-termini via peptide bond(s). Specifically, the invention provides isolated proteins having an amino acid sequence of β-hCG amino acids 45–57 (SEQ ID NO:6) linked at the C-terminus via a peptide bond to the N-terminus of amino acids β-hCG 109–119 (SEQ ID NO:7) or linked at the N-terminus via a peptide bond to the C-terminus of β-hCG amino acids 110–119 (SEQ ID NO:27); or an isolated protein of β-hCG amino acids 47–57 (SEQ ID NO:28) linked at the C-terminus via a peptide bond to the N-terminus of amino acids β-hCG 108–119 (SEQ ID NO:29) of the β-hCG sequence depicted in FIG. 8 (portions of SEQ ID NO:2), i.e., the fused peptides denoted 45–57::109–119, 110–119::45–57, or 47–57::108–119 (SEQ ID NOS:30–32, respectively).

The present invention also relates to certain fractions (i.e. components of a source of native hCG or native β-hCG isolated away from other components in the source of native hCG or native β-hCG by a separation technique known in the art), particularly fractions from gel filtration sizing chromatography, of a source of native hCG or β-hCG, such as commercial preparations of hCG and human (preferably early, i.e. first trimester) pregnancy urine, that have anti-HIV and/or anti-KS activity. Native hCG or native β-hCG refers to naturally occurring hCG or β-hCG, i.e. not recombinantly produced.

The present invention further relates to therapeutic methods and compositions for treatment and prevention of disorders associated with HIV infection based on hCG and β-hCG preparations, therapeutically and prophylactically effective fractions of a source of native hCG or native β-hCG, and therapeutically and prophylactically effective β-hCG peptides. The invention provides for treatment of HIV infection by administration of a therapeutic compound of the invention. The therapeutic compounds of the invention include: hCG, β-hCG, therapeutically and prophylactically effective fractions of a source of native hCG or native β-hCG, therapeutically and prophylactically effective β-hCG peptides, related derivatives and analogs of hCG, β-hCG or β-hCG peptides, and nucleic acids encoding β-hCG and β-hCG peptides, and analogs and derivatives thereof. β-hCG peptides which are effective for treatment and prevention of HIV infection can be identified by in vitro and in vivo assays such as those described herein.

In a preferred embodiment, a therapeutic composition of the invention comprises a β-HCG peptide, the amino acid sequence of which consists of amino acid numbers 41–53, 42–53, 43–53, 44–53, 44–57, 45–53, 46–53, 45–54, 45–55, 45–56, 45–58, 47–54, 47–55, 47–56, 47–58, 48–145, 58–145, 109–145, 7–40, 46–65, or 48–56 (SEQ ID NOS:8–25 or 33–35, respectively) of FIG. 8 (a portion of SEQ ID NO:2), particularly a β-hCG peptide which consists of amino acid numbers 41–54, 45–54 or 109–119 (SEQ ID NOS:3, 4, or 7, respectively), most preferably of a β-hCG peptide which consists of amino acid numbers 47–53 (SEQ ID NO:5) or 45–57 (SEQ ID NO:6).

In another preferred embodiment, a therapeutic composition of the invention comprises a fusion protein comprising two or more β-hCG sequences (either as non-contiguous or contiguous sequences), e.g. having an amino acid sequence of one β-hCG peptide linked via a peptide bond to another β-hCG peptide, in particular a protein, the amino acid sequence of which consists of amino acids 45–57 (SEQ ID NO:6) linked at the C-terminus via a peptide bond to the N-terminus of amino acids 109–119 (SEQ ID NO:7) or linked at the N-terminus via a peptide bond to the C-terminus of amino acids 110–119 (SEQ ID NO:27); or an isolated protein of amino acids 47–57 (SEQ ID NO:28) linked at the C-terminus via a peptide bond to the N-terminus of amino acids 108–119 (SEQ ID NO:29) of the β-hCG sequence depicted in FIG. 8 (portions of SEQ ID NO:2), i.e., the peptides denoted 45–57::109–119, 110–119::45–57, or 47–57::108–119 (SEQ ID NOS:30–32, respectively).

In another preferred embodiments, the therapeutic comprises a β-hCG peptide, the amino acid sequence of which consists of circularized (via a disulfide bond between its amino- and carboxy-terminal cysteines) 44–57 (SEQ ID NO:26) with the valine at position 44 substituted with cysteine ((Val44Cys) 45–57 circularized) (depicted in FIG. 9B), the circularized (via a disulfide bond between its amino- and carboxy-terminal cysteines) fused peptide of amino acids 110–119 (SEQ ID NO:27) linked at the C-terminus by a peptide bond to the N-terminus of amino acids 45–57 (SEQ ID NO:6), or the peptide 45–57 (SEQ ID NO:6) where the amino acid residues at positions 47 and 51 are substituted by a branch, where the branches are made up of diaminobutyric acid peptide bonded to a proline residue (depicted in FIG. 9A). The amino acid sequence of β-hCG is depicted in FIG. 8 (SEQ ID NO:2).

In yet another embodiment, the therapeutic comprises fractions, preferably fractions of a source of hCG or β-hCG, such as commercial hCG preparations and human early pregnancy urine, of material eluting from a gel filtration column with apparent molecular weights of approximately 40 kD, 15 kD or 2–3 kD as determined based on in which fractions native hCG dimer (77 kD) and β-hCG core protein (10 kD) elute.

The present invention further relates to therapeutic methods and compositions for treatment and prevention of wasting syndromes based on hCG and β-hCG preparations, therapeutically and prophylactically effective fractions of a source of hCG or β-hCG, and therapeutically and prophylactically effective β-hCG peptides. The invention provides for treatment of wasting syndrome by administration of a therapeutic compound (termed herein "Therapeutic") of the invention. Such Therapeutics of the invention include but are not limited to: hCG, β-hCG, therapeutically and prophylactically effective fractions of a source of native hCG or native β-hCG, therapeutically and prophylactically effective β-hCG proteins (i.e., those peptides which prevent or treat wasting syndrome), related derivatives and analogs of hCG, β-hCG or β-hCG peptides, and nucleic acids encoding β-hCG and β-hCG peptides, and analogs and derivatives thereof. β-hCG peptides which are effective for treatment and prevention of wasting syndromes can be identified by in vitro and in vivo assays such as those described in herein.

The present invention also relates to therapeutic methods and compositions for treatment and prevention of diseases and disorders in which increased amounts of hematopoietic cells are desirable (e.g., disorders associated with reduced numbers of one or more hematopoietic cell types) by administration of hCG, β-hCG and therapeutically or prophylactically effective proteins (e.g., peptides) having a sequence of one or more portions of β-hCG (β-hCG peptides), and derivatives and analogs thereof, and therapeutically or prophylactically effective fractions of a source of native hCG or native β-hCG (i.e. from a naturally occurring source and not hCG or β-hCG which has been recombinantly produced). The invention provides for treatment and prevention of hematopoietic cell deficiencies by administration either of a therapeutic compound of the invention or of hematopoietic cells, the numbers of which have been increased in vitro by contact with a therapeutic compound of the invention. The invention also provides methods for expansion of hematopoietic cells in vitro by contact with a Therapeutic of the invention. The therapeutic compounds of the invention include, but are not limited to: hCG, β-hCG, therapeutically and prophylactically effective fractions of a source of native hCG or native β-hCG, and therapeutically and prophylactically effective β-hCG peptides, i.e., those fractions and peptides which prevent or treat HIV infection (e.g., as demonstrated in in vitro and in vivo assays described infra), and derivatives and analogs thereof, as well as nucleic acids encoding hCG, β-hCG and therapeutically and prophylactically effective β-hCG peptides and derivatives and analogs thereof (e.g., for use in gene therapy).

In a preferred embodiment, a therapeutic composition of the invention comprises a β-hCG peptide, the amino acid sequence of which consists of amino acid numbers 41–53, 42–53, 43–53, 44–53, 44–57, 45–53, 46–53, 45–54, 45–55, 45–56, 45–58, 47–54, 47–55, 47–56, 47–58, 48–145, 58–145, 109–145, 7–40, 46–65, or 48–56 (SEQ ID NOS:8–25 or 33–35, respectively) of FIG. 8 (a portion of SEQ ID NO:2), particularly a β-hCG peptide which consists of amino acid numbers 41–54, 45–54 or 109–119 (SEQ ID NOS:3, 4, or 7, respectively), most preferably of a β-hCG peptide which consists of amino acids 47–53 (SEQ ID NO:5) or 45–57 (SEQ ID NO:6).

In other preferred embodiments, the therapeutic comprises a β-hCG peptide, the amino acid sequence of which consists of circularized (via a disulfide bond between its amino- and carboxy-terminal cysteines) 44–57 (SEQ ID NO:26) with the valine at position 44 substituted with cysteine ((Val44Cys) 45–57 circularized) (depicted in FIG. 9B), 45–57 (SEQ ID NO:6) where the amino acid residues at positions 47 and 51 are substituted by a branch, where the branches are made up of diaminobutyric acid peptide bonded to a proline residue (depicted in FIG. 9A).

In another embodiment, a protein is used which contains the amino acid sequence of two or more peptides of different portions of the β-hCG sequence (either as non-contiguous or contiguous sequenced), e.g., in which the N-terminus of one portion is linked to the C-terminus of another portion by peptide bond(s). In a specific embodiment, a protein is used, the amino acid sequence of which consists of amino acids 45–57 (SEQ ID NO:6) linked at the C-terminus via a peptide bond to the N-terminus of amino acids 109–119 (SEQ ID NO:7) or linked at the N-terminus via a peptide bond to the C-terminus of amino acids 110–119 (SEQ ID NO:27); or a protein is used that has an amino acid sequence of amino acids 47–57 (SEQ ID NO:28) linked at the C-terminus via a peptide bond to the N-terminus of amino acids 108–119 (SEQ ID NO:29) of the β-hCG sequence; i.e., the fused peptides represented as 45–57::109–119, 110–119::45–57, or 47–57::108–119 (SEQ ID NOS:30–32, respectively). In yet another embodiment a protein is used which is a cyclic, fused peptide, particularly a cyclic, fused peptide having a sequence consisting of β-hCG amino acids 110–119 (SEQ ID NO:27) linked at the C-terminus via a peptide bond to the N-terminus of amino acids 45–57 (SEQ ID NO:6) and being circularized by a disulfide bond between the terminal cysteines at positions 110 and 57.

In another embodiment, a protein is used that (a) comprises a β-hCG amino acid sequence consisting of amino acid numbers 41–54, 45–54, 47–53, 45–57, 109–119, 41–53, 42–53, 43–53, 44–53, 44–57, 45–53, 46–53, 45–54, 45–55, 45–56, 45–58, 47–54, 47–55, 47–56, 47–58, 48–145, 58–145, 109–119, 109–145, 7–40, 46–65 or 48–56 (SEQ ID NOS:3–25 or 33–35, respectively) as depicted in FIG. 8 (a portion of SEQ ID NO:2) and (b) lacks β-hCG amino acids contiguous to said sequence. The amino acid sequence of β-hCG is depicted in FIG. 8 (SEQ ID NO:2).

The present invention further relates to therapeutic methods and compositions for treatment and prevention of cancers based on hCG and β-hCG preparations, therapeutically and prophylactically effective fractions of a source of hCG or β-hCG, and therapeutically and prophylactically effective β-hCG peptides. The invention provides for treatment of cancer by administration of a therapeutic compound (termed herein "Therapeutic") of the invention. Such Therapeutics of the invention include but are not limited to: hCG, β-hCG, therapeutically and prophylactically effective fractions of a source of native hCG or native β-hCG, therapeutically and prophylactically effective β-hCG proteins (i.e., those peptides which prevent or treat cancer), related derivatives and analogs of hCG, β-hCG or β-hCG peptides, and nucleic acids encoding β-hCG and β-hCG peptides, and analogs and derivatives thereof. β-hCG peptides and fractions of a source of native hCG or β-hCG which are effective for treatment and prevention of cancer can be identified by in vitro and in vivo assays such as those described in herein.

In a preferred embodiment, a therapeutic composition of the invention comprises a β-hCG peptide, the amino acid sequence of which consists of amino acid numbers 41–53, 42–53, 43–53, 44–53, 44–57, 45–53, 46–53, 45–54, 45–55, 45–56, 45–58, 47–54, 47–55, 47–56, 47–58, 48–145, 58–145, 109–145, 7–40, 46–65, or 48–56 (SEQ ID NOS:8–25 or 33–35, respectively) of FIG. 8 (a portion of SEQ ID NO:2), particularly a β-hCG peptide which consists of amino acid numbers 41–54, 45–54 or 109–119 (SEQ ID NOS:3, 4, or 7, respectively), most preferably of a β-hCG peptide which consists of amino acid numbers 47–53 (SEQ ID NO:5) or 45–57 (SEQ ID NO:6). In another preferred embodiment, a therapeutic composition of the invention comprises a fusion protein comprising more than one β-hCG sequence (preferably non-contiguous sequences), e.g. having an amino acid sequence of one β-hCG peptide linked via a peptide bond to another β-hCG peptide, in particular a protein, the amino acid sequence of which consists of amino acids 45–57 (SEQ ID NO:6) linked at the C-terminus via a peptide bond to the N-terminus of amino acids 109–119 (SEQ ID NO:7) or linked at the N-terminus via a peptide bond to the C-terminus of amino acids 110–119 (SEQ ID NO:27); or an isolated protein of amino acids 47–57 (SEQ ID NO:28) linked at the C-terminus via a peptide bond to the N-terminus of amino acids 108–119 (SEQ ID NO:29) of the β-hCG sequence depicted in FIG. 8 (portions of SEQ ID NO:2), i.e., the peptides denoted 45–57::109–119, 110–119::45–57, or 47–57::108–119 (SEQ ID NOS:30–32, respectively).

In other preferred embodiments, the therapeutic comprises a β-hCG peptide, the amino acid sequence of which consists of circularized (via a disulfide bond between its amino- and carboxy-terminal cysteines) 44–57 (SEQ ID NO:26) with the valine at position 44 substituted with cysteine ((Val44Cys) 45–57 circularized) (depicted in FIG. 9B), the circularized (via a disulfide bond between its amino- and carboxy-terminal cysteines) fused peptide of amino acids 110–119 (SEQ ID NO:27) linked at the C-terminus by a peptide bond to the N-terminus of amino acids 45–57 (SEQ ID NO:6), or the peptide 45–57 (SEQ ID NO:6) where the amino acid residues at positions 47 and 51 are substituted by a branch, where the branches are made up of diaminobutyric acid peptide bonded to a proline residue (depicted in FIG. 9A). The amino acid sequence of β-hCG is depicted in FIG. 8 (SEQ ID NO:2).

In yet another embodiment, the therapeutic comprises fractions, preferably gel filtration fractions of a source of native hCG or native β-hCG (i.e. from or derived from a naturally occurring source of hCG or β-hCG and not recombinantly produced hCG or β-hCG), such as commercial hCG preparations and human pregnancy (preferably early, i.e. first trimester) urine, of material eluting from a SUPERDEX™ 200 (Pharmacia) gel filtration column with apparent molecular weights of approximately 40 kD, 15 kD or 2–3 kD as determined based on in which fractions native hCG dimer (77 kD) and β-hCG core (10 kD) elute.

For clarity of disclosure, and not by way of limitation, the detailed description of the invention is divided into the subsections which follow.

β-hCG Peptides and Derivatives Thereof

The invention provides isolated proteins (e.g., peptides), the amino acid sequences of which consist of one or more portions of the β-hCG sequence (β-hCG peptides), and derivatives thereof, which are effective for treatment or prevention of HIV infection and resulting disorders. In various specific embodiments, the portions of the β-hCG sequence are at least 3, 5, 10, 20, or 30 amino acids. Effectiveness of the peptides of the invention for treatment or prevention of HIV infection can be determined by any of the methods disclosed herein or by any method known in the art. In a specific embodiment, the peptides inhibit HIV infection or replication. In a preferred embodiment, the invention relates to proteins, the amino acid sequences of which consist of amino acid numbers 41–54, 45–54, 47–53 and 45–57 (SEQ ID NOS:3–6) of the β-hCG sequence depicted in FIG. 8 (a portion of SEQ ID NO:2). In other embodiments, proteins, the amino acid sequences of which consist of amino acid numbers 109–119, 41–53, 42–53, 43–53, 44–53, 44–57, 45–53, 46–53, 45–54, 45–55, 45–56, 45–58, 47–54, 47–55, 47–56, 47–58, 48–145; 58–145, 109–145, 7–40, 46–65, and 48–56 (SEQ ID NOS:7–25 and 33–35, respectively) of FIG. 8 (a portion of SEQ ID NO:2) are also provided.

In another embodiment, the invention provides proteins, the amino acid sequences of which consist of two or more at least 5, 7 or 10 amino acid, non-naturally contiguous portions of the β-hCG sequence (FIG. 8 (SEQ ID NO:2))

linked by peptide bonds between the N-terminus of one portion and the C-terminus of another portion. Specifically, proteins, the amino acid sequences of which consist of amino acids 45–57 (SEQ ID NO:6) linked at the C-terminus via a peptide bond to the N-terminus of a peptide of amino acids 109–119 (SEQ ID NO:7) or linked at the N-terminus via a peptide bond to the C-terminus of amino acids 110–119 (SEQ ID NO:27); or an isolated protein of amino acids 47–57 (SEQ ID NO:28) linked at the C-terminus via a peptide bond to the N-terminus of amino acids 108–119 (SEQ ID NO:29) of the β-hCG sequence depicted in FIG. 8 (portions of SEQ ID NO:2), i.e., the fused peptides denoted as 45–57::109–119, 110–119::45–57, or 47–57::108–119 (SEQ ID NOS:30–32, respectively). Derivatives of the foregoing fusion proteins are also provided (e.g., branched, cyclized, N- or C-terminal chemically modified, etc.). In another embodiment, fusion proteins comprising two or more such portions of the β-hCG sequence are provided; such portions may or may not be contiguous to one another (i.e., an intervening sequence may be present). Molecules comprising such portions linked by hydrocarbon linkages are also provided. In another embodiment, the peptides of the invention (i) have an amino acid sequence consisting of no more than 8 peptides of the β-hCG sequence (FIG. 8 (SEQ ID NO:2)) and (ii) comprise amino acid numbers 47–53 (SEQ ID NO:5) of β-hCG (FIG. 8 (SEQ ID NO:2)).

In another embodiment, the invention provides an isolated protein which protein (a) comprises one or more portions of the amino acid sequence of β-hCG, a peptide consisting of said portion(s) being effective to inhibit HIV infection or replication; and (b) lacks β-hCG amino acids contiguous to said portion(s). In a specific embodiment, the invention provides an isolated protein (a) comprising a β-hCG amino acid sequence consisting of amino acid numbers 41–54, 45–54, 47–53, 45–57, 41–53, 42–53, 43–53, 44–53, 44–57, 45–53, 46–53, 45–54, 45–55, 45–56, 45–58, 47–54, 47–56, 47–58, 58–145, 7–40, 46–65 or 48–56 (SEQ ID NOS:3–6, 8–19, 21, 22, 24, or 33–35, respectively) as depicted in FIG. 8 (a portion of SEQ ID NO:2); and (b) lacking β-hCG amino acids contiguous to said sequence. Peptides containing the above sequences in which only conservative substitutions have been made are also provided by the present invention, as but one example of peptide derivatives within the scope of the invention. Analogs of the above-mentioned proteins and peptides which have one or more amino acid substitutions forming a branched peptide (e.g., by substitution with an amino acid or amino acid analog having a free amino- or carboxy-side chain that forms a peptide bond with a sequence of one or more amino acids, including but not limited to prolines) or allowing circularization of the peptide (e.g., by substitution with a cysteine, or insertion of a cysteine at the amino- or carboxy-terminus or internally), to provide a sulfhydryl group for disulfide bond formation, are also provided.

In specific embodiments, peptides of less than 50, or less than 25, amino acids are provided.

The invention also relates to derivatives, modifications and analogs of β-hCG peptides. In one embodiment, β-hCG peptide derivatives can be made by altering the β-hCG peptide sequence by substitutions, additions or deletions that provide for therapeutically effective molecules. Thus, the β-hCG peptide derivatives include peptides containing, as a primary amino acid sequence, all or part of the particular β-hCG amino acid sequence including altered sequences in which functionally equivalent amino acid residues are substituted for residues within the sequence resulting in a peptide which is functionally active. For example, one or more amino acid residues within the sequence can be substituted by another amino acid of a similar polarity which acts as a functional equivalent, resulting in a silent alteration.

Conservative substitutions for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Such β-hCG peptide derivatives can be made either by chemical peptide synthesis or by recombinant production from nucleic acid encoding the β-hCG peptide which nucleic acid has been mutated. Any technique for mutagenesis known in the art can be used, including but not limited to, chemical mutagenesis, in vitro site-directed mutagenesis (Hutchinson, C., et al., 1978, *J. Biol. Chem* 253:6551), use of TAB® linkers (Pharmacia), etc.

In addition, β-hCG peptides and analogs and derivatives of β-hCG peptides can be chemically synthesized (see, e.g., Merrifield, 1963, *J. Amer. Chem. Soc.* 85:2149–2156). For example, peptides can be synthesized by solid phase techniques, cleaved from the resin, and purified by preparative high performance liquid chromatography (e.g., see Creighton, 1983, Proteins, Structures and Molecular Principles, W. H. Freeman and Co., N.Y., pp. 50–60). β-hCG peptides can also be synthesized by use of a peptide synthesizer. The composition of the synthetic peptides may be confirmed by amino acid analysis or sequencing (e.g., the Edman degradation procedure; see Creighton, 1983, Proteins, Structures and Molecular Principles, W. H. Freeman and Co., N.Y., pp. 34–49). Furthermore, if desired, nonclassical amino acids or chemical amino acid analogs can be introduced as a substitution or addition into the β-hCG peptide. Non-classical amino acids include but are not limited to the D-isomers of the common amino acids, 2,4-diaminobutyric acid, α-amino isobutyric acid, 4-aminobutyric acid, Abu, 2-amino butyric acid, γ-Abu, ε-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, β-alanine, fluoro-amino acids, designer amino acids such as β-methyl amino acids, Cα-methyl amino acids, Nα-methyl amino acids, and amino acid analogs in general. Furthermore, the amino acid can be D (dextrorotary) or L (levorotary).

By way of example but not by way of limitation, peptides of the invention can be chemically synthesized and purified as follows: Peptides can be synthesized by employing the N-α-9-fluorenylmethyloxycarbonyl or Fmoc solid phase peptide synthesis chemistry using a Rainin Symphony Multiplex Peptide Synthesizer. The standard cycle used for coupling of an amino acid to the peptide-resin growing chain generally includes: (1) washing the peptide-resin three times for 30 seconds with N,N-dimethylformamide (DMF); (2) removing the Fmoc protective group on the amino terminus by deprotection with 20% piperdine in DMF by two washes for 15 minutes each, during which process mixing is effected by bubbling nitrogen through the reaction vessel for one second every 10 seconds to prevent peptide-resin settling; (3) washing the peptide-resin three times for 30 seconds with DMF; (4) coupling the amino acid to the peptide resin by addition of equal volumes of a 250 mM solution of the Fmoc derivative of the appropriate amino acid and an activator mix consisting or 400 mM N-methylmorpholine and 250 mM (2-(1H-benzotriazol-1-4))-1,1,3,3-tetramethyluronium hexafluorophosphate (HBTU) in DMF; (5) allowing the solution to mix for 45 minutes; and (6) washing the peptide-resin three times for 30 seconds of DMF. This cycle can be repeated as necessary with the appropriate amino acids in sequence to produce the desired peptide. Exceptions to this cycle program are amino acid couplings predicted to be difficult by nature of their hydrophobicity or predicted inclusion within a helical formation during synthesis. For these situations, the above cycle can be modified by repeating step 4 a second time immediately upon completion of the first 45 minute coupling step to "double couple" the amino acid of interest. Additionally, in the first coupling step in peptide synthesis, the resin can be allowed to swell for more efficient coupling by increasing the time of mixing in the initial DMF washes to three 15 minute washes rather than three 30 second washes.

After peptide synthesis, the peptide can be cleaved from the resin as follows: (1) washing the peptide-resin three times for 30 seconds with DMF; (2) removing the Fmoc protective group on the amino terminus by washing two times for 15 minutes in 20% piperdine in DMF; (3) washing the peptide-resin three times for 30 seconds with DMF; and (4) mixing a cleavage cocktail consisting of 95% trifluoroacetic acid (TFA), 2.4% water, 2.4% phenol, and 0.2% triisopropysilane with the peptide-resin for two hours, then filtering the peptide in the cleavage cocktail away from the resin, and precipitating the peptide out of solution by addition of two volumes of ethyl ether.

To isolate the peptide, the ether-peptide solution can be allowed to sit at −20° C. for 20 minutes, then centrifuged at 6,000×G for 5 minutes to pellet the peptide, and the peptide can be washed three times with ethyl ether to remove residual cleavage cocktail ingredients. The final peptide product can be purified by reversed phase high pressure liquid chromatography (RP-HPLC) with the primary solvent consisting of 0.1% TFA and the eluting buffer consisting of 80% acetonitrile and 0.1% TFA. The purified peptide can then be lyophilized to a powder.

In a preferred embodiment, the invention provides a peptide with branched amino acids (branched peptide), preferably a branched peptide of amino acids 45–57 (SEQ ID NO:6) with branches occurring at positions 47 and 51, respectively, instead of the Gly and Ala residues normally present. Most preferably, diaminobutyric acid is substituted for the gly and ala residues at positions 47 and 51, respectively, and proline bonded to both diaminobutyric acid residues (45–57 branched) as shown in FIG. 9A.

In other specific embodiments, branched versions of the β-hCG peptides listed hereinabove are provided, e.g., by substituting one or more amino acids within the β-hCG sequence with an amino acid or amino acid analog with a free side chain capable of forming a peptide bond with one or more amino acids (and thus capable of forming a "branch").

Branched peptides may be prepared by any method known in the art for covalently linking any naturally occurring or synthetic amino acid to any naturally occurring or synthetic amino acid in a peptide chain which has a side chain group able to react with the amino or carboxyl group on the amino acids so as to become covalently attached to the peptide chain. In particular, amino acids with a free amino side chain group, such as, but not limited to, diaminobutyric acid, lysine, arginine, ornithine, diaminopropionic acid and citrulline, can be incorporated into a peptide so that an amino acid can form a branch therewith, for example, by forming a peptide bond to the free amino side group, from that residue. Alternatively, amino acids with a free carboxyl side chain group, such as, but not limited to, glutamic acid, aspartic acid and homocitrulline, can be incorporated into the peptide so that an amino acid can form a branch therewith, for example, by forming a peptide bond to the free carboxyl side group, from that residue. The amino acid forming the branch can be linked to a side chain group of an amino acid in the peptide chain by any type of covalent bond, including, but not limited to, peptide bonds, ester bonds and disulfide bonds. In a specific embodiment, amino acids, such as those described above, that are capable of forming a branch point, are substituted for β-hCG residues within a peptide having a β-hCG sequence.

Branched peptides can be prepared by any method known in the art. For example, but not by way of limitation, branched peptides can be prepared as follows: (1) the amino acid to be branched from the main peptide chain can be purchased as an N-α-tert-butyloxycarbonyl (Boc) protected amino acid pentafluorophenyl (Opfp) ester and the residue within the main chain to which this branched amino acid will be attached can be an N-Fmoc-α-γ-diaminobutyric acid; (2) the coupling of the Boc protected amino acid to diaminobutyric acid can be achieved by adding 5 grams of each precursor to a flask containing 150 ml DMF, along with 2.25 ml pyridine and 50 mg dimethylaminopyridine and allowing the solution to mix for 24 hours; (3) the peptide can then be extracted from the 150 ml coupling reaction by mixing the reaction with 400 ml dichlormethane (DCM) and 200 ml 0.12 N HCl in a 1 liter separatory funnel, and allowing the phases to separate, saving the bottom aqueous layer and re-extracting the top layer two more times with 200 ml 0.12 N HCl; (4) the solution containing the peptide can be dehydrated by adding 2–5 grams magnesium sulfate, filtering out the magnesium sulfate, and evaporating the remaining solution to a volume of about 2–5 ml; (5) the dipeptide can then be precipitated by addition of ethyl acetate and then 2 volumes of hexanes and then collected by filtration and washed two times with cold hexanes; and (6) the resulting filtrate can be lyophilized to achieve a light powder form of the desired dipeptide. Branched peptides prepared by this method will have a substitution of diaminobutyric acid at the amino acid position which is branched. Branched peptides containing an amino acid or amino acid analog substitution other than diaminobutyric acid can be prepared analogously to the procedure described above, using the N-F-moc coupled form of the amino acid or amino acid analog.

In a preferred embodiment, the peptide is a cyclic peptide, preferably a cyclic peptide of β-hCG amino acids 44–57 with cysteine substituted for valine at position 44 (SEQ ID NO:26) and circularized via a disulfide bond between the cysteine residues at positions 44 and 57 (C[V44C] 45–57) (FIG. 9B), or a cyclic fused peptide of β-hCG amino acids 110–119 (SEQ ID NO:27) linked at the C-terminus by a peptide bond to the N-terminus of amino acids 45–57 (SEQ ID NO:6) and circularized via a disulfide bond between the cysteine residues at positions 110 and 57. In another preferred embodiment, the peptide is a cyclic branched peptide of β-hCG amino acids 44–57 (SEQ ID NO:26) with cysteine substituted for valine at position 44 and circularized via a disulfide bond between the cysteine residues at positions 44 and 57 and positions 47 and 51 substituted with a diaminobutyric acid residue on which a proline is peptide bonded to its free amino sidechain.

Cyclization can be, for example but not by way of limitation, via a disulfide bond between two cysteine residues or via an amide linkage. For example, but not by way of limitation, disulfide bridge formation can be achieved by (1) dissolving the purified peptide at a concentration of between 0.1.–0.5 mg/ml in 0.01 M ammonium acetate, pH 7.5; (2) adding 0.01 M potassium ferricyanide to the dissolved peptide dropwise until the solution appears pale yellow in color and allowing this solution to mix for 24 hours; (3) concentrating the cyclized peptide to 5–10 ml of solution, repurifying the peptide by reverse phase-high pressure liquid chromatography (RP-HPLC) and finally lyophilizing the peptide. In a specific embodiment, in which the peptide does not contain two appropriately situated cysteine residues, cysteine residues can be introduced at the amino-terminus and/or carboxy-terminus and/or internally such that the peptide to be cyclized contains two cysteine residues spaced such that the residues can form a disulfide bridge.

Alternatively, a cyclic peptide can be obtained by generating an amide linkage. An amide linkage can be achieved by, for example, but not limited to, the following procedure: An allyl protected amino acid, such as aspartate, glutamate, asparagine or glutamine, can be incorporated into the peptide as the first amino acid, and then the remaining amino acids coupled on. The allyl protective group can be removed by a two hour mixing of the peptide-resin with a solution of tetrakistriphenylphophine palladium (0) in a solution of chloroform containing 5% acetic acid and 2.5% N-methylmorpholine. The peptide resin can be washed three times with 0.5% N,N-diisopropylethylamine (DIEA) and 0.5% sodium diethyldithiocabamate in DMF. The amino terminal Fmoc group on the peptide chain can be removed by two incubations for 15 minutes each in 20% piperdine in DMF, and washed three times with DMF for 30 seconds each. The activator mix, N-methylmorpholine and HBTU in DMF, can be brought onto the column and allowed to couple the free amino terminal end to the carboxyl group generated by removal of the allyl group to cyclize the peptide. The peptide can cleaved from the resin as described in the general description of chemical peptide synthesis above and the peptide purified by reverse phase-high pressure liquid chromatography (RP-HPLC). In a specific embodiment, in which the peptide to be cyclized does not contain an allyl protected amino acid, an allyl protected amino acid can be introduced into the sequence of the peptide, at the amino-terminus, carboxy-terminus or internally, such that the peptide can be cyclized.

β-hCG peptides can also be obtained by recombinant expression techniques. (See, e.g., Sambrook et al., 1989, Molecular Cloning, A Laboratory Manual, Cold Spring Harbor Laboratory, 2d Ed., Cold Spring Harbor, N.Y., Glover, D. M. (ed.), 1985, DNA Cloning: A Practical Approach, MRL Press, Ltd., Oxford, U.K., Vol. I, II). The nucleic acid sequence encoding hCG has been cloned and the sequence determined (FIG. 8 (SEQ ID NOS:1 and 2) and Xia, H., 1993, *J. Molecular Endocrinology* Jun. 10, 1993:337–343; Sherman, G. B., 1992, *J. Molecular Endocrinology*, Jun. 6, 1992:951–959; Gieseman, L. K. (ed.), 1991, *Basic and Chemical Endocrinology*, pp. 543–567; Ward et al., 1991, in *Reproduction in Domestic Animals*, 4th ed., P. T. Coppos, ed., pp. 25–80, Academic Press, New York) and can be isolated using well-known techniques in the art, such as screening a library, chemical synthesis, or polymerase chain reaction (PCR).

To recombinantly produce a β-hCG peptide, a nucleic acid sequence encoding β-hCG or a β-hCG peptide is operatively linked to a promoter such that β-hCG or a β-hCG peptide is produced from said sequence. For example, a vector can be introduced into a cell, within which cell the vector or a portion thereof is expressed, producing β-hCG or one or more portions thereof. In a preferred embodiment, the nucleic acid is DNA if the source of RNA polymerase is DNA-directed RNA polymerase, but the nucleic acid may also be RNA if the source of polymerase is RNA-directed RNA polymerase or if reverse transcriptase is present in the cell or provided to produce DNA from the RNA. Such a vector can remain episomal or become chromosomally integrated, as long as it can be transcribed to produce the desired RNA. Such vectors can be constructed by recombinant DNA technology methods standard in the art. Vectors can be plasmid, viral, or others known in the art, used for replication and expression in bacterial or mammalian cells. Expression of the sequence encoding β-hCG or the β-hCG peptide can be by any promoter known in the art to act in bacterial or mammalian cells. Such promoters can be inducible or constitutive. Such promoters include, but are not limited to: the SV40 early promoter region (Bernoist and Chambon, 1981, *Nature* 290:304–310), the promoter contained in the 3' long terminal repeat of Rous sarcoma virus (Yamamoto et al., 1980, *Cell* 22:787–797), the HSV-1 (herpes simplex virus-1) thymidine kinase promoter (Wagner et al., 1981, *Proc. Natl. Acad. Sci. USA* 78:1441–1445), the regulatory sequences of the metallothionein gene (Brinster et al., 1982, *Nature* 296:39–42), etc., as well as the following animal transcriptional control regions, which exhibit tissue specificity and have been utilized in transgenic animals: elastase I gene control region which is active in pancreatic acinar cells (Swift et al., 1984, *Cell* 38:639–646; Ornitz et al., 1986, *Cold Spring Harbor Symp. Quant. Biol.* 50:399–409; MacDonald, 1987, *Hepatology* 7:425–515); insulin gene control region which is active in pancreatic beta cells (Hanahan, 1985, *Nature* 315:115–122), immunoglobulin gene control region which is active in lymphoid cells (Grosschedl et al., 1984, *Cell* 38:647–658; Adames et al., 1985, *Nature* 318:533–538; Alexander et al., 1987, *Mol. Cell. Biol.* 7:1436–1444), mouse mammary tumor virus control region which is active in testicular, breast, lymphoid and mast cells (Leder et al., 1986, *Cell* 45:485–495), albumin gene control region which is active in liver (Pinkert et al., 1987, *Genes and Devel.* 1:268–276), alpha-fetoprotein gene control region which is active in liver (Krumlauf et al., 1985, *Mol. Cell. Biol.* 5:1639–1648; Hammer et al., 1987, *Science* 235:53–58), alpha 1-antitrypsin gene control region which is active in the liver (Kelsey et al., 1987, *Genes and Devel.* 1:161–171), beta-globin gene control region which is active in erythroid cells (Mogram et al., 1985, *Nature* 315:338–340; Kollias et al., 1986, *Cell* 46, 89–94), myelin basic protein gene control region which is active in oligodendrocyte cells in the brain (Readhead et al., 1987, *Cell* 48:703–712), myosin light chain-2 gene control region which is active in skeletal muscle (Sani, 1985, *Nature* 314:283–286), and gonadotropin releasing hormone gene control region which is active in the hypothalamus (Mason et al., 1986, *Science* 234:1372–1378). The promoter element which is operatively linked to the nucleic acid encoding β-hCG or a β-hCG peptide can also be a bacteriophage promoter with the source of the bacteriophage RNA polymerase expressed from a gene for the RNA polymerase on a separate plasmid, e.g., under the control of an inducible promoter, for example, the nucleic acid encoding β-hCG or β-hCG peptide operatively linked to the T7 RNA polymerase promoter with a separate plasmid encoding the T7 RNA polymerase.

In a less preferred embodiment, peptides can be obtained by proteolysis of hCG or β-hCG followed by purification using standard techniques such as chromatography (e.g., HPLC), electrophoresis, etc.

Also included within the scope of the invention are β-hCG peptide derivatives which are differentially modified during or after synthesis, e.g., by benzylation, glycosylation, acetylation, phosphorylation, amidation, pegylation, derivatization by known protecting/blocking groups, proteolytic cleavage, linkage to an antibody molecule or other cellular ligand, etc. In specific embodiments, the peptides are acetylated at the N-terminus and/or amidated at the C-terminus.

Any of numerous chemical modifications may be carried out by known techniques, including but not limited to acetylation, formulation, oxidation, reduction; metabolic synthesis in the presence of tunicamycin; etc.

In another embodiment, the β-hCG or β-hCG peptide derivative is a chimeric, or fusion, protein comprising β-hCG or a functional β-hCG peptide (or two or more portions of β-hCG joined by peptide bond(s)) joined at its amino- or carboxy-terminus via a peptide bond to an amino acid sequence of a different protein. In a specific embodiment, the derivative is a fusion protein comprising the β-hCG sequence, or portions thereof, joined at its amino or carboxy-terminus to an amino acid sequence, or portions thereof, of a chemokine which is therapeutically useful in the treatment of AIDS, for example, the chemokines MIP-1α, MIP-1β or Rantes (for amino acid sequences of these chemokines see Shall, 1991, *Cytokine* 3:165–183). In one embodiment, such a chimeric protein is produced by recombinant expression of a nucleic acid encoding the protein (comprising a β-hCG-coding sequence joined in-frame to a coding sequence for a different protein). Such a chimeric product can be made by ligating the appropriate nucleic acid sequences encoding the desired amino acid sequences to each other by methods known in the art, in the proper coding frame, and expressing the chimeric product by methods commonly known in the art. Alternatively, such a chimeric product may be made by protein synthetic techniques, e.g., by use of a peptide synthesizer.

Therapeutic Uses

HIV

The invention provides for treatment or prevention of diseases and disorders associated with HIV infection by administration of a therapeutic compound (termed herein "Therapeutic"). Such "Therapeutics" include, but are not limited to: hCG, β-hCG, therapeutically and prophylactically effective fractions of a source of native hCG or native β-hCG, and therapeutically and prophylactically effective β-hCG peptides, i.e., those fractions and peptides which prevent or treat HIV infection (e.g., as demonstrated in in vitro and in vivo assays described infra), and derivatives and analogs thereof, as well as nucleic acids encoding hCG, β-hCG and therapeutically and prophylactically effective β-hCG peptides and derivatives and analogs thereof (e.g., for use in gene therapy). Examples of Therapeutics are those proteins described herein and nucleic acids encoding such proteins and frations of native hCG and native β-hCG described below.

A preferred embodiment of the invention relates to methods of using a Therapeutic for treatment or prevention of HIV infection, preferably HIV-1 infection, in a human subject. In a specific embodiment, the Therapeutic is used for the treatment or prevention of HIV infection in a human subject that does not suffer from a cancer which secretes hCG or hCG fragments. In another specific embodiment, the Therapeutic is used for the treatment or prevention of HIV infection in a human subject who does not suffer from Kaposi's sarcoma (KS). In the treatment of HIV infection, the Therapeutic of the invention can be used to prevent progression of HIV infection to ARC or to AIDS in a human patient, or to treat a human patient with ARC or AIDS.

In a preferred aspect of the invention, proteins, preferably β-hCG peptides and derivatives are used to treat HIV infection. In particular, proteins, or nucleic acids encoding the proteins, containing an amino acid sequence of one or more portions of β-hCG, preferably containing a sequence from amino acids 41–53, 42–53, 43–53, 44–53, 44–57, 45–53, 46–53, 45–54, 45–55, 45–56, 45–58, 47–54, 47–55, 47–56, 47–58, 48–145, 58–145, 109–145, 7–40, 46–65, or 48–56 (SEQ ID NOS:8–25 or 33–35, respectively) of FIG. 8 (a portion of SEQ ID NO:2), and preferably containing a sequence from amino acids 41–54, 45–54 or 109–119 (SEQ ID NOS:3, 4 or 7, respectively) of FIG. 8 (a portion of SEQ ID NO:2), and most preferably containing a sequence from amino acids 47–53 or 45–57 of FIG. 8 (a portion of SEQ ID NO:2), or circular [C44V]45–57 peptide (SEQ ID NO:26), or branched 45–57 (SEQ ID NO:6) peptide, or branched circular [V44C]45–57 peptide are used to treat HIV infection. In another embodiment, a protein is used which contains the amino acid sequence of two or more peptides of different, non-naturally contiguous portions of the β-hCG sequence (FIG. 8 (SEQ ID NO:2)) in which the N-terminus of one portion is linked to the C-terminus of another portion by peptide bond(s). In a specific embodiment, a protein is used, the amino acid sequence of which consists of amino acids 45–57 (SEQ ID NO:6) linked at the C-terminus via a peptide bond to the N-terminus of amino acids 109–119 (SEQ ID NO:7) or linked at the N-terminus via a peptide bond to the C-terminus of amino acids 110–119 (SEQ ID NO:27); or a protein is used that has an amino acid sequence of amino acids 47–57 (SEQ ID NO:28) linked at the C-terminus via a peptide bond to the N-terminus of amino acids 108–119 (SEQ ID NO:29) of the β-hCG sequence depicted in FIG. 8 (portions of SEQ ID NO:2); i.e., the fused peptides represented as 45–57::109–119, 110–119::45–57, or 47–57::108–119 (SEQ ID NOS:30–32, respectively). In yet another embodiment a protein is used which is a cyclic, fused peptide, particularly a cyclic, fused peptide having a sequence consisting of β-hCG amino acids 110–119 (SEQ ID NO:27) linked at the C-terminus via a peptide bond to the N-terminus of amino acids 45–57 (SEQ ID NO:6) and being circularized by a disulfide bond between the terminal cysteines at positions 110 and 57. In another embodiment, a protein is used that (a) comprises a β-hCG amino acid sequence consisting of amino acid numbers 41–54, 45–54, 47–53, 45–57, 109–119, 41–53, 42–53, 43–53, 44–53, 44–57, 45–53, 46–53, 45–54, 45–55, 45–56, 45–58, 47–54, 47–55, 47–56, 47–58, 48–145, 58–145, 109–119, 109–145, 7–40, 46–65 or 48–56 (SEQ ID NOS:3–25 or 33–35, respectively) as depicted in FIG. 8 (a portion of SEQ ID NO:2) and (b) lacks β-hCG amino acids contiguous to said sequence. In yet another embodiment, a purified derivative of a protein is used to treat or prevent HIV infection, the amino acid sequence of which protein is selected from the group consisting of amino acid numbers 41–54, 45–54, 47–53, 45–57, 109–119, 41–53, 42–53, 43–53, 44–53, 44–57, 45–53, 46–53, 45–54, 45–55, 45–56, 45–58, 47–54, 47–55, 47–56, 47–58, 48–145, 58–145, 109–145, 7–40, 46–65 or 48–56 (SEQ ID NOS:3–25 or 33–35, respectively) as depicted in FIG. 8 (a portion of SEQ ID NO:2). Other β-hCG peptides, and nucleic acids encoding the peptides, and modifications and derivatives thereof, may have utility in the therapeutic methods of the invention.

In yet another embodiment, a fraction, particularly a size fraction, of a source of native hCG or native β-hCG (i.e. naturally occurring, not recombinantly produced, hCG or β-hCG) active in inhibiting HIV infection and replication, particularly a size fraction of approximately 40 kD, 15 kD or 2–3 kD, is used to treat or prevent HIV infection. The utility of β-hCG peptides and fractions of native hCG and native β-hCG sources may be determined by the in vitro and in vivo assays described herein or by any other method known in the art.

Additionally, the present inventors have found that different preparations of native hCG and native β-hCG have variable effects on HIV infection both in vitro and in vivo. Specifically, the inventors found that among the commercial preparations of (non-recombinant) hCG they investigated, hCG from Fujisawa was the most effective, hCG APL™ (Wyeth-Ayerst) the next most effective, and PREGNYL™ (Organon) the next most effective in inhibiting HIV infection and replication. A highly purified hCG preparation and recombinant β-hCG were found not to be active in inhibiting HIV infection in vitro. In fact, the present inventors have shown that specific size fractions of an active hCG preparation (APL™; Wyeth Ayerst) have anti-HIV activity in vitro and anti-KS activity both in vitro and in vivo, as described herein.

These active fractions were eluted from the gel filtration sizing matrix as or close to (i.e., within 5 fractions (where the fractions are 4 ml fractions using a SUPERDEX™ 200 column which is 26 mm$^2$ by 60 mm)) the fractions containing or that would contain material that is approximately 40 kD (±8 kD), 15 kD (±3 kD) and 2–3 kD (±2 kD) molecular weight. One skilled in the art would understand that these fractions could be subjected to further size fractionation to further isolate the component of these fractions having the anti-HIV and/or anti-KS activity. Additionally, other methods of fractionation, such as ion-exchange chromatography, affinity chromatography, etc., are well known in the art; those skilled in the art would be able to use any available fractionation techniques to obtain the active fractions from the active hCG preparations and human early (first trimester) pregnancy urine. hCG preparations and fractions of hCG preparations can be screened for efficacy in treating or preventing HIV infection, cancer, wasting syndrome, and/or hematopoietic deficiencies by the assays described herein or by any method known in the art. In a specific embodiment, the invention provides a first composition comprising one or more first components of a second composition comprising native hCG or native β-hCG, said first components being separated from other components of the hCG or β-hCG sample, said first components being active to inhibit HIV infection or replication or Kaposi's sarcoma or having a pro-hematopoietic activity, and said second composition being active to inhibit HIV infection or replication or Kaposi's sarcoma or having a pro-hematopoietic activity, and said native hCG or native β-hCG not being purified to homogeneity in said second composition. In particular the invention provides a composition comprising components which have been separated from other components of the native hCG or native β-hCG sample by sizing column chromatography, preferably where the components elute from a gel filtration, preferably a SUPERDEX™ 200, sizing column with an apparent approximate molecular weight of 40 kD, 14 kD or 2–3 kD as determined relative to the elution of a native hCG heterodimer, having a molecular weight of 77 kD, and a β-hCG core protein (β-hCG amino acids 6–40 linked via a disulfide bond to β-hCG amino acids 55–92, as depicted in FIG. 8 (SEQ ID NO:2)), having a molecular weight of 10 kD. In a specific embodiment, the therapeutic method of the invention is carried out as monotherapy, i.e., as the only agent provided for treatment or prevention of HIV. In another embodiment, the Therapeutic is administered in combination with one or more anti-viral compounds, for example, protease inhibitors (e.g., saquinavir) and/or reverse transcriptase inhibitors (e.g., azidothymidine (AZT), lamioridine (3TC), dideoxyinosine (ddI), dideoxycytidine (ddC)). The Therapeutic may also be administered in conjunction with chemotherapy (e.g., treatment with adriamycin, bleomycin, vincristine, vinblastine, doxorubicin and/or Taxol) or other therapies known in the art.

In another embodiment, HIV infection is treated or prevented by administration of a Therapeutic of the invention in combination with one or more chemokines. In particular, the Therapeutic is administered with one or more C-C type chemokines, especially one or more from the group RANTES, MIP-1α and MIP-1β.

The invention provides for treatment or prevention of wasting syndrome by administration of a therapeutic compound (termed herein "Therapeutic"). Such "Therapeutics" include, but are not limited to: hCG, β-hCG, therapeutically and prophylactically effective fractions of a source of native hCG or native β-hCG (i.e. naturally occurring hCG or β-hCG and not recombinantly produced hCG or β-hCG), and therapeutically and prophylactically effective β-hCG peptides, i.e., those fractions and peptides which prevent or treat wasting syndrome (e.g., as demonstrated in in vitro and in vivo assays described infra), and derivatives and analogs thereof, as well as nucleic acids encoding hCG, β-hCG and therapeutically and prophylactically effective β-hCG peptides and derivatives and analogs thereof (e.g., for use in gene therapy).

The methods of the invention can be used for treatment or prevention of any disease or disorder characterized by a loss of body cell mass. Particular conditions that can be treated by methods of the invention include, but are not limited to, wasting associated with viral, such as HIV, bacterial or other types of infections, and sepsis; cachexia associated with cancer, chemotherapy, and radiation therapy; wasting associated with chronic cardiovascular disease; wasting caused by exposure to toxic substances; wasting associated with diarrhea and other gastrointestinal disorders.

In a preferred embodiment, a Therapeutic of the invention is administered to treat or prevent a wasting syndrome associated with HIV infection. In another preferred embodiment, a Therapeutic of the invention is administered to treat or prevent a wasting syndrome associated with cancer.

Hematopoiesis

The invention also provides for treatment or prevention of diseases and disorders in which increased numbers of one or more hematopoietic cell types are desirable (e.g., diseases or disorders associated with one or more hematopoietic cell deficiencies) by administration of a therapeutic compound (termed herein "Therapeutic") of the invention or by administration of hematopoietic cells, the production of which has been induced in vitro by contacting the cells with a Therapeutic of the invention. Such "Therapeutics" include but are not limited to: hCG, β-hCG and derivatives thereof, and therapeutically or prophylactically effective fractions of a source of native hCG or native β-hCG and therapeutically or prophylactically effective β-hCG peptides, i.e., those fraction and peptides which prevent or treat hematopoietic deficiencies (e.g., as demonstrated in in vitro and in vivo assays described infra) as well as modifications, derivatives and analogs thereof and nucleic acids encoding hCG, β-hCG and therapeutically and prophylactically effective β-hCG peptides, and derivatives and analogs thereof. In one embodiment, the Therapeutic of the invention is a protein containing an amino acid sequence of a therapeutically and prophylactically effective portion or portions of β-hCG.

In a preferred embodiment, the Therapeutic of the invention is a protein having a sequence of amino acid numbers 41–54, 45–54, 47–53 or 45–57 (SEQ ID NOS:3–6, respectively) of the β-hCG sequence depicted in FIG. 8 (a portion of SEQ ID NO:2). In other embodiments, the Therapeutic of the invention is a protein having a sequence of amino acid numbers 41–53, 42–53, 43–53, 44–53, 44–57, 45–53, 46–53, 45–54, 45–55, 45–56, 45–58, 47–54, 47–55, 47–56, 47–58, 48–145, 58–145, 109–145, 7–40, 46–65, or 48–56 (SEQ ID NOS:8–25 or 33–35, respectively) of the β-hCG sequence of FIG. 8 (a portion of SEQ ID NO:2). Additionally, the present inventors have found that different preparations of hCG and β-hCG have variable effects on hematopoietic cell proliferation in vitro and in vivo. Specifically, the inventors found that among the (non-recombinant) commercial preparations they investigated, hCG from Fujisawa was the most effective, hCG from APL (Wyeth-Ayerst) the next most effective, and pregnyl (Organon) the next most effective. hCG preparations and fractions of hCG and β-hCG preparations can be screened for utility in inducing hematopoiesis in vitro or in vivo by the methods described infra herein or any method known in the art.

In one embodiment of the invention, the Therapeutic is administered directly to a patient suffering from a disease or disorder amenable to treatment by increasing production of one or more hematopoietic cell types (e.g., a disease or disorder associated with a hematopoietic cell deficiency). In another embodiment of the invention, hematopoietic cells, preferably stem and/or progenitor cells, are obtained, contacted with a Therapeutic of the invention in vitro to induce proliferation of the cells, and then administered to a subject suffering from a disease or disorder associated with a hematopoietic cell deficiency. Preferably, autologous hematopoietic cells (obtained from the subject or its identical twin) are reintroduced into the subject after in vitro expansion. In this embodiment, gene therapy methods can be performed by introducing a nucleic acid of interest, e.g., containing a gene which provides a function desired in a subject, into the hematopoietic cells, before or after expansion of the cells by contact with a Therapeutic. Hematopoietic cell subpopulations can be isolated for use, before or after expansion in vitro. For example, blood cells can be isolated and expanded, and optionally also differentiated, in vitro, followed by introduction of all or a portion of the cells (e.g., purified platelets, red blood cells, lymphocytes, etc.) into a patient.

In general, disorders that can be treated by methods of the invention include, but are not limited to, five broad categories. First are diseases resulting from a failure or dysfunction of normal blood cell production and maturation (i.e., aplastic anemia, cytopenias and hypoproliferative stem cell disorders). The second group are neoplastic, malignant diseases in the hematopoietic organs (e.g., leukemia and lymphomas). The third group of disorders comprises those of patients with a broad spectrum of malignant solid tumors of non-hematopoietic origin. Induction of hematopoietic cell proliferation or administration of replacement hematopoietic cells in these patients serves as a bone marrow rescue procedure, which is provided to a patient following otherwise lethal chemotherapy or irradiation of the malignant tumor. The fourth group of diseases consists of autoimmune conditions, where the hematopoietic cells serve as a source of replacement of an abnormal immune system. The fifth group of diseases comprises a number of genetic disorders which can be corrected by infusion of hematopoietic stem cells, preferably syngeneic, which prior to transplantation have undergone gene therapy. Particular diseases and disorders which can be treated by induction of hematopoietic cell production in vivo or by administration of hematopoietic cells expanded in vitro include but are not limited to those listed in Table 1, and described infra.

TABLE 1

DISEASES OR DISORDERS WHICH CAN BE TREATED BY INCREASING PRODUCTION OF HEMATOPOIETIC CELLS

I. Diseases resulting from a failure or dysfunction of normal blood cell production and maturation
    hyperproliferative stem cell disorders
    aplastic anemia
    pancytopenia
    agranulocytosis
    thrombocytopenia
    red cell aplasia
    Blackfan-Diamond syndrome
    due to drugs, radiation, or infection
    idiopathic II. Hematopoietic malignancies
    acute lymphoblastic (lymphocytic) leukemia
    chronic lymphocytic leukemia
    acute myelogenous leukemia
    chronic myelogenous leukemia
    acute malignant myelosclerosis
    multiple myeloma
    polycythemia vera
    agnogenic myelometaplasia
    Waldenstrom's macroglobulinemia
    Hodgkin's lymphoma
    non-Hodgkin's lymphoma III. Immunosuppression in patients with malignant, solid tumors
    malignant melanoma
    carcinoma of the stomach
    ovarian carcinoma
    breast carcinoma
    small cell lung carcinoma
    retinoblastoma
    testicular carcinoma
    glioblastoma
    rhabdomyosarcoma
    neuroblastoma
    Ewing's sarcoma
    Lymphoma IV. Autoimmune diseases
    rheumatoid arthritis
    diabetes type I
    chronic hepatitis
    multiple sclerosis
    systemic lupus erythematosus V. Genetic (congenital) disorders
    anemias
    familial aplastic
    Fanconi's syndrome
    Bloom's syndrome
    pure red cell aplasia (PRCA)
    dyskeratosis congenita
    Blackfan-Diamond syndrome
    congenital dyserythropoietic syndromes I–IV
    Chwachmann-Diamond syndrome
    dihydrofolate reductase deficiencies
    formamino transferase deficiency
    Lesch-Nyhan syndrome
    congenital spherocytosis
    congenital elliptocytosis
    congenital stomatocytosis
    congenital Rh null disease
    paroxysmal nocturnal hemoglobinuria
    G6PD (glucose-6-phosphate dehydrogenase) variants 1,2,3
    pyruvate kinase deficiency
    congenital erythropoietin sensitivity deficiency
    sickle cell disease and trait
    thalassemia alpha, beta, gamma
    met-hemoglobinemia
    congenital disorders of immunity

TABLE 1-continued

DISEASES OR DISORDERS WHICH CAN BE TREATED BY INCREASING PRODUCTION OF HEMATOPOIETIC CELLS severe combined immunodeficiency disease (SCID)
    bare lymphocyte syndrome
    ionophore-responsive combined immunodeficiency
    combined immunodeficiency with a capping abnormality
    nucleoside phosphorylase deficiency
    granulocyte actin deficiency
    infantile agranulocytosis
    Gaucher's disease
    adenosine deaminase deficiency
    Kostmann's syndrome
    reticular dysgenesis
    congenital leukocyte dysfunction syndromes
VI. Others
    osteopetrosis
    myelosclerosis
    acquired hemolytic anemias
    acquired immunodeficiencies
    infectious disorders causing primary or secondary immunodeficiencies
    bacterial infections (e.g., Brucellosis, Listeriosis, tuberculosis, leprosy)
    parasitic infections (e.g., malaria, Leishmaniasis)
    fungal infections
    disorders involving disproportions in lymphoid cell sets and impaired immune functions due to aging
    phagocyte disorders
    Kostmann's agranulocytosis
    chronic granulomatous disease
    Chediak-Higachi syndrome
    neutrophil actin deficiency
    neutrophil membrane GP-180 deficiency
    melabolic storage diseases
    mucopolysaccharidoses
    mucolipidoses
    miscellaneous disorders involving immune mechanisms
    Wiskott-Aldrich Syndrome
    alpha 1-antitrypsin deficiency

Treatment of Malignancies

Malignancies and related disorders that can be treated or prevented by administration of a Therapeutic of the invention include, but are not limited to, those disorders listed in Table 2 (for a review of such disorders, see Fishman et al., 1985, *Medicine,* 2d Ed., J. B. Lippencott Co., Philadelphia):

TABLE 2

MALIGNANCIES AND RELATED DISORDERS

Leukemia
    Acute:
        acute lymphocytic leukemia
        acute myelocytic leukemia
            myeloblastic
            promyelocytic
            myelomonocytic
            monocytic
            erythroleukemia
    Chronic:
        chronic myelocytic (granulocytic) leukemia
        chronic lymphocytic leukemia
Polycythemia vera
Lymphoma
Hodgkin's disease
non-Hodgkin's disease
Multiple myeloma
Waldenstrom's macroglobulinemia

TABLE 2-continued

MALIGNANCIES AND RELATED DISORDERS

Heavy chain disease
Solid tumors
    Sarcomas and Carcinomas:
        fibrosarcoma
        myxosarcoma
        liposarcoma
        chondrosarcoma
        osteogenic sarcoma
        chordoma
        angiosarcoma
        endotheliosarcoma
        lymphangiosarcoma
        Kaposi's sarcoma
        lymphangioendotheliosarcoma
        synovioma
        mesothelioma
        Ewing's tumor
        leiomyosarcoma
        rhabdomyosarcoma
        colon carcinoma
        pancreatic cancer
        breast cancer
        ovarian cancer
        prostate cancer
        squamous cell carcinoma
        basal cell carcinoma
        adenocarcinoma
        sweat gland carcinoma
        sebaceous gland carcinoma
        papillary carcinoma
        papillary adenocarcinomas
        cystadenocarcinoma
        medullary carcinoma
        bronchogenic carcinoma
        renal cell carcinoma
        hepatoma
        bile duct carcinoma
        choriocarcinoma
        seminoma
        embryonal carcinoma
        Wilms' tumor
        cervical cancer
        uterine cancer
        testicular tumor
        lung carcinoma
        small cell lung carcinoma
        bladder carcinoma
        epithelial carcinoma
        glioma
        astrocytoma
        medulloblastoma
        craniopharyngioma
        ependymoma
        pinealoma
        hemangioblastoma
        acoustic neuroma
        oligodendroglioma
        meningioma
        melanoma
        neuroblastoma
        retinoblastoma
Virally induced cancers In specific embodiments, a Therapeutic of the invention is used to treat a neoplasm such as a gestational trophoblastic tumor, or testicular germ cell tumor, or cancer of the bladder, pancreas, cervix, lung, liver, ovary, colon or stomach, or adenocarcinoma or a virally induced cancer. In a preferred embodiment, a Therapeutic of the invention is used to treat neuroblastoma or carcinoma of the ovary or stomach. In a more preferred embodiment, a Therapeutic of the invention is used to treat Kaposi's sarcoma or carcinoma of the breast, lung, prostate, or kidney (renal).

In one aspect of the invention, the Therapeutic is administered in conjunction with other cancer therapy, such as chemotherapy (e.g., treatment with adriamycin, bleomycin, vincristine, vinblastine, doxorubicin and/or Taxol).

The efficacy of a Therapeutic against a particular cancer can be determined by any method known in the art, for example but not limited to, those methods described herein.

The Therapeutics of the invention can also be administered to treat premalignant conditions and to prevent progression to a neoplastic or malignant state, including but not limited to those disorders listed in Table 2. Such prophylactic or therapeutic use is indicated in conditions known or suspected of preceding progression to neoplasia or cancer, in particular, where non-neoplastic cell growth consisting of hyperplasia, metaplasia, or most particularly, dysplasia has occurred (for review of such abnormal growth conditions, see Robbins and Angell, 1976, *Basic Pathology*, 2d Ed., W. B. Saunders Co., Philadelphia, pp. 68–79). Hyperplasia is a form of controlled cell proliferation involving an increase in cell number in a tissue or organ, without significant alteration in structure or function. As but one example, endometrial hyperplasia often precedes endometrial cancer. Metaplasia is a form of controlled cell growth in which one type of adult or fully differentiated cell substitutes for another type of adult cell. Metaplasia can occur in epithelial or connective tissue cells. Atypical metaplasia involves a somewhat disorderly metaplastic epithelium. Dysplasia is frequently a forerunner of cancer, and is found mainly in the epithelia; it is the most disorderly form of non-neoplastic cell growth, involving a loss in individual cell uniformity and in the architectural orientation of cells. Dysplastic cells often have abnormally large, deeply stained nuclei, and exhibit pleomorphism. Dysplasia characteristically occurs where there exists chronic irritation or inflammation, and is often found in the cervix, respiratory passages, oral cavity, and gall bladder.

Alternatively or in addition to the presence of abnormal cell growth characterized as hyperplasia, metaplasia, or dysplasia, the presence of one or more characteristics of a transformed phenotype, or of a malignant phenotype, displayed in vivo or displayed in vitro by a cell sample from a patient, can indicate the desirability of prophylactic/therapeutic administration of a Therapeutic of the invention. Such characteristics of a transformed phenotype include morphology changes, looser substratum attachment, loss of contact inhibition, loss of anchorage dependence, protease release, increased sugar transport, decreased serum requirement, expression of fetal antigens, etc.

In other embodiments, a patient which exhibits one or more of the following predisposing factors for malignancy is treated by administration of an effective amount of a Therapeutic: a chromosomal translocation associated with a malignancy (e.g., the Philadelphia chromosome for chronic myelogenous leukemia, t(14;18) for follicular lymphoma, etc.), familial polyposis or Gardner's syndrome (possible forerunners of colon cancer), benign monoclonal gammopathy (a possible forerunner of multiple myeloma), and a first degree kinship with persons having a cancer or precancerous disease showing a Mendelian (genetic) inheritance pattern (e.g., familial polyposis of the colon, Gardner's syndrome, hereditary exostosis, polyendocrine adenomatosis, medullary thyroid carcinoma with amyloid production and pheochromocytoma, Peutz-Jeghers syndrome, neurofibromatosis of Von Recklinghausen, retinoblastoma, carotid body tumor, cutaneous melanocarcinoma, intraocular melanocarcinoma, xeroderma pigmentosum, ataxia telangiectasia, Chediak-Higashi syndrome, albinism, Fanconi's aplastic anemia, and Bloom's syndrome; see Robbins and Angell, 1976, *Basic Pathology*, 2d Ed., W. B. Saunders Co., Philadelphia, pp. 112–113, etc.)

In another specific embodiment, a Therapeutic of the invention is administered to a human patient to prevent progression to breast, colon, lung, pancreatic, or uterine cancer, or melanoma or sarcoma.

Hyperproliferative malignant stem cell disorders as well as non-hematopoietic malignancies can be treated with chemotherapy or radiation therapy along with rescue of hematopoietic cells by direct administration of a Therapeutic of the invention or by administration of hematopoietic cells induced to proliferate by contacting the cells with a Therapeutic of the invention. The conditions that can be treated according to the invention include, but are not limited to, the leukemias listed in Table 2 and the solid tumors listed in Table 2.

These malignancies are currently treated by, inter alia, chemotherapy and, when feasible, allogeneic bone marrow transplantation. However, allogeneic HLA identical sibling bone marrow is available only to less than one-third of patients, and this treatment is associated with transplantation-related complications such as immunodeficiency and graft versus host disease. Induction of hematopoietic cell proliferation in vivo or provision of autologous hematopoietic stem and progenitor cells expanded by administration of a Therapeutic in vitro permits hematopoietic reconstitution of patients lacking suitable allogeneic donors and eliminates the risks of graft versus host disease arising from allogeneic marrow transplantation. Thus, in a specific embodiment, a Therapeutic is used to induce proliferation in hematopoietic cells which are then administered to a patient who has undergone chemotherapy or radiation therapy for treatment of cancer or an immunological disorder. In another embodiment, a Therapeutic is directly administered to a patient who has undergone chemotherapy or radiation therapy for treatment of cancer or an immunological disorder.

Autoimmune Disorders

Many chronic inflammatory and degenerative diseases are characterized by a continuous immune reaction against the body's own tissues. Such autoimmune disorders include but are not limited to rheumatoid arthritis and other inflammatory osteopathies, diabetes type I, chronic hepatitis, multiple sclerosis, and systemic lupus erythematosus. Autoimmune disorders are often treated by lymphoid irradiation. Administration of a Therapeutic of the invention or of cells produced by exposure to a Therapeutic in vitro can be valuable to repopulate the hematopoietic system after radiotherapy.

Anti-inflammatory drugs such as steroids retard the inflammatory cells which are activated by autoreactive T cells, but do not prevent T cells which recognize self-proteins from activating new inflammatory cells. A more direct approach to treating autoimmune diseases depends on eradication of T cells by irradiation of the lymphoid tissues, and relying on stem cells from the unirradiated bone marrow to repopulate the patient's hematopoietic system. The rationale is that the formation of new populations of mature T cells from bone marrow stem cells may result in absence of T cells that have reactivity to self-specific antigens. This procedure, called total lymphoid irradiation (TLI), has been used to treat intractable rheumatoid arthritis (Strober, S., et al., 1985, *Annals of Internal Medicine* 102:441–449, 450–458). These clinical trials showed that in the majority of otherwise intractable cases, joint disease was significantly alleviated for at least 2–3 years. However, the major drawback to such treatment is failure of stem cells in the bone marrow of these elderly patients to efficiently repopulate the hematopoietic system, resulting in infections and bleeding disorders. Analogous studies have been made of the effects of TLI as an alternative to cytotoxic drugs for treatment of SLE (Strober, S., et al., 1985, *Ann. Internal Med.* 102:450). Studies of the use of TLI to treat intractable SLE have also shown that this treatment alleviates disease activity, but is severely limited by failure of bone marrow stem cells to rapidly and efficiently repopulate the hematopoietic system after irradiation.

Thus, a Therapeutic of the invention can be administered to promote proliferation of the remaining hematopoietic cells to increase the success of TLI therapy. Additionally, hematopoietic stem and progenitor cells can be isolated from the patient before treatment, induced to proliferate in vitro and then introduced into the patient after TLI treatment to repopulate the hematopoietic system.

Diseases Resulting from a Failure or Dysfunction of Normal Blood Cell Production and Maturation In a preferred aspect, a Therapeutic of the invention is used to treat a disease resulting from a failure or dysfunction of normal blood cell production and maturation, such as an aplastic anemia, a cytopenia or a hypoproliferative stem cell disorder. These disorders entail failure of stem cells in bone marrow to provide normal numbers of functional blood cells. The aplastic anemias result from the failure of stem cells to give rise to the intermediate and mature forms of red cells, white cells, and platelets. While red cell production is usually most seriously affected, a marked decrease in production of other mature blood cell elements is also seen as some anemias specifically affect production of white cells and/or platelets. The large majority of these anemias are acquired during adult life, and do not have any apparent genetic predisposition. About half of these acquired anemias arise in the absence of any obvious causative factor such as exposure to poisons, drugs or disease processes that impair stem cell function; these are termed idiopathic aplastic anemias. The remaining cases are associated with exposure to an extremely diverse array of chemicals and drugs and also occur as the consequence of viral infections, such as HIV infection, and after pregnancy. Other specific types of aplastic anemia are termed agranulocytosis or thrombocytopenia to indicate that the major deficiency lies in particular white cells or in platelet production, respectively. These non red blood cell deficiencies are also often associated with HIV infection. Also significantly associated with HIV infection is a severe platelet deficiency, Idiopathic Thrombocytopenic Purpura (ITP). Additionally, agranulocytosis may be associated with autoimmune syndromes such as systemic lupus erythematosus (SLE) or with other infections, such as neonatal rubella.

In addition, immune deficiencies which are the primary or secondary result of infection by pathogenic microorganisms can be treated by administration of a Therapeutic of the invention. For example, immune deficiencies caused by microorganisms which are intracellular pathogens of hematopoietic cells, can be treated by the provision of new hematopoietic cells. These new hematopoietic cells can be generated by contacting hematopoietic stem and/or progenitor cells in vitro with a Therapeutic of the invention to cause proliferation of the cells. Microorganisms causing immune deficiencies which may be treated according to this embodiment of the invention include but are not limited to gram-negative bacilli such as Brucella or Listeria, the mycobacterium which are the etiological agents of tuberculosis or of Hansen's disease (leprosy), parasites such as Plasmodium (the etiological agents of malaria) or Leishmania, and fungi (such as those that cause pneumonia and other lethal infections secondary to immunodeficiencies) (for a discussion of many of these disorders, see Harrison's Principles of Internal Medicine, 1970, 6th Edition, Wintrobe, M. M., et al., eds., McGraw-Hill, New York, pp. 798–1044).

In a preferred embodiment of the invention, a Therapeutic of the invention is administered for the treatment of a cytopenia associated with HIV infection.

The hematopoietic deficiencies associated with HIV infection include reduction in $CD4^+$ T cells and other lymphocytes, red blood cells, platelets, specifically ITP, and neutrophils. Such a disorder is treated by contacting hematopoietic stem and/or progenitor cells in vitro with a Therapeutic of the invention and then infusing the resulting hematopoietic cells into the subject in need of treatment. In a another preferred embodiment, the disorder is treated by direct administration of a Therapeutic of the invention to the subject in need of treatment. Assays for determining the efficacy of particular Therapeutics for treatment of hematopoietic deficiencies associated with HIV infection are detailed herein.

Sources of hCG and β-hCG

Native preparations (i.e. derived from naturally occurring sources and not recombinantly produced) of hCG and β-hCG can be obtained from a variety of sources. Both hCG and β-hCG are commercially available (e.g., Sigma Chemical Company) and hCG is commercially available in a form suitable for therapeutic use in humans (e.g., from Fujisawa, Wyeth-Ayerst Laboratories (APL™), Organon, Inc. (PREGNYL™) and Serono Laboratories, Inc. (PROFASI™)). hCG is also present at particularly high concentrations in the urine of women in the first trimester of pregnancy ("human early pregnancy urine"). Other sources include, but are not limited to, urine from women in the second and third trimesters of pregnancy, urine from patients with proteinuria, urine from patients having hCG secreting tumors or other cancer patients, and from pituitary glands.

Since the inventors have discovered that different sources of hCG have variable effects on HIV infection and cancer cell growth in vitro and in vivo, one aspect of the invention relates to assaying preparations of hCG for efficacy in treatment or prevention of HIV infection. The therapeutic effectiveness of hCG preparations and fractions can be tested by the in vitro or in vivo assays described herein or by any method known in the art. It is preferable to test the hCG preparation or fraction in an in vitro assay, e.g., for HIV replication or transcription from the HIV-1 LTR or in vivo in an animal model, such as HIV transgenic mice or SIV infected monkeys, before assaying the preparation in humans.

In a specific embodiment, a preparation comprising hCG is used that contains not only the hCG heterodimer but also peptide fragments thereof, e.g., β chain peptides.

hCG and β-hCG can also be purified, or preferably partially purified, from any source known to contain hCG or β-hCG, e.g., urine from pregnant women, using conventional techniques well-known in the art, such as affinity chromatography. For example, antibodies prepared against hCG or β-hCG can be used to prepare an affinity chromatography column which can be used to purify the proteins by well-known techniques (see, e.g., Hudson & May, 1986, *Practical Immunology*, Blackwell Scientific Publications, Oxford, United Kingdom).

The β-hCG-related proteins are preferably prepared by any chemical or enzymatic synthesis method known in the art, as described supra herein.

Fractionation of Sources of hCG

The present inventors have found that the component(s) of a source of hCG having therapeutic activity can be further isolated by fractionation of the source of hCG. The inventors have fractionated the active portions of the commercial hCG preparation APL™ (Wyeth-Ayerst) and human early pregnancy urine as described herein. Other sources of hCG include, but are not limited to, urine from women in the second and third trimester of pregnancy, urine from proteinuria patients (both pregnant women with preeclampsia and patients with nephrotic syndromes), urine from patients with hCG secreting tumors, and pituitary glands. However, those skilled in the art will appreciate that any source of hCG or β-hCG having anti-HIV activity and/or anti-KS activity and/or a pro-hematopoietic effect can be fractionated to further isolate the active components. The source of hCG or β-hCG can be fractionated using any technique available in the art for the separation and isolation of molecules, for example but not limited to, sizing chromatography, ion-exchange chromatography, affinity chromatography, etc.

Additionally, the present inventors have found that different preparations of hCG and β-hCG have variable effects on HIV infection, KS cell growth and hematopoiesis both in vitro and in vivo. Specifically, the inventors found that among the commercial preparations of (non-recombinant) hCG they investigated, hCG from Fujisawa was the most effective, hCG APL™ (Wyeth-Ayerst) the next most effective, and PREGNYL™ (Organon) the next most effective in inhibiting HIV infection and replication. A highly purified hCG preparation and recombinant β-hCG were found not to be active in inhibiting HIV infection, KS cell growth and promoting hematopoiesis in vitro. In fact, the present inventors have shown that specific size fractions of an active hCG preparation (APL™; Wyeth Ayerst) and human early (i.e. first trimester) pregnancy urine have anti-HIV and pro-hematopoieitic activities in vitro and anti-KS activity both in vitro and in vivo, as described infra herein.

These active fractions were eluted from the sizing matrix as or close to (i.e., within 5 fractions (where the fractions are 4 ml fractions using a SUPERDEX™ 200 (Pharmacia) column which is 26 mm² by 60 mm)) the fractions containing or that would contain material that is approximately 40 kD (±8 kD), 15 kD (±3 kD) and 2–3 kD (±2 kD) molecular weight. One skilled in the art would understand that these fractions could be subjected to further size fractionation to further isolate the component of these fractions having the anti-HIV and/or anti-KS activity. Additionally, other methods of fractionation, such as ion-exchange chromatography, affinity chromatography are well known in the art; those skilled in the art would be able to use any available fractionation techniques to obtain the active fractions from the active hCG preparations and human early (first trimester) pregnancy urine (or any other preparation containing hCG or β-hCG).

In a specific embodiment, the invention provides a first composition comprising one or more first components of a second composition comprising native hCG or native β-hCG, said first components being separated from other components of the hCG or β-hCG sample, said first components being active to inhibit HIV infection or replication or Kaposi's sarcoma or having a pro-hematopoietic activity, and said second composition being active to inhibit HIV infection or replication or Kaposi's sarcoma or having a pro-hematopoietic activity, and said native hCG or native β-hCG not being purified to homogeneity in said second composition.

In particular the invention provides a composition comprising components which have been separated from other components of the native hCG or native β-hCG sample by sizing column chromatography, preferably where the components elute from a gel filtration, preferably a SUPERDEX™ 200, sizing column with an apparent approximate molecular weight of 40 kD, 14 kD or 2–3 kD as determined relative to the elution of a hCG heterodimer, having a molecular weight of 77 kD, and a β-hCG core protein (β-hCG amino acids 6–40 linked via a disulfide bond to β-hCG amino acids 55–92, as depicted in FIG. 8 (SEQ ID NO:2)), having a molecular weight of 10 kD. hCG preparations and fractions of hCG preparations can be screened for efficacy in inducing proliferation of hematopoietic cells by the assays described herein or by any method known in the art.

Thus, in a preferred embodiment, a fraction, particularly a size fraction, of a source of native hCG or native β-hCG active in promoting hematopoiesis, particularly a size fraction of approximately 40 kD, 15 kD or 2–3 kD, is used to treat or prevent a hematopoietic deficiency.

The inventors have fractionated the active portions of the commercial hCG preparation APL™ (Wyeth-Ayerst) and human early (i.e. first trimester) pregnancy urine as described herein. Other sources of hCG include, but are not limited to, urine from women in the second and third trimester of pregnancy, urine from proteinuria patients (both pregnant women with preeclampsia and patients with nephrotic syndromes), urine from patients with hCG secreting tumors, and pituitary glands. However, those skilled in the art will appreciate that any source of hCG or β-hCG having anti-HIV activity and/or anti-KS activity and/or a pro-hematopoietic effect can be fractionated to further isolate the active components. The source of hCG or β-hCG can be fractionated using any technique available in the art for the separation and isolation of molecules, for example but not limited to, sizing chromatography, ion-exchange chromatography, affinity chromatography, etc.

Briefly, by way of example but not by way of limitation, urine can be prepared for fractionation as follows:

Urine is collected and stored either frozen or refrigerated for not more than two (2) days. Then, sodium azide is then added at a concentration of 1 gram/liter and the sample is stored frozen until sufficient material is collected for the fractionation.

At this point, the urine is thawed over night, the pH adjusted to 7.2 to 7.4 with sodium hydroxide and then centrifuged to remove any precipitate (alternatively, the precipitate can be allowed to sediment, e.g., for 1 hour at room temperature, approximately 75% of the supernatant is decanted, the remainder of the supernatant and the precipitate is centrifuged to pellet the precipitate, and the supernatant decanted and added to the first volume of decanted supernatant). The urine is then filtered through, e.g., a 45 micron filter to remove any remaining particulate matter.

Next, the urine is concentrated using any concentration method available in the art which does not remove higher molecular weight material, e.g., material larger than 3,000 daltons in molecular weight; for example, the material may be concentrated using a Pellicon (Millipore) filtration system with a membrane filter cassette having a molecular weight cut off of 3,000 daltons. Concentration with the Pellicon filtration system using the 3,000 molecular weight membrane filter cut off concentrates 30 liters of urine to 500 ml (i.e., a 60-fold concentration) overnight.

To remove salts and lipids, the concentrate can then be passed over a column containing a large volume of Sephadex G25 resin in 0.05 M ammonium bicarbonate (for example, 250 ml of the concentrate can be passed over a column of approximately 1.7 liters, washing the column with 25% ethanol between runs to remove adsorbed lipids and glycoprotein). The resulting desalted and delipidated urine concentrate is then lyophilized.

The lyophilized urine material or commercial hCG preparation (or any source of native hCG or β-hCG) is resuspended in either phosphate buffered saline (PBS—30 mM sodium phosphate buffer, pH 8.3) or in 0.10 M ammonium bicarbonate at a concentration and in a volume appropriate for the column upon which the sample will be loaded, for example, but not limited to 0.5 grams of protein in 6 ml (i.e., approximately 83 mg/ml). It is within the skill of the skilled artisan to determine the concentration and volume of the sample to be subjected to fractionation.

The sample can then be fractionated by any method known in the art for the separation of proteins. A preferred method is high resolution gel filtration on a Pharmacia pre-packed SUPERDEX™ 200 column (26/60) by HPLC using any available HPLC apparatus, e.g., with a Hewlett Packard 1050 HPLC equipped with a photodiode array detector. The resuspended sample is loaded onto the column in 30 mM phosphate buffer, pH 8.3, and the material can then be eluted from the column with 30 mM sodium phosphate buffer, pH 7.0; 2M NaCl in e.g. 4 ml fractions. Fractionation can also be performed using other types of chromatography matrices e.g., heparin, DEAE-cellulose, Sephadex A50, Sephadex G100, phenyl sepharose, or any sizing, ion-exchange, affinity chromatography or any other chromatography matrix available in the art. The column chromatography can also be run using any method available in the art, e.g., standard gravity flow or low pressure chromatography, FPLC, or reverse phase HPLC.

Many separation techniques are known in the art. Those skilled in the art would understand how to apply these known techniques to the fractionation of hCG preparations.

Once the material has been fractionated, any method known in the art, such as but not limited to, those described herein, can be used to determine which fractions have anti-HIV activity and/or anti-KS activity and/or a pro-hematopoietic effect.

When fractionating by size, such as fractionation on the SUPERDEX™ 200 column, the apparent molecular weight of material in the fractions can be determined by the relative elution of those fractions compared with the elution of specific hCG and β-hCG species having a known molecular weight or with the elution of known protein size markers. In general, proteins elute from a sizing column as a function of their molecular weight. The elution of, for example, hCG and the β-hCG core protein can be determined by assaying the column chromatography fractions for the presence of hCG and the β-hCG core protein, or any hCG or β-hCG species, by any immunoassay technique available in the art, such as radioimmunoassays (either liquid or solid phase), enzyme-linked assays or ELISA assays.

Antibodies, either polyclonal or, preferably, monoclonal, can be generated against hCG or the β-hCG core protein by any method known in the art. Preparation of monoclonal antibodies against hCG and β-hCG species have been described in the art, see, e.g., O'Connor et al., 1994, *Endocrine Reviews* 15:650–683; Krichevsky et al, 1991, *Endocrinology* 128:1255–1264; and Krichevsky et al., 1988, *Endorcrinology* 123:584–593. For the production of antibodies, various host animals can be immunized by injection with hCG, the β-hCG core protein or any other species of hCG, including but not limited to rabbits, mice, rats, etc. Various adjuvants may be used to increase the immunological response, depending on the host species, and including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and corynebacterium parvum. For preparation of monoclonal antibodies, any technique which provides for the production of antibody molecules by continuous cell lines in culture may be used. For example, the hybridoma technique originally developed by Kohler and Milstein (1975, Nature 256:495–497), as well as the trioma technique, the human B-cell hybridoma technique (Kozbor et al., 1983, Immunology Today 4:72), and the EBV-hybridoma technique to produce human monoclonal antibodies (Cole et al., 1985, in Monoclonal Antibodies and Cancer Therapy, Alan R. Liss, Inc., pp. 77–96). Monoclonal cells lines can then be screened for binding to the particular hCG or β-hCG species using the purified species in any type of immunoassay available in the art (see, e.g., Erlich et al., 1985, *Am. J. Reprod Immunol. Microbiol.* 8:48).

The fractions can then be assayed for the presence of the hCG or β-hCG species using a monoclonal antibody specific for the hCG or β-hCG species. The assay can be performed by any method known in the art. For example, an immunoradiometric assay (IRMA) can be used (Krichevsky et al., 1988, *Endocrinology* 123:584–593). Briefly, the IRMA assay is performed by adsorbing an antibody against the hCG or β-hCG species onto the surface of wells of a microtiter plate by incubation in a coating buffer (0.2 M sodium bicarbonate, pH 9.5) overnight at 4° C. The residual non-specific binding sites are blocked by the addition of a 1% bovine serum albumin solution (with 0.1% sodium azide) to the wells for 3 hours at room temperature, and the wells of the microtiter plate are then washed with deionized water. An aliquot of the fraction in assay buffer (0.01 M sodium phosphate, 0.15 M NaCl, 0.01 M EDTA, 0.1% sodium azide, 0.1% bovine γ-globulin, pH 7.4) is incubated in the wells for 24 hours at room temperature. The sample is then removed and the wells washed with deionized water. A solution of a second antibody specific for the hCG or β-hCG species, which antibody has been iodinated with $I^{125}$, (approximately 40,000 cpm/well) is incubated in the wells for 24 hours at room temperature. The iodinated antibody solution is removed and the wells washed five times with deionized water. The level of radioactivity in each well is then determined in a scintillation counter which can measure γ-irradiation.

In a specific embodiment, a preparation comprising hCG is used that contains not only the hCG heterodimer but also peptide fragments thereof, e.g., β chain peptides.

In a preferred embodiment of the invention, proteins (e.g., peptides), the amino acid sequence of which consists of one or more portions effective to increase the production of one or more hematopoietic cell types of the β-hCG sequence (β-hCG peptides) are used to treat or prevent HIV infection, cancer, wasting syndrome and/or hematopoietic deficiencies. In various specific embodiments, the portion(s) of the β-hCG sequence are at least 3, 5, 10, 20, or 30 amino acids. These proteins are preferably β-hCG peptides, or nucleic acids encoding β-hCG peptides, from amino acids 41–54, 45–54, 47–53 and 45–57 (SEQ ID NOS:3–6, respectively) of FIG. 8 (a portion of SEQ ID NO:2). In other embodiments, these proteins are β-hCG peptides, or nucleic acids encoding β-hCG peptides, of amino acids 41–53, 42–53, 43–53, 44–53, 44–57, 45–53, 46–53, 45–54, 45–55, 45–56, 45–58, 47–54, 47–55, 47–56, 47–58, 48–145, 58–145, 109–145, 7–40, 46–65, or 48–56 (SEQ ID NOS:8–25 or 33–35, respectively) of FIG. 8 (a portion of SEQ ID NO:2), and preferably containing a sequence from amino acids 41–54, 45–54 or 109–119 (SEQ ID NOS:3, 4 or 7, respectively) of FIG. 8 (a portion of SEQ ID NO:2), and most preferably containing a sequence from amino acids 47–53 or 45–57 of FIG. 8 (a portion of SEQ ID NO:2), or circular [C44V]45–57 peptide (SEQ ID NO:26), or branched 45–57 (SEQ ID NO:6) peptide, or branched circular [V44C]45–57 peptide are used to treat or prevent hematopoietic deficiencies.

In another embodiment, the invention provides proteins, the amino acid sequences of which consist of two or more at least 5, 7 or 10 amino acid, non-naturally contiguous portions of the β-hCG sequence (FIG. 8 (SEQ ID NO:2)) linked by peptide bonds between the N-terminus of one portion and the C-terminus of another portion. Specifically, proteins, the amino acid sequences of which consist of amino acids 45–57 (SEQ ID NO:6) linked at the C-terminus via a peptide bond to the N-terminus of a peptide of amino acids 109–119 (SEQ ID NO:7) or linked at the N-terminus via a peptide bond to the C-terminus of amino acids 110–119 (SEQ ID NO:27); or an isolated protein of amino acids 47–57 (SEQ ID NO:28) linked at the C-terminus via a peptide bond to the N-terminus of amino acids 108–119 (SEQ ID NO:29) of the β-hCG sequence depicted in FIG. 4 (portions of SEQ ID NO:2), i.e., the fused peptides denoted as 45–57::109–119, 110–119::45–57, or 47–57::108–119 (SEQ ID NOS:30–32, respectively). Derivatives of the foregoing fusion proteins are also provided (e.g., branched, cyclized, N- or C-terminal chemically modified, etc.). In another embodiment, fusion proteins comprising two or more such portions of the β-hCG sequence are provided; such portions may or may not be contiguous to one another (i.e., an intervening sequence may be present). Molecules comprising such portions linked by hydrocarbon linkages are also provided. In another embodiment, the peptides of the invention (i) have an amino acid sequence consisting of no more than 8 peptides of the β-hCG sequence (FIG. 8 (SEQ ID NO:2)) and (ii) comprise amino acid numbers 47–53 (SEQ ID NO:5) of β-hCG (FIG. 8 (SEQ ID NO:2)).

In another embodiment, a protein is used that (a) comprises one or more portions of the amino acid sequence consisting of β-hCG, a peptide having an amino acid sequence consisting of said portion(s) being effective to increase production of one or more hematopoietic cell types; and (b) lacks β-hCG amino acids contiguous to said portion(s). In another embodiment, a protein is used that (a) comprises a β-hCG amino acid sequence consisting of amino acid numbers 41–54, 45–54, 47–53, 45–57, 109–119, 41–53, 42–53, 43–53, 44–53, 44–57, 45–53, 46–53, 45–54, 45–55, 45–56, 45–58, 47–54, 47–55, 47–56, 47–58, 48–145, 58–145, 109–119, 109–145, 7–40, 46–65 or 48–56 (SEQ ID NOS:3–25 or 33–35, respectively) as depicted in FIG. 8 (a portion of SEQ ID NO:2) and (b) lacks β-hCG amino acids contiguous to said sequence. Peptides containing the above sequences in which only conservative substitutions have been made are also provided by the present invention, as but one example of peptide derivatives within the scope of the invention. Analogs of the above-mentioned proteins and peptides which have one or more amino acid substitutions forming a branched peptide (e.g., by substitution with an amino acid or amino acid analog having a free amino- or carboxy-side chain that forms a peptide bond with a sequence of one or more amino acids, including but not limited to prolines) or allowing circularization of the peptide (e.g., by substitution with a cysteine, or insertion of a cysteine at the amino- or carboxy-terminus or internally), to provide a sulfhydryl group for disulfide bond formation, are also provided.

Other β-hCG peptides, and nucleic acids encoding these peptides, may have utility in the therapeutic methods of the invention. The utility of β-hCG peptides may be determined by the in vitro and in vivo assays described in herein or by any other method known in the art.

In specific embodiments, peptides of less than 50, or less than 25, amino acids are provided.

The invention also relates to derivatives, modifications and analogs of β-hCG peptides. One embodiment of the invention provides a purified derivative of a protein effective to increase the production of one or more hematopoietic cell types, which protein contains an amino acid sequence of one or more portions effective to increase the production of one or more hematopoietic cell types of β-hCG. Another embodiment of the invention provides a purified derivative of a protein effective to increase the production of one or more hematopoietic cell types, the amino acid sequence of which protein is selected from the group consisting of amino acid numbers 41–54, 45–54, 47–53, 45–57, 109–119, 41–53, 42–53, 43–53, 44–53, 44–57, 45–53, 46–53, 45–54, 45–55, 45–56, 45–58, 47–54, 47–55, 47–56, 47–58, 48–145, 58–145, 109–145, 7–40, 46–65 or 48–56 (SEQ ID NOS:3–25 or 33–35, respectively) as depicted in FIG. 8 (a portion of SEQ ID NO:2). In another embodiment, β-hCG peptide derivatives can be made by altering the β-hCG peptide sequence by substitutions, additions or deletions that provide for therapeutically effective molecules. Thus, the β-hCG peptide derivatives include peptides containing, as a primary amino acid sequence, all or part of the particular β-hCG peptide sequence including altered sequences in which functionally equivalent amino acid residues are substituted for residues within the sequence resulting in a peptide which is functionally active. For example, one or more amino acid residues within the sequence can be substituted by another amino acid of a similar polarity which acts as a functional equivalent, resulting in a silent alteration. Conservative substitutions for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Such β-hCG peptide derivatives can be made either by chemical peptide synthesis or by recombinant production from a nucleic acid encoding the β-hCG peptide which nucleic acid has been mutated. Any technique for mutagenesis known in the art can be used, including but not limited to, chemical mutagenesis, in vitro site-directed mutagenesis (Hutchinson, C., et al., 1978, *J. Biol. Chem* 253:6551), use of TAB® linkers (Pharmacia), etc.

In addition, β-hCG peptides and analogs and derivatives of β-hCG peptides can be chemically synthesized. (See, e.g., Merrifield, 1963, 1. *Amer. Chem. Soc.* 85:2149–2156.) For example, peptides can be synthesized by solid phase techniques, cleaved from the resin, and purified by preparative high performance liquid chromatography (e.g., see Creighton, 1983, Proteins, Structures and Molecular Principles, W. H. Freeman and Co., N.Y., pp. 50–60). β-hCG peptides can also be synthesized by use of a peptide synthesizer. The composition of the synthetic peptides may be confirmed by amino acid analysis or sequencing (e.g., the Edman degradation procedure; see Creighton, 1983, Proteins, Structures and Molecular Principles, W. H. Freeman and Co., N.Y., pp. 34–49). Furthermore, if desired, nonclassical amino acids or chemical amino acid analogs can be introduced as a substitution or addition into the β-hCG peptide. Non-classical amino acids include but are not limited to the D-isomers of the common amino acids, 2,4-diaminobutyric acid, α-amino isobutyric acid, 4-aminobutyric acid, Abu, 2-amino butyric acid, γ-Abu, ε-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, β-alanine, fluoro-amino acids, designer amino acids such as β-methyl amino acids, Cα-methyl amino acids, Nα-methyl amino acids, and amino acid analogs in general. Furthermore, the amino acid can be D (dextrorotary) or L (levorotary).

By way of example but not by way of limitation, peptides of the invention can be chemically synthesized and purified as follows: Peptides can be synthesized by employing the N-α-9-fluorenylmethyloxycarbonyl or Fmoc solid phase peptide synthesis chemistry using a Rainin Symphony Multiplex Peptide Synthesizer. The standard cycle used for coupling of an amino acid to the peptide-resin growing chain generally includes: (1) washing the peptide-resin three times for 30 seconds with N,N-dimethylformamide (DMF); (2) removing the Fmoc protective group on the amino terminus by deprotection with 20% piperdine in DMF by two washes for 15 minutes each, during which process mixing is effected by bubbling nitrogen through the reaction vessel for one second every 10 seconds to prevent peptide-resin settling; (3) washing the peptide-resin three times for 30 seconds with DMF; (4) coupling the amino acid to the peptide resin by addition of equal volumes of a 250 mM solution of the Fmoc derivative of the appropriate amino acid and an activator mix consisting or 400 mM N-methylmorpholine and 250 mM (2-(1H-benzotriazol-1-4))-1,1,3,3-tetramethyluronium hexafluorophosphate (HBTU) in DMF; (5) allowing the solution to mix for 45 minutes; and (6) washing the peptide-resin three times for 30 seconds of DMF. This cycle can be repeated as necessary with the appropriate amino acids in sequence to produce the desired peptide. Exceptions to this cycle program are amino acid couplings predicted to be difficult by nature of their hydrophobicity or predicted inclusion within a helical formation during synthesis. For these situations, the above cycle can be modified by repeating step 4 a second time immediately upon completion of the first 45 minute coupling step to "double couple" the amino acid of interest. Additionally, in the first coupling step in peptide synthesis, the resin can be allowed to swell for more efficient coupling by increasing the time of mixing in the initial DMF washes to three 15 minute washes rather than three 30 second washes. After peptide synthesis, the peptide can be cleaved from the resin as follows: (1) washing the peptide-resin three times for 30 seconds with DMF; (2) removing the Fmoc protective group on the amino terminus by washing two times for 15 minutes in 20% piperdine in DMF; (3) washing the peptide-resin three times for 30 seconds with DMF; and (4) mixing a cleavage cocktail consisting of 95% trifluoroacetic acid (TFA), 2.4% water, 2.4% phenol, and 0.2% triisopropysilane with the peptide-resin for two hours, then filtering the peptide in the cleavage cocktail away from the resin, and precipitating the peptide out of solution by addition of two volumes of ethyl ether. Specifically, to isolate the peptide, the ether-peptide solution can be allowed to sit at −20° C. for 20 minutes, then centrifuged at 6,000×G for 5 minutes to pellet the peptide, and the peptide can be washed three times with ethyl ether to remove residual cleavage cocktail ingredients. The final peptide product can be purified by reversed phase high pressure liquid chromatography (RP-HPLC) with the primary solvent consisting of 0.1% TFA and the eluting buffer consisting of 80% acetonitrile and 0.1% TFA. The purified peptide can then be lyophilized to a powder.

In a preferred embodiment, the invention provides a peptide with branched amino acids (branched peptide), preferably a branched peptide of amino acids 45–57 (SEQ ID NO:6) with branches occurring at positions 47 and 51, respectively, instead of the Gly and Ala residues normally present. Most preferably, diaminobutyric acid is substituted for the gly and ala residues at positions 47 and 51, respectively, and proline bonded to both diaminobutyric acid residues (45–57 branched) as shown in FIG. 9A.

In other specific embodiments, branched versions of the β-hCG peptides listed hereinabove are provided, e.g., by substituting one or more amino acids within the β-hCG sequence with an amino acid or amino acid analog with a free side chain capable of forming a peptide bond with one or more amino acids (and thus capable of forming a "branch").

Branched peptides may be prepared by any method known in the art for covalently linking any naturally occurring or synthetic amino acid to any naturally occurring or synthetic amino acid in a peptide chain which has a side chain group able to react with the amino or carboxyl group on the amino acids so as to become covalently attached to the peptide chain. In particular, amino acids with a free amino side chain group, such as, but not limited to, diaminobutyric acid, lysine, arginine, ornithine, diaminopropionic acid and citrulline, can be incorporated into a peptide so that an amino acid can form a branch therewith, for example, by forming a peptide bond to the free amino side group, from that residue. Alternatively, amino acids with a free carboxyl side chain group, such as, but not limited to, glutamic acid, aspartic acid and homocitrulline, can be incorporated into the peptide so that an amino acid can form a branch therewith, for example, by forming a peptide bond to the free carboxyl side group, from that residue. The amino acid forming the branch can be linked to a side chain group of an amino acid in the peptide chain by any type of covalent bond, including, but not limited to, peptide bonds, ester bonds and disulfide bonds. In a specific embodiment, amino acids, such as those described above, that are capable of forming a branch point, are substituted for β-hCG residues within a peptide having a β-hCG sequence.

Branched peptides can be prepared by any method known in the art. For example, but not by way of limitation, branched peptides can be prepared as follows: (1) the amino acid to be branched from the main peptide chain can be purchased as an N-α-tert-butyloxycarbonyl (Boc) protected amino acid pentafluorophenyl (Opfp) ester and the residue within the main chain to which this branched amino acid will be attached can be an N-Fmoc-α-γ-diaminobutyric acid; (2) the coupling of the Boc protected amino acid to diaminobutyric acid can be achieved by adding 5 grams of each precursor to a flask containing 150 ml DMF, along with 2.25 ml pyridine and 50 mg dimethylaminopyridine and allowing the solution to mix for 24 hours; (3) the peptide can then be extracted from the 150 ml coupling reaction by mixing the reaction with 400 ml dichlormethane (DCM) and 200 ml 0.12N HCl in a 1 liter separatory funnel, and allowing the phases to separate, saving the bottom aqueous layer and re-extracting the top layer two more times with 200 ml 0.12 N HCl; (4) the solution containing the peptide can be dehydrated by adding 2–5 grams magnesium sulfate, filtering out the magnesium sulfate, and evaporating the remaining solution to a volume of about 2–5 ml; (5) the dipeptide can then be precipitated by addition of ethyl acetate and then 2 volumes of hexanes and then collected by filtration and washed two times with cold hexanes; and (6) the resulting filtrate can be lyophilized to achieve a light powder form of the desired dipeptide. Branched peptides prepared by this method will have a substitution of diaminobutyric acid at the amino acid position which is branched. Branched peptides containing an amino acid or amino acid analog substitution other than diaminobutyric acid can be prepared analogously to the procedure described above, using the N-F-moc coupled form of the amino acid or amino acid analog.

In a preferred embodiment, the peptide is a cyclic peptide, preferably a cyclic peptide of β-hCG amino acids 44–57 (SEQ ID NO:26) with cysteine substituted for valine at position 44 and circularized via a disulfide bond between the cysteine residues at positions 44 and 57 (C[V44C] 45–57) (FIG. 9B) or a cyclic fused peptide of β-hCG amino acids 110–119 (SEQ ID NO:27) linked at the C-terminus by a peptide bond to the N-terminus of amino acids 45–57 (SEQ ID NO:6) and circularized via a disulfide bond between the cysteine residues at positions 110 and 57. In another preferred embodiment, the peptide is a cyclic branched peptide of β-hCG amino acids 44–57 (SEQ ID NO:12) with cysteine substituted for valine at position 44 and circularized via a disulfide bond between the cysteine residues at positions 44 and 57 and positions 47 and 51 substituted with a diaminobutyric acid residue on which a proline is peptide bonded to its free amino sidechain.

Cyclization can be, for example, but not by way of limitation, via a disulfide bond between two cysteine residues or via an amide linkage. For example, but not by way of limitation, disulfide bridge formation can be achieved by (1) dissolving the purified peptide at a concentration of between 0.1.–0.5 mg/ml in 0.01 M ammonium acetate, pH 7.5; (2) adding to the dissolved peptide 0.01 M potassium ferricyanide dropwise until the solution appears pale yellow in color and allowing this solution to mix for 24 hours; (3) concentrating the cyclized peptide to 5–10 ml of solution, repurifying the peptide by reverse phase-high pressure liquid chromatography (RP-HPLC) and finally lyophilizing the peptide. In a specific embodiment, in which the peptide does not contain two appropriately situated cysteine residues, cysteine residues can be introduced at the amino-terminus and/or carboxy-terminus and/or internally such that the peptide to be cyclized contains two cysteine residues spaced such that the residues can form a disulfide bridge. Alternatively, a cyclic peptide can be obtained by generating an amide linkage using, for example but not limited to, the following protocol: An allyl protected amino acid, such as aspartate, glutamate, asparagine or glutamine, can be incorporated into the peptide as the first amino acid, and then the remaining amino acids are coupled on. The allyl protective group can be removed by a two hour mixing of the peptide-resin with a solution of tetrakistriphenylphophine palladium (0) in a solution of chloroform containing 5% acetic acid and 2.5% N-methylmorpholine. The peptide resin can be washed three times with 0.5% N,N-diisopropylethylamine (DIEA) and 0.5% sodium diethyldithiocabamate in DMF. The amino terminal Fmoc group on the peptide chain can be removed by two incubations for 15 minutes each in 20% piperdine in DMF, and washed three times with DMF for 30 seconds each. The activator mix, N-methylmorpholine and HBTU in DMF, can be brought onto the column and allowed to couple the free amino terminal end to the carboxyl group generated by removal of the allyl group to cyclize the peptide. The peptide can cleaved from the resin as described in the general description of chemical peptide synthesis above and the peptide purified by reverse phase-high pressure liquid chromatography (RP-HPLC). In a specific embodiment, in which the peptide to be cyclized does not contain an allyl protected amino acid, an allyl protected amino acid can be introduced into the sequence of the peptide, at the amino-terminus, carboxy-terminus or internally, such that the peptide can be cyclized.

β-hCG peptides can also be obtained by recombinant expression techniques. (See, e.g., Sambrook et al., 1989, *Molecular Cloning, A Laboratory Manual*, Cold Spring Harbor Laboratory, 2d Ed., Cold Spring Harbor, N.Y., Glover, D. M. (ed.), 1985, *DNA Cloning: A Practical Approach*, MRL Press, Ltd., Oxford, U.K., Vol. I, II). The nucleic acid sequence encoding hCG has been cloned and the sequence determined (see FIG. 8 and Xia, H., 1993, *J. Molecular Endocrinology* Jun. 10, 1993:337–343; Sherman, G. B., 1992, *J. Molecular Endocrinology*, Jun. 6, 1992:951–959; Gieseman, L. K. (ed.), 1991, *Basic and Chemical Endocrinology*, pp. 543–567; Ward et al., 1991, in *Reproduction in Domestic Animals*, 4th ed., P. T. Coppos, ed., pp. 25–80, Academic Press, New York) and can be isolated using well-known techniques in the art, such as screening a library, chemical synthesis, or polymerase chain reaction (PCR).

To recombinantly produce a β-hCG peptide, a nucleic acid sequence encoding the β-hCG peptide is operatively linked to a promoter such that the β-hCG peptide is produced from said sequence. For example, a vector can be introduced into a cell, within which cell the vector or a portion thereof is expressed, producing the β-hCG peptide. In a preferred embodiment, the nucleic acid is DNA if the source of RNA polymerase is DNA-directed RNA polymerase, but the nucleic acid may also be RNA if the source of polymerase is RNA-directed RNA polymerase or if reverse transcriptase is present in the cell or provided to produce DNA from the RNA. Such a vector can remain episomal or become chromosomally integrated, as long as it can be transcribed to produce the desired RNA. Such vectors can be constructed by recombinant DNA technology methods standard in the art. Vectors can be plasmid, viral, or others known in the art, used for replication and expression in bacterial or mammalian cells.

Expression of the sequence encoding the β-hCG peptide can be by any promoter known in the art to act in bacterial or mammalian cells. Such promoters can be inducible or constitutive. Such promoters include, but are not limited to: the SV40 early promoter region (Bernoist and Chambon, 1981, *Nature* 290:304–310), the promoter contained in the 3' long terminal repeat of Rous sarcoma virus (Yamamoto et al., 1980, *Cell* 22:787–797), the HSV-1 (herpes simplex virus-1) thymidine kinase promoter (Wagner et al., 1981, *Proc. Natl. Acad. Sci. USA* 78:1441–1445), the regulatory sequences of the metallothionein gene (Brinster et al., 1982, *Nature* 296:39–42), etc., as well as the following animal transcriptional control regions, which exhibit tissue specificity and have been utilized in transgenic animals: elastase I gene control region which is active in pancreatic acinar cells (Swift et al., 1984, *Cell* 38:639–646; Ornitz et al., 1986, *Cold Spring Harbor Symp. Quant. Biol.* 50:399–409; MacDonald, 1987, *Hepatology* 7:425–515); insulin gene control region which is active in pancreatic beta cells (Hanahan, 1985, *Nature* 315:115–122), immunoglobulin gene control region which is active in lymphoid cells (Grosschedl et al., 1984, *Cell* 38:647–658; Adames et al., 1985, *Nature* 318:533–538; Alexander et al., 1987, *Mol. Cell. Biol.* 7:1436–1444), mouse mammary tumor virus control region which is active in testicular, breast, lymphoid and mast cells (Leder et al., 1986, *Cell* 45:485–495), albumin gene control region which is active in liver (Pinkert et al., 1987, *Genes and Devel.* 1:268–276), alpha-fetoprotein gene control region which is active in liver (Krumlauf et al., 1985, *Mol. Cell. Biol.* 5:1639–1648; Hammer et al., 1987, *Science* 235:53–58), alpha 1-antitrypsin gene control region which is active in the liver (Kelsey et al., 1987, *Genes and Devel.* 1:161–171), beta-globin gene control region which is active in erythroid cells (Mogram et al., 1985, *Nature* 315:338–340; Kollias et al., 1986, *Cell* 46, 89–94), myelin basic protein gene control region which is active in oligodendrocyte cells in the brain (Readhead et al., 1987, *Cell* 48:703–712), myosin light chain-2 gene control region which is active in skeletal muscle (Sani, 1985, *Nature* 314:283–286), and gonadotropin releasing hormone gene control region which is active in the hypothalamus (Mason et al., 1986, *Science* 234:1372–1378). The promoter element which is operatively linked to the nucleic acid encoding the β-hCG peptide can also be a bacteriophage promoter with the source of the bacteriophage RNA polymerase expressed from a gene for the RNA polymerase on a separate plasmid, e.g., under the control of an inducible promoter, for example, a nucleic acid encoding the β-hCG peptide operatively linked to the T7 RNA polymerase promoter with a separate plasmid encoding the T7 RNA polymerase.

In a less preferred embodiment, peptides can be obtained by proteolysis of hCG followed by purification using standard techniques such as chromatography (e.g., HPLC), electrophoresis, etc.

Also included within the scope of the invention are β-hCG peptide derivatives which are differentially modified during or after synthesis, e.g., by benzylation, glycosylation, acetylation, phosphorylation, amidation, pegylation, derivatization by known protecting/blocking groups, proteolytic cleavage, linkage to an antibody molecule or other cellular ligand, etc. In specific embodiments, the peptides are acetylated at the N-terminus and/or amidated at the C-terminus. Any of numerous chemical modifications may be carried out by known techniques, including but not limited to acetylation, formylation, oxidation, reduction; metabolic synthesis in the presence of tunicamycin; etc.

In another embodiment, the β-hCG peptide derivative is a chimeric, or fusion, protein comprising a functional β-hCG peptide joined at its amino- or carboxy-terminus via a peptide bond to an amino acid sequence of a different protein. In one embodiment, such a chimeric protein is produced by recombinant expression of a nucleic acid encoding the protein (comprising a β-hCG-coding sequence joined in-frame to a coding sequence for a different protein). Such a chimeric product can be made by ligating the appropriate nucleic acid sequences encoding the desired amino acid sequences to each other by methods known in the art, in the proper coding frame, and expressing the chimeric product by methods commonly known in the art. Alternatively, such a chimeric product may be made by protein synthetic techniques, e.g., by use of a peptide synthesizer.

Gene Therapy

In a specific embodiment, nucleic acids comprising a sequence encoding β-hCG or a β-hCG peptide or fused β-hCG peptides (i.e., two or more β-hCG peptides linked at the N-termini and C-termini via peptide bond(s)), are administered for treatment or prevention of HIV infection, wasting, and/or cancer, and/or promotion of hematopoiesis by way of gene therapy. Gene therapy refers to therapy performed by the administration of a nucleic acid to a subject. In this embodiment of the invention, the nucleic acid produces its encoded protein that mediates a therapeutic effect. For example, any of the methods for gene therapy available in the art can be used according to the present invention. Exemplary methods are described below.

For general reviews of the methods of gene therapy, see Goldspiel et al., 1993, *Clinical Pharmacy* 12:488–505; Wu and Wu, 1991, *Biotherapy* 3:87–95; Tolstoshev, 1993, *Ann. Rev. Pharmacol. Toxicol.* 32:573–596; Mulligan, 1993, *Science* 260:926–932; and Morgan and Anderson, 1993, *Ann. Rev. Biochem.* 62:191–217; May, 1993, *TIBTECH* 11(5):155–215. Methods commonly known in the art of recombinant DNA technology which can be used are described in Ausubel et al. (eds.), 1993, Current Protocols in Molecular Biology, John Wiley & Sons, NY; and Kriegler, 1990, Gene Transfer and Expression, A Laboratory Manual, Stockton Press, NY.

In a preferred aspect, the nucleic acid encoding β-hCG or a β-hCG peptide or fused β-hCG peptides or related fusion protein is part of an expression vector that produces β-hCG protein or a β-hCG peptide or fused β-hCG peptides or related fusion protein in a suitable host. In particular, such a nucleic acid has a promoter operably linked to the nucleic acid sequence coding for β-hCG or a β-hCG peptide or fused β-hCG peptides or related fusion protein, said promoter being inducible or constitutive, and, optionally, tissue-specific. In another particular embodiment, a nucleic acid molecule is used in which the β-hCG sequences and any other desired sequences are flanked by regions that promote homologous recombination at a desired site in the genome, thus providing for intrachromosomal expression of β-hCG (Koller and Smithies, 1989, *Proc. Natl. Acad. Sci. USA* 86:8932–8935; Zijlstra et al., 1989, *Nature* 342:435–438).

Delivery of the nucleic acid into a patient may be either direct, in which case the patient is directly exposed to the nucleic acid or nucleic acid-carrying vector, or indirect, in which case, cells are first transformed with the nucleic acid in vitro, then administered to the patient. These two approaches are known, respectively, as in vivo or ex vivo gene therapy.

In a specific embodiment, the nucleic acid is directly administered in vivo, where it is expressed to produce the encoded product. This can be accomplished by any of numerous methods known in the art, e.g., by constructing it as part of an appropriate nucleic acid expression vector and administering it so that it becomes intracellular, e.g., by infection using a defective or attenuated retroviral or other viral vector (see U.S. Pat. No. 4,980,286), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering it in linkage to a peptide which is known to enter the cell or nucleus, e.g., by administering it in linkage to a ligand subject to receptor-mediated endocytosis (see e.g., Wu and Wu, 1987, *J. Biol. Chem.* 262:4429–4432) (which can be used to target cell types specifically expressing the receptors), etc. In a specific embodiment, the nucleic acid can be targeted in vivo for cell specific uptake and expression, by targeting a specific receptor (see, e.g., PCT Publications WO92/06180 dated Apr. 16, 1992 (Wu et al.); WO92/22635 dated Dec. 23, 1992 (Wilson et al.); WO92/20316 dated Nov. 26, 1992 (Findeis et al.); WO93/14188 dated Jul. 22, 1993 (Clarke et al.), WO93/20221 dated Oct. 14, 1993 (Young)). In another embodiment, a nucleic acid-ligand complex can be formed in which the ligand comprises a fusogenic viral peptide to disrupt endosomes, allowing the nucleic acid to avoid lysosomal degradation. Alternatively, the nucleic acid can be introduced intracellularly and incorporated within host cell DNA for expression, by homologous recombination (Koller and Smithies, 1989, *Proc. Natl. Acad. Sci. USA* 86:8932–8935; Zijlstra et al., 1989, *Nature* 342:435–438).

In a specific embodiment, a viral vector that contains the nucleic acid sequence encoding β-hCG or a β-hCG peptide or fused β-hCG peptides or related fusion protein is used. For example, a retroviral vector can be used (see Miller et al., 1993, *Meth. Enzymol.* 217:581–599). These retroviral vectors have been modified to delete retroviral sequences that are not necessary for packaging of the viral genome. Retroviral vectors are maintained in infected cells by integration into genomic sites upon cell division. The nucleic acid to be used in gene therapy is cloned into the vector, which facilitates delivery of the gene into a patient. More detail about retroviral vectors can be found in Boesen et al., 1994, *Biotherapy* 6:291–302, which describes the use of a retroviral vector to deliver the mdr1 gene to hematopoietic stem cells in order to make the stem cells more resistant to chemotherapy. Other references illustrating the use of retroviral vectors in gene therapy are: Clowes et al., 1994, *J. Clin. Invest.* 93:644–651; Kiem et al., 1994, *Blood* 83:1467–1473; Salmons and Gunzberg, 1993, *Human Gene Therapy* 4:129–141; and Grossman and Wilson, 1993, *Curr. Opin. in Genetics and Devel.* 3:110–114.

Adenoviruses are other viral vectors that can be used in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, 1993, *Current Opinion in Genetics and Development* 3:499–503 present a review of adenovirus-based gene therapy. Bout et al., 1994, *Human Gene Therapy* 5:3–10 demonstrated the use of adenovirus vectors to transfer genes to the respiratory epithelia of rhesus monkeys. Other instances of the use of adenoviruses in gene therapy can be found in Rosenfeld et al., 1991, *Science* 252:431–434; Rosenfeld et al., 1992, *Cell* 68:143–155; and Mastrangeli et al., 1993, *J. Clin. Invest.* 91:225–234.

Adeno-associated virus (AAV) has also been proposed for use in gene therapy (Walsh et al., 1993, *Proc. Soc. Exp. Biol. Med.* 204:289–300.) Herpes viruses are other viruses that can also be used.

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient.

In this embodiment, the nucleic acid is introduced into a cell prior to administration in vivo of the resulting recombinant cell. Such introduction can be carried out by any method known in the art, including, but not limited to, transfection, electroporation, microinjection, infection with a viral vector containing the nucleic acid sequences, cell fusion, chromosome-mediated gene transfer, microcell-mediated gene transfer, spheroplast fusion, etc. Numerous techniques are known in the art for the introduction of foreign genes into cells (see e.g., Loeffler and Behr, 1993, *Meth. Enzymol.* 217:599–618; Cohen et al., 1993, *Meth. Enzymol.* 217:618–644; Cline, 1985, *Pharmac. Ther.* 29:69–92) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a patient by various methods known in the art. In a preferred embodiment, recombinant blood cells (e.g., hematopoietic stem or progenitor cells) are administered intravenously. Additionally, epithelial cells can be injected, e.g., subcutaneously, or recombinant skin cells (e.g., keratinocytes) may be applied as a skin graft onto the patient. The amount of cells envisioned for use depends on the desired effect, patient state, etc., and can be determined by one skilled in the art.

In an embodiment in which recombinant cells are used in gene therapy, a nucleic acid sequence coding for β-hCG or a β-hCG peptide or fused β-hCG peptides or related fusion protein is introduced into the cells such that it is expressible by the cells or their progeny, and the recombinant cells are then administered in vivo for therapeutic effect. In a specific embodiment, stem or progenitor cells, preferably hematopoietic stem or progenitor cells, are used. Any stem and/or progenitor cells which can be isolated and maintained in vitro can potentially be used in accordance with this embodiment of the present invention.

Administration of hematopoietic, preferably hematopoietic stem and progenitor, cells which have been induced to proliferate with a Therapeutic of the invention and have undergone gene therapy, i.e., which have stably incorporated a heterologous gene capable of expression by their progeny cells, can be of great value in the treatment of diseases and disorders affecting cells of hematopoietic lineage. In one embodiment, hematopoietic reconstitution with such recombinant hematopoietic cells can be used in the treatment of genetic disorders of the hematopoietic system. Such genetic disorders include but are not limited to those listed in Table 1, supra. Genetic deficiencies or dysfunctions of hematopoietic cells can be treated by supplying, to a patient, recombinant stem and progenitor cells. In a specific embodiment, patients who have hematopoietic cells which lack a gene or have a mutant gene, can be provided stem and progenitor cells that have incorporated a functional counterpart of the deficient gene. In particular, such genes which can be subject to gene therapy include but are not limited to hemoglobin or enzymes which mediate its synthetic pathway (e.g., for treatment of anemias such as beta-thalassemia, sickle-cell disease).

In another specific embodiment, patients with infections by pathogenic microorganisms which occur in or affect a hematopoietic cell lineage can be treated with recombinant hematopoietic cells. Such recombinant hematopoietic cells can contain a heterologous gene which is expressed as a product which ameliorates disease symptoms, is toxic to the pathogen without significant detriment to the host, or interferes with the pathogen's life cycle, etc. Pathogens which cause infections which may be treated with recombinant stem cells according to this embodiment of the invention include but are not limited to lymphotropic viruses such as HIV; gram-negative bacilli such as Brucella or Listeria; the mycobacterium which cause tuberculosis, or which cause Hansen's disease (leprosy); parasites such as Plasmodium (the etiological agents of malaria), or Leishmania; and fungi (such as those that cause pneumonia and other lethal infections secondary to immunodeficiencies) (for a discussion of many of these disorders, see Harrison's Principles of Internal Medicine, 1970, 6th Edition, Wintrobe, M. M., et al., eds., McGraw-Hill, New York, pp. 798–1044).

As a particular embodiment, it is possible to construct recombinant stem or progenitor cells that express a sequence which is "anti-sense" to the nucleic acid of a hematopoietic cell pathogen. Such a sequence, which is complementary to the pathogen's RNA or DNA, can hybridize to and inactivate such RNA or DNA, inhibiting the function or expression of the nucleic acid and disrupting the pathogen's life cycle. As a particular example, recombinant hematopoietic cells can be used in the treatment of AIDS. Recombinant stem and progenitor cells which express an anti-sense nucleic acid that is complementary to a critical region (e.g., the long-terminal repeat or polymerase sequence) of the HIV genome (Wain-Hobson et al., 1985, *Cell* 40:9–17) can be used for hematopoietic reconstitution for the treatment of AIDS.

Many methods of gene therapy are available in the art (for general reviews of the methods of gene therapy, see Goldspiel et al., 1993, *Clinical Pharmacy* 12:488–505; Wu and Wu, 1991, *Biotherapy* 3:87–95; Tolstoshev, 1993, *Ann. Rev. Pharmacol. Toxicol.* 32:573–596; Mulligan, 1993, *Science* 260:926–932; and Morgan and Anderson, 1993, *Ann. Rev. Biochem.* 62:191–217; May, 1993, *TIBTECH* 11(5) :155–215). Methods commonly known in the art of recombinant DNA technology which can be used are described in Ausubel et al. (eds.), 1993, Current Protocols in Molecular Biology, John Wiley & Sons, NY; and Kriegler, 1990, Gene Transfer and Expression, A Laboratory Manual, Stockton Press, NY.

In a preferred aspect, the nucleic acid which provides a gene product desired in a subject is introduced into an expression vector that produces the gene product. In particular, such a nucleic acid has a promoter operably linked to the nucleic acid sequence of interest, said promoter being inducible or constitutive, and, optionally, tissue-specific. In another particular embodiment, a nucleic acid molecule is used in which the sequences of interest are flanked by regions that promote homologous recombination at a desired site in the genome, thus providing for intrachromosomal expression of the desired protein (Koller and Smithies, 1989, *Proc. Natl. Acad. Sci. USA* 86:8932–8935; Zijistra et al., 1989, *Nature* 342:435–438).

In an embodiment of the invention, the nucleic acid is introduced into a hematopoietic cell that is then expanded by exposure to a Therapeutic of the invention prior to administration in vivo of the resulting recombinant cell. Alternatively, the nucleic acid can be introduced after expansion. Such introduction can be carried out by any method known in the art, including, but not limited to, transfection, electroporation, microinjection, infection with a viral vector containing the nucleic acid sequences, cell fusion, chromosome-mediated gene transfer, microcell-mediated gene transfer, spheroplast fusion, etc. Numerous techniques are known in the art for the introduction of foreign genes into cells (see, e.g., Loeffler and Behr, 1993, *Meth. Enzymol.* 217:599–618; Cohen et al., 1993, *Meth. Enzymol.* 217:618–644; Cline, 1985, *Pharmac. Ther.* 29:69–92) and may be used to construct the recombinant hematopoietic cells for purposes of gene therapy. The technique should provide for the stable transfer of the nucleic acid to the cell, so that the nucleic acid is expressible by the cell and preferably heritable and expressible by its cell progeny. The resulting recombinant cells can be delivered to a patient by various methods known in the art. In a preferred embodiment, recombinant hematopoietic cells are administered intravenously. The amount of cells envisioned for use depends on the desired effect, patient state, etc., and can be determined by one skilled in the art.

Preparation of Hematopoietic Cells in vitro

Sources of hematopoietic stem and progenitor cells, which cells can be induced to proliferate according to one embodiment of the present invention, include but are not limited to bone marrow, fetal and neonatal blood (preferably from the umbilical cord and/or placenta), fetal liver, adult peripheral blood, neonatal thymus, and neonatal spleen. The foregoing list of sources is deemed to include cell samples (e.g., cryopreserved cells, cell lines, long-term cell cultures) derived therefrom. The source is mammalian, e.g., mouse, cow, horse, primate, monkey, and is most preferably human. Techniques for obtaining such stem and progenitor cells are well known in the art. For example, in one particular embodiment, human bone marrow cells can be obtained from the posterior iliac crest by needle aspiration (see, e.g., Kodo et al., 1984, *J. Clin. Invest.* 73:1377–1384). Neonatal blood can be obtained at birth by direct drainage from the umbilical cord and/or by needle aspiration from the delivered placenta at the root and at distended veins (see U.S. Pat. Nos. 5,004,681 and 5,192,553). Fetal blood can be obtained, e.g., by taking it from the fetal circulation at the placental root with the use of a needle guided by ultrasound (Daffos et al., 1985, *Am. J. Obstet. Cynecol.* 153:655–660; Daffos et al., 1983, *Am. J. Obstet. Gynecol.* 146:985), by placentocentesis (Valenti, 1973, *Am. J. Obstet. Gynecol.* 115:851; Cao et al., 1982, *J. Med. Genet.* 19:81), by fetoscopy (Rodeck, C. H., 1984, in *Prenatal Diagnosis,* Rodeck, C. H. and Nicolaides, K. H., eds., Royal College of Obstetricians and Gynaecologists, London), etc.

The method of the invention which comprises contacting hematopoietic stem and/or progenitor cells (or other hematopoietic cells) with a Therapeutic of the invention, can be carried out on unseparated, partially separated, or purified cell populations, before and/or after cryopreservation (and thawing) or in vitro culturing of such cell populations, before and/or after introduction of a recombinant gene, and any other desired manipulations of the cells. In a preferred aspect, samples (e.g. bone marrow or adult blood or neonatal blood) can be subjected to physical and/or immunological cell separation procedures so as to enrich for hematopoietic stem and progenitor cells (e.g., prior to culturing in the presence of a Therapeutic of the invention to induce proliferation of the cells).

Various procedures are known in the art and can be used to enrich for stem and progenitor cells. These include but are not limited to equilibrium density centrifugation, velocity sedimentation at unit gravity, immune rosetting and immune adherence, counterflow centrifugal elutriation, T lymphocyte depletion, and fluorescence-activated cell sorting, alone or in combination. Procedures have been reported for the isolation of very highly enriched populations of stem/progenitor cells. U.S. Pat. No. 5,061,620 dated Oct. 29, 1991 discloses a method for isolation of human hematopoietic stem cells. Murine CFU-S have been purified by several groups using slightly different procedures (Visser et al., 1984, *J. Exp. Med.* 59:1576; Nijhof et al., 1984, *Exp. Cell Res.* 155:583; Bauman et al., 1986,*J. Cell. Physiol.* 128:133; Lord and Spooncer, 1986, *Lymphokine Res.* 5:59). Studies using human (Emerson et al., 1985, *J. Clin. Invest.* 76:1286) or murine (Nicola et al., 1981, *Blood* 58:376) fetal liver cells have yielded highly enriched progenitor cells with up to 90% of them being colony forming cells for multi-, erythroid-, and granulocyte-macrophage lineages. CFU-E have also been very highly enriched (Nijhof et al., 1983, *J. Cell Biol.* 96:386). Purification of adult mouse marrow CFU-GM with cloning efficiencies of up to 99% in semi-solid medium has been accomplished by pretreatment of mice three days prior to sacrifice with cyclophosphamide, density separation of cells on Ficoll-Hypaque, and counter-flow centrifugal elutriation (Williams et al., 1987, *Exp. Hematol.* 15:243). The resulting fraction of cells contained no detectable CFU-GEMM, BFU-E or CFU-MK, but up to 10% of the cells formed CFU-S measured at day 12. These procedures, or modifications thereof, can be used.

Human stem and progenitor cells are present in the non-adherent, low density, T-lymphocyte-depleted fraction of bone marrow, spleen, and adult and cord blood cells. Low density (density less than 1.077 gm/cm$^3$) cells can be separated by use of Ficoll-Hypaque (Pharmacia Fine Chemicals, Piscataway, N.J.) or Percol (Broxmeyer, H. E., 1982, *J. Clin. Invest.* 69:632–642). In this procedure, the mature cells of the granulocytic series, which are not needed for transplantation, are removed in the dense fraction which goes to the bottom of the tube. An adherence/nonadherence separation protocol can also be used for enrichment of hematopoietic stem and progenitor cells.

It is also possible to use cell separation procedures that entail immunological recognition of cells. Stem and progenitor cells can be isolated by positive or negative selection using antibodies that recognize antigenic determinants on the surface of cells. One means is to separate the cells by using monoclonal antibodies which recognize cell surface determinants on these cells, in conjunction with separation procedures such as fluorescence-activated cell sorting or panning (Broxmeyer et al., 1984, *J. Clin. Invest.* 73:939–953). Human hematopoietic stem and progenitor cells contain antigenic determinants that are not present on all other cells, which can be used in antibody selection protocols for enrichment purposes; such antigens include but are not limited to those described infra.

Within the human system, several antigens have been found on stem/progenitor cells. The first antigenic system studied intensively was that of the MHC class II antigens, especially HLA-DR. This antigen has been found on CFU-GEMM, BFU-E, and CFU-GM (Lu et al., 1983, *Blood* 61:250; Winchester et al., 1977, *Proc. Natl. Acad. Sci. U.S.A.* 74:4012; Busch et al., 1987, *Blut* 54:179). Several investigators have suggested that HLA-DR are not found, or are present at a low density on cells earlier than CFU-GEMM (Moore et al., 1980, *Blood* 55:682; Keating et al., 1984, *Blood* 64:1159).

Groups of antibodies have been used to distinguish different progenitors of the granulocyte-macrophage lineage (Ferrero et al., 1983, *Proc. Natl. Acad. Sci. U.S.A.* 80:4114). Type 1 CFU-GM contribute all of the peripheral blood CFU-GM, as well as a small number of bone marrow CFU-GM. They express surface antigens recognized by S3–13 and S17–25 antibodies, but not by R1B19 and WGHS-29-1 antibodies. Type 2 CFU-GM are present only in the marrow and react with S3–13, R1B19, and WGHS-29-1. Culture of type 1 CFU-GM in liquid culture generates type 2 CFU-GM. These antibodies have also been used to characterize CFU-GM from patients with chronic myeloproliferative disorders (Robak et al., 1985, *Leukemia Res.* 9:1023; Ferrero et al., 1986, *Cancer Res.* 46:975).

Other antigens on human stem/progenitor cells include those reactive with the My10 (Leary et al., 1987, *Blood* 69:953; Strauss et al., 1986, *Exp. Hematol.* 14:879), 3C5 (Katz et al., 1985, *Leukemia Res.* 9:191; Katz et al., 1986, *Leukemia Res.* 10:961), RFB-1 (Bodger et al., 1983, *Blood* 61:1006), 12-8 (Andrews et al., 1986, *Blood* 67:842), and L4F3 (Andrews et al., 1986, *Blood* 68:1030) antibodies. The antigen recognized by L4F3 is on CFU-GM, CFU-MK, BFU-E, and CFU-GEMM, but is apparently absent from cells which generate these progenitors in suspension culture (id.). The antigen recognized by the My10 antibody is CD34 (Civin et al., U.S. Pat. No. 4,714,680 dated Dec. 22, 1987.) Two subsets of pluripotent hematopoietic stem cells have been reported, a CD34$^+$ HLA-DR$^+$ CD38$^-$ subset and a more primitive CD34$^+$ HLA-DR$^-$ CD38$^-$ subset, with a gradual increase in CD38 expression as the hematopoietic cells proceed toward a more differentiated state (Huang and Terstappen, 1992, *Nature* 360:745–749; Terstappen et al., 1992, *Leukemia* 6:993–1000). The antigen recognized by another antibody, MyII, is expressed on CFU-GM, but not on BFU-E or CFU-GEMM (Strauss et al., 1986, *Exp. Hematol.* 14:935). Receptors for various lectins are also expressed on stem/progenitor cells (Nicola et al., 1980, *J. Cell Physiol.* 103:217; Reisner et al., 1982, *Blood* 59:360; Reisner et al., 1978, *Proc. Natl. Acad. Sci. U.S.A.* 75:2933; Aizawa and Tavassoli, 1986, *Int. J. Cell Cloning* 4:464).

To expand the numbers of the hematopoietic stem and/or progenitor cells, the hematopoietic stem and/or progenitor cells (or precursor cells thereof) are exposed to or contacted with a composition comprising a Therapeutic of the invention for a sufficient time period, i.e., until the desired number of cells is obtained and the time period should be for as long as it is desired to keep cells self-renewing. Preferably, the cells are contacted with the Therapeutic, for example but not limited to, 200 IU/ml hCG (e.g., hCG APL) or β-hCG preparation or a fraction of a source of hCG or β-hCG or 100 µg/ml β-hCG peptide, preferably a β-hCG peptide having the amino acid sequence of amino acid numbers 45–57 or 109–119 (SEQ ID NOS:6 or 7, respectively), or circularized peptide of amino acid numbers 44–57 (SEQ ID NO:12) with cysteine substituted for valine at position 44, or a branched peptide of amino acid numbers 45–57 (SEQ ID NO:6) with diaminobutyric acid substituted for the amino acids at positions 47 and 51 with proline peptide bonded to the diaminobutyric acid residues, or a circularized branched peptide of amino acids 44–57 (SEQ ID NO:12) with cysteine substituted for valine at position 44 and with diaminobutyric acid substituted for the amino acids at positions 47 and 51 with proline peptide bonded to the diaminobutyric acid residues or a peptide having the sequence of amino acids 45–57 (SEQ ID NO:6) linked at the C-terminus via a peptide bond to the N-terminus of amino acids 109–119 (SEQ ID NO:7) or linked at the N-terminus via a peptide bond to the C-terminus of amino acids 110–119 (SEQ ID NO:27); or an amino acid sequence of amino acids 47–57 (SEQ ID NO:28) linked at the C-terminus via a peptide bond to the N-terminus of amino acids 108–119 (SEQ ID NO:29) or the cyclic, fused peptide, having a sequence of amino acids 110–119 (SEQ ID NO:27) linked at the C-terminus via a peptide bond to the N-terminus of amino acids 45–57 (SEQ ID NO:6) and being circularized by a disulfide bond between the terminal cysteines at positions 110 and 57, where all amino acid numbers are of the β-hCG sequence depicted in FIG. 8 (a portion of SEQ ID NO:2), while under appropriate culture conditions, for a time period in the range of 1–21 or, more preferably, 7–21 days.

The composition comprising the Therapeutic of the invention, to which the stem and progenitor cells are exposed according to the invention, optionally also contains other growth factors and/or cytokines or cell culture materials, including but not limited to erythropoietin (Epo), Steel factor (SLF), IL-1, IL-3, IL-4, IL-6, IL-11, G-CSF, GM-CSF, FBS, adult PB plasma, alone or in combination. Preferably, factors are present that cause proliferation or, less preferably, differentiation of cells that are CFU-GEMM or earlier cells, e.g., IL-3, GM-CSF.

Contacting of the stem and progenitor cells with the Therapeutic preferably occurs during cell culture and thus, the Therapeutic is preferably added to the cell culture medium being used to culture the hematopoietic stem and/or progenitor cells. Such culturing can be by any method known in the art, including, but not limited to, cells grown in culture dishes, test tubes, roller bottles, bioreactors (perfusion system machines wherein cells are grown on a surface with continual perfusion by medium; e.g., as sold by Aastrom Biosciences, Inc., Ann Arbor, Mich.), etc. Various protocols have been described for the growth in vitro of cord blood or bone marrow cells, and it is envisioned that such procedures, or modifications thereof, may be employed (see, e.g. Smith, S. and Broxmeyer, H. E., 1986, *Br. J. Haematol.* 63:29–34; Dexter et al., 1977, *J. Cell. Physiol.* 91:335; Witlock and Witte, 1982, *Proc. Natl. Acad. Sci. U.S.A.* 79:3608–3612). The cell culture medium is supplemented to contain an effective concentration of the Therapeutic, for example but not limited to, 200 I.U. hCG (APL) or β-hCG preparation or 100 μg/ml of a β-hCG peptide or a fraction of a native hCG or native β-hCG preparation.

Progeny cells of hematopoietic stem and progenitor cells of can be generated in vitro; the differentiated progeny cells thus generated can be therapeutically useful. For example, in one embodiment of this aspect of the invention, hematopoietic stem cells and/or CFU-GEMM progenitor cells, can be induced to differentiate into platelets. Such platelets can be used, for example, for infusion into a patient with thrombocytopenia, such as, but not limited to, the ITP associated with HIV infection. In another embodiment, granulocytes can be generated in vitro prior to infusion into a patient. One or more of the hematopoietic progeny cells can be generated in vitro, allowing for the in vitro production of blood components. In one embodiment, the generation of differentiated blood components is accompanied by expansion of the hematopoietic stem and progenitor cell pool, in order to allow for production of a greater quantity of differentiated cells. Various growth factors can be used to promote expansion and/or differentiation of hematopoietic stem and progenitor cells, such as cytokines (growth factors) including, but not limited to, G-CSF, CSF-1, IL-3, IL-5, tumor necrosis factor-β, and α-interferon. The blood components which are thus produced have uses which are not limited to therapeutic uses in vivo. For example, such progeny cells can be used in vitro, e.g., for the production and isolation of hematopoietic cell products such as growth factors, antibodies, etc.

A specific embodiment of the invention relates to a method of increasing the amount of hematopoietic cells, which method comprises contacting in vitro a non-terminally differentiated hematopoietic cell with a composition comprising an amount of a Therapeutic of the invention effective to increase proliferation of the cell, under conditions suitable and for a time period sufficient to increase the numbers of said hematopoietic cell. For example, hematopoietic cell numbers can be increased by contacting a non-terminally differentiated hematopoietic cell (e.g., a cell isolated from bone marrow or blood, adult or fetal or umbilical cord blood) with a composition compris-ing 200 IU/ml hCG (e.g., hCG APL) or β-hCG preparation or a fraction of a source of hCG or β-hCG or 100 μg/ml β-hCG peptide, preferably a β-hCG peptide having the amino acid sequence of amino acid numbers 45–57 or 109–119 (SEQ ID NOS:6 or 7, respectively), or circularized peptide of amino acid numbers 44–57 (SEQ ID NO:12) with cysteine substituted for valine at position 44, or a branched peptide of amino acid numbers 45–57 (SEQ ID NO:6) with diaminobutyric acid substituted for the amino acids at positions 47 and 51 with proline peptide bonded to the diaminobutyric acid residues, or a circularized branched peptide of amino acids 44–57 (SEQ ID NO:12) with cysteine substituted for valine at position 44 and with diaminobutyric acid substituted for the amino acids at positions 47 and 51 with proline peptide bonded to the diaminobutyric acid residues or a peptide having the sequence of amino acids 45–57 (SEQ ID NO:6) linked at the C-terminus via a peptide bond to the N-terminus of amino acids 109–119 (SEQ ID NO:7) or linked at the N-terminus via a peptide bond to the C-terminus of amino acids 110–119 (SEQ ID NO:27); or an amino acid sequence of amino acids 47–57 (SEQ ID NO:28) linked at the C-terminus via a peptide bond to the N-terminus of amino acids 108–119 (SEQ ID NO:29) or the cyclic, fused peptide, having a sequence of amino acids 110–119 (SEQ ID NO:27) linked at the C-terminus via a peptide bond to the N-terminus of amino acids 45–57 (SEQ ID NO:6) and being circularized by a disulfide bond between the terminal cysteines at positions 110 and 57, where all amino acid numbers are of the β-hCG sequence depicted in FIG. 8 (a portion of SEQ ID NO:2), and culturing the cell for at least ten days.

Demonstration of Therapeutic Utility

The Therapeutics of the invention are preferably tested in vitro, and then in vivo for the desired therapeutic or prophylactic activity, prior to use in humans. Any in vitro or in vivo assay known in the art to measure HIV infection or production can be used to test the efficacy of a Therapeutic of the invention. By way of example, and not by way of limitation, one could use any of the in vitro or in vivo assays described herein.

HIV

In an embodiment of the invention, a method of screening a preparation comprising hCG, an hCG alpha or hCG beta chain, fragment or derivative of hCG or said alpha or beta chain, or a fraction of a source of hCG or β-hCG for anti-HIV activity is provided, which assay comprises assaying said preparation or fraction for the ability to inhibit HIV replication or expression of HIV RNA or protein. In one specific embodiment, the hCG preparation or fraction is assayed by a method comprising measuring HIV-1 p24 antigen levels in cultured hematopoietic cells acutely infected with HIV-1, which cells have been contacted with the preparation or fraction; and comparing the measured HIV-1 p24 antigen levels in the cells which have been contacted with the hCG preparation or fraction with said levels in cells not so contacted with the preparation or fraction, wherein a lower level in said contacted cells indicates that the preparation or fraction has anti-HIV activity. In another specific embodiment, the hCG preparation or fraction is assayed by a method comprising measuring the activity of a reporter gene product expressed from a construct in which the HIV-1 LTR is operably linked to said reporter gene, wherein said construct is present in cells which have been contacted with the preparation or fraction; and comparing the measured expression of said reporter gene in the cells which have been contacted with the preparation or fraction with said levels in such cells not so contacted, wherein a lower level in said contacted cells indicates that the preparation or fraction has anti-HIV activity. In another specific embodiment, the hCG preparation or fraction is assayed by a method comprising measuring HIV-1 derived RNA transcripts or HIV-1 antigen levels in HIV-1 transgenic mice administered the preparation or fraction; and comparing the measured transcript or antigen levels in the mice which have been administered the preparation or fraction with said levels in mice not so administered, wherein a lower level in said administered mice indicates that the preparation or fraction has anti-HIV activity. In yet another specific embodiment, the hCG preparation or fraction is assayed by a method comprising measuring SIV p27 antigen levels in the peripheral blood mononuclear cells of SIV infected monkeys administered the preparation or fraction; and comparing the measured antigen levels in the monkeys which have been exposed to the preparation or fraction with said levels in monkeys not so administered, wherein a lower level in said administered monkeys indicates that the preparation or fraction has anti-HIV activity.

By way of example, to assay a Therapeutic in vitro, one can examine the effect of the Therapeutic on HIV replication in cultured cells. Briefly, cultured hematopoietic cells (e.g., primary PBMCs, isolated macrophages, isolated CD4$^+$ T cells or cultured H9 human T cells) are acutely infected with HIV-1 using titers known in the art to acutely infect cells in vitro, such as $10^5$ TCID$_{50}$/ml. Then, appropriate amounts of the Therapeutic are added to the cell culture media. Cultures are assayed 3 and 10 days after infection for HIV-1 production by measuring levels of p24 antigen using a commercially available ELISA assay. Reduction in p24 antigen levels over levels observed in untreated controls indicates the Therapeutic is effective for treatment of HIV infection.

Additionally, assays for HIV-1 LTR driven transcription are useful for testing the efficacy of Therapeutics of the invention. Specifically, a reporter gene, i.e., a gene the protein or RNA product of which is readily detected, such as, but not limited to, the gene for chloramphenicol acetyltransferase (CAT), is cloned into a DNA plasmid construct such that the transcription of the reporter gene is driven by the HIV-1 LTR promoter. The resulting construct is then introduced by transfection, or any other method known in the art, into a cultured cell line, such as, but not limited to, the human CD4$^+$ T cell line HUT 78. After exposure of the transformed cells to the Therapeutic, transcription from the HIV-1 LTR is determined by measurement of CAT activity using techniques which are routine in the art. Reduction in HIV-1 LTR driven transcription demonstrates utility of the Therapeutic for treatment and/or prevention of HIV infection.

Exemplary tests in animal models are described briefly as follows: First, a Therapeutic of the invention is administered to mice transgenic for HIV-1, e.g., mice which have integrated molecular clone pNL4-3 containing 7.4 kb of the HIV-1 proviral genome deleted in the gag and pol genes (Dickie, P., et al., 1991, *Virology* 185:109–119). Skin biopsies taken from the mice are tested for HIV-1 gene expression by RT-PCR (reverse transcription-polymerase chain reaction) or for HIV-1 antigen expression, such as expression of gp120 or NEF, by immunostaining. Additionally, the mice are examined for reduction in the cachexia and growth retardation usually observed in HIV-1 transgenic mice (Franks, R. R., et al., 1995, *Pediatric Res.* 37:56–63).

The efficacy of Therapeutics of the invention can also be determined in SIV infected rhesus monkeys (see Letrin, N. L., and King, N. W., 1990, *J. AIDS* 3:1023–1040), particularly rhesus monkeys infected with SIV$_{mac251}$, which SIV strain induces a syndrome in experimentally infected monkeys which is very similar to human AIDS (Kestler, H., et al., 1990, *Science* 248:1109–1112). Specifically, monkeys can be infected with cell free SIV$_{mac251}$, for example, with virus at a titer of $10^{4.5}$ TCID$_{50}$/ml. Infection is monitored by the appearance of SIV p27 antigen in PBMCs. Utility of the Therapeutic is characterized by normal weight gain, decrease in SIV titer in PBMCs and an increase in CD4$^+$ T cells.

Once the Therapeutic has been tested in vitro, and also preferably in a non-human animal model, the utility of the Therapeutic can be determined in human subjects. The efficacy of treatment with a Therapeutic can be assessed by measurement of various parameters of HIV infection and HIV associated disease. Specifically, the change in viral load can be determined by quantitative assays for plasma HIV-1 RNA using quantitative RT-PCR (Van Gemen, B., et al., 1994, *J. Virol. Methods* 49:157–168; Chen, Y. H., et al., 1992, *AIDS* 6:533–539) or by assays for viral production from isolated PBMCs. Viral production from PBMCs is determined by co-culturing PBMCs from the subject with H9 cells and subsequent measurement of HIV-1 titers using an ELISA assay for p24 antigen levels (Popovic, M., et al., 1984, *Science* 204:497–500). Another indicator of plasma HIV levels and AIDS progression is the production of inflammatory cytokines such as IL-6, IL-8 and TNF-α; thus, efficacy of the Therapeutic can be assessed by ELISA tests for reduction of serum levels of any or all of these cytokines. Administration of the Therapeutic can also be evaluated by assessing changes in CD4$^+$ T cell levels, body weight, or any other physical condition associated with HIV infection or AIDS or AIDS Related Complex (ARC). Reduction in HIV viral load or production, increase in CD4$^+$ T cell or amelioration of HIV-associated symptoms demonstrates utility of a Therapeutic for administration in treatment/prevention of HIV infection.

Wasting

Specific embodiments provide a method for screening a preparation comprising hCG or an hCG α chain or hCG β chain or a derivative of hCG or of said alpha or beta chain or a fraction of native hCG or native β-hCG, for anti-wasting activity comprising assaying said preparation for the ability to promote weight gain in an animal model that exhibits a wasting syndrome. In one specific embodiment, the hCG preparation is screened by a method comprising measuring the weight of an offspring of an HIV-1 transgenic mouse, which offspring has been exposed to the preparation; and comparing the weight of the offspring which has been exposed to the preparation with the weight of an offspring not so exposed, wherein a greater weight in said exposed offspring indicates that the preparation has anti-wasting activity. In another specific embodiment, the hCG preparation is screened by a method comprising measuring the change in weight of an SIV infected monkey which has been exposed to the preparation; and comparing the change in weight of the monkey which has been exposed to the preparation to the change in weight of a monkey which has not been so exposed, wherein a greater weight increase or smaller weight loss in said exposed monkey indicates that the preparation has anti-wasting activity.

Any animal model in which wasting occurs can be used. Exemplary tests in animal models are described briefly as follows: First, a Therapeutic of the invention can be assayed in mice transgenic for HIV-1, e.g., mice which have integrated molecular clone pNL4-3 containing 7.4 kb of the HIV-1 proviral genome deleted in the gag and pol genes (Dickie, P., et al., 1991, *Virology* 185:109–119). These mice exhibit cachexia and growth retardation (Franks, R. R., et al., 1995, *Pediatric Res.* 37:56–63). A Therapeutic which reverses the cachexia and growth retardation in the HIV transgenic mice is predicted to have utility for treatment or prevention of wasting syndromes.

Similarly, the efficacy of Therapeutics of the invention can also be assayed in SIV infected rhesus monkeys (see Letrin, N. L., and King, N. W., 1990, *J. AIDS* 3:1023–1040), particularly rhesus monkeys infected with $SIV_{mac251}$, which SIV strain induces a syndrome in experimentally infected monkeys which is very similar to human AIDS and results in weight loss in the infected monkeys (Kestler, H., et al., 1990, *Science* 248:1109–1112). Specifically, monkeys are infected with cell free $SIV_{mac251}$, for example, with virus at a titer of $10^{4.5}$ $TCID_{50}$/ml and SIV infection is monitored by the appearance of SIV p27 antigen in PBMCs. An increase in the weight of infected monkeys indicates that the Therapeutic has utility in the treatment of wasting syndrome.

Compounds for use in therapy can be tested in suitable animal model systems prior to testing in humans, including but not limited to rats, mice, chicken, cows, monkeys, rabbits, etc. For in vivo testing, prior to administration to humans, any animal model system known in the art may be used.

Once the Therapeutic has been tested in a non-human animal model, the utility of the Therapeutic can be determined in human subjects. Improvement in wasting syndrome, i.e. and increase in body cell mass, can be assessed by any well known clinical techniques available in the art. For example but not limited to, measuring body weight, determination of total body potassium content, determination of intracellular water volume, bioelectrical impedance analysis, anthropometrics and determination of total body nitrogen content (see, e.g., Kotler, D. P. et al., 1985, *Am. J. Clin. Nutr.* 42:1255–65; Ott, M. et al., 1993, *Am. J. Clin. Nutr.* 57:15–19; Miller, T. L. et al., 1993, *Am. J. Clin. Nutr.* 57:588–592). Therapeutics, the administration of which increases body weight or cell mass, should have utility in treatment of wasting syndrome.

Cancer

One embodiment provides a method for screening a preparation comprising a protein, preferably a purified protein, having a sequence of one or more portions of β-hCG or a derivative, preferably in purified form, of said protein, or a fraction of a source of native hCG or native β-hCG for anti-cancer activity comprising assaying said preparation for the ability to inhibit the survival or proliferation of malignant cells. In a specific embodiment, the preparation is screened by a method comprising measuring the survival or proliferation of malignant cells, which cells have been contacted with the preparation; and comparing the survival or proliferation of the cells contacted with the preparation with the survival or proliferation of cells not so contacted with the preparation, wherein a lower level of survival or proliferation in said contacted cells indicates that the preparation has anti-cancer activity. In another specific embodiment, the preparation is screened by a method comprising measuring the survival or proliferation of cells from a cell line which is derived from or displays characteristics associated with a malignant disorder, which cells have been contacted with the preparation; and comparing the survival or proliferation in the cells which have been contacted with the preparation with said survival or proliferation in cells not so contacted, wherein a lower level in said contacted cells indicates that the preparation has anti-tumor activity.

Another embodiment provides a method for screening a preparation comprising a protein having a sequence of a portion of β-hCG or a derivative of said protein or a fraction of a source of native hCG or native β-hCG, for anti-cancer activity comprising assaying said preparation for the ability to convert cells having an abnormal phenotype to a more normal cell phenotype. In a specific embodiment, the preparation is screened by a method comprising assessing the phenotype of cells suspected of being pre-neoplastic in culture, which cells have been contacted with the preparation; and comparing the phenotype in the cells which have been contacted with the preparation with said phenotype in cells not so contacted, wherein a more normal phenotype in said contacted cells indicates that the preparation has anti-cancer activity. In another specific embodiment, the preparation is screened by a method comprising assessing the phenotype of cells from a cell line which is derived from or displays characteristics associated with a pre-malignant disorder, which cells have been contacted with the preparation; and comparing the phenotype in the cells which have been contacted with the preparation with said phenotype in cells not so contacted, wherein a more normal phenotype in said contacted cells indicates that the preparation has anti-cancer activity.

Yet another embodiment provides a method for screening a preparation comprising a protein having a sequence of a portion of β-hCG or a derivative of said protein or a fraction of a source of native hCG or native β-hCG, for activity in treatment or prevention of Kaposi's Sarcoma comprising assaying said preparation for the ability to inhibit Kaposi's Sarcoma cell proliferation or promote Kaposi's Sarcoma cell apoptosis. In a specific embodiment, the preparation is screened by a method comprising measuring proliferation or colony formation in cultured KS Y-1 or KS-SLK cells, which cells have been contacted with the preparation; and comparing the measured proliferation or colony formation in the cells which have been contacted with the preparation with said proliferation or colony formation in cells not so contacted with the preparation, wherein a lower level of proliferation or colony formation in said contacted cells indicates that the preparation has anti-Kaposi's Sarcoma activity.

In another specific embodiment, the preparation is screened by a method comprising measuring apoptosis in a Kaposi's Sarcoma tumor in an immunodeficient mouse, which Kaposi's Sarcoma tumors have been induced by injection with KS Y-1 or KS-SLK cells, and which mouse has been exposed to the preparation; and comparing the degree of apoptosis in the tumor of the mouse which has been exposed to the preparation with a tumor in a mouse not so exposed, wherein a higher in level of apoptosis in the tumor of said exposed mouse indicates that the preparation has anti-Kaposi's Sarcoma activity.

For example, in vitro assays which can be used to determine whether administration of a specific Therapeutic is indicated include in vitro cell culture assays in which a patient tissue sample is grown in culture, and exposed to or otherwise administered a Therapeutic, and the effect of such Therapeutic upon the tissue sample is observed. In one embodiment, where the patient has a malignancy, a sample of cells from such malignancy is plated out or grown in culture, and the cells are then exposed to a Therapeutic. A Therapeutic which inhibits survival or growth of the malignant cells is selected for therapeutic use in vivo. Many assays standard in the art can be used to assess such survival and/or growth; for example, cell proliferation can be assayed by measuring $^3$H-thymidine incorporation, by direct cell count, by detecting changes in transcriptional activity of known genes such as proto-oncogenes (e.g., fos, myc) or cell cycle markers; cell viability can be assessed by trypan blue staining, differentiation can be assessed visually based on changes in morphology, etc.

In various specific embodiments, in vitro assays can be carried out with representative cells of cell types involved in a patient's disorder, to determine if a Therapeutic has a desired effect upon such cell types.

In another embodiment, cells of a patient tissue sample suspected of being pre-neoplastic are similarly plated out or grown in vitro, and exposed to a Therapeutic. The Therapeutic which results in a cell phenotype that is more normal (i.e., less representative of a pre-neoplastic state, neoplastic state, malignant state, or transformed phenotype) is selected for therapeutic use. Many assays standard in the art can be used to assess whether a pre-neoplastic state, neoplastic state, or a transformed or malignant phenotype, is present. For example, characteristics associated with a transformed phenotype (a set of in vitro characteristics associated with a tumorigenic ability in vivo) include a more rounded cell morphology, looser substratum attachment, loss of contact inhibition, loss of anchorage dependence, release of proteases such as plasminogen activator, increased sugar transport, decreased serum requirement, expression of fetal antigens, disappearance of the 250,000 dalton surface protein, etc. (see Luria et al., 1978, *General Virology*, 3d Ed., John Wiley & Sons, New York pp. 436–446).

In other specific embodiments, the in vitro assays described supra can be carried out using a cell line, rather than a cell sample derived from the specific patient to be treated, in which the cell line is derived from or displays characteristic(s) associated with the malignant, neoplastic or pre-neoplastic disorder desired to be treated or prevented, or is derived from the cell type upon which an effect is desired, according to the present invention.

Specifically, Therapeutics can be tested for efficacy in treatment or prevention of Kaposi's sarcoma by any of the methods relating to Kaposi's sarcoma described herein or in Lunardi-Iskandar et al. (1995, *Nature* 375:64–68) or by any other method known in the art. Briefly, KS cell lines, KS Y-1 (Ibid.) or KS-SLK (Siegal, B. et al., 1990, *Cancer* 65:492–498), which will produce malignant tumors in immunodeficient mice, are used to perform in vitro proliferation and clonogenic assays (see, e.g., Lunardi-Iskandar, Y. et al., 1993, *J. Exp. Med.* 177:741–750); methods for performing such assays are well known in the art. A Therapeutic which reduces proliferation or colony formation in the cultured cells can be used in the methods of the invention for treatment or prevention of KS.

Efficacy of a Therapeutic can also be determined by administration of the Therapeutic to immunodeficient mice injected with either the KS-Y-1 or KS-SLK cells, which cause tumor formation in the mice, and assessment of the degree of apoptosis and angiogenesis of tumor cells after treatment with the Therapeutic. Apoptosis is detected by staining fixed tissue samples from the tumor for the presence of cells with DNA fragmentation. For example, this is accomplished by treating tissue slides from formalin-fixed tumors with terminal deoxynucleotide transferase for extension of DNA ends (3' hydroxyl ends) and incorporation of digoxigenin-11-dUTP. Anti-digoxigenin antibody conjugated with the enzyme peroxidase allows detection of apoptotic cells that stain brown whereas viable cells stain blue. An increase in KS tumor cell apoptosis and a decrease in angiogenesis indicates that the Therapeutic has utility in treatment of KS.

The Therapeutic can also be assessed in clinical trials in human patients suffering from KS or any other cancer. To test the efficacy of the Therapeutic in KS patients, either local, i.e. intralesional, or systemic administration of the Therapeutic can be used. Tumors can be examined physically for regression in response to administration of the Therapeutic. Additionally, tissue biopsies can be taken from the tumors, and these tissue samples examined for apoptosis, as described above.

Compounds for use in therapy can be tested in suitable animal model systems prior to testing in humans, including but not limited to rats, mice, chicken, cows, monkeys, rabbits, etc. For in vivo testing, prior to administration to humans, any animal model system known in the art may be used.

Hematopoiesis

The Therapeutics of the invention are preferably tested in vitro, and then in vivo for the desired therapeutic or prophylactic activity, prior to use in humans. Any in vitro or in vivo assay known in the art to measure a pro-hematopoietic effect, i.e. the ability to induce hematopoietic cell proliferation in vitro or production of one or more hematopoietic cell types in vivo, such as those described herein, can be used to test the efficacy of a Therapeutic of the invention.

A specific embodiment provides a method for screening a preparation comprising hCG or an hCG α chain or hCG β chain or a derivative of hCG or of said alpha or beta chain or a fraction of a source of native hCG or native β-hCG, for pro-hematopoietic activity comprising assaying said preparation for the ability to induce an increase in hematopoietic cell numbers. In one embodiment, the preparation is screened by a method comprising measuring the number of colonies formed from hematopoietic stem or progenitor cells, which cells have been contacted with the preparation; and comparing the number of colonies formed from the cells contacted with the preparation with the number of colonies formed from cells not so contacted with the preparation, wherein a higher number of colonies formed from said contacted cells indicates that the preparation has pro-hematopoietic activity. In another embodiment, the preparation is screened by a method comprising measuring the number of $CD4^+$ T cells in an SIV infected monkey, which monkey has been exposed to the preparation; and comparing the number of $CD4^+$ T cells in the monkey which has been exposed to the preparation with the number of $CD4^+$ T cells in a monkey not so exposed, wherein a higher number of $CD4^+$ T cells in said exposed monkey indicates that the preparation has pro-hematopoietic activity.

Specifically, to assay a Therapeutic in vitro, one could examine the effect of the Therapeutic on proliferation of hematopoietic cells in vitro. For example, to assay colony-forming units (a progenitor cell), briefly, the hematopoietic cells are cultured for an appropriate amount of time, such as 5 to 20 days and preferably 10 days, in the presence of (or otherwise exposed to) the Therapeutic to be tested, and then colony assays are performed to determine the number of colonies formed in comparison to the number of colonies formed by cells cultured in the absence of the Therapeutic. For example, hematopoietic progenitor cells can be isolated from bone marrow or cord blood, seeded in methylcellulose in the presence of absence of the Therapeutic, and then colony numbers determined after 10 days of culture. An increase in colony numbers in cells contacted with the Therapeutic indicates that the Therapeutic has activity in inducing proliferation of hematopoietic cells. Thus, for example, depending on the progenitor cell desired to be assayed, CFU-GM, CFU-GEMM, etc., assays can be done.

Therapeutics can also be tested in vivo for activity in increasing the numbers of hematopoietic cells. Preferably, Therapeutics are tested in animal models of hematopoietic disorders before testing them in human patients. For example, but not by way of limitation, a Therapeutic can be tested in rhesus monkeys infected with SIV, particularly $SIV_{mac251}$ which induces a syndrome in monkeys similar to human AIDS (Kestler, H. et al., 1990, *Science* 248:1109–1112), and which are deficient in CD4+ T cells. The Therapeutic to be tested can be administered to the infected monkeys; then the blood or bone marrow of the infected monkeys can be examined for an increase in CD4+ T cells or any other hematopoietic cell type for which the monkey is deficient. An increase in numbers of the hematopoietic cell demonstrates that the Therapeutic is useful for treating diseases and disorders associated with hematopoietic deficiencies. Any animal model of an anemia can be similarly used for testing.

Therapeutics can be tested in human patients, preferably after tests in vitro and/or in vivo in an animal model, with hematopoietic deficiencies, for example but not limited to, deficiencies associated with HIV infection such as anemia, neutropenia, thrombocytopenia, or CD4+ T cell lymphocyte deficiency, for activity in increasing numbers of hematopoietic cells for which the patient is deficient. Briefly, the Therapeutic is administered, for example by intramuscular injection two to three times per week, to the patient suffering from the hematopoietic deficiency. The subject's blood or bone marrow is assayed before and after treatment with the Therapeutic for an increase in the hematopoietic cell numbers. Therapeutics which cause an increase in hematopoietic cell numbers are useful for treatment of diseases and disorders associated with hematopoietic deficiencies.

Assays for hematopoietic cell proliferation in the blood or bone marrow can be accomplished by any method well known in the art. For example, blood can be drawn and blood cell numbers can be determined by routine clinical laboratory tests for red blood cells, platelets, neutrophils, lymphocytes, etc. Additionally, colony assays on isolated bone marrow can be performed to assess increases in stem or progenitor cells. For example, bone marrow can be sampled and bone marrow cells evaluated for stem and progenitor cell colony formation. Briefly, cells are seeded in methylcellulose, cultured for 12 to 14 days, and then scored for colony formation where aggregates containing more than 50 cells are counted as a colony (see, e.g., Lunardi-Iskandar, Y. et al., 1995, *Nature* 375:64–68; Louache, R. et al., 1992, *Blood* 180:2991–2999; Lunardi-Iskandar, Y. et al., 1989, *J. Clin. Invest.* 83:610–615). Bone marrow progenitors which can be evaluated by this colony assay include, but are not limited to, CFU-Mix, BFU-e and CFU-GM. As an alternative to colony assays for detection and quantitation of stem and/or progenitor cells, immunological detection methods can be employed, based on the antigens expressed by the particular cell type (see, e.g., the relevant discussion hereinabove).

Therapeutic Compositions and Methods of Administration

The invention provides methods of treatment and prevention by administration to a subject in need of such treatment of a therapeutically or prophylactically effective amount of a Therapeutic of the invention. The subject is preferably an animal, including, but not limited to, animals such as monkeys, cows, pigs, horses, chickens, cats, dogs, etc., and is preferably a mammal, and most preferably human. In a specific embodiment, the subject is a human not afflicted with a cancer which secretes hCG or hCG fragments and, more particularly, not afflicted with KS.

Various delivery systems are known and can be used to administer a Therapeutic of the invention, e.g., encapsulation in liposomes, microparticles, microcapsules, recombinant cells capable of expressing the Therapeutic, receptor-mediated endocytosis (see, e.g., Wu and Wu, 1987, J. Biol. Chem. 262:4429–4432), construction of a Therapeutic nucleic acid as part of a retroviral or other vector, etc. Methods of introduction include but are not limited to intradermal, intramuscular, intraperitoneal, intravenous, subcutaneous, intranasal, epidural, and oral routes. The compounds may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compositions of the invention locally to the area in need of treatment; this may be achieved, for example and not by way of limitation, by topical application, by injection, by means of a catheter, by means of a suppository, or by means of an implant, said implant being of a porous, non-porous, or gelatinous material, including membranes, such as sialastic membranes, or fibers.

In another embodiment, the Therapeutic can be delivered in a vesicle, in particular a liposome (see Langer, *Science* 249:1527–1533 (1990); Treat et al., in *Liposomes in the Therapy of Infectious Disease and Cancer*, Lopez-Berestein and Fidler (eds.), Liss, New York, pp. 353–365 (1989); Lopez-Berestein, ibid., pp. 317–327; see generally ibid.)

In yet another embodiment, the Therapeutic can be delivered in a controlled release system. In one embodiment, a pump may be used (see Langer, supra; Sefton, *CRC Crit. Ref. Biomed. Eng.* 14:201 (1987); Buchwald et al., *Surgery* 88:507 (1980); Saudek et al., *N. Engl. J. Med.* 321:574 (1989)). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, *J. Macromol. Sci. Rev. Macromol. Chem.* 23:61 (1983); see also Levy et al., *Science* 228:190 (1985); During et al., *Ann. Neurol.* 25:351 (1989); Howard et al., *J. Neurosurg.* 71:105 (1989)). In yet another embodiment, a controlled release system can be placed in proximity of the therapeutic target, thus requiring only a fraction of the systemic dose (see, e.g., Goodson, in Medical Applications of Controlled Release, supra, vol. 2, pp. 115–138 (1984)). Other controlled release systems are discussed in the review by Langer (*Science* 249:1527–1533 (1990)).

In a specific embodiment where the Therapeutic is a nucleic acid encoding a protein Therapeutic, the nucleic acid can be administered by gene therapy methods as described herein.

The present invention also provides pharmaceutical compositions. Such compositions comprise a therapeutically effective amount of a Therapeutic, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans.

The term "carrier" refers to a diluent, adjuvant, excipient, or vehicle with which the Therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol and the like.

The composition, if desired, can also contain minor amounts of wetting or emulsifying agents, or pH buffering agents. These compositions can take the form of solutions, suspensions, emulsion, tablets, pills, capsules, powders, sustained-release formulations and the like.

The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the Therapeutic, preferably in purified form, together with a suitable amount of carrier so as to provide the form for proper administration to the patient. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The Therapeutics of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The amount of the Therapeutic of the invention which will be effective in the treatment of a particular disorder or condition will depend on the nature of the disorder or condition, and can be determined by standard clinical techniques. In addition, in vivo and/or in vitro assays may optionally be employed to help predict optimal dosage ranges. The precise dose to be employed in the formulation will also depend on the route of administration, and the seriousness of the disease or disorder, and should be decided according to the judgment of the practitioner and each patient's circumstances. Doses of, for example but not limited to, at least 15,000 I.U. and up to 45,000 I.U. hCG weekly was effective and well tolerated in humans. Weekly doses of 6,000 I.U. in monkeys and 300–500 I.U. in mice were also effective. Predicted suitable doses of a hCG peptide for treatment or prevention of HIV infection include, but are not limited to, 1 to 1000 micrograms per week. Routes of administration of a Therapeutic include, but are not limited to, intramuscularly, subcutaneously or intravenously. Effective doses may be extrapolated from dose-response curves derived from in vitro or animal model test systems.

Suppositories generally contain active ingredient in the range of 0.5% to 10% by weight; oral formulations preferably contain 10% to 95% active ingredient.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

EXAMPLES

Effects of hCG, β-hCG and β-hCG Peptide Preparations on HIV-1 Infection and Disease As described herein, we have observed beneficial effects of some preparations of human Chorionic Gonadotropin (hCG) and β-hCG against HIV disease including anti-tumor (Kaposi sarcoma, KS), anti-viral, increase in weight and pro-hematopoiesis effects. Our studies document that the same preparations inhibit KS cell growth in vitro and induce apoptosis in a mouse model, inhibit HIV acute infection in vitro, down regulate HIV gene expression in 30 of 30 HIV-1 transgenic mice, inhibit SIV replication in 3 of 3 SIV acutely infected macaque monkeys with no evidence of viral resistance, promote normal hematopoiesis (including $CD4^+$ T cell rise), and reverse the wasting seen in these animals. Examples of these effects were also noted in some HIV-positive patients treated with some hCG preparations. The strength of these effects varied among crude hCG preparations, and highly purified hCG did not retain these activities. However, anti-KS, anti-viral, and pro-hematopoietic effects were mimicked by native β-hCG and synthetic peptides of the beta subunit of hCG having amino acid sequences of amino acid numbers 45–57 (SEQ ID NO:6), 109–119 (SEQ ID NO:7), circularized 44–57, where cysteine is substituted for the amino acid at position 44 (SEQ ID NO:26), and peptides of amino acid numbers 45–57 (SEQ ID NO:6) linked at the C-terminus via a peptide bond to the N-terminus of amino acids 109–119 (SEQ ID NO:7) or linked at the N-terminus via a peptide bond to the C-terminus of amino acids 110–119 (SEQ ID NO:27); or a peptide of amino acids 47–57 (SEQ ID NO:28) linked at the C-terminus via a peptide bond to the N-terminus of amino acids 108–119 (SEQ ID NO:29) of the β-hCG sequence depicted in FIG. 8 (portions of SEQ ID NO:2). The peptides having an amino acid sequence of amino acid numbers 7–45, 47–55, 46–65, and 48–56 (SEQ ID NOS:21 and 33–35, respectively) of β-hCG (FIG. 8 (SEQ ID NO:2) also exhibit activity in in vitro assays.

Effects of hCG Preparations on HIV-1 Transgenic Mice

The HIV-1 transgenic mice used for this study contain 7.4 kb of foreign DNA, including 5.1 kb of the HIV-1 proviral genome deleted in the gag and pol genes and 2.3 kb of vector (Dickie et al., 1991, *Virology* 185:109–119). The birth weights of mice homozygous for the HIV-1 transgene are normal, but soon the mice uniformly display severe growth retardation (FIG. 1A), cachexia, and early mortality from expression of HIV-1 genes (env and regulatory genes) which are highly expressed shortly after birth in homozygotes (Franks et al., 1995, *Pediatric Res.* 37:56–63) (FIG. 1B). In addition, these mice develop severe hyperkeratotic skin lesions with marked expression of gp120 and nef genes (Kopp et al., 1993, *AIDS Res. Hum. Retroviruses* 9:267–275; Vasli et al., 1994, *AIDS Res. Hum. Retroviruses* 10:1241–1250).

To examine the effects of hCG preparations on HIV transgenic Tg26 mice, the mothers of 30 neonatal mice were administered a commercial preparation of native hCG (APL™, Wyeth Ayerst) (300–500 I.U.), and the mothers of other HIV-1 transgenic mice received other commercial native hCG preparations (PREGNYL™ and Sigma (G10), α-chain preparations and partially purified native β-hCG and recombinant β-hCG preparations (all Sigma) (50–100 µg). For studies involving synthetic peptides, heterozygous transgenic mothers of 6 homozygous transgenic mice were given 10 µg of β-hCG peptide 45–57 (SEQ ID NO:6) where the amino acid residues at positions 47 and 51 are substituted by a branch, where the branches are made up of diaminobutyric acid and proline (branched β-hCG 45–57) (prepared by Dr. N. Ambulos, UMAB) subcutaneously, daily for 10 days. Other studies were carried out with other β-hCG peptides (see Table 3).

Heterozygous transgenic mothers were treated with the hCG preparation subcutaneously twice weekly. Pups received hCG via the mother's milk. Blood levels of hCG in the mother and pups were monitored and ranged from 5 IU/ml to over 150 IU/ml over a 96 hour time period (data not shown).

Gene expression was assayed in total RNA extracted from the skin of Tg26 mice with RNAzol. One microgram of RNA was reverse transcribed into cDNA using random hexamer primers and MMTV reverse transcriptase (Life Technologies, MD) in a final volume of 30 µl. One tenth of the cDNA reactions were used for PCR amplification of various HIV gene sequences (env, tat, rev, nef and vif). In addition, glyceraidehyde 3-phosphate dehydrogenase (GAPHD) mRNA was amplified for each sample for normalization. Following 25 cycles of amplification, 10% of the PCR product was resolved by electrophoresis through 2% agarose gels and processed for Southern hybridization using FITC-labeled oligonucleotide probes complementary to internal sequences of the amplicons. Detection was performed by chemiluminescence (Amersham) and relative mRNA levels determined by densitometry after normalization with GAPDH mRNA levels.

Figure 1A:
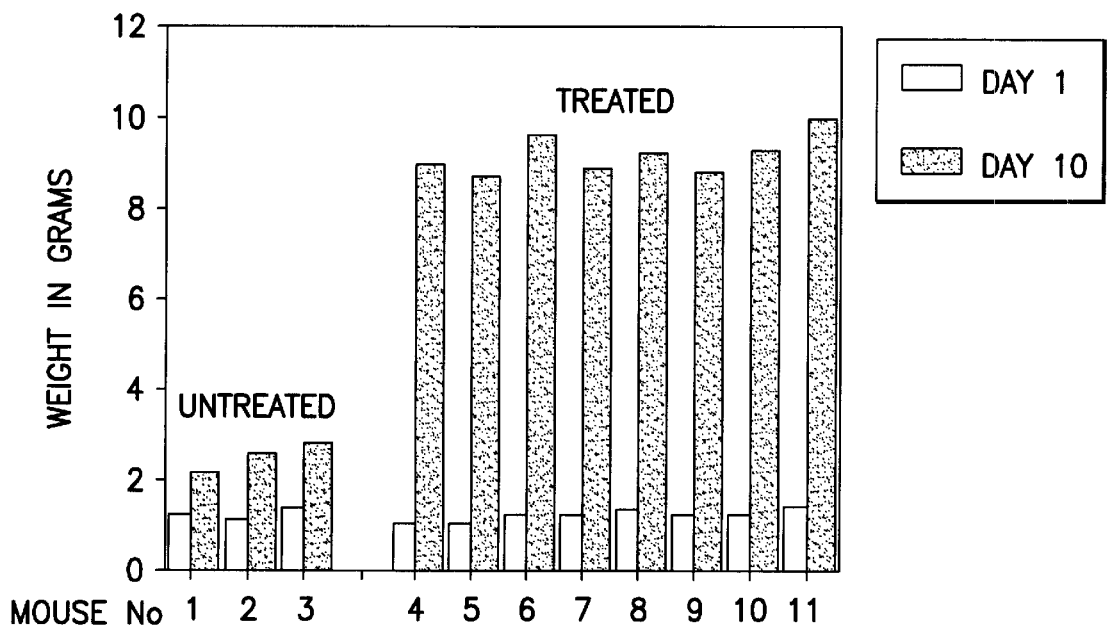
FIGS. 1A–E. Effects of an hCG preparation, APL™ (Wyeth-Ayerst), β-hCG peptides and certain fractions of hCG APL™ and early pregnancy urine on weight and HIV-1 gene expression in HIV-1 transgenic mice. (A) and (C) Weight change in grams in individual HIV-1 transgenic mice after treatment from day 1 to day 10 postpartum is represented as a bar graph with open bars representing the weight at day 1 and solid bars representing the weight at day 10. (B), (D) and (E) Suppression of HIV-1 gene expression in transgenic mice. The bar graph presents the level of expression in pixels, as determined by chemiluminescence assay of the HIV genes env, tat, rev, and nef in the individual HIV transgenic mice. For (B) and (D), the black bars represent tat expression, the striped bars represent rev expression, the lightly stippled bars represent env expression, the open bars represent nef expression. For (E), the striped bars represent env expression, the solid bars represent rev expression, and the open bars represent nef expression. In (A) and (B), bars 1–3 represent untreated control transgenic mice; bars 4–6 represent mice whose mothers received (subjects were administered through the mothers' milk) 200 μg circularized β-hCG peptide 44–57 (with cysteine substituted at position 44; SEQ ID NO:26) per day; bars 7–9 represent mice whose mothers received 300 IU per day hCG-APL™; and bars 9–11 represent mice whose mothers received 200 μg per day of the fused β-hCG peptide 45–57::109–119 (SEQ ID NO:30). In (C) and (D), the bars labeled "untreated" represent mice receiving only PBS; and the bars labeled "treated" or "treated with HAFc" represent mice administered 300 IU per day of hCG APL™. In (E), the set of bars labeled "1" represents mice treated with PBS alone; "2" represents mice treated with 100 μg β-hCG core peptide per day; "3" represents mice treated with 100 μg per day oc-hCG; "4" represents mice treated with 200 μl per day of fraction 61 of the hCG APL™ fractionation; and "5" represents mice treated with 200 μl per day of fraction 65 of the early pregnancy urine fractionation.
Figure 1B:
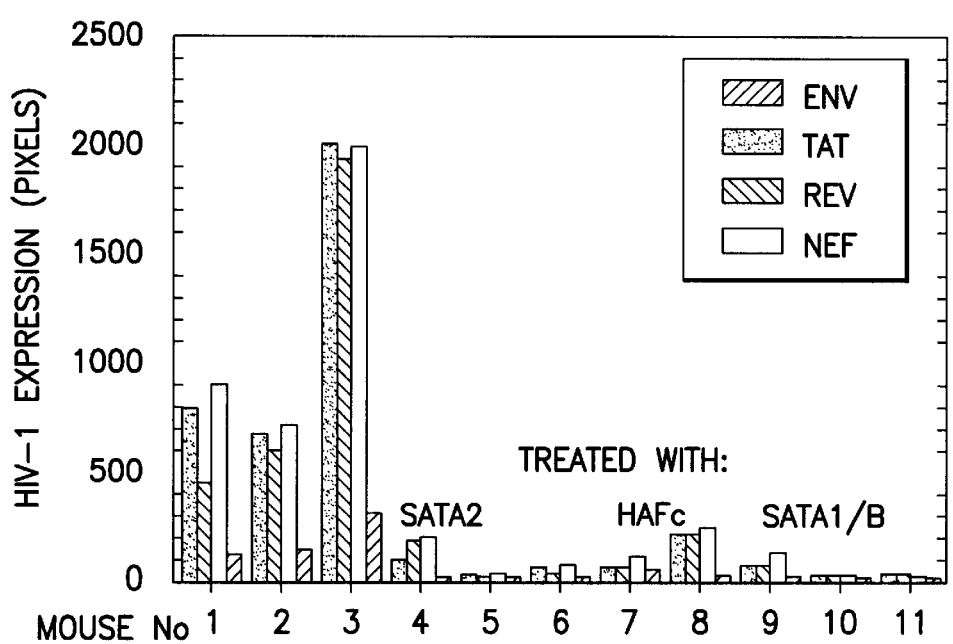
Figure 1C:
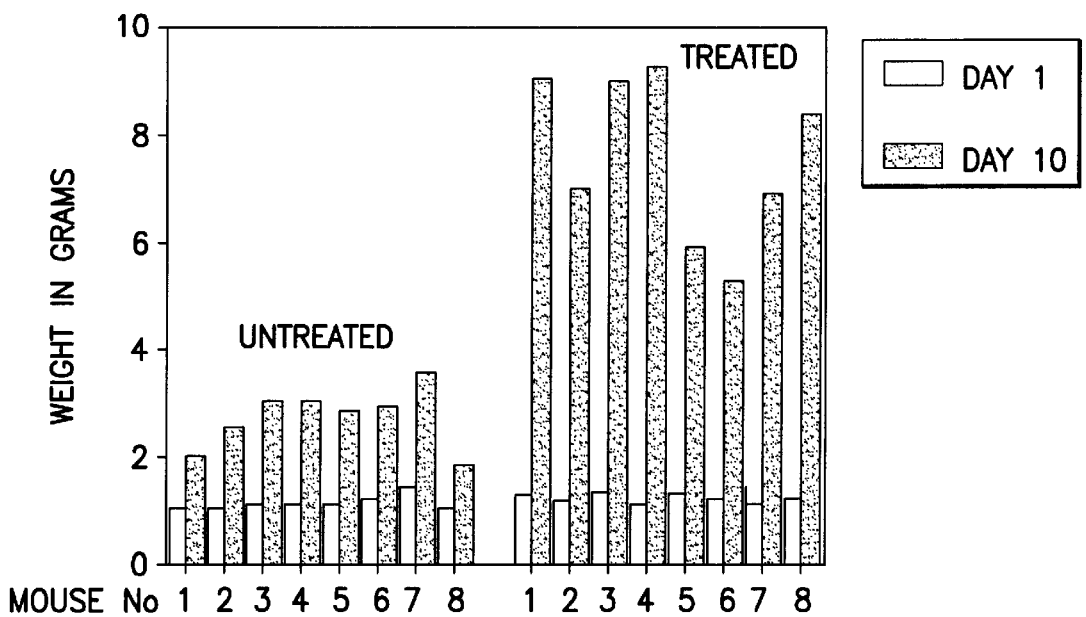
Figure 1D:
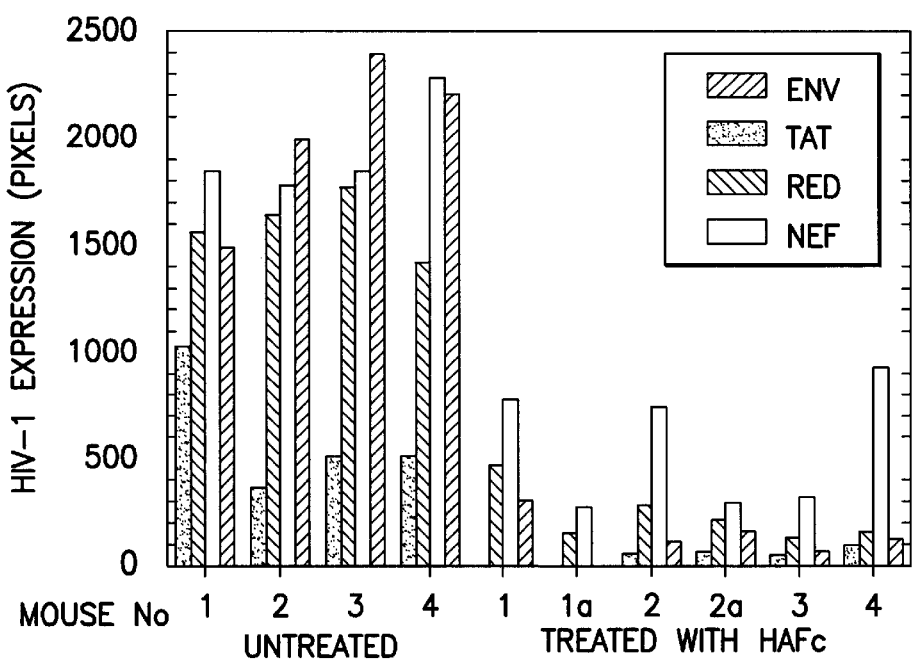

The hCG (APL™) treatments resulted in marked down regulation of HIV-1 gene expression in skin biopsies as determined by the RT-PCR technique (FIG. 1D). The 25 cycles of amplification employed in these experiments readily detected abundantly expressed genes (e.g., env and rev) while the tat gene in treated animals was at low levels, and more readily detected with more cycles of amplification (not shown). Other skin biopsies were examined for HIV viral proteins using mouse monoclonal antibodies against gp120 and Nef by an immunostaining technique. A marked decrease in viral proteins occurred after 2 weeks treatment and no detectable HIV proteins were found after 30 days of hCG treatment (not shown) and the hyperkeratosis of the skin regressed. When the treatment was halted, reappearance of viral protein expression occurred after 2 weeks (not shown).

Associated with the decrease in HIV-1 gene expression (FIG. 1D) was a reversal of the growth retardation and cachexia (FIG. 1C). As described immediately below, native β-hCG and some synthetic peptides of the β-subunit also reversed the adverse effects of the viral genes in these transgenic animals (Table 3). In contrast, native α-hCG had no effect on HIV gene expression or the retarded postnatal growth and cachexia (Table 3).

Table 3 and FIGS. 1A and B also provide results from the administration of various β-hCG peptides and β-hCG peptide derivatives, i.e. the peptides of amino acids 45–57 (SEQ ID NO:6) ("Satellin A1"), circularized 44–57 with cysteine substituted at position 44 (SEQ ID NO:26) ("Satellin A2"), 47–57 linked at the C-terminus via a peptide bond to the N-terminus of 108–119 (SEQ ID NO:32) ("Satellin A1/B$^G$"), 45–57 linked at the C-terminus via a peptide bond to the N-terminus of 109–119 (SEQ ID NO:30)("Satellin A1/B"), 41–54, 6–16, 47–55 (SEQ ID NO:20), and 48–56 (SEQ ID NO:35). All animals born to HIV-1 transgenic mothers which did not receive preparations containing β-hCG peptide or derivative thereof died within 10 days, showed high level of gp120 and nef protein as measured by antibody staining, and exhibited characteristic hyperkeratosis. The pups receiving the β-hCG peptides 45–57, circularized 44–57 with cysteine substituted at position 44, 47–57 linked by peptide bond to 108–119, 45–57 linked by peptide bond to 109–119 (SEQ ID NOS:6, 26, 32 and 30, respectively) all exhibited considerable inhibition of HIV-1 transcription and protein expression and higher weight gain than untreated mice. The peptides 47–55 and 48–56 (SEQ ID NOS:20 and 32, respectively) also elicited inhibition. The scrambled peptide 45–57::109–119 and the scrambled circularized 44–57, administered as controls, showed no inhibitory effect while, surprisingly, the scrambled 45–57 peptide did exhibit some inhibition (Table 3).

TABLE 3

ACTIVITIES OF hCG AND hCG SUBUNIT PREPARATIONS AND hCG PEPTIDES.

| Sources | HIV in vitro Inhibition | HIV transgenic mice | KS in vitro | KS in vivo | Pro-hematopoiesis in vitro Enhancement |
|---|---|---|---|---|---|
| hCG preparations | | | | | |
| APL ™ | +++ | +++ | +++ | +++ | +++ |
| PREGNYL ™ | ++ | ++ | ++ | ++ | ++ |

TABLE 3-continued

ACTIVITIES OF hCG AND hCG SUBUNIT PREPARATIONS AND hCG PEPTIDES.

| Sources | HIV in vitro Inhibition | HIV transgenic mice | KS in vitro | KS in vivo | Pro-hematopoiesis in vitro Enhancement |
|---|---|---|---|---|---|
| ORGANON | − | ND | − | − | ND |
| PROFASI ™ | + | ND | + | + | + |
| GOLDLINE | + | ND | − | − | − |
| STERIS ™ | ++ | ND | ++ | ND | ++ |
| SHEIN | + | ND | − | − | − |
| SIGMA | +++ | +++ | +++ | +++ | +++ |
| SIGMA[2] | − | ND | − | − | − |
| CR127 | − | ND | − | ND | − |
| CR1XY17V | − | ND | − | ND | − |
| CR1XY17B | − | ND | − | − | − |
| rhCG | − | − | − | − | − |
| hCG subunits | | | | | |
| α Chain | | | | | |
| αhCG | − | − | − | − | − |
| rαhCG | − | − | − | − | − |
| αfp1769A | − | ND | − | ND | − |
| β Chain | | | | | |
| rβhCG | − | − | − | − | − |
| βhCG | ++ | ++ | ++ | ++ | ++ |
| Synthetic peptides β-chain hCG | | | | | |
| 1. 109–119 | + | ND | + | + | + |
| 2. 109–145 | + | ND | + | + | + |
| 3. 45–57 | ++ | ++ | ++ | ++ | ++ |
| 4. Circ 44–57 | +++ | +++ | +++ | +++ | +++ |
| 5. 47–57::108–119 | ++ | ++ | ++ | +++ | ND |
| 6. 45–57::109–119 | ++ | ++ | ++ | ++ | ++ |
| 7. 45–57 + 109–119 | ++ | ND | ++ | ND | ++ |
| 8. 41–54 | − | − | − | − | − |
| 9. 38–57 | − | ND | − | − | − |
| 10. Scrambled 45–57::109–119 | − | − | − | − | − |
| 11. Scrambled 45–57 | ++ | ND | ++ | ND | ND |
| 12. Scrambled circ. 44–57 | − | ND | − | ND | − |
| 13. 6–16 | − | − | − | − | − |
| 14. 1–20 | − | ND | − | ND | ND |
| 15. 20–47 | − | ND | − | ND | − |
| 16. 31–50 | − | ND | − | ND | − |
| 17. 46–65 | + | ND | + | ND | ND |
| 18. 91–112 | ND | ND | − | ND | − |
| 19. 93–100 | − | ND | − | ND | ND |
| 20. 110–145 | ND | ND | − | ND | − |
| 21. 74–95 | − | ND | − | ND | − |
| 22. 7–40 | + | ND | + | ND | − |
| 23. 57–93 | − | ND | − | ND | − |
| 24. 34–39 | − | ND | − | ND | ND |
| 25. 123–145 | − | ND | − | ND | ND |
| 26. 134–144 | − | ND | − | ND | − |
| 27. 100–110 | − | ND | − | ND | ND |
| 28. 113–132 | ND | ND | − | ND | − |
| 29. 128–145 | − | ND | − | ND | −V |
| 30. 37–55 | + | + | + | + | + |
| 31. 51 . 59 | − | ND | − | ND | − |
| 32. 48–56 | + | + | + | + | + |
| 33. Trimers | − | ND | − | ND | − |
| Synthetic peptides α-chain hCG | | | | | |
| 34. 88–92 | − | ND | − | ND | ND |
| 35. 1–15 | − | ND | − | − | − |
| 36. 16–30 | − | ND | − | ND | − |
| 37. 26–45 | − | ND | − | ND | − |
| 38. 41–61 | − | ND | − | ND | ND |
| 39. 57–76 | − | ND | − | ND | ND |
| 40. 72–92 | − | ND | − | ND | − |
| 41. 1–95 | − | − | − | − | − |

In Table 3, "−" represents less than 10% effect; "+" represents greater than 15% effect; "++" represents greater than 40% effect; "+++" represents greater than 70% effect; and "ND" represents no data available. The "HIV: in vitro" column reports results from assays of the inhibition of HIV-1 replication in vitro (HIV-1 strains and HIV-1 primary isolates) as described herein. The "HIV transgenic mice" column reports data from the inhibition of HIV RNA and protein expression in HIV-1 transgenic mice as described herein. Columns labeled "KS:in vitro" and "KS:in vivo" report on the inhibition of Kaposi's Sarcoma cell growth in vitro in cultured cells and of Kaposi's Sarcoma induced in mice, respectively, as described herein. Column 5 provides data on the relative increase of hematopoietic colony cell number in vitro clonogenic assays as described herein. The commercial hCG preparations tested were APL™ (Wyeth Ayerst), PREGNYL™ (Organon), ORGANON (a highly purified preparation obtained from Organon) PROFASI™ (Serono), Goldline, STERIS™, and Shein, and two preparations from Sigma, Sigma$^1$ (GHO) and Sigma$^2$ (C1063). The hCG preparations CR127 and CR1XY17V are highly purified hCG preparations and CR1 XY17B is a mixture of highly purified α-hCG and β-hCG, all three preparations were obtained from the National Institute of Child Health and Human Development (NICHD) at the National Institute of Health (NIH) and the rhCG is recombinant hCG expressed in a mouse cell line (Sigma). For the hCG subunits "αhCG" and "βhCG" are purified native subunits (Sigma); "rαhCG" and "rβhCG" all the recombinant subunits expressed in mouse cells (Sigma); and αfp1769A is purified, native α subunit (NICHD, NIH). The peptide "scrambled A1" has the sequence Cys-Val-Ala-Gln-Pro-Gly-Pro-Gln-Val-Leu-Leu-Val-Leu-Cys (SEQ ID NO:36) and "Scrambled A2"has the sequence Cys-Val-Ala-Gln-Gly-Val-Leu-Pro-Ala-Leu-Pro-Gln-Val-Val-Cys (SEQ ID NO:37). "Scrambled A1/B" has the sequence of β-hCG amino acids 45–57 (SEQ ID NO:6) and 109–119 (SEQ ID NO:7) which has been scrambled. "Trimers" is a mixture of tripeptides from the β-hCG sequence of amino acids 45–57: Leu-Gln-Gly, Leu-Gln-Pro, Gln-Gly-Val, Gln-Pro-Val, Gln-Val-Leu, Val-Leu-Pro, Leu-Pro-Ala, Leu-Pro-Pro, Pro-Ala-Leu, Pro-Pro-Leu, Ala-Leu-Pro, Pro-Leu-Pro, Leu-Pro-Gln, Pro-Gln-Val, Gln-Val-Val, and Val-Val-Cys (SEQ ID NOS: 38–53, respectively). Peptides were synthesized by Dr. N. Ambulos (University of Maryland Biomedicine Center), Becham (CA) or Peptide Technologies Corp. (Gaithersburg, Md.).

Considerable pro-hematopoietic activity was found with the native partially purified hCG heterodimer and whole β-chain, however, variability in the pro-hematopoietic effect was observed for different hCG preparations and no pro-hematopoietic activity was observed with highly purified (to homogeneity) hCG heterodimer in vitro. The lower molecular weight species may retain the pro-hematopoietic effect and that some purification procedure may not eliminate those species.

The available clinically used native hCG and native β-chain preparations are not homogenous and may be contaminated with one or more other active molecules. In this respect, it is noteworthy that though the effects of some preparations of hCG described here were obtained with two different commercial sources of hCG (APL and Pregnyl), one was usually more active (APL) at lower concentrations than any other preparation. The differences in activities of commercial preparations might be explained by variation in the amount of β-hCG fragments. This could be the consequence of different methods of preparation or different sources of human urine. For example, free β is more abundant in the earliest weeks of pregnancy. Consequently, we initiated studies with a variety of synthetic peptides, and our results show that all the in vitro activities of the preparations of native hCG are mimicked by the β-hCG peptides 45–57 and 109–119 but not other β- or α-peptides or scrambled 45–57 peptide. Thus, β-hCG may contain structural motifs that produce effects which probably work by mechanisms which differ from those currently known for hCG, and β-hCG peptides may have biological functions quite distinct from the conventional effects of the heterodimer.

Effects of hCG Preparations in SIV Infected Rhesus Monkeys

Events early in HIV infection are thought to be critical to subsequent AIDS pathogenesis. Although the early events in HIV infection are difficult to study in humans, they can be readily investigated in the SIV infected rhesus monkey animal model (Letvin et al., 1990, *J. AIDS* 3:1023–1040). SIV and HIV-1 are similar in many of their biological and physical properties including their genomic structure. In addition, $SIV_{mac251}$, unlike several other SIV isolates, induces a syndrome in experimentally infected rhesus macaques that is similar to human AIDS (Kestler et al., 1990, *Science* 248:1109–1112).

The effect of the same commercially available hCG preparation (APL™, Wyeth Ayerst), which had been pre-screened for anti-viral and anti-KS activity, was studied in five adult male rhesus monkeys who were intravenously inoculated with cell free $SIV_{mac251}$ ($10^{4.5}$ $TCID_{50}$/ml). In all animals, SIV p27 was apparent in plasma 14 days after infection, reaching a maximum by about day 20 (not shown). Treatment with systemic injections (3,000 IU, 2 times weekly) of the active commercial preparation of hCG (APL™), was initiated 3 weeks after SIV inoculation. Two months post-inoculation, the characteristic increase of SIV p27 antigen (FIG. 2A), reduction of CD4$^+$ T cells (FIG. 2B), and weight loss (FIG. 2C) occurred in 2 of 2 untreated infected monkeys. In contrast, the 3 infected monkeys treated with this hCG preparation showed weight gain characteristic of uninfected animals of this age (FIG. 2C), a marked decrease in SIV p27 (FIG. 2A) and an increase in CD4$^+$ T cells to normal levels (FIG. 2B). These effects were maintained over the 7 months the animals were followed. These results show that this commercially available hCG preparation can control $SIV_{mac251}$ acute infection, increase CD4$^+$ T cells, and promote weight gain in SIV infected rhesus monkeys and that these effects can be maintained. The animals were followed for 7 months, and no evidence of disease or SIV resistance to the hCG preparation developed.

Figure 2D:
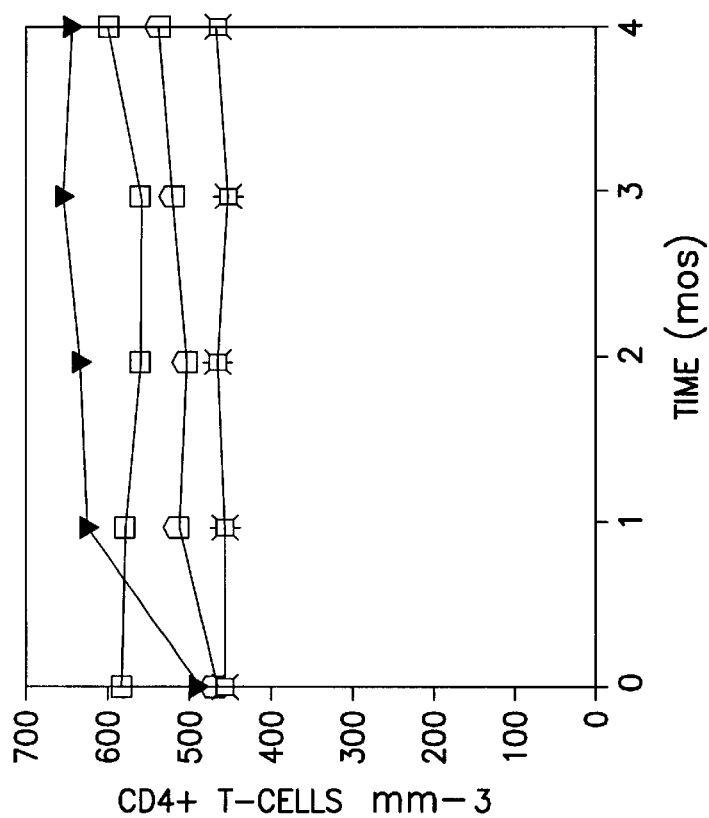
Figure 2C:
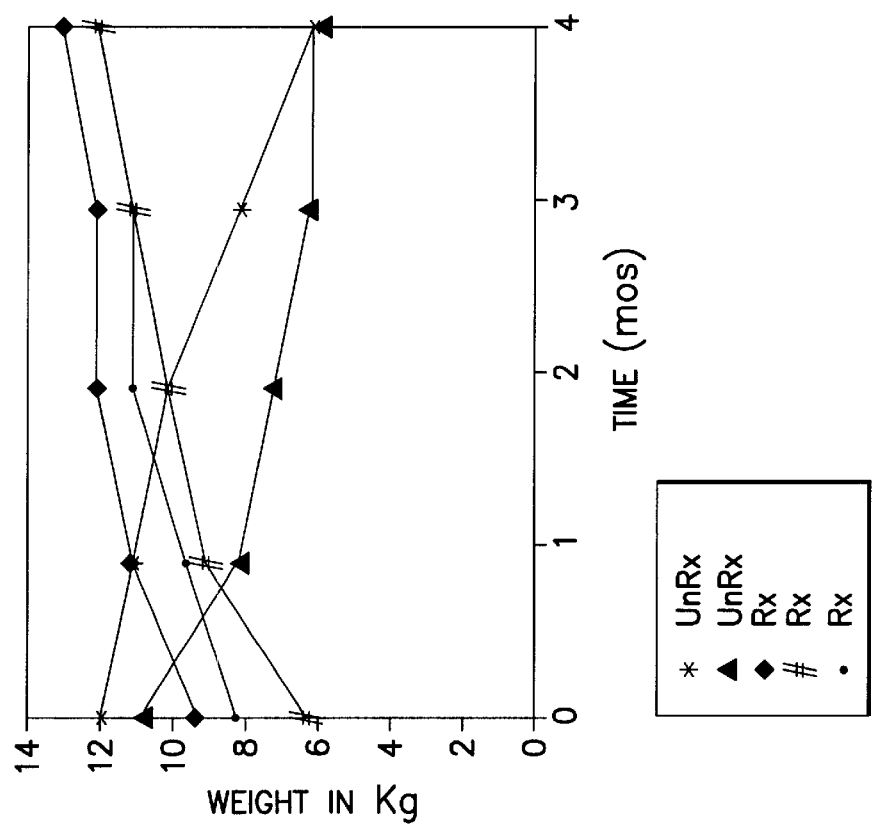

In FIG. 2D, results are shown from 4 uninfected controls: 2 received the hCG preparation and 2 received the diluent without the hCG. There is a slight increase in the CD4$^+$ T cells in the treated animals (increasing from 460 mm$^3$ to 520 mm$^3$ and from 470 mm$^3$ to 650 mm$^3$) (FIG. 2D). The 2 treated animals also showed a 1 to 2 kg weight gain (not shown).

Early Studies of Some hCG Preparationsin Patients with HIV-1 Disease

The incidence of KS is greatly increased in HIV-infected persons (Friedman-Kien et al., 1981, *J. Am. Acad. Dermatol.* 5:468–473). Based on experimental studies of the killing effect of some hCG preparations on KS Y-1 cells, clinical trials with some commercially available preparations of hCG given either intralesionally (Hermans et al., 1995, *Cellular and Molecular Biology* 3:357–364; Gill et al., 1996, *New Engl. J. Med.* 335:1261–1269, Harris, P. J., 1995, *The Lancet* 346:118–119) or systemically to KS patients have shown that cutaneous KS lesions were reduced via cell killing by apoptosis following intralesional inoculation (Lunardi-Iskandar et al., 1995, *Nature* 375:64–68; Hermans et al., 1995, *Cellular and Molecular Biology* 3:357–364; Gill et al., 1996, *New Engl. J. Med* 335: 1261–1269) and induced regression of advanced KS disease treated by systemic delivery.

Clinical trials reported herein were undertaken in Belgium and California to evaluate the anti-KS properties of systemic hCG therapy with or with out concomitant intralesional therapy. Use of anti-viral protease and non-protease inhibitors was not restricted. A total of 47 patients were enrolled under protocols of compassionate use sanctioned by the Institutional Review Boards of the respective centers. 29 patients were treated in Belgium, either on a protocol to investigate intralesional and systemic treatment of cutaneous KS (n=15), or in the pre-clinical phase of that protocol (n=4), or on compassionate use for systemic KS or HIV infection (n=10). The protocol involved intralesional administration of 500 IU hCG (PREGNYL™) to 4 lesions for 2 weeks, followed by subcutaneous administration of 2,500 IU hCG (PREGNYL™) 5 days per week for 4 to 6 weeks. Additional systemic intramuscular or subcutaneous hCG treatment with either PREGNYL™, APL™, or STERIS™ (one patient) was provided as ongoing therapy in some patients or as part of compassionate use protocols.

A total of 18 patients were treated in California with at least 1 month of follow-up as part of an ongoing protocol to evaluate systemic hCG therapy for cutaneous KS. These patients received either 5000 IU of APL™ subcutaneously 7 days per week, 10,000 IU subcutaneously 3 times per week, or 10,000 IU subcutaneously 7 days per week.

Overall 30 patients were on pre-existing, anti-viral therapy (19 on RT inhibitors and 11 on protease inhibitors), 11 were on no anti-virals and 8 were missing information. One patient, PH-RF, was on 3TC therapy before hCG therapy, and despite poor compliance, had an hCG response for visceral KS and viral load, which declined to undetectable on hCG alone.

Thirty-six patients survived the study, 7 (PH-LFA, PH-DD, PH-PJ, PO-BO, PO-RB, PH-JJ, PH-MH) died either from opportunistic infections or multiple organ failure. The vital status of 1 patient is unknown. Two patients, PH-DD and PH-OJ, discontinued hCG treatment because of cholestasis. PH-DD was on concomitant anti-mycobacterial therapy which was felt to be a contributing factor. PH-OJ had preexisting cholestasis, which was exacerbated by the hCG treatment with a marked increase in alkaline phosphatase and rise in bilirubin which required hospitalization (PH). These values declined by 2-fold following discontinuation of hCG therapy. These cases raise the possibility that liver toxicity may be a rare complication of hCG therapy.

Early clinical experience with relatively low dose intralesional hCG administration for KS indicated partial or complete regression of treated lesions, including 3 of the first 4 patients in the initial pilot study in Belgium (Hermans et al.,1995, *Cellular and Molecular Biology* 3:357–364) as well as a dose dependent effect between 16% (250 IU) and 83% (2,000 IU) in patients reported from California (Gill et al., 1996, *New Engl. J. Med.* 335:1261–1269), and other cases showing striking clearance of visceral (lung and gastrointestinal) KS in very advanced disease following systemic therapy with hCG APL™ or PREGNYL™ within 1 to 3 months of initiating therapy.

Among the 30 cases with cutaneous Kaposi's Sarcoma, 12 were treated with intralesional followed by systemic therapy in Belgium and 18 with systemic therapy only in California. Complete (2/12, Belgium; 2/18, California) and partial (5/12, Belgium; 4/18, California) responses were observed while progressive disease was noted among 2/12 from Belgium and 10/18 in California. The overall response rate for the study (CR+PR) was 43% (13/30). The response rate in the group administered hCG both intralesionally plus systemicly group was 58%, while the response rate was 33% in the group receiving only the systemic treatment. Among 8 patients with both visceral and cutaneous KS treated in Belgium with very advanced pulmonary or gastric lesions, 3 patients experienced complete remissions, 2 patients exhibited tumor stabilization and 3 progressed, in each case after failure of conventional cytotoxic therapy.

AIDS patients treated with hCG therapy were tested for increases in $CD4^+$ T cell levels (in numbers of cells per $mm^3$) and decrease in viral load by one of the following assays for determining viral load: NASBA (Louache, et al., 1992, *Blood* 180:2991–2999; Geller, et al., 1985, *Archs. Path. Lab. Met.* 109:138–145), which has a lower detection limit of 4,000 copies; Roche Amplicor, with a lower detection limit of 200 copies; RT-PCR, with a lower detection limit of 100 copies; or TCID assay in which the infection of PBMCs in co-culture is determined (Popovic et al., 1984, *Science* 204:497–500). As viral load was assayed retrospectively, the viral load results were not a factor in guiding choice of therapy or changes in therapy. Each patient served as their own control and change in viral load (0.7 log change between baseline and subsequent post hCG viral load, scored as significant) was the endpoint measurement for this analysis. For analysis of the anti-viral effect, in addition to the 10 patients undergoing with synchronous hCG and other anti-viral therapy, 6 patients were excluded because of a lack of base line viral load or insufficient follow up before hCG therapy was stopped or additional anti-viral therapy was started.

Figure 3C:
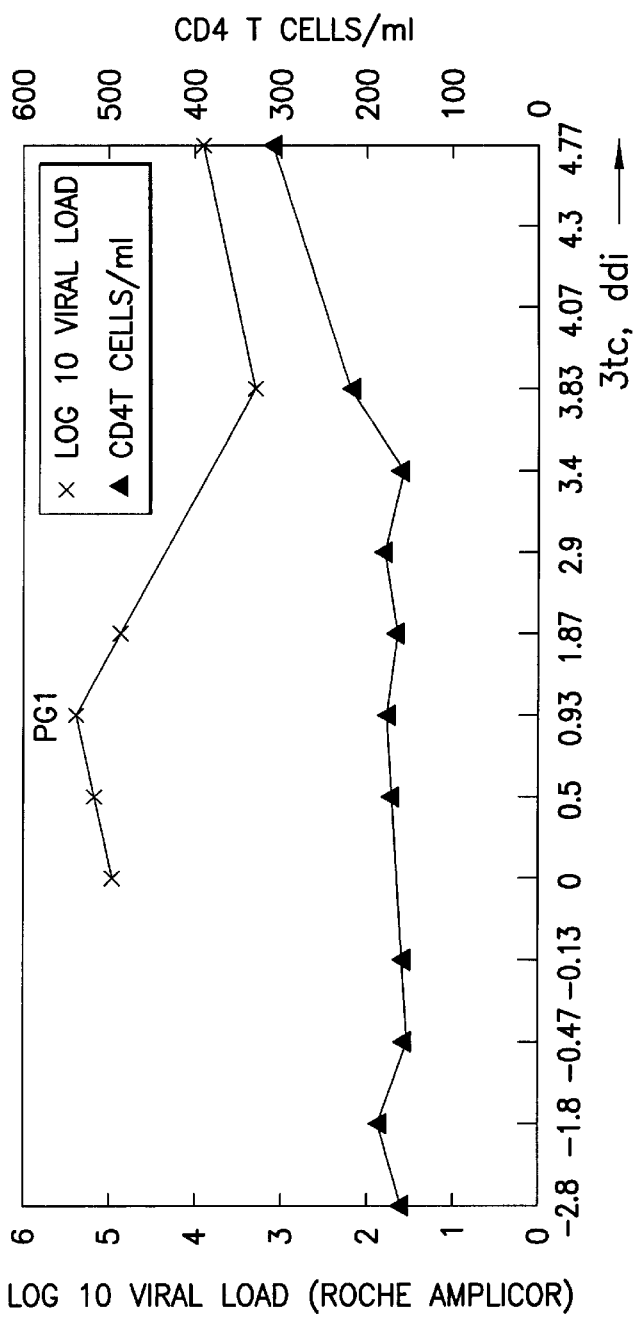
Figure 3D:
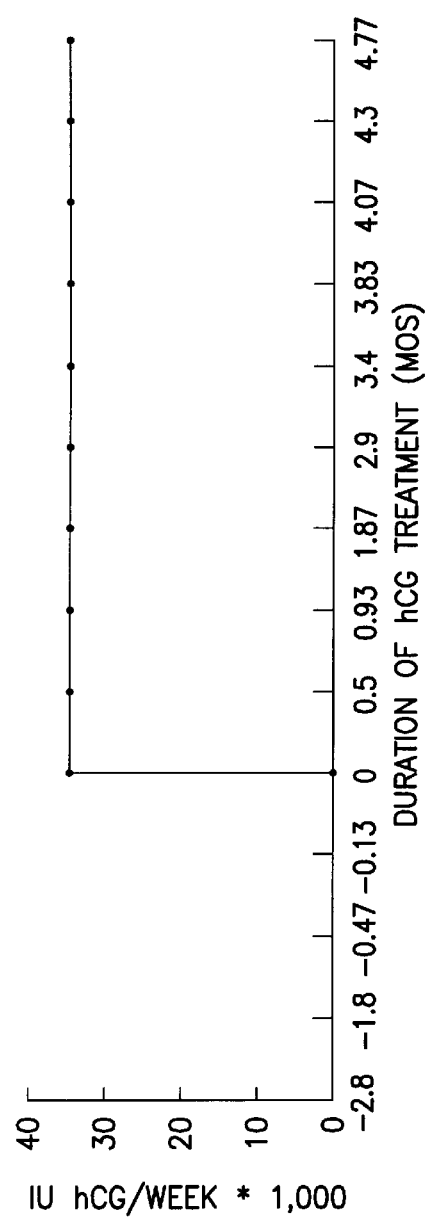

Among the 16 cases, 1 (PH-OJ) experienced a fall in viral load of 0.7 log on 2 successive tests at least 1 month apart while on stable anti-viral therapy (see FIGS. 3A and B), 11 were non responding and 2 (PH-VE and PHGRX) manifested an increase in viral load of at least 0.7 log after hCG therapy on 2 successive tests at least 1 month apart. As illustrated in FIGS. 3C and D, another patient (PG-1), initially on hCG alone and classified as non responsive by study criteria (2 consecutive values of 0.7 log decrease in viral load over 1 month) on hCG alone, experienced a steady decline in viral load but the second qualifying >0.7 log viral load drop was measured 2 weeks after non protease inhibitor therapy was begun. Because of this short window, it is likely that this second stable viral load point is accounted for by hCG rather than the newly introduced anti-virals. It is noteworthy that $CD4^+$ T cell levels were not significantly altered in this case but, the patient's KS progressed, documenting a dissociation of various hCG effects.

Among the 6 cases being treated with hCG alone (i.e. without other anti-viral therapies) with analyzable data, all were scored as non responsive to the hCG therapy by the scoring criteria although one case (PG-1) noted above (and illustrated in FIGS. 3C and D) is a probable responder. An additional patient on hCG alone (PG-8; FIGS. 3E and F) experienced a sustained fall in viral load of 0.5 log over a 2.8 month period of treatment on hCG alone until KS lesions progressed, at which time hCG therapy was discontinued. Thus of the 7 analyzable patients on hCG alone, 4 exhibited a downward trend in viral load, 2 patients showed an increase in viral load, and 1 patient was stable.

To more fully evaluate all data from patients on hCG alone or with stable antiviral therapy, all eligible data points were plotted, as shown in FIG. 15A, indicating the coordinates for each data point pre and post therapy, with values on the line representing no change in viral load. Values are distributed more or less equally above and below the line with no obvious trend to suggest a strong anti viral effect. To evaluate a dose response relationship between hCG and viral load, regression analysis for patients on hCG, alone or with stable antiviral therapy is shown in FIG. 15C. There was no detectable effect of higher hCG dose on viral load level (r=−0.089, p=0.285, N=147 measurements). An analysis by different CD4 strata did not show any significant trends to suggest that level of immunity impacted the hCG effect.

Figure 3G:
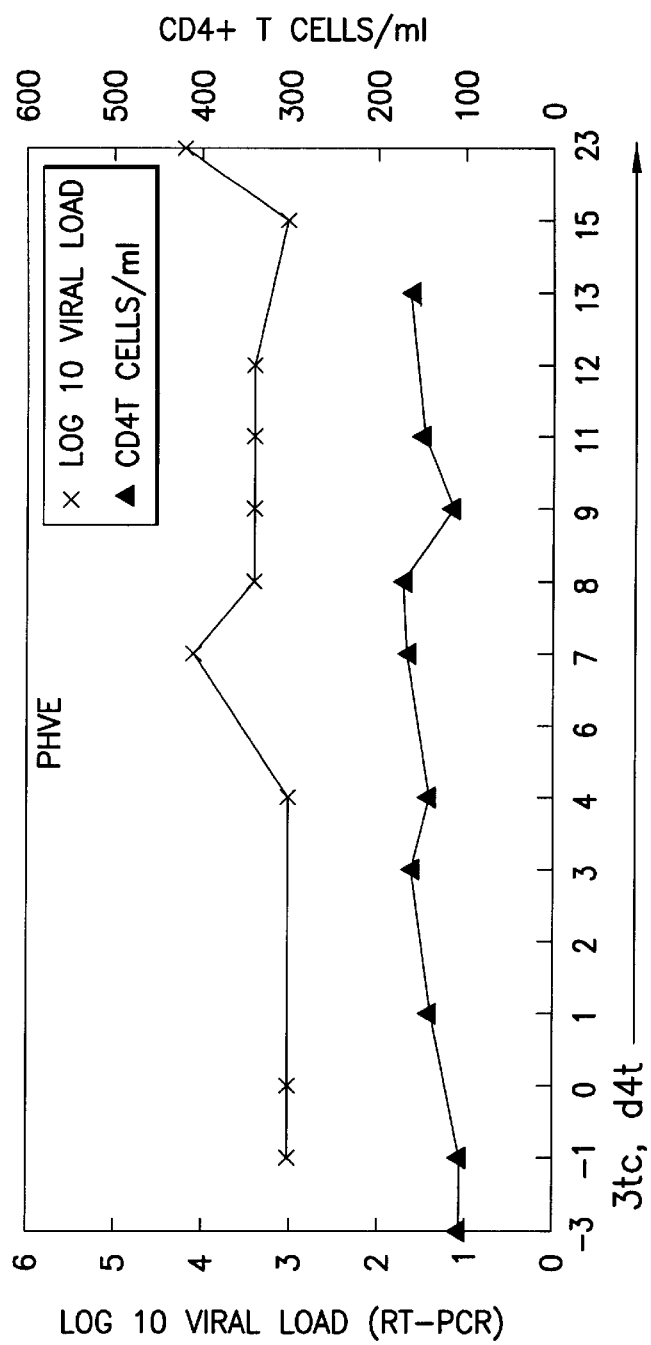
Figure 3H:
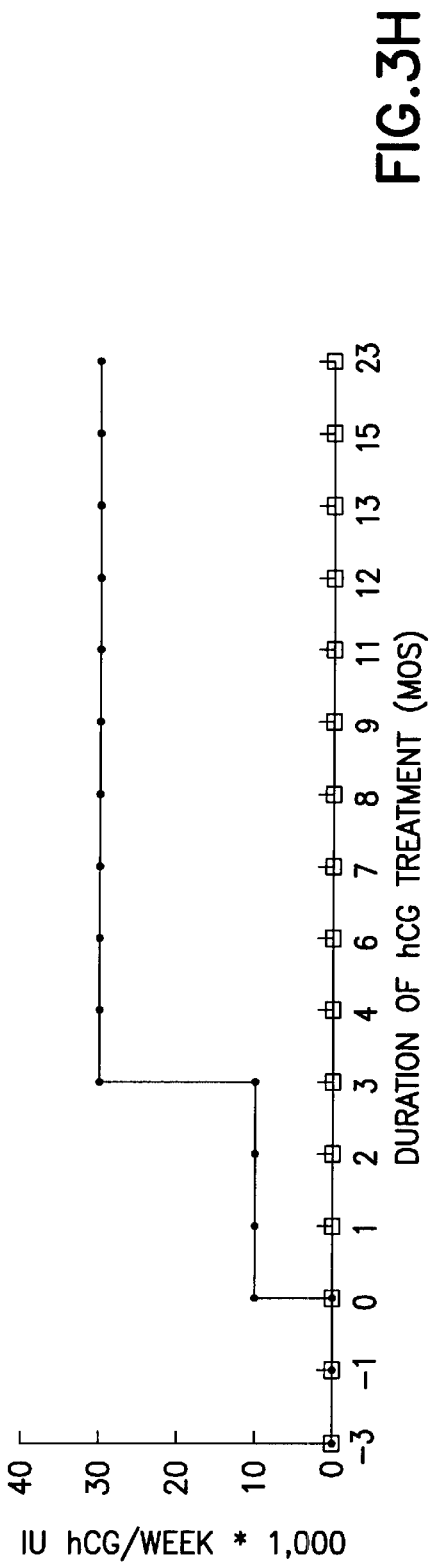
Figure 3I:
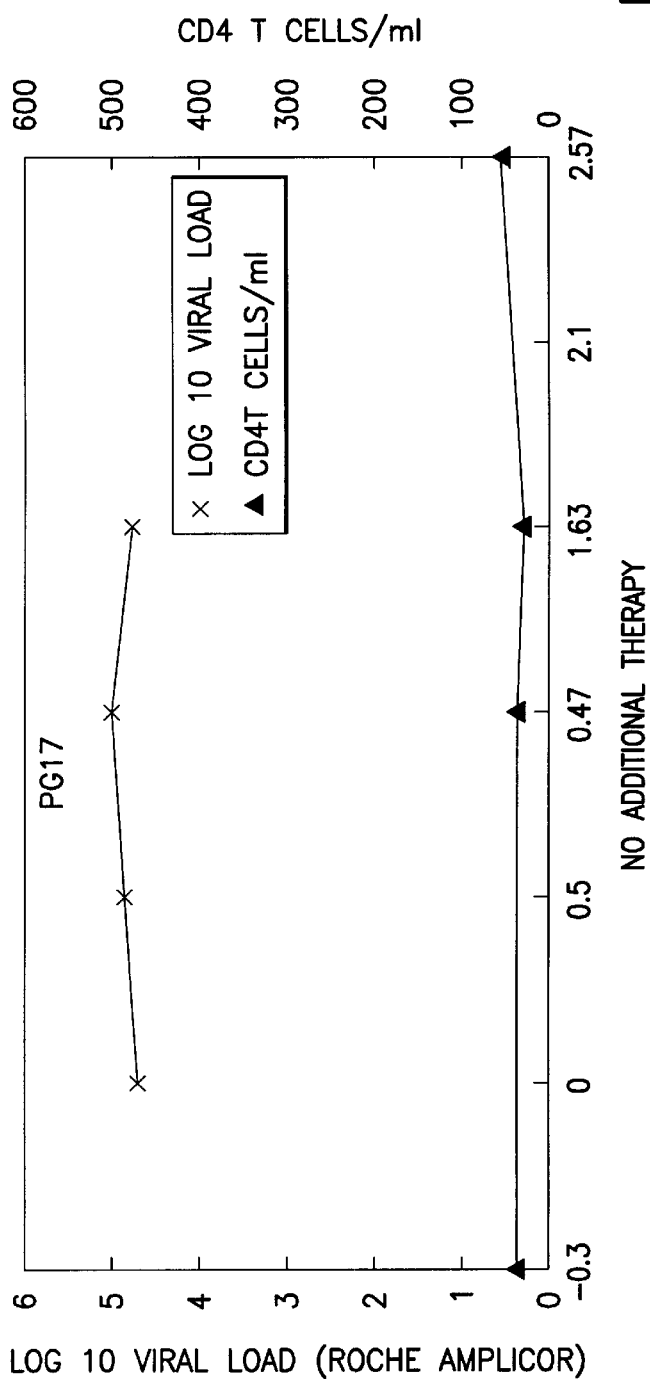
Figure 3J:
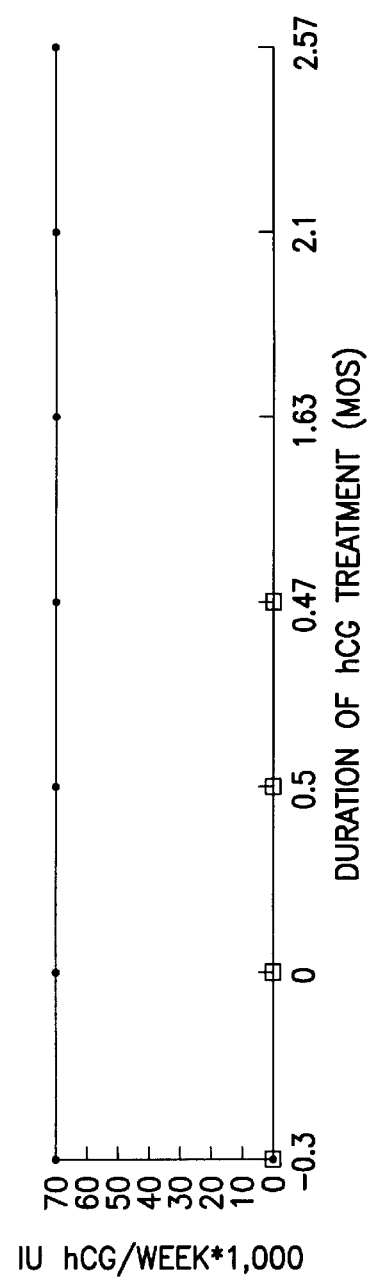

Among the 22 patients with analyzable CD4$^+$ T cell data, 5 demonstrated a pro-CD4$^+$ T cell effect (PH-VE, PH-RF, PG-9, PG-17, and PG-19) characterized by a 50% rise in CD4$^+$ T cell count sustained over at least a one month period, as demonstrated by plotting the data from at least two patients (PH-VE—FIGS. 3G and H and PG-17—FIGS. 3I and J). Of these 5 patients, concomitant stable non protease anti-virals were administered to 2 patients, stable protease inhibitors in 2 cases and hCG preparation alone in 1 case. Thus of the 6 cases with valid CD4$^+$ T cell data on hCG preparation alone, 1 manifested a significant response. No patient experienced an adverse fall in CD4$^+$ T cell on hCG preparation therapy, although patient PH-VE experienced an 0.7 log rise in viral load with a sustained 50% fall in CD4$^+$ T cell numbers and a partial anti KS response (FIGS. 3G and H). Similarly, patient PG-17 experienced a significant rise in CD4$^+$ T cells and no change in viral load on hCG therapy alone, yet experienced progression of KS after 2.5 months (FIGS. 3I and J). All CD4$^+$ T cell values (except for 2 patients on hCG alone) were at or above baseline, with the most significant rises in those on concomitant stable protease inhibitor or non protease drugs (FIG. 15B). There is no correlation between a change in the CD4$^+$ T cells count and the dosage of hCG (r=0.101, p=0.339, N=92) (data not shown).

Among the 26 patients analyzable for weight gain (patients who started hCG preparation therapy coincident with or shortly after starting other anti-viral therapy were excluded), 14 gained weight, 3 experienced weight loss, and 9 remained stable. There was no correlation between weight change and dosage of hCG (data not shown). There was however a pattern observed in some patients where an initial weight gain was followed by a return to baseline levels while others experienced sustained weight gain over several months.

hCG therapy was well tolerated clinically by patients and there was no evidence for an adverse effect of hCG on viral load or CD4$^+$ T cell level. In two cases with advanced HIV disease hCG was discontinued because of coincident cholestasis probably due to other medications in one case and opportunistic infections in the other.

Certain preparations of hCG and β-hCG were particularly efficacious in reversing wasting associated with HIV or SIV infection although variability among different preparations was observed. The native hCG and native β-chain preparations available for clinical use are not homogenous and may be contaminated with one or more other active molecules. In this respect, it is noteworthy that though the effects of some preparations of hCG described here were obtained with two different commercial sources of hCG (APL and Pregnyl), one was usually more active (APL) at lower concentrations than any other preparation despite the fact that identical amounts (International Units) were used, as assessed by the manufacturer's standard bioassays for the conventional use of hCG. The differences in activities of commercial preparations might be explained by variation in the amount of β-hCG peptide fragments. This could be the consequence of different methods of preparation or different sources of human urine. For example, free β chain is more abundant in the earliest weeks of pregnancy.

Effects of hCG Preparations on HIV-1 Infection in vitro

To prepare HIV infected cells for the in vitro assay of hCG preparations and -β-hCG peptides and derivatives, primary PBMCs, macrophages, and CD4$^+$ T cells isolated from peripheral blood and the H9 human T cell line, were acutely or chronically infected with 8 different HIV-1 strains: 4 cell line adapted viruses, namely the macrophage tropic Ba-L strain (Gartner et al., 1986, *Science* 233:215–219) and the CD4$^+$ T cell tropic MN, RF, and IIIB strains ($10^5$ TCID$_{50}$/ml) (Popovic et al., 1984, *Science* 204:497–500; Gallo et al., 1984, *Science* 224:500–503); 2 isolates, Ju1083 and G3, from Nigerian AIDS patients passed once in a CD4$^+$ T cell line (Sub-T1); and 2 primary ("clinical") isolates from AIDS patients from Trinidad which were never passed in any cell line and were used at a titer of 7.5×10$^4$ TCID$_{50}$/ml. In all experiments, HIV-1 ($10^5$ TCID$_{50}$/ml) was added to the cells ($10^6$ cells/ml) for a 2 hour incubation after which the virus infected cells were washed with 10 ml phosphate buffered saline (PBS) three times to eliminate extracellular virus. The test inhibitor, i.e. the hCG or β-hCG peptide preparation was then added and the cells were incubated with the test inhibiter for 9 to 10 days with serial sampling. Cultures were assayed for p24 antigen on days 3 to 10. The inhibition of HIV production by the active preparations was not due to cell toxicity since, at the concentrations used, there was little or no effect on $^3$HTdR incorporation, or cell viability as assessed by cell counts and 3-[4,5 dimethylthiazol-2-y], 2,5 diphenyltetrazolium, and bromide thiazoylblue (MTT) assays (data not shown).

Figure 4A:
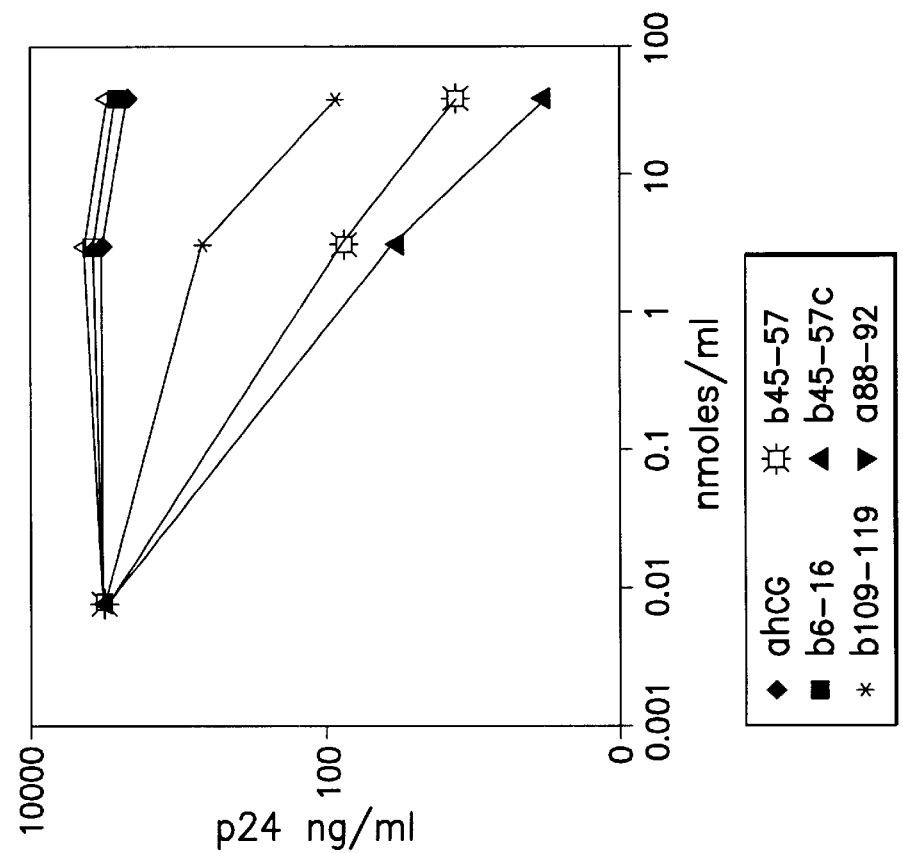
FIGS. 4A–D. Effects of hCG preparations and peptides on HIV replication in vitro. (A and B) These graphs depict the concentration dependence of inhibition of HIV-1 IIIB infection of $CD4^+$ T cells or total PBMCs from peripheral blood of normal donors (infection is expressed in nanograms (ng) of p24/ml plasma) as a function of nmol per ml α-hCG subunit, β-hCG peptide or α-hCG peptide over a concentration of 0.05 to 50 nmol/ml. Graphs present data on infection of (A) $CD4^+$ T cells infected by HIV-1 IIIB and (B) PBMCs infected with HIV-1 IIIB. In both graphs, results with α-hCG subunit are represented by lines with diamonds, results with the β-hCG peptide 6–16 by lines with squares, results with the β-hCG peptide 109–119 by lines with stars, results with the circularized β-hCG peptide 44–57 (with cysteine substituted for the amino acid at position 44) (SEQ ID NO:26) by lines with triangles, and results with the α-hCG peptide 88–92 by lines with inverted triangles. (C and D) These graphs depict data on the effect of α-hCG, hCG peptides and commercial hCG preparations on the infection of primary macrophages by HIV-1 Ba-L. (C) Effect of different concentrations of hCG a subunits and various hCG peptides (0.05 to 50 nmol/ml) on infection in peripheral blood macrophages from a normal donor infected with HIV-1 Ba-L. The results are averages of triplicate samples with less than 15% variation. Results with α-hCG subunit are represented by lines with diamonds, results with the β-hCG peptide 6–16 by lines with squares, results with the β-hCG peptide 109–119 (SEQ ID NO:7) by lines with stars, results with the circularized β-hCG peptide 44–57 (with cysteine substituted for the amino acid at position 44) (SEQ ID NO:26) by lines with triangles, and results with the α-hCG peptide 88–92 by lines with inverted triangles. (D) A comparison of the inhibition of HIV Ba-L infection of macrophages by different commercial native hCG preparations (APL™, Wyeth Ayerst; STERIS™, Steris; PREGNYL™, Organon) and by purified hCG (CR127) over a concentration range of 0.05 IU to 1,000 IU/ml. Results are shown at day 10. Results with APL™ hCG are indicated by a line with inverted triangles, results with STERIS™ hCG are indicated by a line with circles, results with PREGNYL™ hCG are indicated by a line with squares, and results with hCG-CR127 are indicated by a line with X's.
Figure 4B:
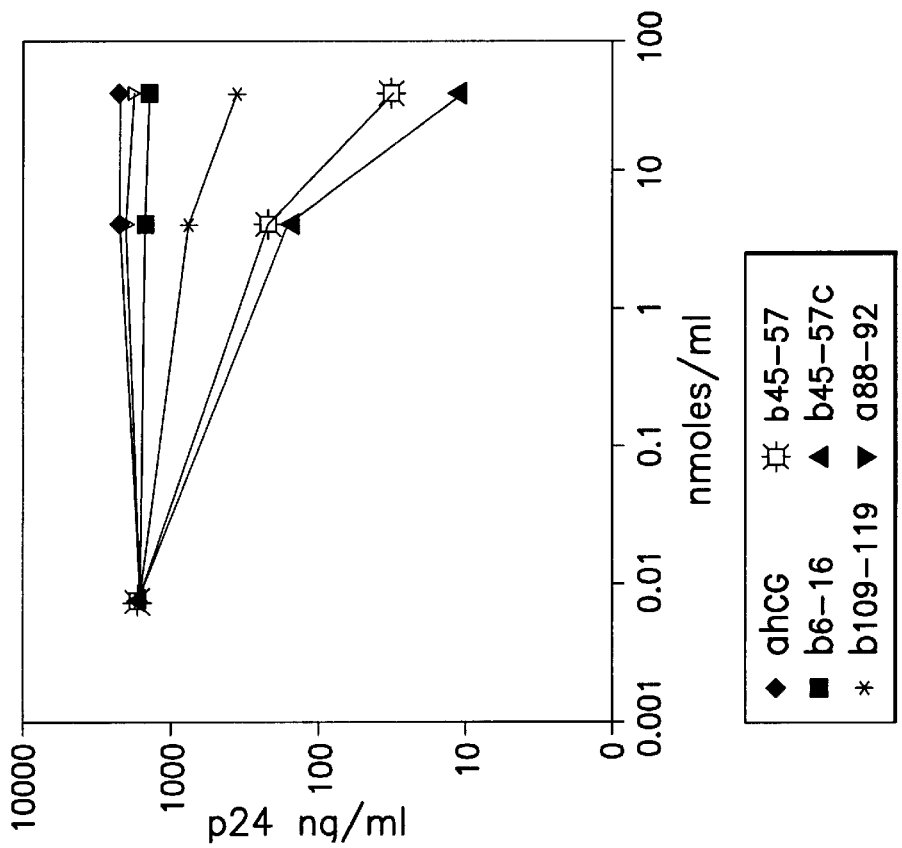
Figure 4D:
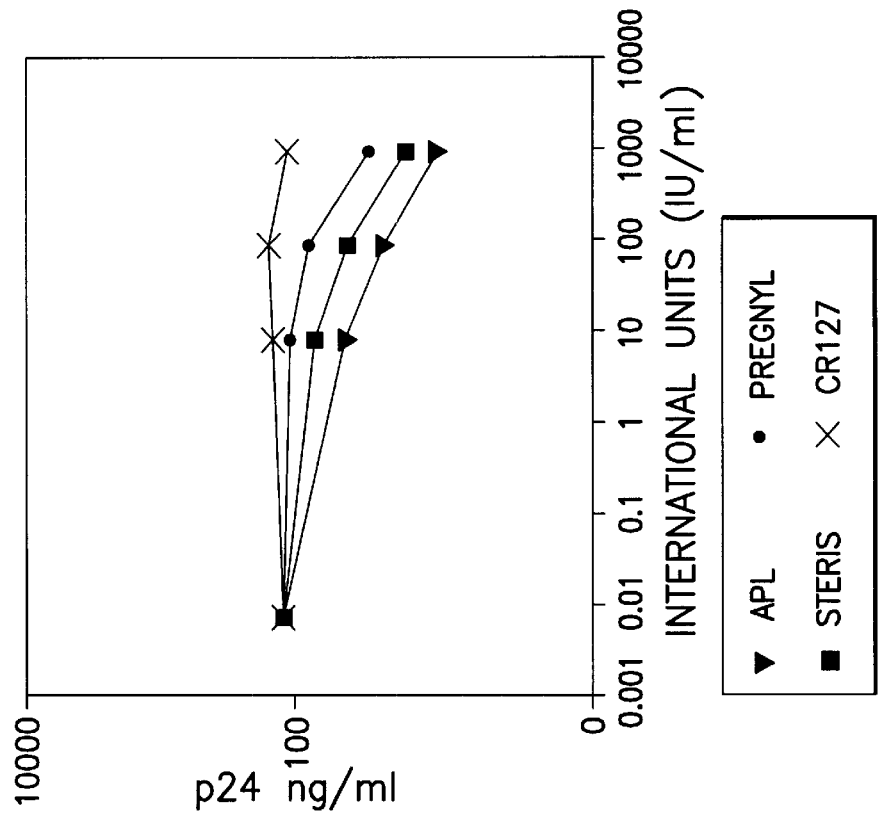
Figure 4C:
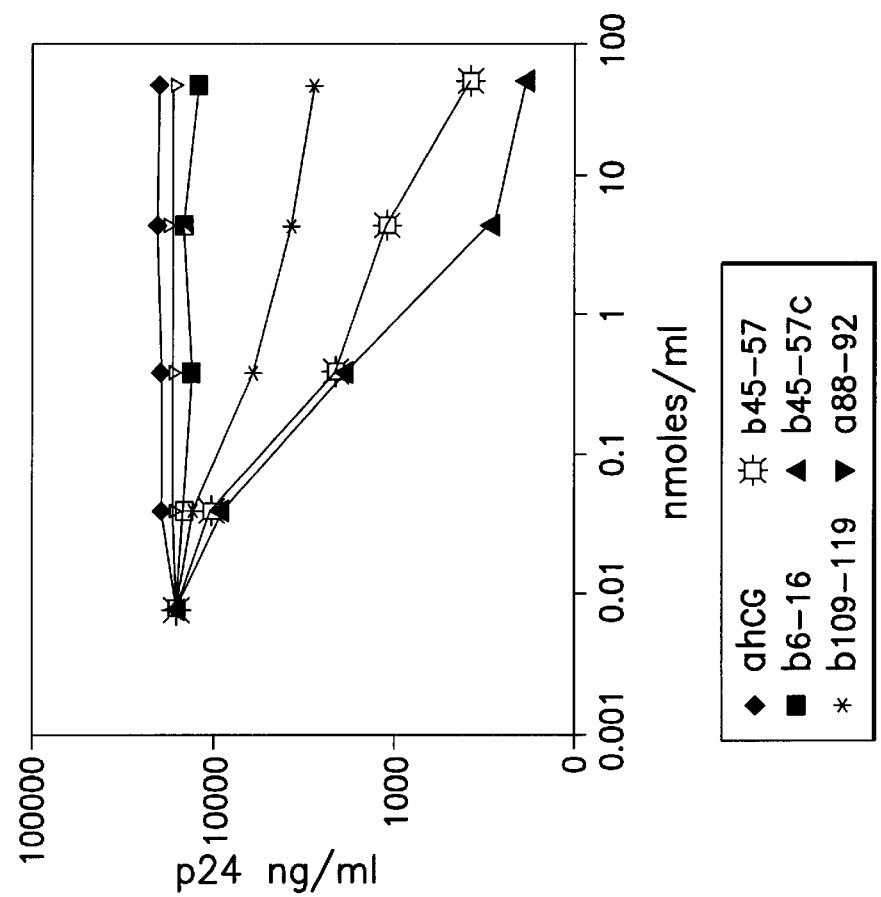

There were no significant differences in the results with the different strains of HIV-1 (not shown). For illustrative purposes, the data presented are from the assays with the HIV-1 IIIB infected isolated CD4$^+$ T cells (FIG. 4A), IIIB infected PBMCs (FIG. 4B) and HIV-1 Ba-L infected isolated macrophages (FIGS. 4C and D). As shown in FIGS. 4A–D, the inhibitory effects of the peptides or hCG preparations were approximately the same for macrophage tropic (FIGS. 4C and D) or T cell tropic strains (FIGS. 4A and B). Infection with primary isolates showed similar inhibition (data not shown). In contrast to the potent inhibition of acute HIV-1 infection in vitro by the active hCG preparations or synthetic peptides, there was slight or moderate inhibition (20–40%) of virus production (HIV-1 IIIB) from chronically infected CD4$^+$ T cell lines (not shown). All target cells had similar patterns of inhibition with the expected variation in p24 antigen expression (FIGS. 4A–D).

As already noted, there is significant variation in the activity of various commercial preparations of native hCG to kill KS tumor cells (Lunardi-Iskandar et al., 1995, *Nature* 375:64–68; Hermans et al., 1995, *Cellular and Molecular Biology* 3:357–364; Gill et al., 1996, *New Engl. J. Med* 335:1261–1269). As shown in FIG. 4D, there is similar variation in the anti-HIV activities of these preparations. For example, for the native heterodimer preparations, the most active preparation was usually hCG APL™ (Wyeth Ayerst) and Sigma hCG (CG10) followed by hCG PREGNYL™ (Organon) (FIG. 4D and Table 3).

Employing APL™ hCG, there is a dose dependent inhibition of HIV-1 replication (FIG. 4A). Surprisingly, there was little or no inhibition with the highly purified native hCG heterodimer preparations CRIXY17B (data not shown) and CR127 (FIGS. 4C and D) (generously supplied by the National Hormone and Pituitary Program and Center for Population Research, NIH) nor with purified recombinant α- or β-chains (Sigma). However, commercially available hCG (APL™, Wyeth Ayerst) and partially purified native β-hCG (NβhCG) (dissociated from hCG, Sigma) was active while native α-hCG was not (FIGS. 4A–D and Table 3).

Effect of hCG Preparations on HIV-1 Transcription

Figure 5A:
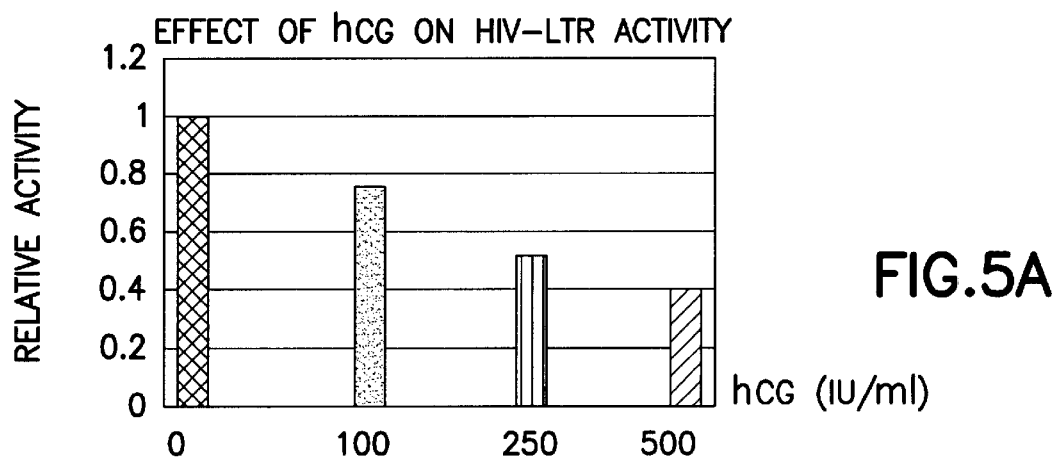
FIGS. 5A–C. Effect of preparations of hCG on HIV-LTR activity. (A) The CAT activity of cells containing the HIV-LTR construct and treated with hCG concentrations of 0 IU/ml, 100 IU/ml, 250 IU/ml and 500 IU/ml was calculated relative to the untreated control. (B) Relative CAT activity of the unrelated SV40 promoter in response to hCG at 0 IU/ml, 250 IU/ml and 500 IU/ml was similarly calculated. Data in both A and B represents the mean+/−S.E.M. of 3 to 7 independent experiments and is presented as a bar graph. The different hCG concentrations are indicated in both A and B as depicted below.
Figure 5B:
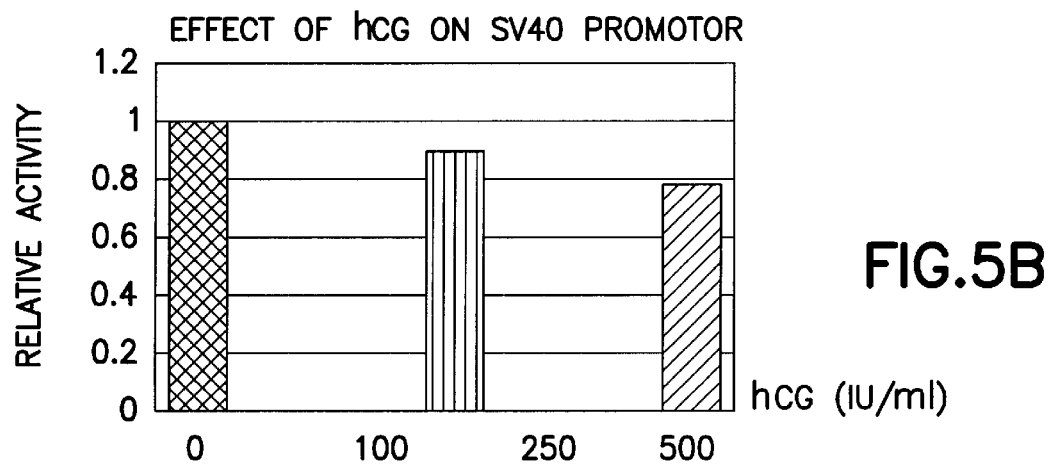
Figure 5C:
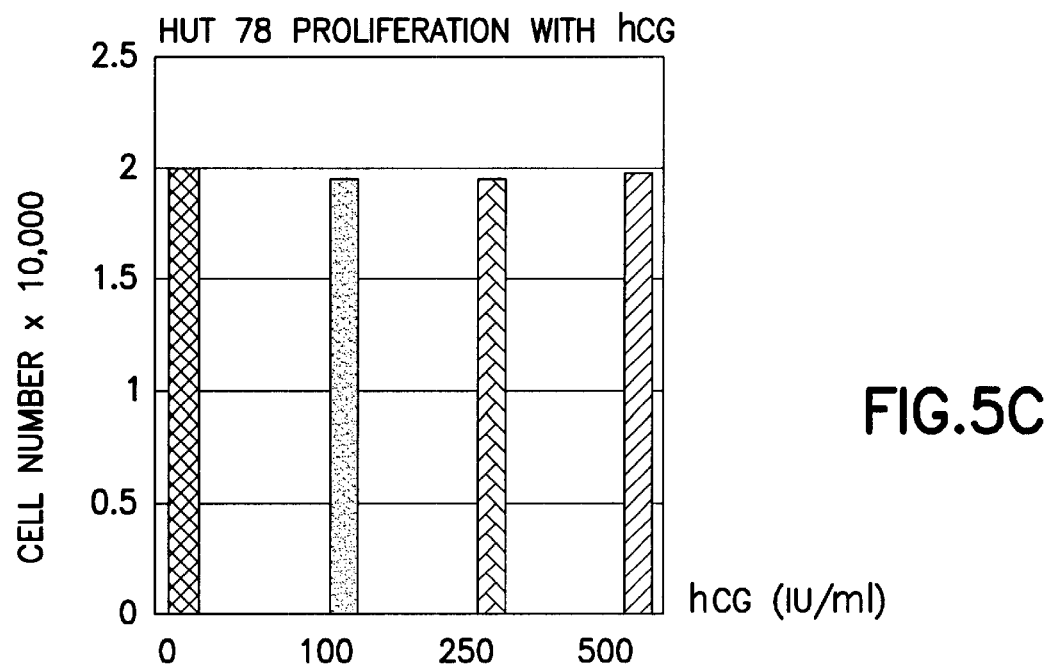

To further elucidate the anti-HIV effects of crude hCG preparations, we studied the effect of APL™ hCG on a HIV-1 LTR driven expression of a reporter gene, chloramphenicol acetyltransferase (CAT) (FIGS. 5A–C). The T-lymphocyte cell line HUT 78 was transiently transfected with the HIV-LTR construct 174WTIICAT by electroporation. $1 \times 10^7$ cells were resuspended in 0.4 ml RPMI 1640 medium supplemented with 10% fetal calf serum (FCS), and 20 μg of the test plasmid with 2 μg of the Tat expression vector pDEX/Tat were introduced into the cells by a pulse from a Biorad GenePulser II apparatus of 250 V and 950 μF at 4° C. (Plasmids were the generous gift of Dr. Richard Gaynor, University of Texas Southwestern Medical Center.) Cells were then divided into three aliquots and maintained at 37° C., 5% $CO_2$ for 40 hours in the presence of drug, or an equal volume of diluent. Transiently transfected cells were harvested, lysed and a standard amount (4 μg) of heat-treated extract was incubated in the presence of 0.6 mM acetyl coenzyme A and 0.1 μCi [$^{14}$C]chloramphenicol in 0.25 mM Tris, pH 7.9 at 37° C. for 1 hour. The amount of acetylated [$^{14}$C] chloramphenicol converted to acetyl [$^{14}$C] chloramphenicol was determined by thin layer chromatography in chloroform: methanol 95:5 (v/v) to fractionate the reaction mixture. Results were quantified by phosphorimage analysis on a Molecular Dynamics Phosphor Imager 445 SI. For each assay the amount of acetylated chloramphenicol was determined as a fraction of total [$^{14}$C] in the sample to determine the activity of the CAT enzyme.

The expression of CAT driven by the HIV-1 LTR was inhibited in a dose-dependent manner such that 78% of normal transcription from the LTR was detected in cells treated with 100 IU/ml hCG (APL™) and 36% of normal transcription was detected in cells treated with 500 IU/ml hCG (APL™) (FIG. 5A). hCG had no effect on transcription of the SV-40 driven CAT construct (FIG. 5B). The hCG preparation also had no inhibitory or cytotoxic effect on these cells even after 40-hour incubation with 500 IU/ml hCG (FIG. 5C), as previously shown (Lunardi-Iskandar, Y., et al., 1995, Nature 375:64–68).

Results from constructs with point mutations in the enhancer (NFkB), SP-1 and TAR regions of the promoter showed essentially the same response to hCG; therefore, none of these important regulatory elements was demonstrated to be necessary for the response to hCG (not shown). These results are in accord with the transgenic mice results and indicate that at least part of the inhibitory effect of these hCG preparations is on transcription of the HIV-1 provirus.

Effects of β-hCG Peptides on HIV-1 Infection

Since it is known that hCG has proteolytic products which may co-purify with the heterodimer or its β-chain, a series of α- and β-subunits and various synthetic peptides were compared to the active preparations of the native heterodimer (FIGS. 4A–D; see also Table 3). Peptides of the α- and β-subunits (0.05 to 50 nmoles/ml), native a chain preparation, and various crude preparations of the native hCG heterodimer (0.01 to 1,000 IU) and the native β-hCG subunit (100 to 1,000 μg) were tested for effects on HIV-1 replication in acutely infected cells by measuring change in viral antigen levels in response to the above noted preparations (FIGS. 4A–D and Table 3).

The effect of β-hCG synthetic peptides β-hCG 45–57 (SEQ ID NO:6; "satellin A1"), circularized β-hCG 45–57 with cysteine at position 44 (SEQ ID NO:26; "satellin A2"), the peptide β-hCG 109–119 (SEQ ID NO:7; "satellin B"), and the fused peptides of amino acids 47–57 (SEQ ID NO:28) linked by a peptide bond to the N-terminus of 108–119 (SEQ ID NO:29), and 45–57 (SEQ ID No:6) linked at C-terminus by a peptide bond to the N-terminus of 109–119 (SEQ ID NO:7) all inhibit HIV-1 replication in vitro (Table 3). The first three of these peptides were shown to inhibit HIV infection in a dose dependent fashion (FIGS. 4A, B and C) and had comparable activity in various cell systems (FIGS. 4A, B and C) and against various viral strains (not shown), including primary field isolates. Additionally, the β-hCG peptides of amino acids 109–145, 46–65, 7–40, 47–55 and 48–56 (SEQ ID NOS:25, 34, 33, 20 and 35, respectively) also inhibited HIV-1 replication (Table 3). Surprisingly, the "Scrambled Satellin A1", with a sequence of Cys-Val-Gln-Pro-Gly-Pro-Gly-Val-Leu-Leu-Val-Leu-Cys (SEQ ID NO: 36) also had an inhibitory effect (Table 3). Native α-hCG, the α-hCG peptides of 88–92 and 1–95, and several other β-hCG peptides had little or no effect (FIGS. 4A, B and C and Table 3).

Effects of β-hCG Peptides on Kaposi Sarcoma Cells

Neoplastic Kaposi's Sarcoma tumor cells with a characteristic chromosomal abnormality have been reported (Delli-Bovi et al., 1986, Cancer Res. 46:6333–6338; Siegal, et al., 1990, Cancer 65:492–498; Popescu et al., 1995, JNCI 88:450–454) and provide a model system for studying the in vitro effects of hCG on KS cells. In our prior studies employing immune deficient mice injected with KS tumor cells, some commercial preparations of native hCG killed KS tumor cells in vivo apparently by inducing apoptosis and inhibiting angiogenesis. In vitro tumor cell colonies were also suppressed in clonogenic assays by the hCG preparations (Lunardi-Iskandar et al., 1995, Nature 375:64–68; Nakamura et al., 1988, Science 242:426–430; Ensoli et al., 1989, Science 243:223–226; Salahuddin et al., 1988, Science 242:430–433; Masood, et al., 1984, AIDS Res. Hum. Retroviruses 10:969–976). In the current study, experiments were performed to investigate whether the anti-viral effect of the active peptides (FIGS. 4A–D and Table 3) correlated with the anti-KS effect of native hCG both in vitro in clonogenic assays on cultured KS Y-1 cells and in vivo in KS tumors induced in nude mice by injection of cultured Kaposi's Sarcoma cells.

Briefly, the KS Y-1 cells were obtained from mononuclear cells isolated from pleural effusion of an AIDS patient with KS in the lungs. After the depletion of T lymphocytes, monocytes/macrophages and fibroblasts using monoclonal antibodies against CD2, CD3, CD4, CD8, CD10 and CD14 membrane antigens and baby rabbit complement, the cells were cultured in the absence of exogenous growth factors to select for transformed cells. Immunological characterization of the KS Y-1 cells showed that CD34, CD31 and endoglin were expressed. Clonogenic assays were performed by seeding the KS Y-1 or KS-SLK cells in methylcellulose (0.8%, v/v), incubating the cells for 10 days in the presence or absence of the hCG, β-hCG or β-hCG peptide preparations and then counting the number of well-formed colonies of triplicate wells formed after seeding with $5 \times 10^4$ cells.

Figure 6A:
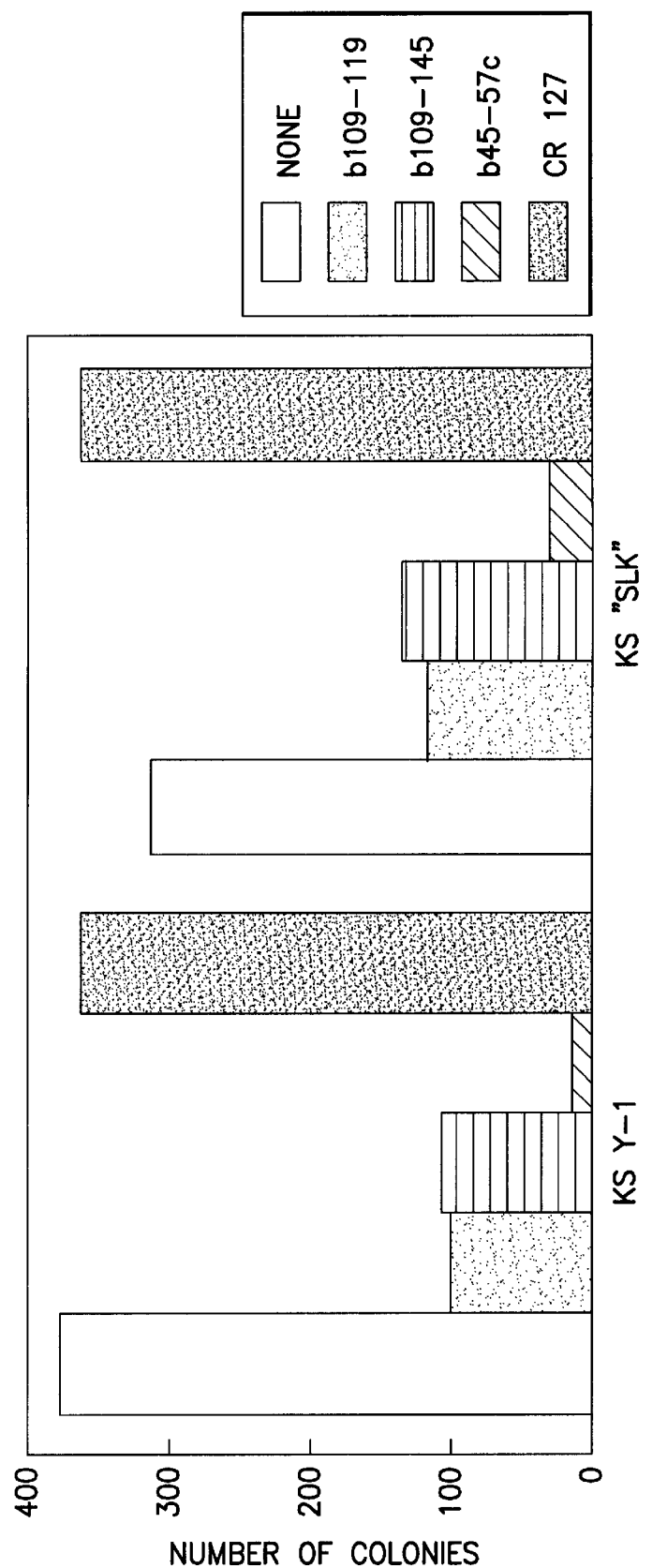
Figure 6B:
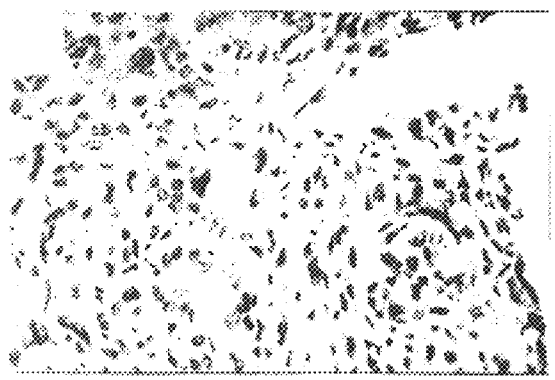

As shown in FIG. 6A and Table 3, the peptides used in the assay at a concentration of (50 nmoles/ml) with the strongest anti-viral effects (peptides of amino acids 45–57 (SEQ ID NO:6), cyclic 44–57, with cysteine substituted at position 44 (SEQ ID NO:26), 109–119 (SEQ ID NO:7), 109–145 (SEQ ID NO:25), and 47–57 linked at the C-terminus by a peptide bond to the N-terminus of 108–119 (SEQ ID NO:32), and 45–57 linked at the C-terminus by a peptide bond to the N-terminus of 109–119 (SEQ ID NO:30)) also had the strongest anti-tumor effects (i.e., anti-KS effect) on the two KS neoplastic cell lines. It is notable that the highly purified hCG heterodimer (CR127 2 use data concentrations of nmoles/ml) was inactive, as in the in vitro HIV assay. There was no anti-KS effect with the highly purified α- and β-chains and the α-hCG peptides, and other β-hCG peptides showed little or no inhibition in clonogenic assays (Table 3). Again, the "Scrambled Satellin A1" peptide (SEQ ID NO:36) exhibited activity while the others scrambled peptides did not.

The effects of the peptides on KS tumor cells were also evaluated in vivo in the KS mouse model. To induce KS tumors in the mice, $1 \times 10^6$/ml KS Y-1 cells in 50 μl PBS or saline were injected subcutaneously into immunodeficient mice (beige-XID-BNX mice). After one week, tumors ranged in size from 2 mm×3 mm to 3 mm×5 mm. Methods for detection of apoptosis (from tissue biopsies) were used, as described in Lunardi-Iskandar et al.(1995, *Nature* 375:64–68). Briefly, the samples were stained in situ for the presence of cells with DNA fragmentation. Tissue slides from formalin-fixed tumors were treated with terminal deoxynucleotide transferase for extension of DNA ends (hydroxyl 3') and incorporation of digoxigenin-11-dUTP according to the manufacturer's instructions (Oncor, Gaithersburg, Md.). Anti-digoxigenin antibody conjugated with the enzyme peroxidase allowed detection of apoptotic cells, which stain brown, whereas viable cells stain blue.

Figure 6C:
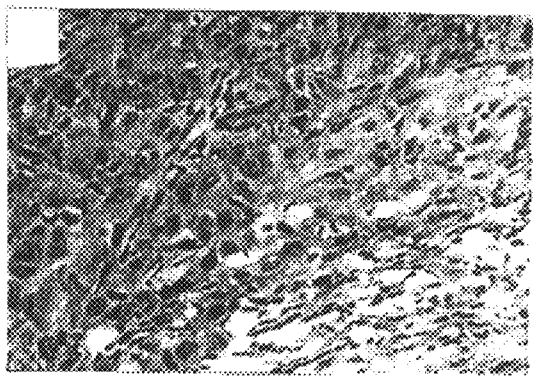
Figure 6D:
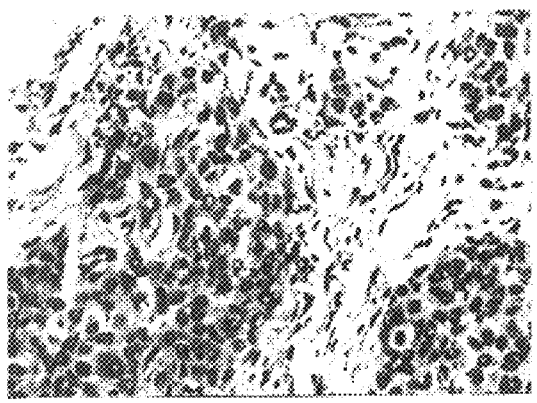
Figure 6E:
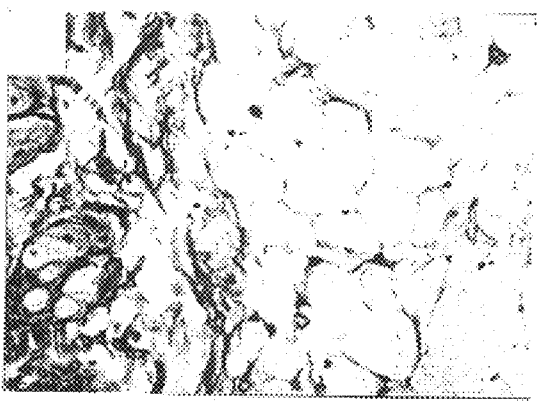

Shown in FIGS. 6B–E are representative examples of the effects of hCG and the β-hCG peptides on KS Y-1 tumors in mice. One week after injection with the tumor cells, the mice were treated with crude hCG (APL™, Wyeth Ayerst) or with β-chain peptides 45–57 (SEQ ID NO:6) and cyclic 44–57 [Cys44] (SEQ ID NO:26). FIGS. 6B–E show hematoxylin and eosin staining of thin tissue sections of KS Y-1 induced tumors. Compared to the frequent mitotic activity in the controls (FIG. 6B), there is evidence of extensive cell death in the tumors of the animals treated with the β-hCG peptides which are comparable to the findings in animals treated with active hCG preparations (FIGS. 6C–E). Table 3 presents data showing that the β-hCG peptides with an amino acid sequence of 47–57 linked at the C-terminus by a peptide bond to the N-terminus of 108–119 (47–57::108–119; SEQ ID NO:32) and 45–57 linked at the C-terminus by a peptide bond to the N-terminus of 109–119 (45–57::109–1 19; SEQ ID NO:30) also had significant anti-KS activity. Additionally, β-hCG peptides of amino acid numbers 109–119, 109–145, 47–55 and 48–56 (SEQ ID NOS:7, 25, 20 and 35, respectively) exhibited some anti-KS activity. Other α-hCG and β-hCG peptides showed no activity (Table 3).

As noted above, some AIDS-KS patients treated by intralesional or systemic injection of some preparations of hCG experience regression of tumor lesions of the skin as well as visceral KS (Hermans et al., 1995, *Cellular and Molecular Biology* 3:357–364; Gill et al., 1996, *New Engl. J. Med.* 335:1261–1269). Patients receiving these preparations showed macroscopic regression and flattening of KS lesions. In situ immunostaining specific for apoptosis detection in tumor biopsies showed evidence of apoptosis and/or, histologically, complete absence of the KS tumor after 2–3 weeks of hCG therapy as shown in FIGS. 6F, G and H, similar to that seen in the experimental mouse model with the active β-hCG peptides. In control KS tumors treated with diluent only or untreated KS tumor tissues (not shown), there was little evidence of cell death (FIG. 6F).

Effects of hCG and β-hCG Peptides on Hematopoiesis

In addition to the typical decline in CD4+ T cells, cytopenias can occur in HIV infected people affecting one or more hematopoietic lineages associated with deficient progenitor cell growth. This deficiency is often made worse by some of the anti-viral therapies currently in use. In contrast, hCG preparations do not inhibit hematopoiesis.

The effect of hCG preparations and peptides was assayed on hematopoietic progenitor cells in vitro. Hematopoietic progenitor cells ($2 \times 10^5$ cell/ml) were isolated from normal bone marrow and cord blood and seeded in methylcellulose. The following hCG preparations and peptides were used in these clonogenic assays were: hCG (APL™); hCG alpha subunit (Sigma); purified hCG heterodimer CR 127; β-hCG peptide 109–119 (SEQ ID NO:7) (Bachem); β-hCG peptide 45–57 (SEQ ID NO:6); β-hCG peptide 45–57 circularized (44–57 with cysteine substituted for the amino acid at position 44, SEQ ID NO:26); mixture of scrambled β-hCG peptides 45–57 and 109–119; and crude preparation of native β-hCG. Also tested were the peptides 45–57 linked at the C-terminus via a peptide bond to the N-terminus of 109–119 (45–57::109–119; SEQ ID NO:30), 47–55 (SEQ ID NO:20) and 48–56 (SEQ ID NO:35) as well as other hCG, α-hCG and β-hCG preparations and α-hCG and β-hCG peptides (Table 3). The hCG preparations were administered at 200 IU/ml and the β- and α-subunits and peptides were administered at 100 μg/ml. The native commercial preparation of hCG (APL™, Wyeth Ayerst) was pre-tested for anti-HIV and anti-KS activities. Aggregates containing more than 50 cells after 10 days of culture were counted as colonies.

As shown in FIGS. 7A–C and in Table 3, the growth of hematopoietic progenitors (Lunardi-Iskandar et al., 1989, *Leukemia Res.* 13:573–581) is directly promoted by a commercial preparation of partially purified hCG (APL™, Wyeth Ayerst), partially purified native β-chain, and by the synthetic peptides, β-hCG peptide 45–57 (SEQ ID NO:6), β-hCG peptide 109–119 (SEQ ID NO:7), circularized 44–57 with cysteine substituted for the amino acid at position 44 (SEQ ID NO:26), the peptide 45–57 linked at the C-terminus via a peptide bond to the N-terminus of 109–119 (45–57::109–119; SEQ ID NO:30), and a mixture of the β-hCG peptides 45–57 and 109–119 (SEQ ID NOS:6 and 7, respectively), but not by the highly purified hCG heterodimer (CR127) nor by the recombinant hCG β-chain or the α-chain preparations. The β-hCG peptides 47–55 and 48–56 (SEQ ID NOS:20 and 35, respectively) also exhibited a pro-hematopoietic effect (Table 3). Additionally, scrambled β-hCG peptides 45–57 and 109–119 as well as other β-hCG peptides showed little inhibition (Table 3). Thus, these results recapitulate the anti-KS and anti-HIV effects. Each activity is chiefly effected by the satellin peptides (45–57 and 109–119; SEQ ID NOS:6 and 7, respectively). A series of other peptides of the α- and β-chain had no effect (data not shown).

Some partially purified preparations of hCG and β-hCG and some β-chain fragments stimulate the growth of hematopoietic progenitors, for example β-hCG peptides having amino acid sequences of amino acid numbers 45–57 (SEQ.ID NO:6), 109–119 (SEQ ID NO:7), circularized 44–57, where cysteine is substituted for the amino acid at position 44 (SEQ ID NO:26), and peptides of amino acid numbers 45–57 (SEQ ID NO:6) linked at the C-terminus via a peptide bond to the N-terminus of amino acids 109–119 (SEQ ID NO:7) or linked at the N-terminus via a peptide bond to the C-terminus of amino acids 110–119 (SEQ ID NO:27); or a peptide of amino acids 47–57 (SEQ ID NO:28)

linked at the C-terminus via a peptide bond to the N-terminus of amino acids 108–119 (SEQ ID NO:29) of the β-hCG sequence depicted in FIG. 8 (portions of SEQ ID NO:2). The peptides having an amino acid sequence of amino acid numbers 7–45, 47–55, 46–65, and 48–56 (SEQ ID NOS:21 and 33–35, respectively) of β-hCG (FIG. 8 (SEQ ID NO:2) also exhibit activity in in vitro assays.

Furthermore, in 3 of 3 SIV acutely infected rhesus macaque monkeys the same preparation of hCG (pre-screened for anti viral activity) at a dose of 6,000 IU per week, led to a reduction of SIV in plasma, an increase in $CD4^+$ T cells and weight gain. Examples of pro-hematopoietic effects are observed in preliminary studies of a limited number of patients treated with some commercial hCG products. Factors such as patient stage, total weekly dose, and manufacturer source very likely play a role in the variability of response.

New treatment regimens for HIV-1 show that a combination of anti-HIV compounds which target reverse transcriptase (RT) such as azidothymidine (AZT), lamivudine (3TC), dideoxyinosine (ddI), dideoxycytodine (ddC) used in combination with an HIV-1 protease inhibitor, have a far greater effect (2 or more logs reduction) on viral load compared to AZT alone (about 1 log reduction) (Perelson et al., 1996, *Science* 15:1582–1586). However, long-term use of combinations of these chemicals may lead to toxicity, especially to the bone marrow and suppression of $CD8^+$ T cells, which may be essential to the control of HIV via killer cell activity (Blazevic et al., 1995, *AIDS Res Hum Retroviruses* 11:1335–1342) and by the release of suppressive factors, notably the C-C chemokines (Cocchi et al., 1995, *Science* 270:1811–1815). Other concerns in long-term chemical anti-retroviral therapy are the possible development of HIV mutations with partial or complete resistance (Lange, 1995, *AIDS Res Hum Retroviruses* 10:S77–82) and cost.

The discovery of an anti-KS effect of "hCG" was observed in vivo in pregnant Bg-nude mice which did not develop KS as did their male litter mates inoculated at the same time with the KS Y-1 tumor cells. This observation led to clinical trials of intralesional therapy for KS which documented responses in 83% of treated lesions in a dose dependent manner (Hermans et al., 1995, *Cellular and Molecular Biology* 3:357–364; Gill et al., 1996, *New Engl. J. Med.* 335:1261–1269).

As shown herein, some patients treated intralesionally with an hCG preparation for KS were noted to have a reduction in viral load, and in vitro human cell culture and in vivo animal model data show that some preparations of partially purified hCG, partially purified β-hCG and the active β-hCG peptides and fused β-hCG peptides have anti-viral, anti-KS and pro-hematopoietic effects.

We found considerable activity with some preparations of the partially purified native heterodimer and the native partially purified whole β-chain, whereas recombinant β-hCG (purified) and highly purified native hCG heterodimer (CRIXY17B and CR127) were inactive. Based on our results with the β-hCG peptides and fused β-hCG peptides reported here, we suspect that the lower molecular weight species, active portions of them, or possibly larger fragments which include the active amino acid sequences accompany hCG and the β-chain and are not eliminated by some of the purification procedures, thus retaining the anti-viral, anti-KS and pro-hematopoietic effects, but varying among commercial sources. In this respect, it is noteworthy that, although the clinical effects of some preparations of hCG described here were obtained with two different commercial sources (APL™ and PREGNYL™), one was usually more active in laboratory tests (APL™) at lower concentrations than any other preparation. This hCG preparation, however, also varied from lot to lot in the immunodeficient mouse KS system (data not shown) despite the fact that identical amounts (International Units) were used as assessed by the manufacturer's standard bioassays for the conventional use of hCG.

Consequently, we next began studies with a variety of synthetic peptides, and our results show that all the in vitro activities of the preparations of native hCG and the in vivo mouse data are mimicked strongly by satellin A1 (β-hCG peptide 45–57 (SEQ ID NO:6)), but not other β- or α-peptides or scrambled 45–57 peptide.

The mechanism of the anti-HIV effect of some preparations of native hCG, and native β-hCG, and of the β fragments appear, at least in part, to be direct. This is suggested by: 1) the in vitro inhibition of HIV-1 infectivity of $CD4^+$ T cells and macrophages; 2) the inhibition of HIV-1 gene transcription in HIV-1 transgenic mice; 3) the rapid clearance of p27 antigen in the acutely SIV infected monkeys treated with hCG; and 4) the decline of plasma virus in some patients treated with some hCG preparations. However, there was a greater inhibition of in vitro infection of cells with various strains of HIV-1 compared to inhibition of HIV-1 production from chronically infected cells suggesting that mechanisms, in addition to inhibition of transcription, are also involved. Indirect effects also cannot be excluded for the anti-SIV/HIV effects observed in the monkey experiments and among responding patients. HIV has anti-hematopoiesis effects (Lunardi-Iskandar et al., 1989, *J. Clin. Invest.* 83:610–615; Louache et al., 1992, *Blood* 180:2991–2999; Geller et al., 1985, *Archs. Path. Lab. Met.* 109:138–145). Based on the findings that hCG and the peptides have pro-hematopoietic effects on progenitors cells of the bone marrow, it is possible that enhanced immune function also may have contributed to the in vivo results.

Some preparations of hCG have beneficial effects against the range of core problems associated with HIV-1 infection. In laboratory tests, KS cells were killed and regression occurred of transplanted KS tumors in mice (Lunardi-Iskandar et al., 1995, *Nature* 375:64–68). A recent clinical study of escalating dose by intralesional injection of hCG (APL™, Wyeth Ayerst) for cutaneous KS skin lesions demonstrated tumor regression in a dose-dependent manner, with 8% responding at the lowest dose (250 IU, 3 times weekly) and 83% at the highest intralesional dose (2000 IU, 3 times weekly) (Gill et al., 1996, *New Engl. J. Med.* 335:1261–1269). Results described here also showed regression of KS lesions in a substantial proportion of cases including cases treated with systemic therapy, and even regression of newly developed lesions while on hCG therapy when higher doses were given. It is also noteworthy that regression of visceral lesions occurred in several KS patients with advanced KS.

The clinical data reviewed herein illustrate many of the beneficial effects observed in the laboratory pre-clinical studies. Since the protocols were not designed to systematically study the various beneficial effects of some preparations of hCG as a treatment for HIV infection and since there is variability in dose and source of product, the inferences to be drawn are illustrative of the potential for some commercial preparations of hCG or related products in HIV and KS treatment. As reported elsewhere (Hermans et al., 1995, *Cellular and Molecular Biology* 3:357–364; Gill et al., 1996, *New Engl. J. Med.* 335:1261–1269), and confirmed herein, some preparations of hCG induced partial or complete regression of KS lesions in patients treated intralesionally (Hermans et al., 1995, *Cellular and Molecular Biology* 3:357–364) and systemically, including advanced visceral disease. In some HIV-1 positive patients at various stages of HIV infection there was a 0.5 to 2 log reduction in plasma viremia level, and in some cases this effect was sustained with no evidence of development of resistance or toxicity and $CD4^+$ T cell levels increased in some as well. Non-fluid weight gain was a very frequent benefit to patients even with far advanced disease. It is noteworthy that patients such as PH-VE have experienced long term benefits from hCG therapy without toxicity over more than 80 weeks of therapy documenting the safety of this therapeutic approach.
Fractionation of Active hCG Preparations and Human Early Pregnancy Urine The present inventors have found that certain commercial preparations of hCG, for example, hCG APL™ (Wyeth-Ayerst), had higher anti-HIV, anti-Kaposi's Sarcoma, anti-wasting and pro-hematopoietic activity than other commercial preparations of hCG (see discussion herein). Further, the inventors have also shown that highly purified preparations of native and recombinant hCG and β-hCG had no activity against HIV infection or replication or against Kaposi's Sarcoma. Accordingly, the inventors postulated that there must be an activity in the hCG commercial preparations that is not the hCG dimer or the β-hCG subunit, responsible for the anti-HIV, anti-Kaposi's Sarcoma, anti-wasting and pro-hematopoietic activities. This section presents results of the fractionation of the APL™ hCG commercial preparation and urine from women in the first trimester of pregnancy ("human early pregnancy urine") which also contains hCG. Particular sizing column chromatography fractions were shown to have activity, thus demonstrating that the active components could be fractionated.
Materials and Methods Both human early pregnancy urine and the APL™ (Wyeth-Ayerst) hCG commercial preparation were subjected to fractionation. For the human early pregnancy urine, 5 liters of urine were collected from women in the first trimester of pregnancy. Twenty-four hour collections were stored frozen or refrigerated for up to 2 days. Upon delivery of the urine to the laboratory, sodium azide was added at 1 g/liter and the urine frozen until five liters had been collected. At this time, all the urine was thawed overnight, and the pH was adjusted to 7.2–7.4 with NaOH, which causes some precipitation. The precipitate was allowed to sediment for 1 hour at room temperature, most of the supernatant decanted and the remaining supernatant centrifuged to remove any additional precipitate with that supernatant being added to the first supernatant decanted. Next, the urine was concentrated with a Pellicon (Millipore) filtration system using a membrane cassette with a 3,000 MW cut off, which concentrates the urine approximately 60 to 80 fold. Next, the urine was desalted and delipidated by passing 500 ml of the material at a time through a Sephadex G25 column with a volume of 1.7 liters in 0.05 M ammonium bicarbonate (the column was washed between runs with 25% ethanol to remove absorbed lipids and glycoprotein). The material was lyophilized and stored for further fractionation. The urinary material was then reconstituted in 6 ml of 30 mM sodium phosphate buffer, pH 8.3 fractionation.

For the APL™ hCG, the lyophilized hCG preparation from eleven vials (each vial containing 20,000 IU hCG) was resuspended in 6 ml of 30 mM sodium phosphate buffer, pH 8.3 and filtered twice through the 0.45 μm particle filter. For both the lyophilized urine and the hCG APL™, the prepared sample was then loaded onto a pre-packed SUPERDEX™ 200 HiLoad Column (Pharmacia 26 mm²×60 cm) in the 30 mM sodium phosphate buffer, pH 8.3 and then eluted from the column with a solution containing 30 mM sodium phosphate buffer, pH 7.0 and 2 M NaCl. For the first ten minutes, the column flow rate was 1 ml/minute (due to the viscosity of the hCG APL™ material; this flow rate scheme was also used for the urine material); after the first 10 minutes, the flow rate was 2 ml/minute. The column was run on a Hewlett Packard 1050 HPLC equipped with a photodiode array detector. Four ml fractions were collected and frozen until further analysis.

The protein concentration in each fraction was determined by amino acid analysis. A 50 μl aliquot of alternate column fractions was processed for anlysis by hydrolysis in vapors of 6N HCl with 0.1% phenol at 110° C. for 24 hours in a Waters Associates Pico-Tag Workstation (Waters, Milford, Mass.). An internal standard, norleucine, was added to all fraction samples before hydrolysis to correct for any losses during hydrolysis or liquid transfer. The hydrolyzed samples were then analyzed on a Beckman Instruments 6300 amino acid analyzer and the data was collected on the PE Nelson Data System (Perkin-Elmer) and transformed using PE Nelson Turbochrome software.

The column fractions were monitored with immunoassays to heterodimeric hCG as well as to the hCG beta core fragment (O'Connor et al., 1994, *Endocrin. Rev* 15:650–683; Krichevsky et al., 1994, *Endocrinology* 134:1139–145; Krichevsky et al., 1991, *Endocrinology* 128:1255–1264; O'Connor et al., 1988, *Cancer Res.* 48:1361–1366; Krichevsky, 1988, *Endocrinology* 128:584–593). These two assays permit placement of two internal standard sizes for the gel filtration column: 70,000 kD (hCG) and 10,000 kD (hCG beta core fragment which is amino acids 6–40 of β-hCG linked via a disulfide bond to amino acids 55–92 of β-hCG). External molecular weight standards were also employed to calibrate the column elution positions. In addition, MALDI-TOF mass spectrometry was used to evaluate the ions observed in certain active fractions. Mass spectrometry did indicate that some peptides separated at anomalous positions, showing that they were being carried by other proteins to earlier elution positions in some cases, or interacting with the column matrix and eluting much later than their molecular size would indicate. For example, 3,000 and 6,000 molecular weight materials eluted from the gel filtration column with material of 14,000 molecular weight while 11,000 molecular weight material eluted with material of approximately 1,000–2,000 molecular weight, hCG and hCG-related molecules eluted at their expected positions.

The fractions were then tested for anti-HIV, anti-KS and pro-hematopoietic activities in vitro. To assay for inhibition of HIV-1 replication in vitro, the HIV-1 IIID viral strain was used to infect PBMCs and PM-1 cells (derived from the HUT-78 T-cell lymphoma cell line) at $10^3$ $TCID_{50}$/ml as described in detail herein. The infected cells were incubated for three days in 100 IU/ml of the hCG APL™ or β-hCG C-Sigma preparations; 50–100 μl per ml of the hCG APL™ or early pregnancy urine fractions; 50 μl/ml β-core protein or α-hCG preparation; 200 IU/ml of the highly purified CR127 hCG preparation; or 100 μl/ml of the circularized β-hCG peptide 44–57 (with cysteine substituted at position 44; SEQ ID NO:26).

To assay for activity against Kaposi's sarcoma cell growth in vitro, the clonogenic assay described herein was used with the KS Y-1 and KS-SLK cultured Kaposi's Sarcoma cell lines. The cells were incubated in 200 IU/ml of commercial hCG preparations; 50 μl/ml of certain fractions from the hCG preparation of early pregnancy urine fractionation; or 100 µg/ml β- and α-hCG chains, β-hCG core protein, β-hCG peptides or LH (leuteinizing hormone).

Pro-hematopoietic activity was assayed in in-vitro clonogenic assays as described herein. Cells were assayed for colony formation in the presence of 200 IU/ml hCG APL™ or highly purified hCG preparation CR 127; 100 µl/ml of the fractions of the hCG commercial preparation of early pregnancy urine; or 100 µg/ml β-hCG core protein or cyclized β-hCG peptide of amino acids 44–57 (with cysteine substituted at position 44; SEQ ID NO:26).

Certain fractions were tested for activity in reducing Kaposi's Sarcoma lesions in the Kaposi's Sarcoma mouse model as described herein. In this assay, starting one week after injection of the KS Y-1 cells to induce Kaposi's sarcoma formation, the mice were injected subcutaneously with 100 IU hCG APL™; 200 IU highly purified hCG preparation CR127; 100 µg α-hCG, β-hCG, recombinant β-hCG, LH (luteinizing hormone), or β-core protein; 200 µl of fractions of commercial hCG preparation or early pregnancy urine; or 200 µg cyclized β-hCG peptide of amino acids 44–57 (with cysteine substituted at position 44; SEQ ID NO:26) per day for one week. After one week of the week of treatment with the hCG fractions, the KS lesions were examined for cell apoptosis and regression as described herein.

Finally, certain fractions were tested for their ability to increase survival, promote weight gain and reduce HIV-1 gene expression in HIV-1 transgenic mice as described herein. The mothers the mice were administered 300 IU hCG APL™ by osmotic pump or 200 IU hCG APL™ by slow release; 200 µl of certain fractions of hCG commercial preparation or of early pregnancy urine; 200 µg of the cyclized β-hCG peptide of amino acids 44–57 (with cysteine substituted at position 44; SEQ ID NO:26) or the fused peptide of amino acids 45–57::109–119 (SEQ ID NO:30); or 100 µg β-hCG core peptide or the α-hCG sub unit per day, and the pups were dosed through the mother's milk.

The unfractionated APL™ hCG preparation, PREGNYL™ (Organon) hCG preparation, purified β-core and phenol were also tested in certain assays. Phenol, which is an additive in the hCG APL™ preparation, was tested to control for any effect on cell growth or viral inhibition.

Active Fractions

Figure 10A:
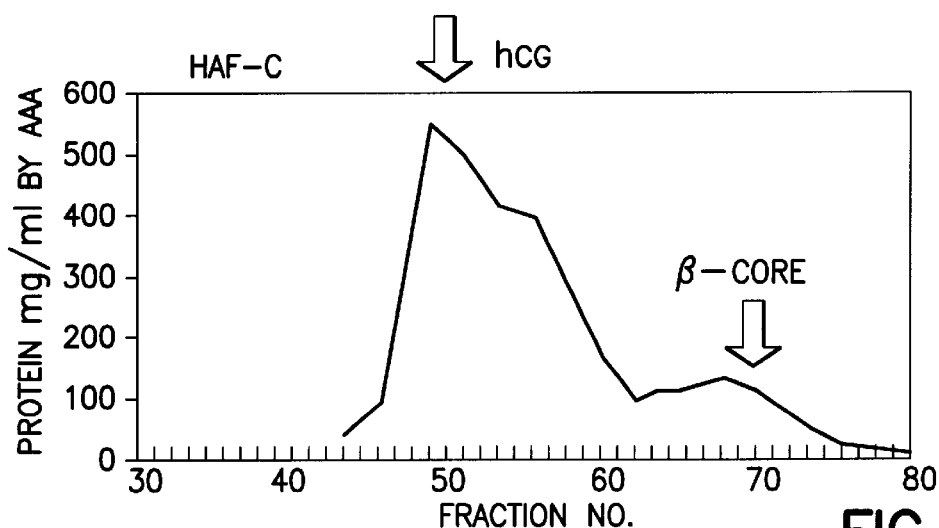

Fractionation of both the APL™ hCG preparation and the human early pregnancy urine resulted in a significant protein peak at approximately 158 kD with diminishing, but still detectable, protein in the rest of the fractions, even those containing small molecular weight material (FIGS. 10A and D). Fractions containing the hCG dimer (77 kD) and the β-hCG core (10 kD) were identified by immunoprecipitation using antibodies that specifically recognize these particular species, as described in the materials and methods herein. The elution profile of the commercial hCG material was also plotted in comparison to the elution of standard molecular weight markers (FIGS. 16A and B). Additionally, Fractions 61, 63, 64, 65 and 67 from the fractionation of the commercial hCG material was analyzed by MALDI-TOF mass spectrometry (FIGS. 17A–E, respectively).

Figure 10B:
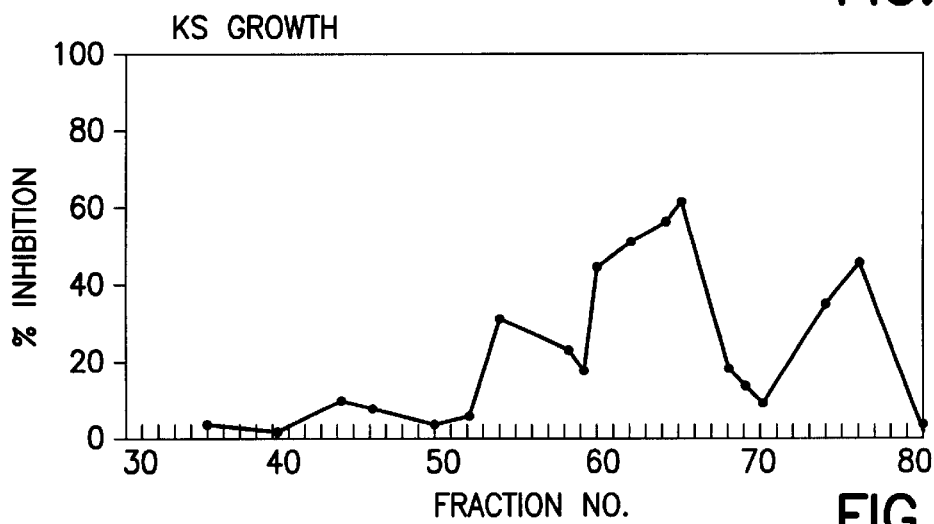
Figure 10C:
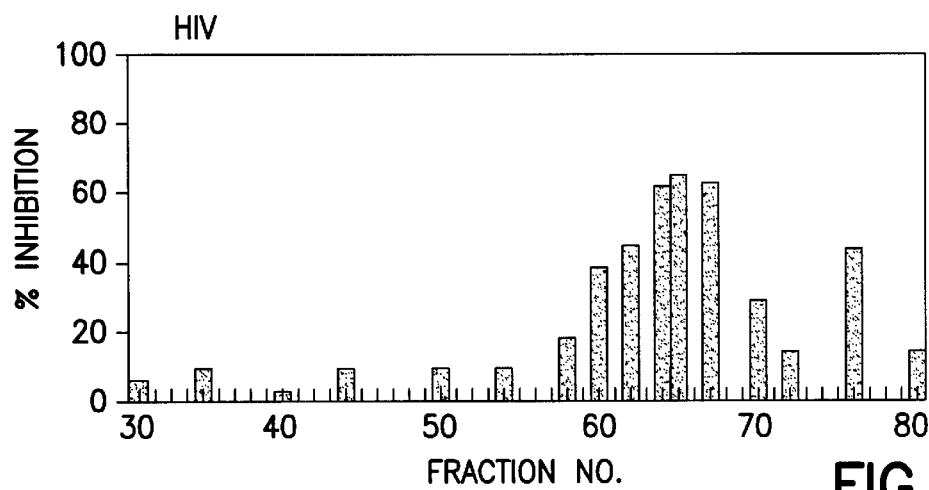
Figure 10D:
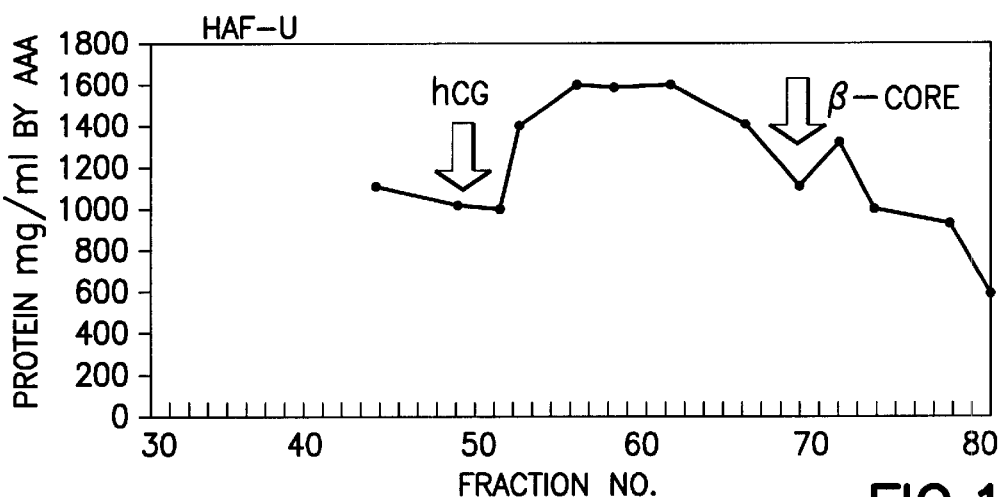

Effect of Fractions of Commercia; hCG Preparations and Early Pregnancy Urine on HIV-1 Replication In Vitro The fractions of both the APL™ hCG preparation and the human early pregnancy urine were assayed for inhibition of HIV-1 IIID replication in PBMCs and PM-1 cells as described herein. Many of the APL™ hCG preparation fractions exhibited significant inhibition of HIV-1 IIID replication (FIG. 10C). In particular, fractions containing material of approximately 70 kD to approximately 2–3 kD exhibited HIV-1 inhibitory activity. The fractions effecting the highest percent inhibition of HIV-1 replication were fractions 62, 63, 65, and 73, with the three main peaks of activity eluting with apparent molecular weights of approximately 40 kD, approximately 15 kD, and approximately 2–3 kD, as determined by comparison with the elution of hCG (77 kD) and β-core protein (10 kD).

Figure 10E:
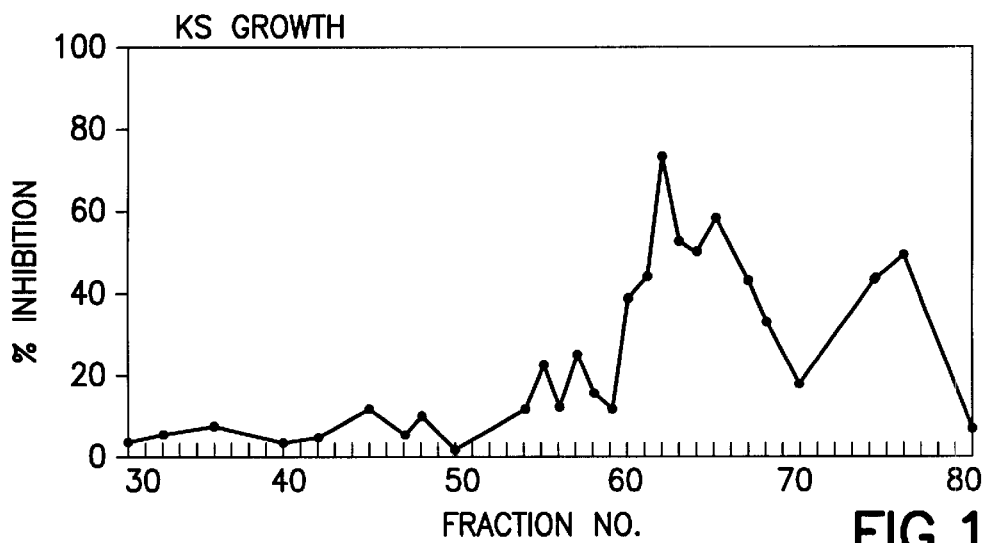
Figure 10F:
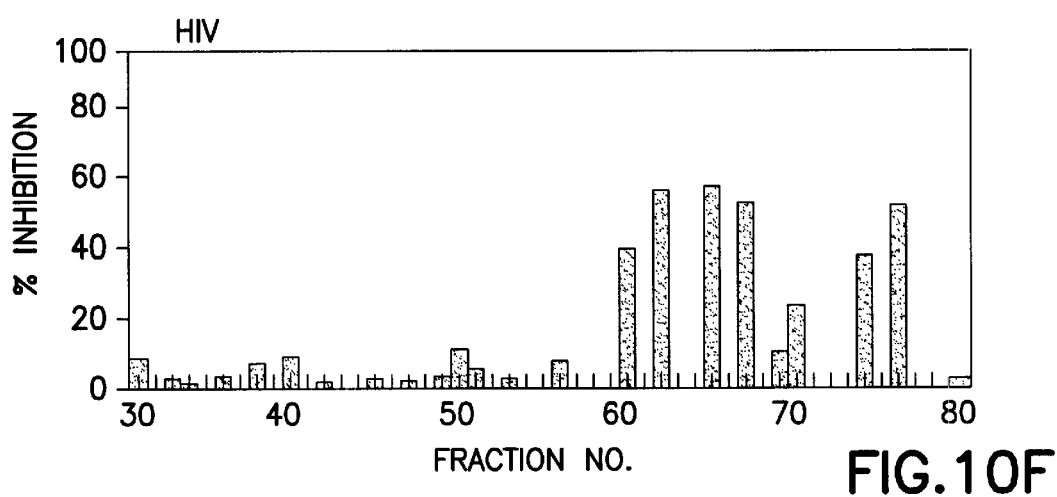

The fractions of human early pregnancy urine were also assayed for ability to inhibit HIV-1 IIID replication in the PBMCs and the PM-1 cells. Again, several fractions had at least some HIV-1 replication-inhibitory activity. Fractions 64 and 67 caused more than twice the inhibition of HIV-1 IIID replication than any of the other fractions (FIG. 10F). There were approximately two peaks of activity eluting from the gel filtration column with apparent molecular weights of approximately 15 kD and 3 kD, as determined by comparison with the elution of hCG (77 D) and S-core protein (10 kD) identified by immunoassay.

Additionally, phenol had no effect on HIV-1 replication, demonstrating that the anti-HIV activity of the APL™ hCG is not due to the presence of phenol in the APL™ m hCG preparation, and purified β-hCG core protein (the peptide of amino acids to 6–40 of β-hCG linked via a disulfide bond to the peptide of amino acids 55–92 of β-hCG as depicted in FIG. 8 (SEQ ID NO:2)) was also found not to inhibit HIV-1 replication (data not shown).

Effect of Fractions of Commercia; hCG and Early Pregnancy Urine on Kaposo's Sarcoma Cell Growth in Vitro The fractions of APL™ hCG and human early pregnancy urine were also tested for inhibition of the proliferation of cultured Kaposi's Sarcoma cells. FIG. 10B depicts the results of assays of the APL™ hCG fractions for inhibition of KS Y-1 cell growth. There were three major peaks of KS cell growth inhibitory activity which eluted from the gel filtration column with apparent molecular weights of approximately 40 kD, approximately 15 kD, and approximately 2–3 kD, as compared with the elutions of fractions containing hCG dimer (77 kD) and β-core protein (10 kD). A fraction containing material about the same size as the β-hCG core protein exhibited the highest level of inhibition; however, purified β-hCG core was found not to inhibit KS cell growth (data not shown).

Fractions of human early pregnancy urine were also assayed for inhibition of KS Y-1 cell growth. Fractions containing material which eluted from the gel filtration column with apparent molecular weights of approximately 15 kD and approximately 2–3 kD as compared with the elution of fractions containing hCG dimer (77 kD) and the β-hCG core (10 kD) as identified by immunoprecipitation assay were the most effective at inhibiting KS cell growth, with the approximately 15 kD fractions having the highest activity (FIG. 10E).

FIG. 11 presents additional data on the inhibitory effects of hCG and hCG-related preparations in KS cultured cell clonogenic assays using both the KS Y-1 and KS SLK assays. Fraction 65 (from the peak eluting with an apparent molecular weight of approximately 15 kD) and 76 (from the peak eluting with an apparent molecular weight of approximately 2–3 kD) from the fractionation of both the APL™ hCG preparation (fraction 65 and 76 are represented by bars 12 and 13, respectively,) and the early pregnancy urine (fraction 65 and 76 are represented by bars 10 and 11, respectively) inhibited growth of both cell lines. The fractions containing material eluting with an apparent molecular weight of approximately 2–3 kD (i.e. fraction 76 of both fractionations) inhibited KS cell growth marginally more effectively than the fractions containing material eluting with an apparent molecular weight of approximately 15 kD (i.e. fraction 65 of both fractionations). Although the active fractions elute close to the fractions containing the β-hCG core protein, purified β-hCG core protein (bar 5) exhibited almost no inhibition of KS cell growth.

The results confirm that the APL™ hCG commercial preparation (bar 1) inhibited KS cell growth better than the other commercial hCG preparations (bars 2–4). Additionally, while native β-hCG (bar 6) inhibited KS cell growth moderately well, α-hCG, the highly purified hCG preparation CR 127 and recombinant hCG (Sigma) (bars 7–9, respectively) inhibit the KS cell growth negligibly. The results also confirm that the cyclized β-hCG peptide of amino acids 44–57 (cysteine substituted at position 44; SEQ ID NO: 26) also inhibited KS cell growth.

Effect of Commercial hCG and Early Pregnancy Urine Fractions on Hematopoiesis In Vivo FIGS. 12A–C presents data on the effect of hCG and hCG-related preparations on hematopoiesis in in vitro clonogenic assays for numbers of colony forming units of granulocytes, erythrocytes, megakaryocytes and monocytes (CFU-GEMM), burst forming units of erythrocytes (BFU-e) and colony forming units of granulocytes and macrophages (CFU-GM). FIG. 12 shows that fraction 65 of both the hCG APL™ and early pregnancy urine fractionation (bars 7 and 8, respectively; fraction 65 contains material with an apparent molecular weight of approximately 15 kD) promoted hematopoiesis in all three assays. Fraction 26 of the early pregnancy urine fractionation (bar 9) did not promote hematopoiesis in any of the assays. The purified β-core protein (bar 10) likewise exhibited no stimulation of hematopoiesis.

These results also confirm that the hCG APL™ preparation, native β-hCG and the cyclized β-hCG peptide of amino acids 44–57 (cysteine substituted at position 44; SEQ ID NO: 26) (bars 3, 5 and 6, respectively) all have pro-hematopoietic activity. The α-subunit of hCG, highly purified hCG preparation CR127 and PBS alone (bars 2, 4 and 1, respectively) did not promote hematopoiesis.

Effects of hCG and β-hCG Preparations and β-hCG Peptides on Kaposi's Sarcoma

As described herein, we have observed beneficial effects of some preparations of human Chorionic Gonadotropin (hCG) against HIV disease including anti-tumor (Kaposi sarcoma, KS), anti-viral, increase in weight and pro-hematopoiesis effects. Our studies document that the same preparations inhibit KS cell growth in vitro and induce apoptosis in a mouse model. Examples of these effects were also noted in some HIV-positive patients treated with some hCG preparations. The strength of these effects varied among crude hCG preparations, and highly purified hCG did not retain these activities. However, the anti-KS, anti-viral, and pro-hematopoietic effects were mimicked by native β-hCG and synthetic peptides of the beta subunit of hCG having amino acid sequences of amino acid numbers 45–57 (SEQ ID NO:6), 109–119 (SEQ ID NO:7), circularized 44–57, where cysteine is substituted for the amino acid at position 44 (SEQ ID NO:26), and peptides of amino acid numbers 45–57 (SEQ ID NO:6) linked at the C-terminus via a peptide bond to the N-terminus of amino acids 109–119 (SEQ ID NO:7) or linked at the N-terminus via a peptide bond to the C-terminus of amino acids 110–119 (SEQ ID NO:27); or a peptide of amino acids 47–57 (SEQ ID NO:28) linked at the C-terminus via a peptide bond to the N-terminus of amino acids 108–119 (SEQ ID NO:29) of the β-hCG sequence depicted in FIG. 8 (portions of SEQ ID NO:2). The peptides having an amino acid sequence of amino acid numbers 7–45, 47–55, 46–65, and 48–56 (SEQ ID NOS:21 and 33–35, respectively) of β-hCG (FIG. 8 (SEQ ID NO:2) also exhibit activity in in vitro assays.

The discovery of an anti-KS effect of the pregnancy hormone, hCG, was observed in vivo in pregnant Bg-nude mice who did not develop KS as did their male litter mates inoculated at the same time with the KS Y-1 KS tumor line. This observation led to clinical trials of intralesional therapy for KS which documented responses in 83% of treated lesions at the higher dose schedule (Gill, P. S., et al., 1996, submitted). We show herein that some patients treated intralesionally with hCG for KS were noted to have a reduction in viral load and in vitro and in vivo animal model data show that some hCG preparations, partially purified β-hCG, and the active β-hCG fragments (β-hCG peptides 45–57 and 109–119) have anti-KS effects.

We found considerable anti-KS activity with the native partially purified whole β-chain, but recombinant β-hCG (purified) had little or no effect. We suspect that the lower molecular weight species may retain the effect and that some purification procedure may not eliminate those species.

The native hCG and native β-chain preparations available for clinical use are not homogenous and may be contaminated with one or more other active molecules. In this respect, it is noteworthy that though the effects of some preparations of hCG described here were obtained with two different commercial sources of hCG (APL and Pregnyl), one was usually more active (APL) at lower concentrations than any other preparation, although it too varied from lot to lot as detected in the immunodeficient mouse KS system (data not shown) despite the fact that we used identical amounts (International Units) as assessed by the manufacturer's standard bioassays for the conventional use of hCG. The differences in activities of commercial preparations might be explained by variation in the amount of β-hCG fragments. This could be the consequence of different methods of preparation or different sources of human urine. For example, free β-hCG is more abundant in the earliest weeks of pregnancy. Consequently, we initiated studies with a variety of synthetic peptides, and our results show that all the in vitro activities of the preparations of native hCG are mimicked by the β-hCG peptides 45–57, and 109–119 but not other β- or α-peptides or scrambled 45–57 peptide. Thus, we suggest that β-hCG contains structural motifs that produce effects which probably work by mechanisms which differ from those currently known for hCG. We suspect that β-hCG fragments have biological functions quite distinct from the conventional effects of the heterodimer. The structural features of hCG (Lapthorn, A. J., et al., 1994, Nature 369:455–461) and appearance in very early pregnancy (Fan, C., et al., 1987, J. Clin. Endo. Metab. 64:313–318) combined with some of our observed effects of the β-chain peptides on Kaposi's Sarcoma tumors involving induction of apoptosis (Lunardi-Iskandar, Y., et al., 1995, Nature 375:64–68), suggest that the structural similarity to some growth factors may be important and might also be relevant to the hematopoietic growth promoting and anti-viral effects observed here. In view of the evidence that the a subunits are needed for binding to the hCG receptor, we are uncertain how the β peptides initiate these effects. Thus, whether the effects we have observed (anti-viral, anti-tumor, anti-wasting and pro-hematopoietic) are mediated by known hCG receptors is unknown. Given that the mechanism of action of these hCG fragments is likely to involve pathways distinctive from normal hCG hormonal pathways, it is proposed that these active peptides represent a new class of active molecules which we named Satellins. The first members of this class are Satellin A for the active moiety from the β-hCG peptide 45–57 and Satellin B for the β-hCG peptide 109–119.

In laboratory tests, KS cells were killed and regression occurred of transplanted KS tumors in mice (Lunardi-Iskandar, Y., et al., 1995, *Nature* 375:64–68). A recent clinical study of escalating dose by intralesional injection of hCG (APL, Wyeth Ayerst) for cutaneous KS skin lesions, demonstrated tumor regression in a dose-dependent manner with 8% responding at the lowest dose (250 IU three times per week) and 83% at the highest intralesional dose (2000 IU three times per week) (Gill, P. S., et al., 1996, submitted). It is also noteworthy that regression of visceral lesions occurred in 2 KS patients with advanced KS (Hermans, P., et al., 1995, *AIDS. Res. Hum. Retroviruses S:*96).

The clinical data reported herein confirms many of the beneficial effects observed in the laboratory preclinical studies. As discussed above, some preparations of hCG induced partial or complete regression of KS lesions in patients treated intralesionally when the hCG (APL, Wyeth Ayerst) was used at dose levels of 250 to 2000 IU three times per week.

The intrinsic variability of native hCG preparations led to the discovery that certain β-hCG peptides (satellins) reproduce the anti viral and anti KS effects in vitro as well as the anti-KS effect in mice with transplanted KS tumors.

Effect of Fractions of Commercial hCG and Early Pregnancy Urine on Kaposi's Sarcoma Cell Growth In Vitro The fractions of APL™ hCG and human early pregnancy urine were also tested for inhibition of the proliferation of cultured Kaposi's Sarcoma cells. FIG. 10B depicts the results of assays of the APL™ hCG fractions for inhibition of KS Y-1 cell growth. There were three major peaks of KS cell growth inhibitory activity which eluted from the gel filtration column with apparent molecular weights of approximately 40 kD, approximately 15 kD, and approximately 2–3 kD, as compared with the elutions of fractions containing hCG dimer (77 kD) and β-core protein (10 kD). A fraction containing material about the same size as the β-hCG core protein exhibited the highest level of inhibition; however, purified β-hCG core was found not to inhibit KS cell growth (data not shown).

Fractions of human early pregnancy urine were also assayed for inhibition of KS Y-1 cell growth. Fractions containing material which eluted from the gel filtration column with apparent molecular weights of approximately 15 kD and approximately 2–3 kD as compared with the elution of fractions containing hCG dimer (77 kD) and the β-hCG core (10 kD) as identified by immunoprecipitation assay were the most effective at inhibiting KS cell growth, with the approximately 15 kD fractions having the highest activity (FIG. 10E).

FIG. 11 presents additional data on the inhibitory effects of hCG and hCG-related preparations in KS cultured cell clonogenic assays using both the KS Y-1 and KS SLK assays. Fraction 65 (from the peak eluting with an apparent molecular weight of approximately 15 kD) and 76 (from the peak eluting with an apparent molecular weight of approximately 2–3 kD) from the fractionation of both the APL™ hCG preparation (fraction 65 and 76 are represented by bars 12 and 13, respectively,) and the early pregnancy urine (fraction 65 and 76 are represented by bars 10 and 11, respectively) inhibited growth of both cell lines. The fractions containing material eluting with an apparent molecular weight of approximately 2–3 kD (i.e. fraction 76 of both fractionations) inhibited KS cell growth marginally more effectively than the fractions containing material eluting with an apparent molecular weight of approximately 15 kD (i.e. fraction 65 of both fractionations). Although the active fractions elute close to the fractions containing the β-hCG core protein, purified β-hCG core protein (bar 5) exhibited almost no inhibition of KS cell growth.

The results confirm that the APL™ hCG commercial preparation (bar 1) inhibited KS cell growth better than the other commercial hCG preparations (bars 2–4). Additionally, while native β-hCG (bar 6) inhibited KS cell growth moderately well, α-hCG, the highly purified hCG preparation CR 127 and recombinant hCG (Sigma) (bars 7–9, respectively) inhibit the KS cell growth negligibly. The results also confirm that the cyclized β-hCG peptide of amino acids 44–57 (cysteine substituted at position 44; SEQ ID NO: 26) also inhibited KS cell growth.

Effect of Commercial hCG and Early Pregnancy Urine Fractions on Kaposi's Sarcoma In Vivo Certain fractions of the APL™ hCG and early pregnancy urine were assayed for their ability to elicit apoptosis in Kaposi's Sarcoma lesions induced by injection of KS Y-1 cells in mice (n=3 mice for each treatment). The mice were administered 100 μl subcutaneously of the particular fraction each day for one week. Table 4 presents data on the size of the Kaposi's Sarcoma lesions and the percentage of apoptotic cells within the lesion after one week of treatment with fractions 60, 64, 64, 74, 82 and 85 of the APL™ hCG fractions and the unfractionated APL™ hCG preparation. The negative control treated with no hCG or fractionated hCG material exhibited little cell apoptosis or Kaposi's Sarcoma lesion regression (Table 4). Treatment with fractions 82 and 85 (containing material with apparent molecular weights smaller than approximately 2–3 kD) of the APL™ hCG material also elicited almost no Kaposi's Sarcoma lesion regression or apoptosis (Table 4). The unfractionated APL™ hCG, as well as fractions 60 and 74 (fractions within the peaks containing material with apparent molecular weight of approximately 15 kD and 2–3 kD, respectively) of the APL™ hCG fractionated material, caused about 50% apoptosis within the lesion and significant lesion regression (Table 4). Moreover, fractions 64 and 65 (within the peak containing material with apparent molecular weight of approximately 15 kD) of the APL™ hCG showed even higher percentage of apoptosis and more significant lesion regression than the unfractionated APL™ (Table 4).

Additionally, FIG. 13 presents results on the effects of certain fractions of the APL™ hCG and the early pregnancy urine on KS tumors induced in mice. Those fractions from the anti-HIV and anti-KS (in vitro) peaks containing material having apparent molecular weight of approximately 15 kD (fraction 65 of the early pregnancy urine ("HAF-UF#") and fractions 62 and 65 of the APL™ hCG preparation ("HAF-CF#")) and of approximately 2–3 kD (fraction 76 of the early pregnancy urine and fractions 74 and 76 of the APL™ hCG preparation) diminished KS tumors in mice as well or better than the unfractionated APL™ hCG ("APL"). However, the fractions tested that were outside these peaks of anti-HIV and anti-KS (in vitro) activities, i.e., fraction 35 of the APL™ hCG (having an apparent molecular weight much larger than the hCG dimer (77 kD)) and fractions 26 and 82 of the early pregnancy urine (having apparent molecular weights much larger than the hCG dimer and smaller than 2–3 kD, respectively) did not cause tumor regression in the mouse model.

Thus, these results correlate with the results from the HIV replication and KS clonogenic assays, that the activity elutes from the gel filtration column in peaks with apparent molecular weights of approximately 15 kD and 2–3 kD (fractions, with an apparent molecular weight of approximately 44 kD were not assayed).

TABLE 4

| Fraction | Kaposi's Sarcoma Lesion Size After Treatment (mm × mm) | Percentage Apoptosis Within Lesion |
|---|---|---|
| None | 14 × 10, 12 × 17, 13 × 16 | 3%, 2%, 5% |
| APL#60 | 4 × 3, 3 × 2, 2 × 2 | >50% |
| APL#64 | 1 × 2, 1 × 3, 2 × 3 | >60% |
| APL#65 | 2 × 4, 2 × 3, 2 × 1 | >60% |
| APL#74 | 3 × 5, 2 × 5, 3 × 4 | >50% |
| APL#82 | 15 × 16, 13 × 19, 16 × 14 | 2%, 4%, 6% |
| APL#85 | 11 × 24, 13 × 16, 10 × 13 | 5%, 6%, 4% |
| APL prep | 2 × 3, 3 × 3, 3 × 5 | >50% |

The above-described experiments demonstrate that the factor(s) responsible for the anti-HIV and anti-KS activities can be further isolated from the hCG preparations by gel filtration on a SUPERDEX™ 200 gel filtration column. The factor(s) were fractionated from both the commercial APL™ hCG preparation and urine from women in early pregnancy (first trimester). The fractions of highest anti-HIV and anti-KS activity contained material eluting from the gel filtration column with an apparent molecular weights of approximately 40 kD, 15 kD and 2–3 kD. Although certain active fractions contained material of approximately the size of the β-hCG core protein (~10 kD), purified β-hCG core protein was found to have neither anti-HIV nor anti-KS activity. The fractions exhibiting anti-HIV and anti-KS activity in vitro also caused regression of KS tumors induced in mice. Furthermore, phenol, an additive in the APL™ hCG preparation, had no anti-HIV activity.

Effects of hCG Preparations, hCG Fractions and β-hCG Peptides on Prostate, Lung, Breast and Kidney Cancer Cells The hCG preparations, fractions of the early pregnancy urine and hCG APL™ SUPERDEX™ 200 fractionations (described herein), and certain β-hCG peptides were tested on prostate, lung, breast, and kidney cancer cells in vitro, and on prostate tumors in nude mice. The preparations, fractions and peptides were assayed in trypan blue dye assays by seeding cells in liquid culture and then testing for the viability of cells after treatment by trypan blue dye exclusion (viable cells do not stain for trypan blue). The preparations, fractions and peptides were also assayed using a clonogenic assay in which cells were seeded in methylcellulose in the presence or absence of test substance and then colonies were counted after a certain period of time. Cells were also examined for apoptosis by confocal microscopy.

Effect of hCG Preparations, hCG Fractions and β-hCG Peptides on Prostate Cancer Cells The effects of hCG preparations, hCG fractions and β-hCG peptides were tested in prostate cancer cells both in vitro and in vivo. Cells were incubated in either 10% fetal bovine serum (FBS) or 3% fetal bovine serum plus hCG preparations, hCG fractions and β-hCG peptides. Table 5 presents data on the percentage of cell death as determined by the trypan blue assay.

TABLE 5

| Treatment | 10% FBS | 3% FBS |
|---|---|---|
| PBS | 7% | 10% |
| 200 IU hCG APL | 38% | 48% |
| 500 IU hCG APL | 44% | 68% |
| Circ. β-hCG 44[Cys]-57 (200 µg/ml) | 29% | 39% |
| Circ. β-hCG 44[Cys]-57 (300 µg/ml) | 38% | 50% |
| Urine Fraction 60 | 43% | 62% |
| Urine Fraction 64 | 30% | 58% |
| Urine Fraction 74 | 33% | 55% |
| Urine Fraction 23 | 9% | 13% |
| Urine Fraction 80 | 8% | 15% |
| APL Fraction 64 | 26% | 42% |
| APL Fraction 65 | 27% | 43% |
| APL Fraction 67 | 23% | 39% |
| APL Fraction 72 | 22% | 32% |
| APL Fraction 74 | 35% | 52% |
| APL Fraction 75 | 28% | 40% |
| PBS | 5% | 9% |

Table 5 shows that the hCG APL™ preparations, fractions 60, 64 and 74 of the human early pregnancy urine SUPERDEX™ 200 fractionation and fractions 64, 65, 67, 72, 74, and 75 of the hCG APL™ fractionation and the circularized β-hCG peptide 44–57 (with cysteine substituted for position 44; SEQ ID NO:26), all significantly caused cell death of the prostate cancer cells (all hCG fractions were added at a concentration of 200 µl/ml). Note that fractions 26 and 80 of the early pregnancy urine fractionation, which fractions did not have anti-HIV, anti-KS or pro-hematopoietic activity, did not increase prostate cancer cell death.

Figure 18A:
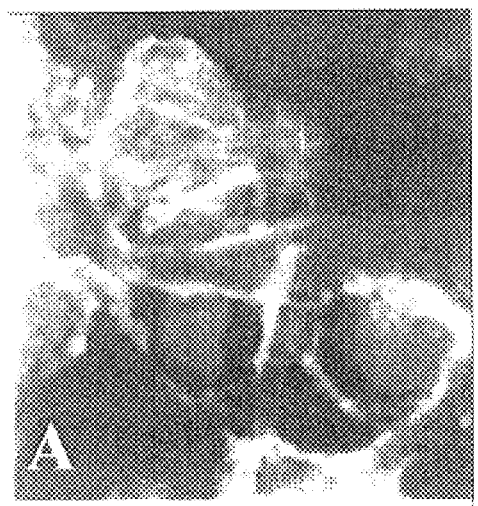
Figure 18B:
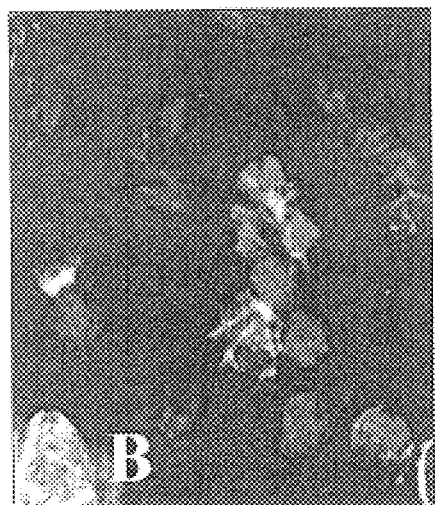
Figure 18C:
Figure 18D:
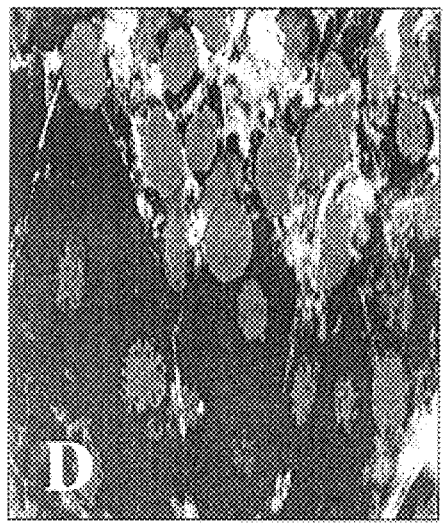
Figure 18E:
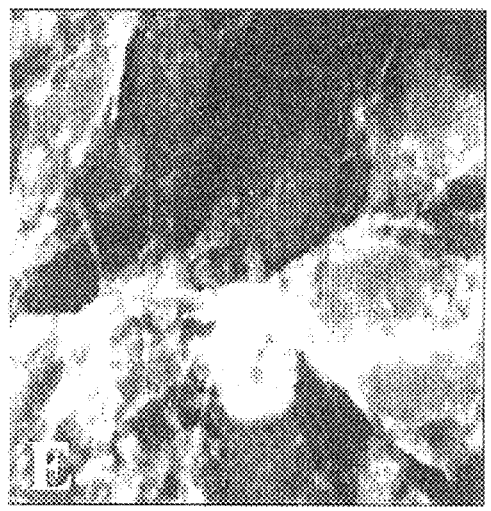
Figure 18F:
Figure 18G:
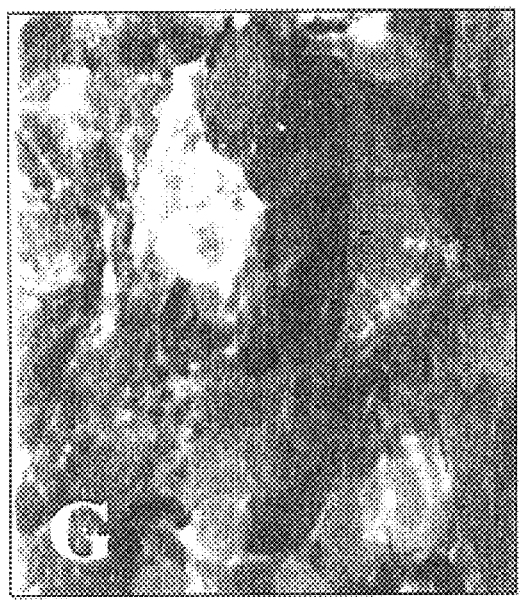
Figure 18H:
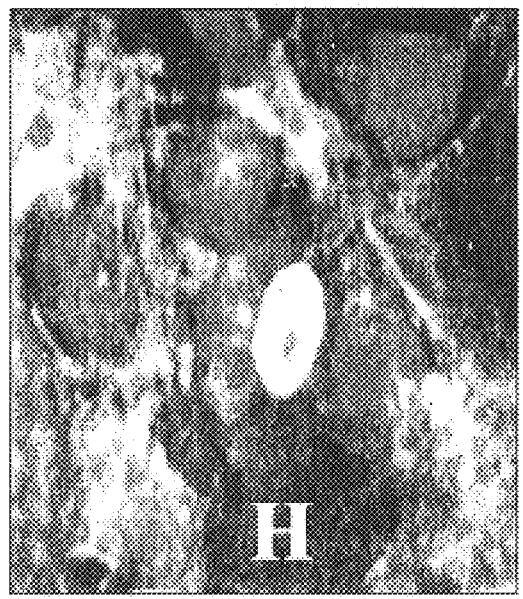

FIGS. 18A–H show confocal micrographs of prostate cancer cells treated with an hCG or hCG related preparation and then stained with FITC-labelled actin monoclonal antibody to visualize the cytoskeleton and propidium iodine to visualize the cell nucleus. Condensation of the nucleus and damage to the cytoskeleton are indications of apoptosis. These micrographs demonstrate increased apoptosis in cells treated with hCG APL™ (FIG. 18B), the β-hCG peptide 44–57 (with cysteine substituted at position 44; SEQ ID NO:26) (FIG. 18C); and fraction 64 of the human early pregnancy urine SUPERDEX™ 200 fractionation (described herein) (FIG. 18D) compared to controls (FIGS. 18A and E–H).

FIG. 19 presents data on the inhibition of colony formation in the clonogenic assay. All of the hCG APL™ fractions, as well as 200 IU and 500 IU of the hCG APL™ preparation inhibited prostate cancer cell colony formation as compared to PBS alone.

The circularized β-hCG peptide 44–57 (with cysteine substituted at position 44; SEQ ID NO:26) (200 µg per day), and the hCG APL™ preparation (100 IU per day) were administered systemically to nude mice in which prostate cancers were induced and also caused apoptosis of the prostate cancer cells in vivo (FIGS. 20A–C).

Effect of hCG Preparations, hCG Fractions and β-hCG Peptides on Lung Cancer Cells The effects of hCG preparations, hCG fractions and β-hCG peptides were tested in lung cancer cells in vitro. Lung cancer cells were incubated with the hCG preparations, hCG fractions and β-hCG peptides in both the trypan blue viability assay and the clonogenic assay. Table 6 presents data on the percentage of cell death as determined by the trypan blue assay.

TABLE 6

| Treatment | % dead cells |
| --- | --- |
| PBS | 11% |
| 200 IU hCG APL | 44% |
| 500 IU hCG APL | 66% |
| 200 µg/ml β-hCG 44[Cys]-57 | 42% |
| 300 µg/ml β-hCG 44[Cys]-57 | 59% |
| Urine Fraction 60 | 53% |
| Urine Fraction 64 | 59% |
| Urine Fraction 74 | 48% |
| Urine Fraction 23 | 13% |
| Urine Fraction 80 | 16% |
| APL Fraction 64 | 39% |
| APL Fraction 65 | 36% |
| APL Fraction 67 | 29% |
| APL Fraction 72 | 28% |
| APL Fraction 74 | 40% |
| APL Fraction 75 | 38% |

Table 6 shows that the hCG APL™ preparations, fractions 60, 64 and 74 of the human early pregnancy urine SUPERDEX™ 200 fractionation and fractions 64, 65, 67, 72, 74, and 75 of the hCG APL™ fractionation and the circularized β-hCG peptide 44–57 (with cysteine substituted for position 44; SEQ ID NO:26), all significantly caused cell death of the lung cancer cells. All hCG fractions were added at a concentration of 200 µl/ml. Note that fractions 26 and 80 of the early pregnancy urine fractionation, which fractions did not have anti-HIV, anti-KS or pro-hematopoietic activity (as shown herein), did not increase lung cancer cell death. These results are also presented as a bar graph in FIG. 21.

Figure 23A:
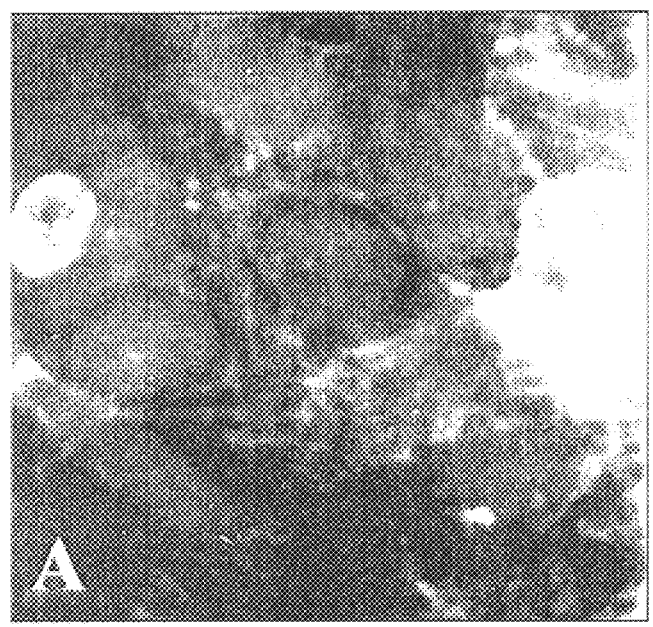
Figure 23B:
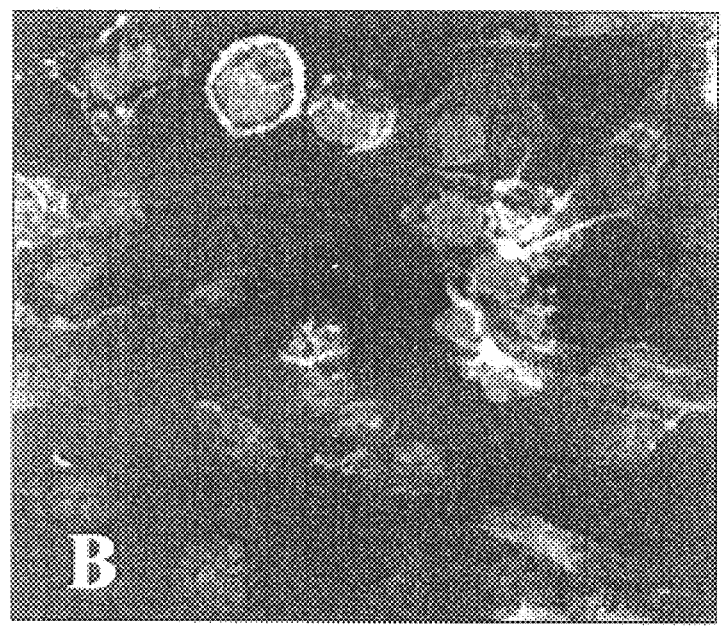
Figure 23C:
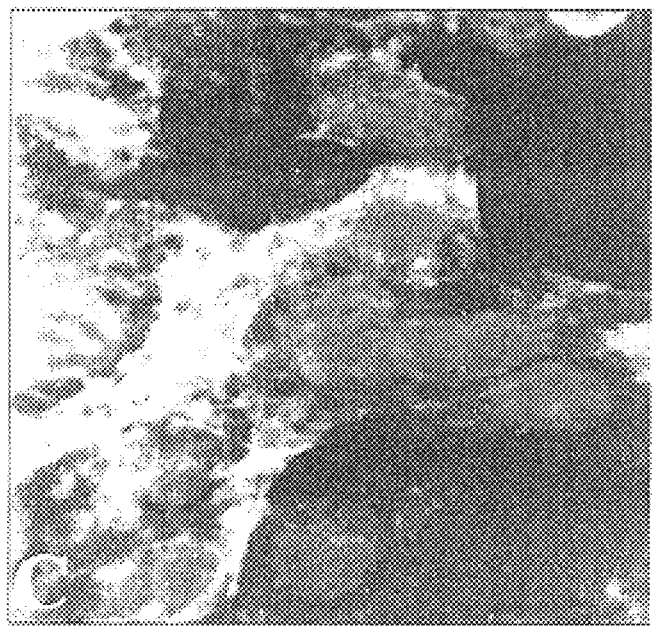
Figure 23D:
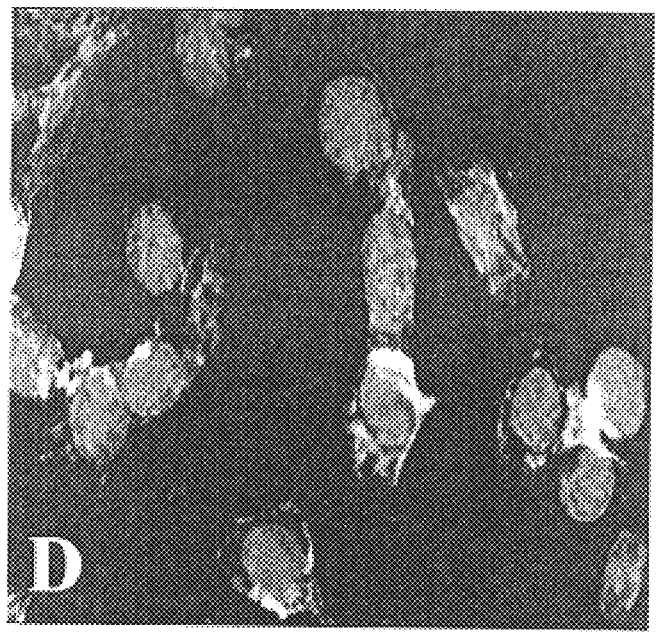
Figure 23E:
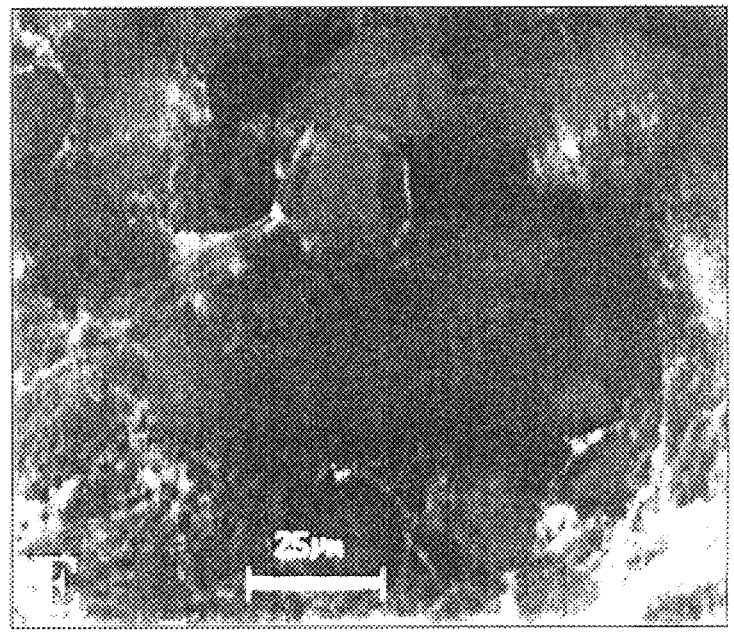
Figure 23F:
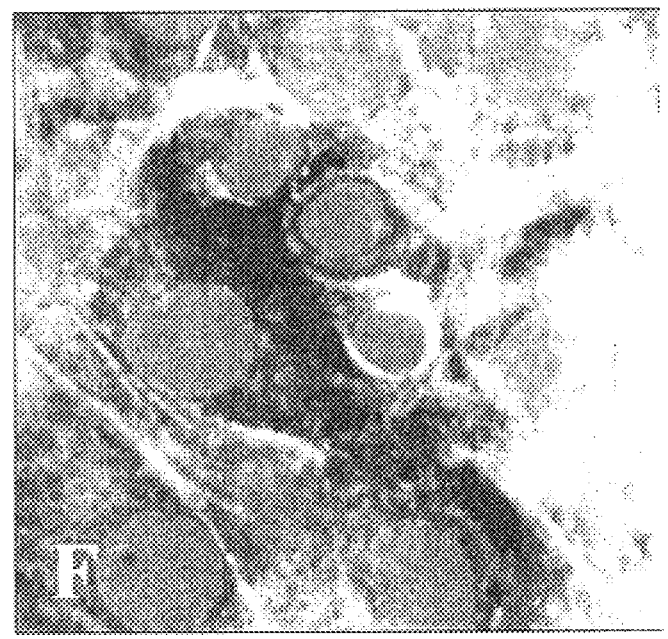

FIGS. 23A–F show confocal micrographs of lung cancer cells treated with the hCG or hCG related preparation and then stained with FITC-labelled actin monoclonal antibody to visualize the cytoskeleton and propidium iodine to visualize the cell nucleus. Condensation of the nucleus and damage to the cytoskeleton are indications of apoptosis. The micrographs show increased apoptosis in cells treated with hCG APL™ (FIG. 23B) and the β-hCG peptide 44–57 (with cysteine substituted at position 44; SEQ ID NO:26) (FIG. 23C) compared to controls (FIGS. 23A and D–E).

FIGS. 22A–C present data on the inhibition of colony formation in the clonogenic assay. The hCG APL™, fractions 60, 64 and 74 of the human early pregnancy urine SUPERDEX 200 fractionation and fractions 60, 64, and 74 of the hCG APL™ fractionation all significantly inhibited lung cancer cell colony formation as compared to PBS alone controls (FIGS. 22A and C). Furthermore, the β-hCG peptides circularized β-hCG 44–57 (with cysteine substituted for position 44; SEQ ID NO:26—"SATA2"), β-hCG 45–57 (SEQ ID NO:6—"SATA1"), and fused β-hCG peptides of 45–57::109–119 (SEQ ID NO:30—"SATAB") also inhibited colony formation of the lung cancer cells as compared to controls (FIGS. 22A–C).

Effect of hCG Preparations, hCG Fractions and β-hCG Peptides on Breast Cancer Cells The effects of hCG preparations, hCG fractions and β-hCG peptides were also tested in breast cancer cells in vitro. Breast cancer cells were incubated with the hCG preparations, hCG fractions and β-hCG peptides in both the trypan blue viability assay and the clonogenic assay. Table 7 presents data on the percentage of cell death as determined by the trypan blue assay.

TABLE 7

| Treatment | % dead cells |
| --- | --- |
| PBS | 4% |
| 100 IU hCG APL | 34% |
| APL Fraction 26 | 3% |
| APL Fraction 55 | 13.3% |
| APL Fraction 65 | 44% |
| APL Fraction 76 | 40% |
| APL Fraction 82 | 5.4% |
| Urine Fraction 26 | 7% |
| Urine Fraction 55 | 12% |
| Urine Fraction 64 | 25% |
| Urine Fraction 65 | 42% |
| Urine Fraction 76 | 44% |
| Urine Fraction 82 | 7% |
| 100 ug/ml Circ β-hCG 44[Cys]-57 | 42% |
| Scramble 45–57::109–119 | 8.6% |

Table 7 shows that the hCG APL™ preparations, fractions 60, 64 and 76 of the human early pregnancy urine SUPERDEX™ 200 fractionation and fractions 65 and 76 of the hCG APL™ fractionation and the circularized β-hCG peptide 44–57 (with cysteine substituted for position 44; SEQ ID NO:26), all significantly caused cell death of the breast cancer cells. All hCG fractions were added at a concentration of 200 µl/ml. The scrambled fused β-hCG peptide of amino acids 45–57 and 109–119 did not cause cell death. Note that fractions 26, 55 and 82 of the early pregnancy urine fractionation and fractions 55 and 82 of the hCG APL™ fractionation, which fractions did not have anti-HIV, anti-KS or pro-hematopoietic activity, did not increase breast cancer cell death.

The hCG preparation, hCG fractions and β-hCG peptides were also tested for the inhibition of breast cancer cell colony formation in the clonogenic assay. The data is presented in Table 8.

TABLE 8

| Treatment | % inhibition |
| --- | --- |
| PBS | 98.3% |
| hCG-APL-100 IU/ml | 50% |
| APL Fraction 26 | 0% |
| APL Fraction 55 | 12.5% |
| APL Fraction 65 | 50.4% |
| APL Fraction 76 | 56.3% |
| Urine Fraction 26 | 0% |
| Urine Fraction 55 | 15.2% |
| Urine Fraction 65 | 51% |
| 100 ug/ml Circ β-hCG 44[Cys]-57 | 45% |
| Scramble 45–57::109–119 | 0% |

The hCG APL™, fraction 65 of the human early pregnancy urine SUPERDEX™ 200 fractionation and fractions 65 and 76 of the hCG APL™ fractionation, and the circularized β-hCG peptide 44–57 (with cysteine substituted for position 44; SEQ ID NO:26) all significantly inhibited colony formation of the breast cancer cells as compared to PBS alone controls. The scrambled fused peptide of amino acids 45–57 (SEQ ID NO:6) and 109–119 (SEQ ID NO:7) did not significantly inhibit of colony formation. Note that fractions 26 and 55 of the early pregnancy urine fractionation and fractions 26 and 55 of the hCG APL™ fractionation, which fractions did not have anti-HIV, anti-KS or pro-hematopoietic activity, did not inhibit breast cancer colony formation.

Effect of hCG Preparations on Kidney Cancer Cells

Figure 1E:
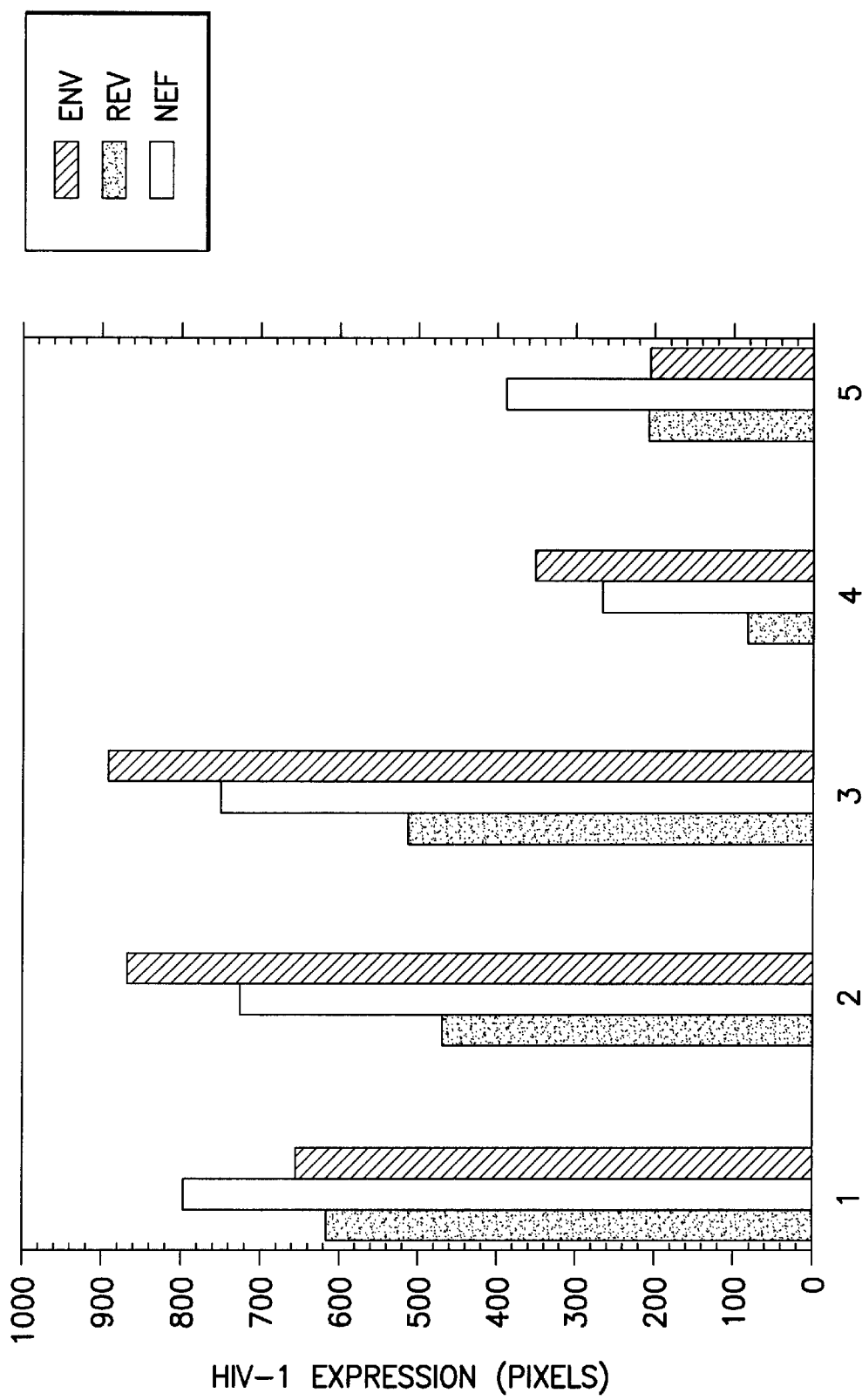
Figure 24A:
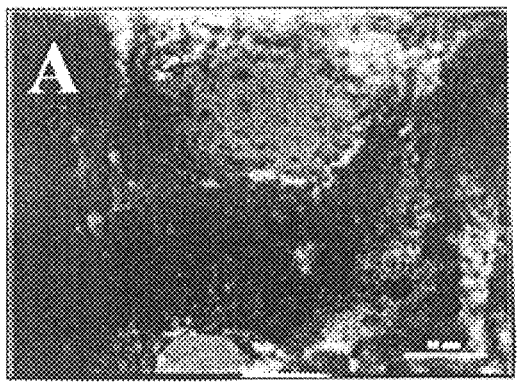
Figure 24B:
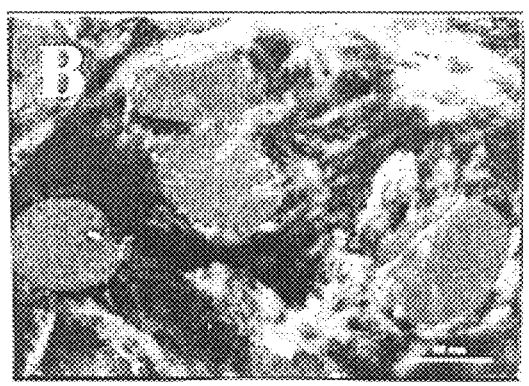
Figure 24C:
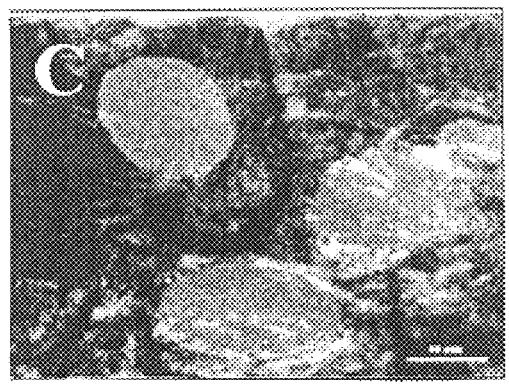
Figure 24D:
Figure 24E:
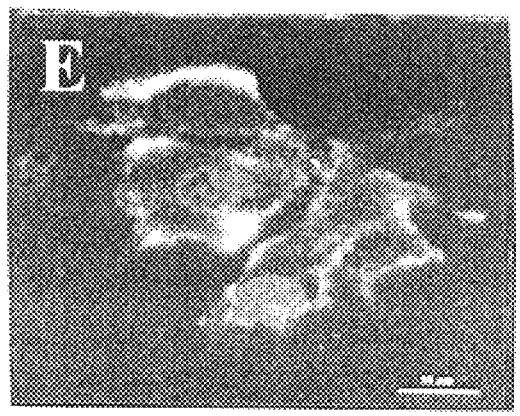
Figure 24F:
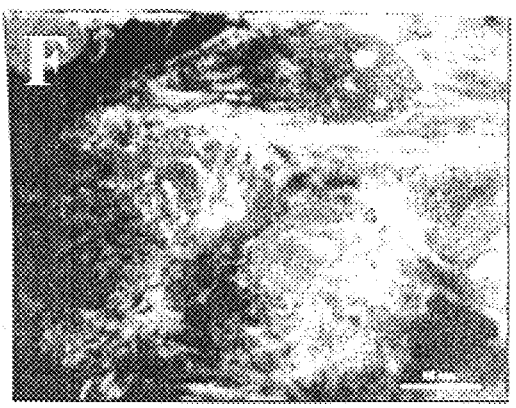
Figure 24G:
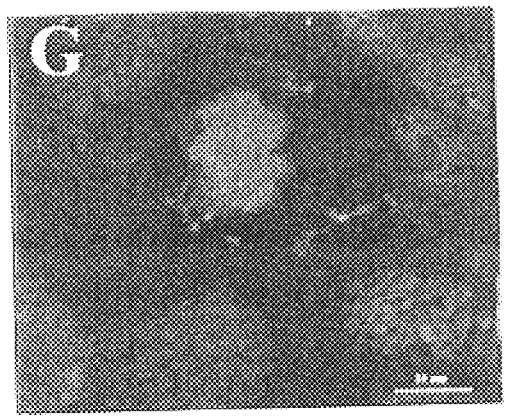
Figure 24H:
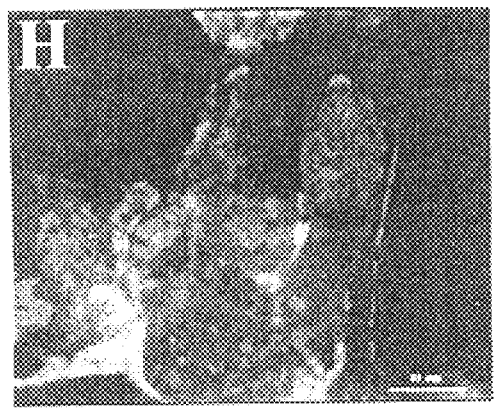
Figure 24I:
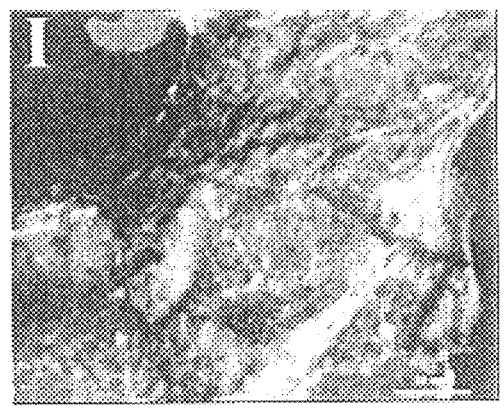

Two different concentrations of the hCG APL™ preparation were tested for the ability to induce apoptosis in kidney cancer cells. FIGS. 24A–I show confocal micrographs of kidney cancer cells treated with the hCG APL™ preparation and then stained with FITC-labelled actin monoclonal antibody to visualize the cytoskeleton and propidium iodine to visualize the cell nucleus. Condensation of the nucleus and damage to the cytoskeleton are indications of apoptosis. The micrographs show increased apoptosis in cells treated with 100 IU hCG APL™ (FIGS. 24D–F) and even higher levels of apoptosis in cultured kidney cancer cells treated with 300 IU hCG APL™ (FIGS. 24G–I) compared to controls treated only with PBS (FIGS. 24A–C). Effect of Fractions of a Commercial hCG Preparation and Early Pregnancy Urine on HIV Gene Expression in HIV-I Transgenic Mice Finally, fractions from the APL™ hCG and early pregnancy urine fractionation were tested for their ability to improve survival and to reduce HIV-I gene expression in HIV-I transgenic mice. FIG. 1E presents results of administration of 200 µl of fraction 61 of the APL™ hCG fractionation (bar 4) and fraction 65 of the early pregnancy urine fractionation (bar 5). These two fractions, both of which are within the peak of anti-HIV and anti-KS activity that contains material with an apparent molecular weight of approximately 15 kD, significantly suppressed HIV-I gene expression in the HIV-I transgenic mice (as measured in the skin and the kidney) in comparison to PBS alone (bar 1), β-hCG core peptide (bar 2) and α-hCG subunit (bar 3).

HIV-I transgenic pups administered hCG and hCG-related preparations for the first 5 days after birth through the mothers milk were monitored for survival at 10 days after birth. All the pups receiving the unfractionated APL™ hCG (bar 2), fraction 65 from both the APL™ hCG fractionation and the early pregnancy urine fractionation (bars 4 and 5, respectively), and fraction 76 of the early pregnancy urine fractionation (bar 6) survived (FIG. 14). These fractions 65 and 76 are within the anti-HIV and anti-KS activity peaks containing material with apparent molecular weights of approximately 15 kD and 2–3 kD, respectively. None of the pups receiving fraction 26 of either the APL™ hCG or the early pregnancy urine (bars labelled as "HAF-CF#26" and "HAF-UF#26", respectively) survived (FIG. 14). These fractions contain material with an apparent molecular weight larger than the hCG heterodimer (77 kD). FIG. 14 also presents data showing that native β-hCG (bar 1) and the β-hCG peptide of amino acids 44–57 (with cysteine substituted at position 44; SEQ ID NO: 26—bar 7) and to a lesser extent LH (bar 3) promote survival of the HIV-I transgenic pups while the α-hCG subunit, the highly purified hCG preparation CR127, recombinant β-hCG and the β-hCG core protein (bars labelled as "ahCG", "CR127", "rβhCG", and "b-core", respectively) failed to promote survival of the transgenic mouse pups.

The above-described experiments demonstrate that the factor(s) responsible for the anti-HIV and anti-KS activities can be further isolated from the hCG preparations by gel filtration on a SUPERDEX™ 200 gel filtration column. The factor(s) were fractionated from both the commercial APL™ hCG preparation and urine from women in early pregnancy (first trimester). The fractions of highest anti-HIV and anti-KS activity contained material eluting from the gel filtration column with an apparent molecular weights of approximately 40 kD, 15 kD and 2–3 kD. Although certain active fractions contained material of approximately the size of the β-hCG core protein (~10 kD), purified β-hCG core protein was found to have neither anti-HIV nor anti-KS activity. The fractions exhibiting anti-HIV and anti-KS activity in vitro also had pro-hematopoietic activity in vitro, caused regression of KS tumors induced in mice, and promoted survival and reduced HIV-I gene expression in HIV-I transgenic mice. Furthermore, phenol, an additive in the APL™ hCG preparation, had no anti-HIV activity.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims. Various references are cited herein, the disclosures of which are incorporated by reference in their entireties.

What is claimed is:

1. An isolated protein or peptide:
  (a) comprising at least one amino acid segment selected from the group consisting of:
    (i) a 5 to 50 amino acid segment of the sequence of β-hCG (SEQ ID NO:2); and
    (ii) a derivative of the segment of (a) having one or more conservative substitutions relative to the sequence of β-hCG (SEQ ID NO:2);
  (b) exhibiting at least one therapeutic effect selected from the group consisting of:
    (i) reduction of HIV viral load or prevention of progression of HIV infection in a subject infected with HIV;
    (ii) reduction of cancer cells or prevention of progression of cancer in a subject with cancer; and
    (iii) promotion of hematopoiesis resulting in an increased hematopoietic cell count or slowed progression of a degenerative hematopoeitic deficiency in a subject in need thereof;
with the proviso that the protein or peptide does not comprise the full-length native sequence of β-hCG (SEQ ID NO: 2) and with the proviso that the protein or peptide does not consist of β-hCG 109–119 (segment of SEQ ID NO: 2) or 109–145 (segment of SEQ ID NO: 2).

2. The protein or peptide of claim 1 wherein the therapeutic effect comprises reduction of HIV viral load or prevention of progression of HIV infection in a subject infected with HIV.

3. The protein or peptide of claim 1 wherein the therapeutic effect comprises reduction of cancer cells or prevention of progression of cancer in a subject with cancer.

4. The protein or peptide of claim 1 wherein the therapeutic effect comprises promotion of hematopoiesis resulting in an increased hematopoietic cell count or slowed progression of a degenerative hematopoeitic deficiency in a subject in need thereof.

5. The protein or peptide of claim 1 wherein the therapeutic effect comprises two or more therapeutic effects of said group.

6. The protein or peptide of claim 1 wherein the segment is selected from residues 40–145 of β-hCG (SEQ ID NO:2).

7. The protein or peptide of claim 1 wherein the segment is selected from residues 40–60 of β-hCG (SEQ ID NO:2).

8. The protein or peptide of claim 1 wherein the segment is from 5 to 25 amino acid residues in length.

9. The protein or peptide of claim 1 wherein the segment is from 5 to 15 amino acid residues in length.

10. The protein or peptide of claim 1 wherein the segment:
    (a) begins at any β-hCG (SEQ ID NO: 2) amino acid residue from residue 40 to residue 48; and
    (b) ends at any β-hCG (SEQ ID NO: 2) amino acid residue from residue 53 to residue 60.

11. The protein or peptide of claim 1 wherein the segment:
    (a) begins at any β-hCG (SEQ ID NO: 2) amino acid residue from residue 41 to residue 48; and
    (b) ends at any β-hCG (SEQ ID NO: 2) amino acid residue from residue 53 to residue 59.

12. The protein or peptide of claim 1 wherein the segment:
    (a) begins at any β-hCG (SEQ ID NO: 2) amino acid residue from residue 42 to residue 48; and
    (b) ends at any β-hCG (SEQ ID NO: 2) amino acid residue from residue 53 to residue 58.

13. The protein or peptide of claim 1 wherein the segment:
    (a) begins at any β-hCG (SEQ ID NO: 2) amino acid residue from residue 43 to residue 48; and
    (b) ends at any β-hCG (SEQ ID NO: 2) amino acid residue from residue 53 to residue 57.

14. The protein or peptide of claim 1 wherein the segment is β-hCG 41–54 (SEQ ID NO: 3).

15. The protein or peptide of claim 1 wherein the segment is β-hCG 45–54 (SEQ ID NO: 4).

16. The protein or peptide of claim 1 wherein the segment is β-hCG 47–53 (SEQ ID NO: 5).

17. The protein or peptide of claim 1 wherein the segment is β-hCG 45–57 (SEQ ID NO: 6).

18. The protein or peptide of claim 1 wherein the segment is β-hCG 41–53 (SEQ ID NO: 8).

19. The protein or peptide of claim 1 wherein the segment is β-hCG 42–53 (SEQ ID NO: 9).

20. The protein or peptide of claim 1 wherein the segment is β-hCG 43–53 (SEQ ID NO: 10).

21. The protein or peptide of claim 1 wherein the segment is β-hCG 44–53 (SEQ ID NO: 11).

22. The protein or peptide of claim 1 wherein the segment is β-hCG 44–57 (SEQ ID NO: 12).

23. The protein or peptide of claim 1 wherein the segment is β-hCG 45–53 (SEQ ID NO: 13).

24. The protein or peptide of claim 1 wherein the segment is β-hCG 46–53 (SEQ ID NO: 14).

25. The protein or peptide of claim 1 wherein the segment is β-hCG 45–55 (SEQ ID NO: 16).

26. The protein or peptide of claim 1 wherein the segment is β-hCG 45–56 (SEQ ID NO: 17).

27. The protein or peptide of claim 1 wherein the segment is β-hCG 45–58 (SEQ ID NO: 18).

28. The protein or peptide of claim 1 wherein the segment is β-hCG 47–54 (SEQ ID NO: 19).

29. The protein or peptide of claim 1 wherein the segment is β-hCG 47–57 (SEQ ID NO: 20).

30. The protein or peptide of claim 1 wherein the segment is β-hCG 47–56 (SEQ ID NO: 21).

31. The protein or peptide of claim 1 wherein the segment is β-hCG 47–58 (SEQ ID NO: 22).

32. The protein or peptide of claim 1 wherein the segment is β-hCG 48–145 (SEQ ID NO: 23).

33. The protein or peptide of claim 1 wherein the segment is β-hCG 58–145 (SEQ ID NO: 24).

34. The protein or peptide of claim 1 wherein the segment is β-hCG 7–40 (SEQ ID NO: 33).

35. The protein or peptide of claim 1 wherein the segment is β-hCG 46–65 (SEQ ID NO: 34).

36. The protein or peptide of claim 1 wherein the segment is β-hCG 48–56 (SEQ ID NO: 35).

37. The protein or peptide of claim 1 wherein the segment is β-hCG 41–54 (SEQ ID NO: 36).

38. The protein or peptide of any of claims 14 to 37 wherein the protein or peptide lacks β-hCG amino acid residues contiguous to the segment.

39. The protein or peptide of claim 1 which is N-acetylated or has a C-terminal amide or is both N-acetylated and has a C-terminal amide.

40. The protein or peptide of claim 1 comprising an insertion of or substitution with one or more non-classical amino acid residues or one or more D-amino acid residues.

41. The protein or peptide of claim 40 comprising an insertion of or substitution with one or more D-amino acid residues selected from the group consisting of D-glycine, D-alanine, D-valine, D-leucine, D-isoleucine, D-serine, D-threonine, D-phenylalanine, D-tyrosine, D-tryptophan, D-cysteine, D-methionine, D-proline, D-asparagine, D-glutamine, D-aspartate, D-glutamine, D-lysine, D-arginine, and D-histidine.

42. The protein or peptide of claim 40 comprising an insertion of or substitution with one or more non-classical amino acid residues selected from the group consisting of 2,4-diaminobutyric acid, α-amino isobutyric acid, 4-aminobutyric acid, Abu, 2-amino butyric acid, γ-Abu, ε-Ahx, 6-aminohexanoic acid, Aib, 2-aminoisobutyric acid, 3-amino propionic acid, omithine, norleucine, norvaline, hydroxyproline, sarcosine, citrulline, homocitrulline, cysteic acid, t-butylglycine, t-butylalanine, phenylglycine, cyclohexylalanine, β-alanine, flouro-amino acid residues, β-methyl amino acid residues, Cα-methyl amino acid residues and amino acid analogues.

43. The protein or peptide of claim 1 comprising two or more segments from the group set forth in 84(a).

44. The protein or peptide of claim 1 comprising two or more segments from the group set forth in 84(a), wherein the segments are linked via a peptide bond between the N-terminus of a first segment and the C-terminus of a second segment.

45. The protein or peptide of claim 44 wherein the amino acid sequence of the protein or peptide is comprises a segment selected from the group consisting of:
    (a) β-hCG 45–57 (SEQ ID NO:6) linked at the C-terminus via a peptide bond to the N-terminus of β-hCG 109–119 (SEQ ID NO:7);
    (b) β-hCG 110–119 (SEQ ID NO:27) linked at the C-terminus via a peptide bond to the N-terminus of β-hCG 45–57 (SEQ ID NO:6); and
    (c) β-hCG 47–57 (SEQ ID NO:28) linked at the C-terminus via a peptide bond to the N-terminus of β-hCG 108–119 (SEQ ID NO:29).

46. The protein or peptide of claim 43 wherein one or more of the segments is joined via a covalent bond to a heterologous amino acid sequence.

47. The protein or peptide of claim 43 wherein one or more of the segments is joined via a peptide bond to a heterologous amino acid sequence.

48. The protein or peptide of claim 1 wherein at least two amino acids are linked by a covalent bond to form a circularized protein or peptide.

49. The protein or peptide of claim 48 wherein the segment is selected from residues 40–145 of the β-hCG amino acid sequence (SEQ ID NO:2).

50. The protein or peptide of claim 48 wherein the segment is selected from residues 40–60 of the β-hCG amino acid sequence (SEQ ID NO:2).

51. The protein or peptide of claim 48 wherein the segment is from 5 to 25 amino acid residues in length.

52. The protein or peptide of claim 48 wherein the segment is from 5 to 15 amino acid residues in length.

53. The protein or peptide of claim 48 wherein the segment is selected from the group consisting of β-hCG 41–54, 45–54, 47–53, 45–57, 109–119, 41–53, 42–53, 43–53, 44–53, 44–57, 45–53, 46–53, 45–55, 45–56, 45–58, 47–54, 47–57, 47–56, 47–58, 48–145, 58–145, 109–145, 7–40, 46–65 and 48–56 (SEQ ID NOS: 3–14, 16–25 and 33–35, respectively).

54. The protein or peptide according to claim 48 comprising at least two cysteine residues linked by a disulfide bond, and optionally satisfying one or more of the following conditions:
(a) at least one cysteine residue is inserted between two non-cysteine residues;
(b) at least one cysteine residue is coupled at an end of the amino acid sequence; and
(c) at least one non-cysteine residue is replaced by a cysteine residue.

55. The protein or peptide of claim 48:
(a) comprising two or more of the segments;
(b) wherein the segments are at least 5 amino acid residues in length and are non-naturally contiguous.

56. The protein or peptide of claim 48:
(a) comprising two or more of the segments;
(b) wherein the segments are at least 5 amino acid residues in length and are non-naturally contiguous; and
(c) wherein the segments are linked end-to-end via peptide bond(s).

57. The protein or peptide of claim 1 wherein the segment is linked by a side chain to a second sequence of one or more amino acid residues.

58. The protein or peptide of claim 57 wherein the side chain comprises an amino or carboxyl group and forms a peptide bond with the second sequence of one or more amino acid residues.

59. The protein or peptide of claim 57 wherein the segment is selected from residues 40–145 of β-hCG (SEQ ID NO:2).

60. The protein or peptide of claim 57 wherein the segment is selected from residues 40–60 of β-hCG (SEQ ID NO:2).

61. The protein or peptide of claim 57 wherein the segment is from 5 to 25 residues in length.

62. The protein or peptide of claim 57 wherein the segment is from 5 to 15 amino acid residues in length.

63. The protein or peptide of claim 57 wherein the segment is selected from the group consisting of β-hCG 41–54, 45–54, 47–53, 45–57, 109–119, 41–53, 42–53, 43–53, 44–53, 44–57, 45–53, 46–53, 45–55, 45–56, 45–58, 47–54, 47–57, 47–56, 47–58, 48–145, 58–145, 109–145, 7–40, 46–65, and 48–56 (SEQ ID NOS: 3–14, 16–25 and 33–35, respective).

64. The protein or peptide of claim 57 wherein at least two amino acid residues of the segment are linked by a covalent bond to form a circularized protein or peptide.

65. The protein or peptide of claim 64 wherein at least two amino acid residues of the segment are linked by a disulfide bond to form a circularized protein or peptide.

66. The protein or peptide of claim 64 wherein the segment is selected from the group consisting of 5 to 50 amino acid segments from the β-hCG amino acid sequence (SEQ ID NO:2).

67. The protein or peptide of claim 64 wherein the segment is selected from residues 40–145 of the β-hCG amino acid sequence (SEQ ID NO:2).

68. The protein or peptide of claim 64 wherein the segment is selected from residues 40–60 of the β-hCG amino acid sequence (SEQ ID NO:2).

69. The protein or peptide of claim 64 wherein the segment is selected from the group consisting of 5 to 25 amino acid segments of the β-hCG amino acid sequence (SEQ ID NO:2).

70. The protein or peptide of claim 64 wherein the segment is selected from the group consisting of β-hCG 41–54, 45–54, 47–53, 45–57, 109–119, 41–53, 42–53, 43–53, 44–53, 44–57, 45–53, 46–53, 45–55, 45–56, 45–58, 47–54, 47–57, 47–56, 47–58, 48–145, 58–145, 109–145, 7–40, 46–65 and 48–56 (SEQ ID NOS: 3–14, 16–25 and 33–35, respectively).

71. The protein or peptide according to claim 64 comprising at least two cysteine residues linked by a disulfide bond, and optionally satisfying one or more of the following conditions:
(a) at least one cysteine residue is inserted between two non-cysteine residues;
(b) at least one cysteine residue is coupled at an end of the amino acid sequence; and
(c) at least one non-cysteine residue is replaced by a cysteine residue.

72. The protein or peptide of claim 64,
(a) comprising two or more of the segments;
(b) wherein the segments are at least 5 amino acid residues in length and are non-naturally contiguous.

73. The protein or peptide of claim 64,
(a) comprising two or more of the segments;
(b) wherein the segments are at least 5 amino acid residues in length and are non-naturally contiguous; and
(c) wherein the segments are linked end-to-end via peptide bond(s).

74. A pharmaceutical composition comprising the protein or peptide of claim 1 and a pharmaceutically acceptable carrier.

75. A pharmaceutical composition comprising the protein or peptide of claim 2 and a pharmaceutically acceptable carrier.

76. A pharmaceutical composition comprising the protein or peptide of claim 7 and a pharmaceutically acceptable carrier.

77. A pharmaceutical composition comprising the protein or peptide of claim 8 and a pharmaceutically acceptable carrier.

78. A pharmaceutical composition comprising the protein or peptide of claim 9 and a pharmaceutically acceptable carrier.

79. A peptide consisting of the amino acid sequence of β-hCG 41–54 (SEQ ID NO: 3).

80. A peptide consisting of the amino acid sequence of β-hCG 45–54 (SEQ ID NO: 4).

81. A peptide consisting of the amino acid sequence of β-hCG 47–53 (SEQ ID NO: 5).

82. A peptide consisting of the amino acid sequence of β-hCG 45–57 (SEQ ID NO: 6).

83. A peptide consisting of the amino acid sequence of β-hCG 41–53 (SEQ ID NO: 8).

84. A peptide consisting of the amino acid sequence of β-hCG 42–53 (SEQ ID NO: 9).

85. A peptide consisting of the amino acid sequence of β-hCG 43–53 (SEQ ID NO: 10).

86. A peptide consisting of the amino acid sequence of β-hCG 44–53 (SEQ ID NO: 11).

87. A peptide consisting of the amino acid sequence of β-hCG 44–57 (SEQ ID NO: 12).

88. A peptide consisting of the amino acid sequence of β-hCG 45–53 (SEQ ID NO: 13).

89. A peptide consisting of the amino acid sequence of β-hCG 46–53 (SEQ ID NO: 14).

90. A peptide consisting of the amino acid sequence of β-hCG 45–55 (SEQ ID NO: 16).

91. A peptide consisting of the amino acid sequence of β-hCG 45–56 (SEQ ID NO: 17).

92. A peptide consisting of the amino acid sequence of β-hCG 45–58 (SEQ ID NO: 18).

93. A peptide consisting of the amino acid sequence of β-hCG 47–54 (SEQ ID NO: 19).

94. A peptide consisting of the amino acid sequence of β-hCG 47–57 (SEQ ID NO: 20).

95. A peptide consisting of the amino acid sequence of β-hCG 47–56 (SEQ ID NO: 21).

96. A peptide consisting of the amino acid sequence of β-hCG 47–58 (SEQ ID NO: 22).

97. A peptide consisting of the amino acid sequence of β-hCG 48–145 (SEQ ID NO: 23).

98. A peptide consisting of the amino acid sequence of β-hCG 58–145 (SEQ ID NO: 24).

99. A peptide consisting of the amino acid sequence of β-hCG 7–40 (SEQ ID NO: 33).

100. A peptide consisting of the amino acid sequence of β-hCG 46–65 (SEQ ID NO: 34).

101. A peptide consisting of the amino acid sequence of β-hCG 48–56 (SEQ ID NO: 35).

102. A peptide consisting of the amino acid sequence of β-hCG 41–54 (SEQ ID NO: 36).

* * * * *